US007741028B2

(12) United States Patent
Dunlop et al.

(10) Patent No.: US 7,741,028 B2
(45) Date of Patent: Jun. 22, 2010

(54) METHODS OF IDENTIFYING GENETIC MARKERS IN THE HUMAN CYSTIC FIBROSIS TRANSMEMBRANE CONDUCTANCE REGULATOR (CFTR) GENE

(75) Inventors: Charles L. M. Dunlop, Irvine, CA (US); James M. Weisel, Manhatton Beach, CA (US)

(73) Assignee: Ambry Genetics, Aliso Viejo, CA (US)

( * ) Notice: Subject to any disclaimer, the term of this patent is extended or adjusted under 35 U.S.C. 154(b) by 1873 days.

(21) Appl. No.: 10/300,683

(22) Filed: Nov. 19, 2002

(65) Prior Publication Data
US 2003/0235834 A1     Dec. 25, 2003

Related U.S. Application Data

(63) Continuation-in-part of application No. 10/142,722, filed on May 8, 2002, now abandoned, which is a continuation of application No. PCT/US00/30493, filed on Nov. 3, 2000, application No. 10/300,683, which is a continuation-in-part of application No. 09/851,501, filed on May 8, 2001, now abandoned.

(60) Provisional application No. 60/165,301, filed on Nov. 12, 1999, provisional application No. 60/333,531, filed on Nov. 19, 2001.

(51) Int. Cl.
*C12Q 1/68* (2006.01)
*C12P 19/34* (2006.01)
(52) U.S. Cl. .......................... 435/6; 435/91.1; 435/91.2
(58) Field of Classification Search .................. 435/6, 435/91.1, 91.2
See application file for complete search history.

(56) References Cited

U.S. PATENT DOCUMENTS

| | | | |
|---|---|---|---|
| 5,407,796 A | 4/1995 | Cutting et al. | 435/6 |
| 5,585,236 A | 12/1996 | Bonn et al. | 435/5 |
| 5,795,976 A | 8/1998 | Oefner et al. | 536/25.4 |
| 5,814,491 A | 9/1998 | Vijg et al. | 435/91.2 |
| 6,007,231 A | 12/1999 | Vijg et al. | 364/497 |
| 6,024,878 A | 2/2000 | Gjerde et al. | 210/635 |
| 6,183,958 B1 | 2/2001 | Stanton, Jr. | 435/6 |
| 6,210,885 B1 | 4/2001 | Gjerde et al. | 435/6 |
| 6,268,147 B1 | 7/2001 | Beattie et al. | 435/6 |

OTHER PUBLICATIONS

Costes et al., Human Mutation 2, 185-191 (1993).*
Buck et al., BioTechniques 27, 528-536 (1999).*
Lowe et al., Nucleic Acids Research 18(7), 1757-1761 (1990).*
Agirre, et al., "Exon Concatenation to Increase the Efficiency of Mutation Screening by DGGE," BioTechniques, 32:1054-1070 2002.
Bjørheim, et al., "Mutation analyses of KRAS exon 1 comparing three different techniques: temporal temperature gradient electrophoresis, constant denaturant capillary electrophoresis and allele specific polymerase chain reaction," Mutation Research, 403:103-112, 1998.
Buyse, et al., "Diagnostic Testing for Rett Syndrome by DHPLC and Direct Sequencing Analysis of the MECP2 Gene: Identification of Several Novel Mutations and Polymorphisms," Am. J. Hum. Genet., 67:1428-1436, 2000.
Chen, et al., "Detection of Mitochondrial DNA Mutations by Temporal Temperature Gradient Gel Electrophoresis," Clinical Chemistry 45(8):1162-1167, 1999.
Choy, et al., "Superiority of Denaturing High Performance Liquid Chromatography over single-stranded conformation and conformation-sensitive gel electrophoresis for mutation detection in TSC2," Ann Hum Genet., 63:383-391, 1999.
Ellis, et al., "A Comparison of Fluorescent SSCP and Denaturing HPLC for High Throughput Mutation Scanning," Hum. Mutat., 15:556-564, 2000.
Escary, et al., "Evaluation of DHPLC Analysis in Mutational Scanning of Notch3, a Gene With a High G-C Content," Hum. Mutat., 16:518-526, 2000.
Giordano, et al., "Identification by Denaturing High-performance Liquid Chromatography of Numerous Polymorphisms in a Candidate Region for Multiple Sclerosis Susceptibility," Genomics, 56:247-253, 1999.
Hayward-Lester, et al., "Accurate and Absolute Quantitative Measurement of Gene Expression by Single-tube RT-PCR and HPLC," Genome Research, 5:494-499, 1995.
Hecker, et al., "Analysis and purification of nucleic acids by ion-pair reversed-phase high-performance liquid chromatography," J. Biochem. Biophys. Methods, 46:83-93, 2000.
Higashimoto, et al., "Rapid Detection of FGFR Mutations in Syndromic Craniosynostosis by Temporal Temperature Gradient Gel Electrophoresis," Clinical Chemistry 45(11):2005-2006, 1999.
Hoogendoom, et al., "Cheap, accurate and rapid allele frequency estimation of single nucleotide polymorphisms by primer extension and DHPLC in DNA pools," Hum. Genet., 107:488-493, 2000.
Huber, et al., "High-Resolution Liquid Chromatography of Oligonucleotides on Nonporous Alkylated Styrene-Divinylbenzene Copolymers," Analytical Biochemistry, 212:351-358, 1993.
Huber, et al., "Mutation detection by capillary denaturing high-performance liquid chromatography using monolithic columns," J. Biochem. Biophys. Methods, 47:5-19, 2001.
Huber, et al., "Rapid Analysis of Biopolymers on Modified Non-Porous Polystyrene-Divinylbenzene Particles," Chromatographia, 37(11/12):653-658, 1993.

(Continued)

Primary Examiner—Kenneth R. Horlick
(74) Attorney, Agent, or Firm—Biotech Beach Law Group PC; Raymond Wagenknecht

(57) ABSTRACT

The present invention relates to the field of genetic screening. More specifically, the described embodiments concern methods to screen multiple samples, in a single assay, for the presence or absence of mutations or polymorphisms in a plurality of genes. Approaches to screen for the presence or absence of mutations that are associated with cystic fibrosis and approaches to design primers that generate extension products that facilitate the resolution of multiple extension products in a single lane of a gel or in a single run on a column are also provided.

11 Claims, 4 Drawing Sheets

OTHER PUBLICATIONS

Huber, et al., "Rapid and Accurate Sizing of DNA Fragments by Ion-Pair Chromatography on Alkylated Nonporous Poly(styrene-divinylbenzene) Particles," *Anal. Chem.*, 67:578-585, 1995.

Jones, et al., "Application and evaluation of denaturing HPLC for molecular genetic analysis in tuberous sclerosis," *Hum. Genet.*, 106:663-668, 2000.

Jones, et al., "Optimal Temperature Selection for Mutation Detection by Denaturing HPLC and Comparison to Single-Stranded Conformation Polymorphism and Heteroduplex Analysis," *Clinical Chemistry*, 45(8):1133-1140, 1999.

Kaler, et al., "Novel Method for Molecular Detection of the Two Common Hereditary Hemochromatosis Mutations," *Genetic Testing*, 4(2):125-129, 2000.

Lipsky, et al., "DNA Melting Analysis for Detection of Single Nuclotide Polymorphisms," *Clinical Chemistry*, 47(4):635-644, 2001.

Liu, et al, "Denaturing high performance liquid chromatography (DHPLC) used in the detection of germline and somatic mutations," *Nucleic Acids Research*, 26(6):1396-1400, 1998.

Liu, et al., "Denaturing HPLC-Identified Novel FBN1 Mutations, Polymorphisms, and Sequence Variants in Marfan Syndrome and Related Connective Tissue Disorders," *Genetic Testing*, 1(4):237-242, 1997/98.

Nickerson, et al., "Random Mutagenesis-PCR to Introduce Alterations Into Defined DNA Sequences for Validation of SNP and Mutation Detection Methods," *Human Mutation*, 17:210-219, 2001.

O'Donovan, et al., "Blind Analysis of Denaturing High-Performance Liquid Chromatography as a Tool for Mutation Detection," *Genomics*, 52:42-49, 1998.

Sauer, et al., "A novel procedure for efficient genotyping of single nucleoide polymorphisms," *Nucleic Acids Research*, 28(5):i-viii, 2000.

Schriml, et al., "Use of Denaturing HPLC to Map Human and Murine Genes and to Validate Single-Nucleotide Polymorphisms," *Biotechniques*, 28:740-745, 2000.

Skopek, et al., "Analysis of sequence alterations in a defined DNA region: comparison of temperature-modulated heteroduplex analysis and denaturing gradient gel electrophoresis," *Mutation Research*, 430:12-21, 1999.

Spiegelman, et al., "High-Accuracy DNA Sequence Variation Screening by DHPLC," *BioTechniques*, 29:1084-1092, 2000.

Underhill, et al., "A pre-Columbian Y chromosome-specific transition and its implications for human evolutionary history," *Proc. Natl. Acad. Sci. USA*, 93:196-200, 1996.

Underhill, et al., "Detection of Numerous Y Chromosome Biallelic Polymorphisms by Denaturing High-Performance Liquid Chromatography," *Genome Research*, 7:996-1005, 1997.

van den Bosch, et al., "Mutation analysis of the entire mitochondrial genome using denaturing high performance liquid chromatography," *Nucleic Acid Research*, 28(20):1-8, 2000.

Wolford, at al., "High-throughput SNP detection by using DNA pooling and denaturing high performance liquid chromatography (DHPLC)," *Hum. Genet*, 107:483-487, 2000.

Zoller, et al., "Temporal Temperature Gradient Gel Electrophoresis of Cystic Fibrosis Samples on the DCode System," *Bio-Rad*, Bulletin 2103 US/EG.

\* cited by examiner

SEQUENCE LISTING

<160> NUMBER OF SEQ ID NOS: 554

<210> SEQ ID NO 1
<211> LENGTH: 58
<212> TYPE: DNA
<213> ORGANISM: Artificial Sequence
<220> FEATURE:
<223> OTHER INFORMATION: Diagnostic Oligonucleotide

<400> SEQUENCE: 1
cgcccgccgc gccccgcgcc cgcccgcccg ccccgcccg ggatgataat tggaggca      58

<210> SEQ ID NO 2
<211> LENGTH: 20
<212> TYPE: DNA
<213> ORGANISM: Artificial Sequence
<220> FEATURE:
<223> OTHER INFORMATION: Diagnostic Oligonucleotide

<400> SEQUENCE: 2
taggagaagt gtgaataaag      20

<210> SEQ ID NO 3
<211> LENGTH: 60
<212> TYPE: DNA
<213> ORGANISM: Artificial Sequence
<220> FEATURE:
<223> OTHER INFORMATION: Diagnostic Oligonucleotide

<400> SEQUENCE: 3
cgcccgccgc gccccgcgcc cgcccgcccg ccccCgcccg ctgttctgtg atattatgtg      60

<210> SEQ ID NO 4
<211> LENGTH: 60
<212> TYPE: DNA
<213> ORGANISM: Artificial Sequence
<220> FEATURE:
<223> OTHER INFORMATION: Diagnostic Oligonucleotide

<400> SEQUENCE: 4
cgcccgccgc gccccgcgcc cgcccgcccg ccccCgcccg tttgcttctc cagttgaaca      60

<210> SEQ ID NO 5
<211> LENGTH: 60
<212> TYPE: DNA
<213> ORGANISM: Artificial Sequence
<220> FEATURE:
<223> OTHER INFORMATION: Diagnostic Oligonucleotide

<400> SEQUENCE: 5
cgcccgccgc gccccgcgcc cgcccgcccg ccccCgcccg ttgaagtgtc caccaaaatg      60

<210> SEQ ID NO 6
<211> LENGTH: 61
<212> TYPE: DNA
<213> ORGANISM: Artificial Sequence
<220> FEATURE:
<223> OTHER INFORMATION: Diagnostic Oligonucleotide

<400> SEQUENCE: 6
cgcccgccgc gccccgcgcc cgccctgcc gccccCgccc ggtactatcc ccaagtaacc      60
t      61

<210> SEQ ID NO 7
<211> LENGTH: 67
<212> TYPE: DNA
<213> ORGANISM: Artificial Sequence
<220> FEATURE:
<223> OTHER INFORMATION: Diagnostic Oligonucleotide

<400> SEQUENCE: 7
cgcccgccgc gccccgcgcc cgcccgcccg ccccCgcccg tacagtggat atagaaagga      60
caatttt      67

<210> SEQ ID NO 8
<211> LENGTH: 25
<212> TYPE: DNA
<213> ORGANISM: Artificial Sequence
<220> FEATURE:
<223> OTHER INFORMATION: Diagnostic Oligonucleotide

<400> SEQUENCE: 8
cagattctct acttcatagc catag      25

```
<210> SEQ ID NO 9
<211> LENGTH: 62
<212> TYPE: DNA
<213> ORGANISM: Artificial Sequence
<220> FEATURE:
<223> OTHER INFORMATION: Diagnostic Oligonucleotide

<400> SEQUENCE: 9
cgcccgccgc gccccgcgcc cgcccgccg ccccgcccg ctatttatgg ttttgcttgt    60
gg                                                                 62

<210> SEQ ID NO 10
<211> LENGTH: 60
<212> TYPE: DNA
<213> ORGANISM: Artificial Sequence
<220> FEATURE:
<223> OTHER INFORMATION: Diagnostic Oligonucleotide

<400> SEQUENCE: 10
cgcccgccgc gccccgcgcc cgcccgccg ccccgcccg gctcagtata actgaggctg    60

<210> SEQ ID NO 11
<211> LENGTH: 59
<212> TYPE: DNA
<213> ORGANISM: Artificial Sequence
<220> FEATURE:
<223> OTHER INFORMATION: Diagnostic Oligonucleotide

<400> SEQUENCE: 11
cgcccgccgc gccccgcgcc cgcccgccg ccccgcccg caaaagttga tggcagagt     59

<210> SEQ ID NO 12
<211> LENGTH: 18
<212> TYPE: DNA
<213> ORGANISM: Artificial Sequence
<220> FEATURE:
<223> OTHER INFORMATION: Diagnostic Oligonucleotide

<400> SEQUENCE: 12
tgtcaggcca attacaga                                                18

<210> SEQ ID NO 13
<211> LENGTH: 58
<212> TYPE: DNA
<213> ORGANISM: Artificial Sequence
<220> FEATURE:
<223> OTHER INFORMATION: Diagnostic Oligonucleotide

<400> SEQUENCE: 13
cgcccgccgc gccccgcgcc cgcccgccg ccccgcccg ggggtgagga attttgaa      58

<210> SEQ ID NO 14
<211> LENGTH: 59
<212> TYPE: DNA
<213> ORGANISM: Artificial Sequence
<220> FEATURE:
<223> OTHER INFORMATION: Diagnostic Oligonucleotide

<400> SEQUENCE: 14
cgcccgccgc gccccgcgcc cgcccgccg ccccgcccg atacccttat tccctgtgg     59

<210> SEQ ID NO 15
<211> LENGTH: 20
<212> TYPE: DNA
<213> ORGANISM: Artificial Sequence
```

```
<220> FEATURE:
<223> OTHER INFORMATION: Diagnostic Oligonucleotide

<400> SEQUENCE: 15
cactggttgg gctagtatgt                                              20

<210> SEQ ID NO 16
<211> LENGTH: 58
<212> TYPE: DNA
<213> ORGANISM: Artificial Sequence
<220> FEATURE:
<223> OTHER INFORMATION: Diagnostic Oligonucleotide

<400> SEQUENCE: 16
cgcccgccgc gccccgcgcc cgccccgccg ccccccgcccg cccagtgttg agcctttg    58

<210> SEQ ID NO 17
<211> LENGTH: 21
<212> TYPE: DNA
<213> ORGANISM: Artificial Sequence
<220> FEATURE:
<223> OTHER INFORMATION: Diagnostic Oligonucleotide

<400> SEQUENCE: 17
gctcccagta gggtcagcat c                                            21

<210> SEQ ID NO 18
<211> LENGTH: 20
<212> TYPE: DNA
<213> ORGANISM: Artificial Sequence
<220> FEATURE:
<223> OTHER INFORMATION: Diagnostic Oligonucleotide

<400> SEQUENCE: 18
atggccaagt actaggttgg                                              20

<210> SEQ ID NO 19
<211> LENGTH: 20
<212> TYPE: DNA
<213> ORGANISM: Artificial Sequence
<220> FEATURE:
<223> OTHER INFORMATION: Diagnostic Oligonucleotide

<400> SEQUENCE: 19
ctaaccgatt gaatatggag                                              20

<210> SEQ ID NO 20
<211> LENGTH: 60
<212> TYPE: DNA
<213> ORGANISM: Artificial Sequence
<220> FEATURE:
<223> OTHER INFORMATION: Diagnostic Oligonucleotide

<400> SEQUENCE: 20
cgcccgccgc gccccgcgcc cgccccgccg ccccccgcccg atactttgtt acttgtctga 60

<210> SEQ ID NO 21
<211> LENGTH: 20
<212> TYPE: DNA
<213> ORGANISM: Artificial Sequence
<220> FEATURE:
<223> OTHER INFORMATION: Diagnostic Oligonucleotide

<400> SEQUENCE: 21
gttatcaaga attacaaggg                                              20
```

<210> SEQ ID NO 22
<211> LENGTH: 20
<212> TYPE: DNA
<213> ORGANISM: Artificial Sequence
<220> FEATURE:
<223> OTHER INFORMATION: Diagnostic Oligonucleotide

<400> SEQUENCE: 22
cgatcagacc ctacaggaca                                               20

<210> SEQ ID NO 23
<211> LENGTH: 27
<212> TYPE: DNA
<213> ORGANISM: Artificial Sequence
<220> FEATURE:
<223> OTHER INFORMATION: Diagnostic Oligonucleotide

<400> SEQUENCE: 23
gatacccaat tcataaata gcattca                                        27

<210> SEQ ID NO 24
<211> LENGTH: 22
<212> TYPE: DNA
<213> ORGANISM: Artificial Sequence
<220> FEATURE:
<223> OTHER INFORMATION: Diagnostic Oligonucleotide

<400> SEQUENCE: 24
catagaatga caggacaata gg                                            22

<210> SEQ ID NO 25
<211> LENGTH: 27
<212> TYPE: DNA
<213> ORGANISM: Artificial Sequence
<220> FEATURE:
<223> OTHER INFORMATION: Diagnostic Oligonucleotide

<400> SEQUENCE: 25
tgcttatttc atctcaatcc tacgctt                                       27

<210> SEQ ID NO 26
<211> LENGTH: 67
<212> TYPE: DNA
<213> ORGANISM: Artificial Sequence
<220> FEATURE:
<223> OTHER INFORMATION: Diagnostic Oligonucleotide

<400> SEQUENCE: 26
cgcccgccgc gccccgcgcc cgccccgccg ccccogcccg aatattcatt ttaaagatcc   60
aagatat                                                             67

<210> SEQ ID NO 27
<211> LENGTH: 25
<212> TYPE: DNA
<213> ORGANISM: Artificial Sequence
<220> FEATURE:
<223> OTHER INFORMATION: Diagnostic Oligonucleotide

<400> SEQUENCE: 27
taaggggaca tacactgaga atgaa                                         25

<210> SEQ ID NO 28
<211> LENGTH: 20
<212> TYPE: DNA
<213> ORGANISM: Artificial Sequence

```
<220> FEATURE:
<223> OTHER INFORMATION: Diagnostic Oligonucleotide

<400> SEQUENCE: 28
ctctgagtca gttaaacagt                                              20

<210> SEQ ID NO 29
<211> LENGTH: 18
<212> TYPE: DNA
<213> ORGANISM: Artificial Sequence
<220> FEATURE:
<223> OTHER INFORMATION: Diagnostic Oligonucleotide

<400> SEQUENCE: 29
atgactttat ggcaggga                                                18

<210> SEQ ID NO 30
<211> LENGTH: 60
<212> TYPE: DNA
<213> ORGANISM: Artificial Sequence
<220> FEATURE:
<223> OTHER INFORMATION: Diagnostic Oligonucleotide

<400> SEQUENCE: 30
cgcccgccgc gccccgcgcc cgccccgccg ccccgcccg tacggaaatg gtataggaaa   60

<210> SEQ ID NO 31
<211> LENGTH: 19
<212> TYPE: DNA
<213> ORGANISM: Artificial Sequence
<220> FEATURE:
<223> OTHER INFORMATION: Diagnostic Oligonucleotide

<400> SEQUENCE: 31
ggtgaggggt gtaatggtt                                               19

<210> SEQ ID NO 32
<211> LENGTH: 21
<212> TYPE: DNA
<213> ORGANISM: Artificial Sequence
<220> FEATURE:
<223> OTHER INFORMATION: Diagnostic Oligonucleotide

<400> SEQUENCE: 32
atggctctat gtcatcttgt c                                            21

<210> SEQ ID NO 33
<211> LENGTH: 58
<212> TYPE: DNA
<213> ORGANISM: Artificial Sequence
<220> FEATURE:
<223> OTHER INFORMATION: Diagnostic Oligonucleotide

<400> SEQUENCE: 33
cgcccgccgc gccccgcgcc cgccccgccg ccccgcccg taggttgagg gttgggac     58

<210> SEQ ID NO 34
<211> LENGTH: 21
<212> TYPE: DNA
<213> ORGANISM: Artificial Sequence
<220> FEATURE:
<223> OTHER INFORMATION: Diagnostic Oligonucleotide

<400> SEQUENCE: 34
cctcgtggtg tagagtgatg t                                            21
```

<210> SEQ ID NO 35
<211> LENGTH: 60
<212> TYPE: DNA
<213> ORGANISM: Artificial Sequence
<220> FEATURE:
<223> OTHER INFORMATION: Diagnostic Oligonucleotide

<400> SEQUENCE: 35
cgcccgccgc gccccgcgcc cgcccgccg ccccgcccg gagcccagga gcccagaaat         60

<210> SEQ ID NO 36
<211> LENGTH: 60
<212> TYPE: DNA
<213> ORGANISM: Artificial Sequence
<220> FEATURE:
<223> OTHER INFORMATION: Diagnostic Oligonucleotide

<400> SEQUENCE: 36
cgcccgccgc gccccgcgcc cgcccgccg ccccgcccg gagggccata gactatagca         60

<210> SEQ ID NO 37
<211> LENGTH: 20
<212> TYPE: DNA
<213> ORGANISM: Artificial Sequence
<220> FEATURE:
<223> OTHER INFORMATION: Diagnostic Oligonucleotide

<400> SEQUENCE: 37
tttctgtccc tgctctggtc                                                   20

<210> SEQ ID NO 38
<211> LENGTH: 60
<212> TYPE: DNA
<213> ORGANISM: Artificial Sequence
<220> FEATURE:
<223> OTHER INFORMATION: Diagnostic Oligonucleotide

<400> SEQUENCE: 38
cgcccgccgc gccccgcgcc cgcccgccg ccccgcccg tcccacgagc tccaattcca         60

<210> SEQ ID NO 39
<211> LENGTH: 58
<212> TYPE: DNA
<213> ORGANISM: Artificial Sequence
<220> FEATURE:
<223> OTHER INFORMATION: Diagnostic Oligonucleotide

<400> SEQUENCE: 39
cgcccgccgc gccccgcgcc cgcccgccg ccccgcccg ggtgaggtct gggaagtg           58

<210> SEQ ID NO 40
<211> LENGTH: 19
<212> TYPE: DNA
<213> ORGANISM: Artificial Sequence
<220> FEATURE:
<223> OTHER INFORMATION: Diagnostic Oligonucleotide

<400> SEQUENCE: 40
tgcctccttg agtatctgc                                                    19

<210> SEQ ID NO 41
<211> LENGTH: 60
<212> TYPE: DNA
<213> ORGANISM: Artificial Sequence
<220> FEATURE:
<223> OTHER INFORMATION: Diagnostic Oligonucleotide

```
<400> SEQUENCE: 41
cgcccgccgc gccccgcgcc cgccccgccg ccccgcccg cagccaagcc ctacctctcg        60

<210> SEQ ID NO 42
<211> LENGTH: 20
<212> TYPE: DNA
<213> ORGANISM: Artificial Sequence
<220> FEATURE:
<223> OTHER INFORMATION: Diagnostic Oligonucleotide

<400> SEQUENCE: 42
cttcatcacc ccctccctgc                                                   20

<210> SEQ ID NO 43
<211> LENGTH: 60
<212> TYPE: DNA
<213> ORGANISM: Artificial Sequence
<220> FEATURE:
<223> OTHER INFORMATION: Diagnostic Oligonucleotide

<400> SEQUENCE: 43
cgcccgccgc gccccgcgcc cgccccgccg ccccgcccg cttgatgact tcctatccat        60

<210> SEQ ID NO 44
<211> LENGTH: 21
<212> TYPE: DNA
<213> ORGANISM: Artificial Sequence
<220> FEATURE:
<223> OTHER INFORMATION: Diagnostic Oligonucleotide

<400> SEQUENCE: 44
aacctccatc cagtgcctag c                                                 21

<210> SEQ ID NO 45
<211> LENGTH: 1577
<212> TYPE: DNA
<213> ORGANISM: Artificial Sequence
<220> FEATURE:
<223> OTHER INFORMATION: Diagnostic Oligonucleotide

<400> SEQUENCE: 45
ccacccttgg agttcactca cctaaacctc aaactaataa agcttggttc ttttctccga        60
cacgcaaagg aagcgctaag gtaaatgcat cagacccaca ctgccgcgga acttttcggc      120
tctctaaggc tgtattttga tatacgaaag gcacattttc cttccctttt caaaatgcac      180
cttgcaaacg taacagggac ccgactagga tcatcgggaa aaggaggagg aggaggaagg      240
caggctccgg ggaagctggt ggcagcgggt cctgggtctg gcggaccctg acgcgaagga      300
gggtctagga agctctccgg ggagccgttc tcccgccggt ggcttcttct gtcctccagc      360
gttgccaact ggacctaaag agaggccgcg actgtcgccc acctgcggga tgggcctggt      420
gctgggcggt aaggacacgg acctggaagg agcgcgcgcg agggagggag gctgggagtc      480
agaatcggga aagggaggtg cggggcgcg agggagcgaa ggaggagagg aggaaggagc       540
gggaggggtg ctggcggggg tgcgtagtgg gtggagaaag ccgctagagc aaatttgggg      600
ccggaccagg cagcactcgg cttttaacct gggcagtgaa ggcggggaa agagcaaaag       660 gaaggggtgg tgtgcggagt agggtgggt gggggaatt ggaagccaaa tgacatcaca        720
gcaggtcaga gaaaagggt tgagcggcag gcacccagag tagtaggtct ttggcattag       780
gagcttgagc ccagacggcc ctagcaggga ccccagcgcc cagagaccat gcagaggtcg      840
```

-continued

```
cctctggaaa aggccagcgt tgtctccaaa ctttttttca ggtgagaagg tggccaaccg    900
agcttcggaa agacacgtgc ccacgaaaga ggagggcgtg tgtatgggtt gggtttgggg    960
taaaggaata agcagttttt aaaaagatgc gctatcattc attgttttga aagaaaatgt   1020
gggtattgta gaataaaaca gaaagcatta agaagagatg gaagaatgaa ctgaagctga   1080
ttgaatagag agccacatct acttgcaact gaaaagttag aatctcaaga ctcaagtacg   1140
ctactatgca cttgttttat ttcattttc taagaaacta aaaatacttg ttaataagta    1200
cctagtatgg tttattggtt ttccccttc atgccttgga cacttgattg tcttcttggc    1260
acatacaggt gccatgcctg catatagtaa gtgctcagaa acatttctt gactgaattc     1320 agccaacaaa aattttgggg taggtagaaa atatatgctt aaagtattta ttgttatgag   1380
actggatata tctagtattt gtcacaggta aatgattctt caaaaattga aagcaaattt   1440
gttgaaatat ttattttgaa aaaagttact tcacaagcta taaattttaa aagccatagg   1500
aatagatacc gaagttatat ccaactgaca tttaataaat tgtattcata gcctaatgtg   1560
atgagccaca gaagctt                                                  1577
```

```
<210> SEQ ID NO 46
<211> LENGTH: 20
<212> TYPE: DNA
<213> ORGANISM: Artificial Sequence
<220> FEATURE:
<223> OTHER INFORMATION: Diagnostic Oligonucleotide

<400> SEQUENCE: 46
taatggatca tgggccatgt                                                 20

<210> SEQ ID NO 47
<211> LENGTH: 60
<212> TYPE: DNA
<213> ORGANISM: Artificial Sequence
<220> FEATURE:
<223> OTHER INFORMATION: Diagnostic Oligonucleotide

<400> SEQUENCE: 47
cgcccgccgc gccccgcgcc cgccccgccg ccccccgcccg aagagacatg gacaccaaat   60

<210> SEQ ID NO 48
<211> LENGTH: 62
<212> TYPE: DNA
<213> ORGANISM: Artificial Sequence
<220> FEATURE:
<223> OTHER INFORMATION: Diagnostic Oligonucleotide

<400> SEQUENCE: 48
cgcccgccgc gccccgcgcc cgccccgccg ccccccgcccg ggaagccaaa tgacatcaca   60
gc                                                                    62

<210> SEQ ID NO 49
<211> LENGTH: 24
<212> TYPE: DNA
<213> ORGANISM: Artificial Sequence
<220> FEATURE:
<223> OTHER INFORMATION: Diagnostic Oligonucleotide

<400> SEQUENCE: 49
tgaaaaaaag tttggagaca acgc                                            24

<210> SEQ ID NO 50
<211> LENGTH: 17
```

```
<212> TYPE: DNA
<213> ORGANISM: Artificial Sequence
<220> FEATURE:
<223> OTHER INFORMATION: Diagnostic Oligonucleotide

<400> SEQUENCE: 50
cccagcgccc agagacc                                                    17

<210> SEQ ID NO 51
<211> LENGTH: 62
<212> TYPE: DNA
<213> ORGANISM: Artificial Sequence
<220> FEATURE:
<223> OTHER INFORMATION: Diagnostic Oligonucleotide

<400> SEQUENCE: 51
cgcccgccgc gccccgcgcc cgcccgccg ccccgcccg actgcttatt cctttacccc       60
aa                                                                    62

<210> SEQ ID NO 52
<211> LENGTH: 63
<212> TYPE: DNA
<213> ORGANISM: Artificial Sequence
<220> FEATURE:
<223> OTHER INFORMATION: Diagnostic Oligonucleotide

<400> SEQUENCE: 52
cgcccgccgc gccccgcgcc cgcccgccg ccccgcccg ccagaaaagt tgaatagtat       60
cag                                                                   63

<210> SEQ ID NO 53
<211> LENGTH: 19
<212> TYPE: DNA
<213> ORGANISM: Artificial Sequence
<220> FEATURE:
<223> OTHER INFORMATION: Diagnostic Oligonucleotide

<400> SEQUENCE: 53
agattgtcag cagaatcaa                                                  19

<210> SEQ ID NO 54
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 54
ataccaaatc ccttctg                                                    17

<210> SEQ ID NO 55
<211> LENGTH: 59
<212> TYPE: DNA
<213> ORGANISM: Artificial Sequence
<220> FEATURE:
<223> OTHER INFORMATION: Diagnostic Oligonucleotide

<400> SEQUENCE: 55
cgcccgccgc gccccgcgcc cgcccgccg ccccgcccg tgctttctct tctctaaat        59

<210> SEQ ID NO 56
<211> LENGTH: 56
<212> TYPE: DNA
<213> ORGANISM: Artificial Sequence
<220> FEATURE:
```

<223> OTHER INFORMATION: Diagnostic Oligonucleotide

<400> SEQUENCE: 56
cgcccgccgc gccccgcgcc cgccccgccg ccccgcccg tggtgttgta tggtct    56

<210> SEQ ID NO 57
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 57
aacataaatc tccagaa    17

<210> SEQ ID NO 58
<211> LENGTH: 22
<212> TYPE: DNA
<213> ORGANISM: Artificial Sequence
<220> FEATURE:
<223> OTHER INFORMATION: Diagnostic Oligonucleotide

<400> SEQUENCE: 58
gctggcttca agaaaaatc cc    22

<210> SEQ ID NO 59
<211> LENGTH: 62
<212> TYPE: DNA
<213> ORGANISM: Artificial Sequence
<220> FEATURE:
<223> OTHER INFORMATION: Diagnostic Oligonucleotide

<400> SEQUENCE: 59
gcccgccgcg ccccgcgccc gccccgccgc ccccgcccgc accagatttc gtagtctttt    60
ca    62

<210> SEQ ID NO 60
<211> LENGTH: 61
<212> TYPE: DNA
<213> ORGANISM: Artificial Sequence
<220> FEATURE:
<223> OTHER INFORMATION: Diagnostic Oligonucleotide

<400> SEQUENCE: 60
cgcccgccgc gccccgcgcc cgccccgccg ccccgcccg aatttctctg ttttccct    60 t    61

<210> SEQ ID NO 61
<211> LENGTH: 22
<212> TYPE: DNA
<213> ORGANISM: Artificial Sequence
<220> FEATURE:
<223> OTHER INFORMATION: Diagnostic Oligonucleotide

<400> SEQUENCE: 61
agctattctc atctgcattc ca    22

<210> SEQ ID NO 62
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 62

```
gacactgctc ctacacc                                                    17

<210> SEQ ID NO 63
<211> LENGTH: 57
<212> TYPE: DNA
<213> ORGANISM: Artificial Sequence
<220> FEATURE:
<223> OTHER INFORMATION: Diagnostic Oligonucleotide

<400> SEQUENCE: 63
cgcccgccgc gccccgcgcc cgccccgccg ccccgcccg tcagcattta tccctta       57

<210> SEQ ID NO 64
<211> LENGTH: 66
<212> TYPE: DNA
<213> ORGANISM: Artificial Sequence
<220> FEATURE:
<223> OTHER INFORMATION: Diagnostic Oligonucleotide

<400> SEQUENCE: 64
cgcccgccgc gccccgcgcc cgccccgccg ccccgcccg ataatatatt tgtattttgt    60
ttgttg                                                                66

<210> SEQ ID NO 65
<211> LENGTH: 20
<212> TYPE: DNA
<213> ORGANISM: Artificial Sequence
<220> FEATURE:
<223> OTHER INFORMATION: Diagnostic Oligonucleotide

<400> SEQUENCE: 65
aatttgttca ggttgttgga                                                 20

<210> SEQ ID NO 66
<211> LENGTH: 18
<212> TYPE: DNA
<213> ORGANISM: Artificial Sequence
<220> FEATURE:
<223> OTHER INFORMATION: Diagnostic Oligonucleotide

<400> SEQUENCE: 66
agctgtcaag ccgtgttc                                                   18

<210> SEQ ID NO 67
<211> LENGTH: 59
<212> TYPE: DNA
<213> ORGANISM: Artificial Sequence
<220> FEATURE:
<223> OTHER INFORMATION: Diagnostic Oligonucleotide

<400> SEQUENCE: 67
cgcccgccgc gccccgcgcc cgccccgccg ccccgcccg atctgaccca ggaaaactc     59

<210> SEQ ID NO 68
<211> LENGTH: 60
<212> TYPE: DNA
<213> ORGANISM: Artificial Sequence
<220> FEATURE:
<223> OTHER INFORMATION: Diagnostic Oligonucleotide

<400> SEQUENCE: 68
cgcccgccgc gccccgcgcc cgccccgccg ccccgcccg ttgttagttt ctaggggtgg    60

<210> SEQ ID NO 69
```

-continued

```
<211> LENGTH: 21
<212> TYPE: DNA
<213> ORGANISM: Artificial Sequence
<220> FEATURE:
<223> OTHER INFORMATION: Diagnostic Oligonucleotide

<400> SEQUENCE: 69
aaggactatc aggaaaccaa g                                              21

<210> SEQ ID NO 70
<211> LENGTH: 20
<212> TYPE: DNA
<213> ORGANISM: Artificial Sequence
<220> FEATURE:
<223> OTHER INFORMATION: Diagnostic Oligonucleotide

<400> SEQUENCE: 70
gctaatctgg gagttgttac                                                20

<210> SEQ ID NO 71
<211> LENGTH: 61
<212> TYPE: DNA
<213> ORGANISM: Artificial Sequence
<220> FEATURE:
<223> OTHER INFORMATION: Diagnostic Oligonucleotide

<400> SEQUENCE: 71
cgcccgccgc gccccgcgcc cgccccgccg ccccgcccg agttatgaaa ataggttgca      60
c                                                                    61

<210> SEQ ID NO 72
<211> LENGTH: 58
<212> TYPE: DNA
<213> ORGANISM: Artificial Sequence
<220> FEATURE:
<223> OTHER INFORMATION: Diagnostic Oligonucleotide

<400> SEQUENCE: 72
cgcccgccgc gccccgcgcc cgccccgccg ccccgcccg gggagaatga tgatgaag       58

<210> SEQ ID NO 73
<211> LENGTH: 21
<212> TYPE: DNA
<213> ORGANISM: Artificial Sequence
<220> FEATURE:
<223> OTHER INFORMATION: Diagnostic Oligonucleotide

<400> SEQUENCE: 73
acactgaaga tcactgttct a                                              21

<210> SEQ ID NO 74
<211> LENGTH: 63
<212> TYPE: DNA
<213> ORGANISM: Artificial Sequence
<220> FEATURE:
<223> OTHER INFORMATION: Diagnostic Oligonucleotide

<400> SEQUENCE: 74
cgcccgccgc gccccgcgcc cgccccgccg ccccgcccg ccttgagcag ttcttaatag      60
ata                                                                  63

<210> SEQ ID NO 75
<211> LENGTH: 21
<212> TYPE: DNA
<213> ORGANISM: Artificial Sequence
```

```
<220> FEATURE:
<223> OTHER INFORMATION: Diagnostic Oligonucleotide

<400> SEQUENCE: 75
atgccttaac agattggata t                                           21

<210> SEQ ID NO 76
<211> LENGTH: 21
<212> TYPE: DNA
<213> ORGANISM: Artificial Sequence
<220> FEATURE:
<223> OTHER INFORMATION: Diagnostic Oligonucleotide

<400> SEQUENCE: 76
gaaaatatcc aatctgttaa g                                           21

<210> SEQ ID NO 77
<211> LENGTH: 58
<212> TYPE: DNA
<213> ORGANISM: Artificial Sequence
<220> FEATURE:
<223> OTHER INFORMATION: Diagnostic Oligonucleotide

<400> SEQUENCE: 77
cgcccgccgc gccccgcgcc cgccccgccg ccccgcccg tgaggtggaa gtctacca    58

<210> SEQ ID NO 78
<211> LENGTH: 59
<212> TYPE: DNA
<213> ORGANISM: Artificial Sequence
<220> FEATURE:
<223> OTHER INFORMATION: Diagnostic Oligonucleotide

<400> SEQUENCE: 78
cgcccgccgc gccccgcgcc cgccccgccg ccccgcccg agaccatgct cagatcttc   59

<210> SEQ ID NO 79
<211> LENGTH: 24
<212> TYPE: DNA
<213> ORGANISM: Artificial Sequence
<220> FEATURE:
<223> OTHER INFORMATION: Diagnostic Oligonucleotide

<400> SEQUENCE: 79
gctgccttcc gagtcagttt cagt                                        24

<210> SEQ ID NO 80
<211> LENGTH: 56
<212> TYPE: DNA
<213> ORGANISM: Artificial Sequence
<220> FEATURE:
<223> OTHER INFORMATION: Diagnostic Oligonucleotide

<400> SEQUENCE: 80
cgcccgccgc gccccgcgcc cgccccgccg ccccgcccg actgaaactg actcgg      56

<210> SEQ ID NO 81
<211> LENGTH: 26
<212> TYPE: DNA
<213> ORGANISM: Artificial Sequence
<220> FEATURE:
<223> OTHER INFORMATION: Diagnostic Oligonucleotide

<400> SEQUENCE: 81
atggtacatt acctgtattt tgttta                                      26
```

```
<210> SEQ ID NO 82
<211> LENGTH: 26
<212> TYPE: DNA
<213> ORGANISM: Artificial Sequence
<220> FEATURE:
<223> OTHER INFORMATION: Diagnostic Oligonucleotide

<400> SEQUENCE: 82
ctgtacaaac atggtatgac tctctt                                   26

<210> SEQ ID NO 83
<211> LENGTH: 65
<212> TYPE: DNA
<213> ORGANISM: Artificial Sequence
<220> FEATURE:
<223> OTHER INFORMATION: Diagnostic Oligonucleotide

<400> SEQUENCE: 83
cgcccgccgc gccccgcgcc cgcccgccg ccccgcccg gtgaaggaaa tttcttttc   60 tatct                                                          65

<210> SEQ ID NO 84
<211> LENGTH: 62
<212> TYPE: DNA
<213> ORGANISM: Artificial Sequence
<220> FEATURE:
<223> OTHER INFORMATION: Diagnostic Oligonucleotide

<400> SEQUENCE: 84
cgcccgccgc gccccgcgcc cgccccgccg ccccgcccg gcacaatgag agtataaagt 60
ag                                                             62

<210> SEQ ID NO 85
<211> LENGTH: 21
<212> TYPE: DNA
<213> ORGANISM: Artificial Sequence
<220> FEATURE:
<223> OTHER INFORMATION: Diagnostic Oligonucleotide

<400> SEQUENCE: 85
ccatcactac ttctgtagtc g                                        21

<210> SEQ ID NO 86
<211> LENGTH: 27
<212> TYPE: DNA
<213> ORGANISM: Artificial Sequence
<220> FEATURE:
<223> OTHER INFORMATION: Diagnostic Oligonucleotide

<400> SEQUENCE: 86
ctctctttta taaataggat ttccttac                                 27

<210> SEQ ID NO 87
<211> LENGTH: 65
<212> TYPE: DNA
<213> ORGANISM: Artificial Sequence
<220> FEATURE:
<223> OTHER INFORMATION: Diagnostic Oligonucleotide

<400> SEQUENCE: 87
cgcccgccgc gccccgcgcc cgccccgccg ccccgcccg ttccagttct accagttata 60
tcatc                                                          65
```

```
<210> SEQ ID NO 88
<211> LENGTH: 65
<212> TYPE: DNA
<213> ORGANISM: Artificial Sequence
<220> FEATURE:
<223> OTHER INFORMATION: Diagnostic Oligonucleotide

<400> SEQUENCE: 88
cgcccgccgc gccccgcgcc cgcccgccg ccccgcccg acaatagaaa aacttctaat    60
ggtga                                                              65

<210> SEQ ID NO 89
<211> LENGTH: 22
<212> TYPE: DNA
<213> ORGANISM: Artificial Sequence
<220> FEATURE:
<223> OTHER INFORMATION: Diagnostic Oligonucleotide

<400> SEQUENCE: 89
aaaaaagaga catggacacc aa                                           22

<210> SEQ ID NO 90
<211> LENGTH: 18
<212> TYPE: DNA
<213> ORGANISM: Artificial Sequence
<220> FEATURE:
<223> OTHER INFORMATION: Diagnostic Oligonucleotide

<400> SEQUENCE: 90
cctgagcgtg atttgata                                                18

<210> SEQ ID NO 91
<211> LENGTH: 60
<212> TYPE: DNA
<213> ORGANISM: Artificial Sequence
<220> FEATURE:
<223> OTHER INFORMATION: Diagnostic Oligonucleotide

<400> SEQUENCE: 91
cgcccgccgc gccccgcgcc cgcccgccg ccccgcccg atgtagacta accgattgaa    60

<210> SEQ ID NO 92
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 92
gggagaactg gagcct                                                  16

<210> SEQ ID NO 93
<211> LENGTH: 58
<212> TYPE: DNA
<213> ORGANISM: Artificial Sequence
<220> FEATURE:
<223> OTHER INFORMATION: Diagnostic Oligonucleotide

<400> SEQUENCE: 93
cgcccgccgc gccccgcgcc cgcccgccg ccccgcccg aaccgattga atatggag      58

<210> SEQ ID NO 94
<211> LENGTH: 61
<212> TYPE: DNA
<213> ORGANISM: Artificial Sequence
<220> FEATURE:
```

-continued

<223> OTHER INFORMATION: Diagnostic Oligonucleotide

<400> SEQUENCE: 94
cgcccgccgc gccccgcgcc cgccccgccg ccccgcccg gatatatgat tacattagaa    60
g    61

<210> SEQ ID NO 95
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 95
accttctcca agaacta    17

<210> SEQ ID NO 96
<211> LENGTH: 18
<212> TYPE: DNA
<213> ORGANISM: Artificial Sequence
<220> FEATURE:
<223> OTHER INFORMATION: Diagnostic Oligonucleotide

<400> SEQUENCE: 96
ataggacatc tccaagtt    18

<210> SEQ ID NO 97
<211> LENGTH: 59
<212> TYPE: DNA
<213> ORGANISM: Artificial Sequence
<220> FEATURE:
<223> OTHER INFORMATION: Diagnostic Oligonucleotide

<400> SEQUENCE: 97
cgcccgccgc gccccgcgcc cgccccgccg ccccgcccg gcaatagaga aatgtctgt    59

<210> SEQ ID NO 98
<211> LENGTH: 63
<212> TYPE: DNA
<213> ORGANISM: Artificial Sequence
<220> FEATURE:
<223> OTHER INFORMATION: Diagnostic Oligonucleotide

<400> SEQUENCE: 98
cgcccgccgc gccccgcgcc cgccccgccg ccccgcccg gtgaactgtt taaggcaaat    60
cat    63

<210> SEQ ID NO 99
<211> LENGTH: 21
<212> TYPE: DNA
<213> ORGANISM: Artificial Sequence
<220> FEATURE:
<223> OTHER INFORMATION: Diagnostic Oligonucleotide

<400> SEQUENCE: 99
tgatgggaca gtctgtcttt c    21

<210> SEQ ID NO 100
<211> LENGTH: 25
<212> TYPE: DNA
<213> ORGANISM: Artificial Sequence
<220> FEATURE:
<223> OTHER INFORMATION: Diagnostic Oligonucleotide

<400> SEQUENCE: 100

-continued aatacgagac atattgcaat aaagt    25

<210> SEQ ID NO 101
<211> LENGTH: 62
<212> TYPE: DNA
<213> ORGANISM: Artificial Sequence
<220> FEATURE:
<223> OTHER INFORMATION: Diagnostic Oligonucleotide

<400> SEQUENCE: 101
cgcccgccgc gccccgcgcc cgcccgccg ccccgcccg ctggctgtag attttggagt    60
tc    62

<210> SEQ ID NO 102
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 102
aggtagcagc tattttt    17

<210> SEQ ID NO 103
<211> LENGTH: 57
<212> TYPE: DNA
<213> ORGANISM: Artificial Sequence
<220> FEATURE:
<223> OTHER INFORMATION: Diagnostic Oligonucleotide

<400> SEQUENCE: 103
cgcccgccgc gccccgcgcc cgcccgccg ccccgcccg ggacagcctt ctctcta    57

<210> SEQ ID NO 104
<211> LENGTH: 61
<212> TYPE: DNA
<213> ORGANISM: Artificial Sequence
<220> FEATURE:
<223> OTHER INFORMATION: Diagnostic Oligonucleotide

<400> SEQUENCE: 104
cgcccgccgc gccccgcgcc cgcccgccg ccccgcccg atgggacatt ttcagaactc    60
c    61

<210> SEQ ID NO 105
<211> LENGTH: 19
<212> TYPE: DNA
<213> ORGANISM: Artificial Sequence
<220> FEATURE:
<223> OTHER INFORMATION: Diagnostic Oligonucleotide

<400> SEQUENCE: 105
cctcttcgat gccattcat    19

<210> SEQ ID NO 106
<211> LENGTH: 60
<212> TYPE: DNA
<213> ORGANISM: Artificial Sequence
<220> FEATURE:
<223> OTHER INFORMATION: Diagnostic Oligonucleotide

<400> SEQUENCE: 106
cgcccgccgc gccccgcgcc cgcccgccg ccccgcccg tgatgagcct ttagagagaa    60

<210> SEQ ID NO 107
<211> LENGTH: 19
<212> TYPE: DNA
<213> ORGANISM: Artificial Sequence
<220> FEATURE:
<223> OTHER INFORMATION: Diagnostic Oligonucleotide

<400> SEQUENCE: 107
ccagttcagt caagtttgc                                        19

<210> SEQ ID NO 108
<211> LENGTH: 54
<212> TYPE: DNA
<213> ORGANISM: Artificial Sequence
<220> FEATURE:
<223> OTHER INFORMATION: Diagnostic Oligonucleotide

<400> SEQUENCE: 108
cgcccgccgc gccccgcgcc cgcccgcccg ccccgcccg cagcgtgatc agca    54

<210> SEQ ID NO 109
<211> LENGTH: 18
<212> TYPE: DNA
<213> ORGANISM: Artificial Sequence
<220> FEATURE:
<223> OTHER INFORMATION: Diagnostic Oligonucleotide

<400> SEQUENCE: 109
tttgttacat gctacata                                         18

<210> SEQ ID NO 110
<211> LENGTH: 62
<212> TYPE: DNA
<213> ORGANISM: Artificial Sequence
<220> FEATURE:
<223> OTHER INFORMATION: Diagnostic Oligonucleotide

<400> SEQUENCE: 110
cgcccgccgc gccccgcgcc cgcccgcccg ccccgcccg ttcatatatt aaaaataaaa    60
cc                                                          62

<210> SEQ ID NO 111
<211> LENGTH: 21
<212> TYPE: DNA
<213> ORGANISM: Artificial Sequence
<220> FEATURE:
<223> OTHER INFORMATION: Diagnostic Oligonucleotide

<400> SEQUENCE: 111
taatatatcg aaggtatgtg t                                     21

<210> SEQ ID NO 112
<211> LENGTH: 22
<212> TYPE: DNA
<213> ORGANISM: Artificial Sequence
<220> FEATURE:
<223> OTHER INFORMATION: Diagnostic Oligonucleotide

<400> SEQUENCE: 112
gagcatacca gcagtgacta ca                                    22

<210> SEQ ID NO 113
<211> LENGTH: 69
<212> TYPE: DNA
<213> ORGANISM: Artificial Sequence

```
<220> FEATURE:
<223> OTHER INFORMATION: Diagnostic Oligonucleotide

<400> SEQUENCE: 113
cgcccgccgc gccccgcgcc cgccccgccg ccccgcccg gtaatactttt acaatagaac      60 attcttacc                                                              69

<210> SEQ ID NO 114
<211> LENGTH: 20
<212> TYPE: DNA
<213> ORGANISM: Artificial Sequence
<220> FEATURE:
<223> OTHER INFORMATION: Diagnostic Oligonucleotide

<400> SEQUENCE: 114
accagcagtg actacatgga                                                  20

<210> SEQ ID NO 115
<211> LENGTH: 68
<212> TYPE: DNA
<213> ORGANISM: Artificial Sequence
<220> FEATURE:
<223> OTHER INFORMATION: Diagnostic Oligonucleotide

<400> SEQUENCE: 115
cgcccgccgc gccccgcgcc cgccccgccg ccccgcccg atatttatgt gtgtgcatat       60
atatgtat                                                               68

<210> SEQ ID NO 116
<211> LENGTH: 57
<212> TYPE: DNA
<213> ORGANISM: Artificial Sequence
<220> FEATURE:
<223> OTHER INFORMATION: Diagnostic Oligonucleotide

<400> SEQUENCE: 116
cgcccgccgc gccccgcgcc cgccccgccg ccccgcccg gtgtaccttg atattgg          57

<210> SEQ ID NO 117
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 117
ctcactttcc aaggag                                                      16

<210> SEQ ID NO 118
<211> LENGTH: 15
<212> TYPE: DNA
<213> ORGANISM: Artificial Sequence
<220> FEATURE:
<223> OTHER INFORMATION: Diagnostic Oligonucleotide

<400> SEQUENCE: 118
gctgtggctc cttgg                                                       15

<210> SEQ ID NO 119
<211> LENGTH: 58
<212> TYPE: DNA
<213> ORGANISM: Artificial Sequence
<220> FEATURE:
<223> OTHER INFORMATION: Diagnostic Oligonucleotide
```

```
<400> SEQUENCE: 119
cgcccgccgc gccccgcgcc cgccccgccg ccccgcccg actacagccc tgaactcc        58

<210> SEQ ID NO 120
<211> LENGTH: 66
<212> TYPE: DNA
<213> ORGANISM: Artificial Sequence
<220> FEATURE:
<223> OTHER INFORMATION: Diagnostic Oligonucleotide

<400> SEQUENCE: 120
cgcccgccgc gccccgcgcc cgccccgccg ccccgcccg catgtattgg aaattcagta       60
agtaac                                                                66

<210> SEQ ID NO 121
<211> LENGTH: 24
<212> TYPE: DNA
<213> ORGANISM: Artificial Sequence
<220> FEATURE:
<223> OTHER INFORMATION: Diagnostic Oligonucleotide

<400> SEQUENCE: 121
ttcgacactg tgattagagt atgc                                            24

<210> SEQ ID NO 122
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 122
cgtgggagta gccgac                                                     16

<210> SEQ ID NO 123
<211> LENGTH: 58
<212> TYPE: DNA
<213> ORGANISM: Artificial Sequence
<220> FEATURE:
<223> OTHER INFORMATION: Diagnostic Oligonucleotide

<400> SEQUENCE: 123
cgcccgccgc gccccgcgcc cgccccgccg ccccgcccg cattagaaaa ccaacaaa        58

<210> SEQ ID NO 124
<211> LENGTH: 56
<212> TYPE: DNA
<213> ORGANISM: Artificial Sequence
<220> FEATURE:
<223> OTHER INFORMATION: Diagnostic Oligonucleotide

<400> SEQUENCE: 124
cgcccgccgc gccccgcgcc cgccccgccg ccccgcccg ctgaatgcgt ctactg          56

<210> SEQ ID NO 125
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 125
catccaaaat tgctata                                                    17
```

```
<210> SEQ ID NO 126
<211> LENGTH: 23
<212> TYPE: DNA
<213> ORGANISM: Artificial Sequence
<220> FEATURE:
<223> OTHER INFORMATION: Diagnostic Oligonucleotide

<400> SEQUENCE: 126
ttgaggaatt tgtcatcttg tat                                          23

<210> SEQ ID NO 127
<211> LENGTH: 63
<212> TYPE: DNA
<213> ORGANISM: Artificial Sequence
<220> FEATURE:
<223> OTHER INFORMATION: Diagnostic Oligonucleotide

<400> SEQUENCE: 127
cgcccgccgc gccccgcgcc cgccccgccg ccccgcccg caaaatcaca tttgcttttc    60
tta                                                                63

<210> SEQ ID NO 128
<211> LENGTH: 58
<212> TYPE: DNA
<213> ORGANISM: Artificial Sequence
<220> FEATURE:
<223> OTHER INFORMATION: Diagnostic Oligonucleotide

<400> SEQUENCE: 128
cgcccgccgc gccccgcgcc cgccccgccg ccccgcccg aaagaaataa atcactga     58

<210> SEQ ID NO 129
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 129
gtaaaactgc gacaac                                                  16

<210> SEQ ID NO 130
<211> LENGTH: 26
<212> TYPE: DNA
<213> ORGANISM: Artificial Sequence
<220> FEATURE:
<223> OTHER INFORMATION: Diagnostic Oligonucleotide

<400> SEQUENCE: 130
ccaacatgtt ttctttgatc ttacag                                       26

<210> SEQ ID NO 131
<211> LENGTH: 67
<212> TYPE: DNA
<213> ORGANISM: Artificial Sequence
<220> FEATURE:
<223> OTHER INFORMATION: Diagnostic Oligonucleotide

<400> SEQUENCE: 131
cgcccgccgc gccccgcgcc cgccccgccg ccccgcccg agaatctcaa atagctctta   60
tagcttt                                                            67

<210> SEQ ID NO 132
<211> LENGTH: 62
<212> TYPE: DNA
```

```
<213> ORGANISM: Artificial Sequence
<220> FEATURE:
<223> OTHER INFORMATION: Diagnostic Oligonucleotide

<400> SEQUENCE: 132
cgcccgccgc gccccgcgcc cgcccgccg ccccgcccg ttaaccaatg acatttgtga    60
ta                                                                  62

<210> SEQ ID NO 133
<211> LENGTH: 21
<212> TYPE: DNA
<213> ORGANISM: Artificial Sequence
<220> FEATURE:
<223> OTHER INFORMATION: Diagnostic Oligonucleotide

<400> SEQUENCE: 133
gtgtccatag tccttttaag c                                             21

<210> SEQ ID NO 134
<211> LENGTH: 61
<212> TYPE: DNA
<213> ORGANISM: Artificial Sequence
<220> FEATURE:
<223> OTHER INFORMATION: Diagnostic Oligonucleotide

<400> SEQUENCE: 134
cgcccgccgc gccccgcgcc cgcccgccg ccccgcccg atatttcaca ggcaggagtc    60
c                                                                   61

<210> SEQ ID NO 135
<211> LENGTH: 25
<212> TYPE: DNA
<213> ORGANISM: Artificial Sequence
<220> FEATURE:
<223> OTHER INFORMATION: Diagnostic Oligonucleotide

<400> SEQUENCE: 135
aaaatcattt ctattctcat ttgga                                         25

<210> SEQ ID NO 136
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 136
acttcgtgcc ttcggac                                                  17

<210> SEQ ID NO 137
<211> LENGTH: 62
<212> TYPE: DNA
<213> ORGANISM: Artificial Sequence
<220> FEATURE:
<223> OTHER INFORMATION: Diagnostic Oligonucleotide

<400> SEQUENCE: 137
cgcccgccgc gccccgcgcc cgcccgccg ccccgcccg cagcaatgaa gaagatgaca    60
aa                                                                  62

<210> SEQ ID NO 138
<211> LENGTH: 17
<212> TYPE: DNA
<213> ORGANISM: Artificial Sequence
```

```
<220> FEATURE:
<223> OTHER INFORMATION: Diagnostic Oligonucleotide

<400> SEQUENCE: 138
ctggttccaa atgagaa                                                    17

<210> SEQ ID NO 139
<211> LENGTH: 59
<212> TYPE: DNA
<213> ORGANISM: Artificial Sequence
<220> FEATURE:
<223> OTHER INFORMATION: Diagnostic Oligonucleotide

<400> SEQUENCE: 139
cgcccgccgc gccccgcgcc cgccccgccg ccccccgcccg taacctatag aatgcagca    59

<210> SEQ ID NO 140
<211> LENGTH: 60
<212> TYPE: DNA
<213> ORGANISM: Artificial Sequence
<220> FEATURE:
<223> OTHER INFORMATION: Diagnostic Oligonucleotide

<400> SEQUENCE: 140
cgcccgccgc gccccgcgcc cgccccgccg ccccccgcccg ttaatgtgat atgtgcccta   60

<210> SEQ ID NO 141
<211> LENGTH: 21
<212> TYPE: DNA
<213> ORGANISM: Artificial Sequence
<220> FEATURE:
<223> OTHER INFORMATION: Diagnostic Oligonucleotide

<400> SEQUENCE: 141
agatgataag acttaccaag c                                              21

<210> SEQ ID NO 142
<211> LENGTH: 21
<212> TYPE: DNA
<213> ORGANISM: Artificial Sequence
<220> FEATURE:
<223> OTHER INFORMATION: Diagnostic Oligonucleotide

<400> SEQUENCE: 142
gagaaggaga aggaagagtt g                                              21

<210> SEQ ID NO 143
<211> LENGTH: 63
<212> TYPE: DNA
<213> ORGANISM: Artificial Sequence
<220> FEATURE:
<223> OTHER INFORMATION: Diagnostic Oligonucleotide

<400> SEQUENCE: 143
cgcccgccgc gccccgcgcc cgccccgccg ccccccgcccg cttcctcatg ctattactca   60
tac                                                                   63

<210> SEQ ID NO 144
<211> LENGTH: 61
<212> TYPE: DNA
<213> ORGANISM: Artificial Sequence
<220> FEATURE:
<223> OTHER INFORMATION: Diagnostic Oligonucleotide

<400> SEQUENCE: 144
```
cgcccgccgc gccccgcgcc cgcccgcccg ccccgcccg aagttatttt ttaggaagca    60
t                                                                   61

<210> SEQ ID NO 145
<211> LENGTH: 19
<212> TYPE: DNA
<213> ORGANISM: Artificial Sequence
<220> FEATURE:
<223> OTHER INFORMATION: Diagnostic Oligonucleotide

<400> SEQUENCE: 145
gaacttaaag actcggctc                                                19

<210> SEQ ID NO 146
<211> LENGTH: 61
<212> TYPE: DNA
<213> ORGANISM: Artificial Sequence
<220> FEATURE:
<223> OTHER INFORMATION: Diagnostic Oligonucleotide

<400> SEQUENCE: 146
cgcccgccgc gccccgcgcc cgcccgcccg ccccgcccg gaaattgtct gccattctta    60
a                                                                   61

<210> SEQ ID NO 147
<211> LENGTH: 20
<212> TYPE: DNA
<213> ORGANISM: Artificial Sequence
<220> FEATURE:
<223> OTHER INFORMATION: Diagnostic Oligonucleotide

<400> SEQUENCE: 147
gagttggcca ttcttgtatg                                               20

<210> SEQ ID NO 148
<211> LENGTH: 56
<212> TYPE: DNA
<213> ORGANISM: Artificial Sequence
<220> FEATURE:
<223> OTHER INFORMATION: Diagnostic Oligonucleotide

<400> SEQUENCE: 148
cgcccgccgc gccccgcgcc cgcccgcccg ccccgcccg tgtgagccga gtcttt         56

<210> SEQ ID NO 149
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 149
atggcatttc cacctt                                                   16

<210> SEQ ID NO 150
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 150
cgtgaagaaa gatgac                                                   16

<210> SEQ ID NO 151
<211> LENGTH: 59
<212> TYPE: DNA
<213> ORGANISM: Artificial Sequence
<220> FEATURE:
<223> OTHER INFORMATION: Diagnostic Oligonucleotide

<400> SEQUENCE: 151
cgcccgccgc gccccgcgcc cgcccgcccg ccccgcccg taatgttaca aatagattc    59

<210> SEQ ID NO 152
<211> LENGTH: 56
<212> TYPE: DNA
<213> ORGANISM: Artificial Sequence
<220> FEATURE:
<223> OTHER INFORMATION: Diagnostic Oligonucleotide

<400> SEQUENCE: 152
cgcccgccgc gccccgcgcc cgcccgcccg ccccgcccg cttgatttct ggagac       56

<210> SEQ ID NO 153
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 153
ctagctgtaa ttgcat                                                 16

<210> SEQ ID NO 154
<211> LENGTH: 59
<212> TYPE: DNA
<213> ORGANISM: Artificial Sequence
<220> FEATURE:
<223> OTHER INFORMATION: Diagnostic Oligonucleotide

<400> SEQUENCE: 154
cgcccgccgc gccccgcgcc cgcccgcccg ccccgcccg ctgaattatg tttatggca    59

<210> SEQ ID NO 155
<211> LENGTH: 18
<212> TYPE: DNA
<213> ORGANISM: Artificial Sequence
<220> FEATURE:
<223> OTHER INFORMATION: Diagnostic Oligonucleotide

<400> SEQUENCE: 155
ccttttttct ggctaagt                                               18

<210> SEQ ID NO 156
<211> LENGTH: 60
<212> TYPE: DNA
<213> ORGANISM: Artificial Sequence
<220> FEATURE:
<223> OTHER INFORMATION: Diagnostic Oligonucleotide

<400> SEQUENCE: 156
cgcccgccgc gccccgcgcc cgcccgcccg ccccgcccg agttattcat actttcttct   60

<210> SEQ ID NO 157
<211> LENGTH: 16
<212> TYPE: DNA
<213> ORGANISM: Artificial Sequence
<220> FEATURE:
<223> OTHER INFORMATION: Diagnostic Oligonucleotide

```
<400> SEQUENCE: 157
agccttacct catctg                                                    16

<210> SEQ ID NO 158
<211> LENGTH: 56
<212> TYPE: DNA
<213> ORGANISM: Artificial Sequence
<220> FEATURE:
<223> OTHER INFORMATION: Diagnostic Oligonucleotide

<400> SEQUENCE: 158
cgcccgccgc gccccgcgcc cgcccgccgg ccccgcccg tttctggaac atttag         56

<210> SEQ ID NO 159
<211> LENGTH: 18
<212> TYPE: DNA
<213> ORGANISM: Artificial Sequence
<220> FEATURE:
<223> OTHER INFORMATION: Diagnostic Oligonucleotide

<400> SEQUENCE: 159
gaatgatgtc agctatat                                                  18

<210> SEQ ID NO 160
<211> LENGTH: 58
<212> TYPE: DNA
<213> ORGANISM: Artificial Sequence
<220> FEATURE:
<223> OTHER INFORMATION: Diagnostic Oligonucleotide

<400> SEQUENCE: 160
cgcccgccgc gccccgcgcc cgcccgccgg ccccgcccg tgagctgtca aggttgta       58

<210> SEQ ID NO 161
<211> LENGTH: 19
<212> TYPE: DNA
<213> ORGANISM: Artificial Sequence
<220> FEATURE:
<223> OTHER INFORMATION: Diagnostic Oligonucleotide

<400> SEQUENCE: 161
caggaaactg ttctatcac                                                 19

<210> SEQ ID NO 162
<211> LENGTH: 64
<212> TYPE: DNA
<213> ORGANISM: Artificial Sequence
<220> FEATURE:
<223> OTHER INFORMATION: Diagnostic Oligonucleotide

<400> SEQUENCE: 162
cgcccgccgc gccccgcgcc cgcccgccgg ccccgcccg gaatgtcaac tgcttgagtg     60
tttt                                                                 64

<210> SEQ ID NO 163
<211> LENGTH: 27
<212> TYPE: DNA
<213> ORGANISM: Artificial Sequence
<220> FEATURE:
<223> OTHER INFORMATION: Diagnostic Oligonucleotide

<400> SEQUENCE: 163
aagtaacaga acatctgaaa ctcacac                                        27
```

<210> SEQ ID NO 164
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 164
cttgctgctt gatgaac                                                17

<210> SEQ ID NO 165
<211> LENGTH: 63
<212> TYPE: DNA
<213> ORGANISM: Artificial Sequence
<220> FEATURE:
<223> OTHER INFORMATION: Diagnostic Oligonucleotide

<400> SEQUENCE: 165
cgcccgccgc gccccgcgcc cgccccgccg ccccgcccg tgggcaatta tttcatatct    60
tgg                                                               63

<210> SEQ ID NO 166
<211> LENGTH: 58
<212> TYPE: DNA
<213> ORGANISM: Artificial Sequence
<220> FEATURE:
<223> OTHER INFORMATION: Diagnostic Oligonucleotide

<400> SEQUENCE: 166
cgcccgccgc gccccgcgcc cgccccgccg ccccgcccg tatcaaggta aatacaga     58

<210> SEQ ID NO 167
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 167
gcttctatcc tgtgttc                                                17

<210> SEQ ID NO 168
<211> LENGTH: 21
<212> TYPE: DNA
<213> ORGANISM: Artificial Sequence
<220> FEATURE:
<223> OTHER INFORMATION: Diagnostic Oligonucleotide

<400> SEQUENCE: 168
gatattatgt gtggtatttt c                                           21

<210> SEQ ID NO 169
<211> LENGTH: 59
<212> TYPE: DNA
<213> ORGANISM: Artificial Sequence
<220> FEATURE:
<223> OTHER INFORMATION: Diagnostic Oligonucleotide

<400> SEQUENCE: 169
cgcccgccgc gccccgcgcc cgccccgccg ccccgcccg gaacttgtac attgttgca    59

<210> SEQ ID NO 170
<211> LENGTH: 56
<212> TYPE: DNA
<213> ORGANISM: Artificial Sequence
<220> FEATURE:

<223> OTHER INFORMATION: Diagnostic Oligonucleotide

<400> SEQUENCE: 170
cgcccgccgc gccccgcgcc cgcccgcccg ccccgcccg cctttgagcc tgtcgg    56

<210> SEQ ID NO 171
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 171
gcttgagttc cggtgg    16

<210> SEQ ID NO 172
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 172
catcagcccc tccgac    16

<210> SEQ ID NO 173
<211> LENGTH: 57
<212> TYPE: DNA
<213> ORGANISM: Artificial Sequence
<220> FEATURE:
<223> OTHER INFORMATION: Diagnostic Oligonucleotide

<400> SEQUENCE: 173
cgcccgccgc gccccgcgcc cgcccgcccg ccccgcccg tttctgaggc agaggta    57

<210> SEQ ID NO 174
<211> LENGTH: 659
<212> TYPE: DNA
<213> ORGANISM: Artificial Sequence
<220> FEATURE:
<223> OTHER INFORMATION: Diagnostic Oligonucleotide

<400> SEQUENCE: 174
gggaggggtg ctggcggggt gcgtagtggg tggagaaagc cgctagagca aatttggggc    60
cggaccaggc agcactcggc ttttaacctg ggcagtgaag gcggggggaaa gagcaaaagg   120 aagggggtggt gtgcggagta ggggtgggtg ggggggaattg gaagccaaat gacatcacag   180
caggtcagag aaaaagggtt gagcggcagg cacccagagt agtaggtctt tggcattagg   240
agcttgagcc cagacggccc tagcagggac cccagcgccc agagaccatg cagaggtcgc    300
ctctggaaaa ggccagcgtt gtctccaaac ttttttttcag gtgagaaggt ggccaaccga   360
gcttcggaaa gacacgtgcc cacgaaagag gagggcgtgt gtatgggttg ggttttggggt   420 aaaggaataa gcagtttttta aaaagatgcg ctatcattca ttgttttgaa agaaaatgtg    480
ggtattgtag aataaaacag aaagcattaa gaagagatgg aagaatgaac tgaagctgat   540
tgaatagaga gccacatcta cttgcaactg aaaagttaga atctcaagac tcaagtacgc    600
tactatgcac ttgttttatt tcattttttct aagaaactaa aatacttgt taataagta    659

<210> SEQ ID NO 175
<211> LENGTH: 62
<212> TYPE: DNA
<213> ORGANISM: Artificial Sequence
<220> FEATURE:
<223> OTHER INFORMATION: Diagnostic Oligonucleotide

<400> SEQUENCE: 175
cgcccgccgc gccccgcgcc cgcccgccg ccccgcccg ggaagccaaa tgacatcaca    60
gc    62

<210> SEQ ID NO 176
<211> LENGTH: 24
<212> TYPE: DNA
<213> ORGANISM: Artificial Sequence
<220> FEATURE:
<223> OTHER INFORMATION: Diagnostic Oligonucleotide

<400> SEQUENCE: 176
tgaaaaaaag tttggagaca acgc    24

<210> SEQ ID NO 177
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 177
cccagcgccc agagacc    17

<210> SEQ ID NO 178
<211> LENGTH: 62
<212> TYPE: DNA
<213> ORGANISM: Artificial Sequence
<220> FEATURE:
<223> OTHER INFORMATION: Diagnostic Oligonucleotide

<400> SEQUENCE: 178
cgcccgccgc gccccgcgcc cgcccgccg ccccgcccg actgcttatt cctttacccc    60
aa    62

<210> SEQ ID NO 179
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 179
gggtggtgtg cggagta    17

<210> SEQ ID NO 180
<211> LENGTH: 20
<212> TYPE: DNA
<213> ORGANISM: Artificial Sequence
<220> FEATURE:
<223> OTHER INFORMATION: Diagnostic Oligonucleotide

<400> SEQUENCE: 180
caaaacaatg aatgatagcg    20

<210> SEQ ID NO 181
<211> LENGTH: 630
<212> TYPE: DNA
<213> ORGANISM: Artificial Sequence
<220> FEATURE:
<223> OTHER INFORMATION: Diagnostic Oligonucleotide -continued

```
<400> SEQUENCE: 181
aaaccatact attattccct cccaatccct ttgacaaagt gacagtcaca ttagttcaga      60
gatattgatg tttatacag gtgtagcctg taagagatga agcctggtat ttatagaaat     120
tgacttattt tattctcata tttacatgtg cataattttc catatgccag aaaagttgaa    180
tagtatcaga ttccaaatct gtatggagac caaatcaagt gaatatctgt tcctcctctc    240
tttattttag ctggaccaga ccaattttga ggaaaggata cagacagcgc ctggaattgt    300
cagacatata ccaaatccct tctgttgatt ctgctgacaa tctatctgaa aaattggaaa    360
ggtatgttca tgtacattgt ttagttgaag agagaaattc atattattaa ttatttagag    420
aagagaaagc aaacatatta taagtttaat tcttatattt aaaaatagga gccaagtatg    480
gtggctaatg cctgtaatcc caactatttg ggaggccaag atgagaggat tgcttgagac    540
caggagtttg ataccagcct gggcaacata gcaagatgtt atctctacac aaaataaaaa    600
gttagctggg aatggtagtg catgcttgta                                      630

<210> SEQ ID NO 182
<211> LENGTH: 63
<212> TYPE: DNA
<213> ORGANISM: Artificial Sequence
<220> FEATURE:
<223> OTHER INFORMATION: Diagnostic Oligonucleotide

<400> SEQUENCE: 182
cgcccgccgc gccccgcgcc cgccccgccg ccccccgcccg ccagaaaagt tgaatagtat    60
cag                                                                   63

<210> SEQ ID NO 183
<211> LENGTH: 19
<212> TYPE: DNA
<213> ORGANISM: Artificial Sequence
<220> FEATURE:
<223> OTHER INFORMATION: Diagnostic Oligonucleotide

<400> SEQUENCE: 183
agattgtcag cagaatcaa                                                  19

<210> SEQ ID NO 184
<211> LENGTH: 19
<212> TYPE: DNA
<213> ORGANISM: Artificial Sequence
<220> FEATURE:
<223> OTHER INFORMATION: Diagnostic Oligonucleotide

<400> SEQUENCE: 184
gacagtcaca ttagttcag                                                  19

<210> SEQ ID NO 185
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 185
tgtttgcttt ctcttct                                                    17

<210> SEQ ID NO 186
<211> LENGTH: 17
<212> TYPE: DNA
<213> ORGANISM: Artificial Sequence
```

```
<220> FEATURE:
<223> OTHER INFORMATION: Diagnostic Oligonucleotide

<400> SEQUENCE: 186
ataccaaatc ccttctg                                                    17

<210> SEQ ID NO 187
<211> LENGTH: 59
<212> TYPE: DNA
<213> ORGANISM: Artificial Sequence
<220> FEATURE:
<223> OTHER INFORMATION: Diagnostic Oligonucleotide

<400> SEQUENCE: 187
cgcccgccgc gccccgcgcc cgcccgcccg ccccgcccg tgctttctct tctctaaat     59

<210> SEQ ID NO 188
<211> LENGTH: 454
<212> TYPE: DNA
<213> ORGANISM: Artificial Sequence
<220> FEATURE:
<223> OTHER INFORMATION: Diagnostic Oligonucleotide

<400> SEQUENCE: 188
aggaatctgc cagatatctg gctgagtgtt tggtgttgta tggtctccat gagattttgt    60
ctctataata cttgggttaa tctccttgga tatacttgtg tgaatcaaac tatgttaagg   120
gaaataggac aactaaaata tttgcacatg caacttattg gtcccacttt ttattctttt   180
gcagagaatg ggatagagag ctggcttcaa agaaaaatcc taaactcatt aatgcccttc   240
ggcgatgttt tttctggaga tttatgttct atggaatctt tttatattta ggggtaagga   300
tctcatttgt acattcatta tgtatcacat aactatatgc attttgtga ttatgaaaag    360 actacgaaat ctggtgaata ggtgtaaaaa tataaggat gaatccaact ccaaacacta    420
agaaaccacc taaaactcta gtaaggataa gtaa                                454

<210> SEQ ID NO 189
<211> LENGTH: 56
<212> TYPE: DNA
<213> ORGANISM: Artificial Sequence
<220> FEATURE:
<223> OTHER INFORMATION: Diagnostic Oligonucleotide

<400> SEQUENCE: 189
cgcccgccgc gccccgcgcc cgcccgcccg ccccgcccg tggtgttgta tggtct         56

<210> SEQ ID NO 190
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 190
aacataaatc tccagaa                                                    17

<210> SEQ ID NO 191
<211> LENGTH: 21
<212> TYPE: DNA
<213> ORGANISM: Artificial Sequence
<220> FEATURE:
<223> OTHER INFORMATION: Diagnostic Oligonucleotide

<400> SEQUENCE: 191
```

```
gctggcttca aagaaaaatc c                                              21
```

<210> SEQ ID NO 192
<211> LENGTH: 63
<212> TYPE: DNA
<213> ORGANISM: Artificial Sequence
<220> FEATURE:
<223> OTHER INFORMATION: Diagnostic Oligonucleotide

<400> SEQUENCE: 192

```
cgcccgccgc gccccgcgcc cgccccgccg ccccgcccg caccagattt cgtagtcttt    60
tca                                                                  63
```

<210> SEQ ID NO 193
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 193

```
tggtgttgta tggtctc                                                   17
```

<210> SEQ ID NO 194
<211> LENGTH: 19
<212> TYPE: DNA
<213> ORGANISM: Artificial Sequence
<220> FEATURE:
<223> OTHER INFORMATION: Diagnostic Oligonucleotide

<400> SEQUENCE: 194

```
ttaggtggtt ttcttagtg                                                 19
```

<210> SEQ ID NO 195
<211> LENGTH: 664
<212> TYPE: DNA
<213> ORGANISM: Artificial Sequence
<220> FEATURE:
<223> OTHER INFORMATION: Diagnostic Oligonucleotide

<400> SEQUENCE: 195

```
ccactattca ctgtttaact taaaatacct catatgtaaa cttgtctccc actgttgcta    60
taacaaatcc caagtcttat ttcaaagtac caagatattg aaaatagtgc taagagtttc   120
acatatggta tgaccctcta ttttaagtct cctctaaaga tgaaaagtct tgtgttgaaa   180
ttctcagggt attttatgag aaataaatga aatttaattt ctctgttttt cccttttgt    240 aggaagtcac caaagcagta cagcctctct tactgggaag aatcatagct tcctatgacc   300
cggataacaa ggaggaacgc tctatcgcga tttatctagg cataggctta tgccttctct   360
ttattgtgag gacactgctc ctacacccag ccatttttgg ccttcatcac attggaatgc   420
agatgagaat agctatgttt agtttgattt ataagaaggt aatacttcct tgcacaggcc   480
ccatggcaca tatattctgt atcgtacatg ttttaatgtc ataaattagg tagtgagctg   540
gtacaagtaa gggataaatg ctgaaattaa tttaatatgc ctattaaata aatggcagga   600
ataattaatg ctcttaatta tccttgataa tttaattgac ttaaactgat aattattgag   660
tatc                                                                664
```

<210> SEQ ID NO 196
<211> LENGTH: 61
<212> TYPE: DNA
<213> ORGANISM: Artificial Sequence

```
<220> FEATURE:
<223> OTHER INFORMATION: Diagnostic Oligonucleotide

<400> SEQUENCE: 196
cgcccgccgc gccccgcgcc cgcccgcccg ccccgcccg aatttctctg tttttcccct    60
t                                                                   61

<210> SEQ ID NO 197
<211> LENGTH: 22
<212> TYPE: DNA
<213> ORGANISM: Artificial Sequence
<220> FEATURE:
<223> OTHER INFORMATION: Diagnostic Oligonucleotide

<400> SEQUENCE: 197
agctattctc atctgcattc ca                                            22

<210> SEQ ID NO 198
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 198
gacactgctc ctacacc                                                  17

<210> SEQ ID NO 199
<211> LENGTH: 57
<212> TYPE: DNA
<213> ORGANISM: Artificial Sequence
<220> FEATURE:
<223> OTHER INFORMATION: Diagnostic Oligonucleotide

<400> SEQUENCE: 199
cgcccgccgc gccccgcgcc cgcccgcccg ccccgcccg tcagcattta tccctta       57

<210> SEQ ID NO 200
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 200
ataacaaatc ccaagtc                                                  17

<210> SEQ ID NO 201
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 201
tgtaccagct cactacc                                                  17

<210> SEQ ID NO 202
<211> LENGTH: 600
<212> TYPE: DNA
<213> ORGANISM: Artificial Sequence
<220> FEATURE:
<223> OTHER INFORMATION: Diagnostic Oligonucleotide

<400> SEQUENCE: 202
```

```
taattatttc tgcctagatg ctgggaaata aaacaactag aagcatgcca gtataatatt      60
gactgttgaa agaaacattt atgaacctga gaagatagta agctagatga atagaatata     120
attttcatta cctttactta ataatgaatg cataataact gaattagtca tattataatt     180
ttacttataa tatatttgta ttttgtttgt tgaaattatc taacttttcca ttttttctttt    240 agactttaaa gctgtcaagc cgtgttctag ataaaataag tattggacaa cttgttagtc     300
tcctttccaa caacctgaac aaatttgatg aagtatgtac ctattgattt aatcttttag     360
gcactattgt tataaattat acaactggaa aggcggagtt ttcctgggtc agataatagt     420
aattagtggt taagtcttgc tcagctctag cttccctatt ctggaaacta agaaaggtca     480
attgtatagc agagcaccat tctggggtct ggtagaacca cccaactcaa aggcacctta    540
gcctgttgtt aataagattt ttcaaaactt aattcttatc agaccttgct tcttttaaac     600
```

<210> SEQ ID NO 203
<211> LENGTH: 66
<212> TYPE: DNA
<213> ORGANISM: Artificial Sequence
<220> FEATURE:
<223> OTHER INFORMATION: Diagnostic Oligonucleotide

<400> SEQUENCE: 203

```
cgcccgccgc gccccgcgcc cgcccgcccg ccccccgcccg ataatatatt tgtattttgt     60
ttgttg                                                                66
```

<210> SEQ ID NO 204
<211> LENGTH: 20
<212> TYPE: DNA
<213> ORGANISM: Artificial Sequence
<220> FEATURE:
<223> OTHER INFORMATION: Diagnostic Oligonucleotide

<400> SEQUENCE: 204

```
aatttgttca ggttgttgga                                                 20
```

<210> SEQ ID NO 205
<211> LENGTH: 18
<212> TYPE: DNA
<213> ORGANISM: Artificial Sequence
<220> FEATURE:
<223> OTHER INFORMATION: Diagnostic Oligonucleotide

<400> SEQUENCE: 205

```
agctgtcaag ccgtgttc                                                   18
```

<210> SEQ ID NO 206
<211> LENGTH: 59
<212> TYPE: DNA
<213> ORGANISM: Artificial Sequence
<220> FEATURE:
<223> OTHER INFORMATION: Diagnostic Oligonucleotide

<400> SEQUENCE: 206

```
cgcccgccgc gccccgcgcc cgcccgcccg ccccccgcccg atctgaccca ggaaaactc     59
```

<210> SEQ ID NO 207
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 207
tgctgggaaa taaaac                                              16

<210> SEQ ID NO 208
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 208
agaatggtgc tctgct                                              16

<210> SEQ ID NO 209
<211> LENGTH: 720
<212> TYPE: DNA
<213> ORGANISM: Artificial Sequence
<220> FEATURE:
<223> OTHER INFORMATION: Diagnostic Oligonucleotide

<400> SEQUENCE: 209
gacatgatac ttaagatgtc caatcttgat tccactgaat aaaaatatgc ttaaaaatgc    60
actgacttga aatttgtttt ttgggaaaac cgattctatg tgtagaatgt ttaagcacat   120
tgctatgtgc tccatgtaat gattacctag attttagtgt gctcagaacc acgaagtgtt   180
tgatcatata agctcctttt acttgctttc tttcatatat gattgttagt ttctaggggt   240
ggaagataca atgacacctg tttttgctgt gctttattt tccagggact tgcattggca    300
catttcgtgt ggatcgctcc tttgcaagtg gcactcctca tggggctaat ctgggagttg   360
ttacaggcgt ctgccttctg tggacttggt ttcctgatag tccttgccct ttttcaggct   420
gggctaggga gaatgatgat gaagtacagg tagcaaccta tttttcataac ttgaaagttt   480 taaaaattat gttttcaaaa agcccacttt agtaaaacca ggactgctct atgcatagaa   540
cagtgatctt cagtgtcatt aaattttttt ttttttttt tttgagacag agtctagatc    600
tgtcacccag gctggagtgc agtggcacga tcttggctca ctgcactgca acttctgcct   660
cccaggctca agcaattctc ctgcctcagc ctccggagta gctgggatta gaggcgcatg   720

<210> SEQ ID NO 210
<211> LENGTH: 60
<212> TYPE: DNA
<213> ORGANISM: Artificial Sequence
<220> FEATURE:
<223> OTHER INFORMATION: Diagnostic Oligonucleotide

<400> SEQUENCE: 210
cgcccgccgc gccccgcgcc cgcccgcccg ccccccgcccg ttgttagttt ctagggtgg    60

<210> SEQ ID NO 211
<211> LENGTH: 21
<212> TYPE: DNA
<213> ORGANISM: Artificial Sequence
<220> FEATURE:
<223> OTHER INFORMATION: Diagnostic Oligonucleotide

<400> SEQUENCE: 211
aaggactatc aggaaaccaa g                                        21

<210> SEQ ID NO 212
<211> LENGTH: 20
<212> TYPE: DNA
<213> ORGANISM: Artificial Sequence
<220> FEATURE:

<223> OTHER INFORMATION: Diagnostic Oligonucleotide

<400> SEQUENCE: 212
gctaatctgg gagttgttac                                               20

<210> SEQ ID NO 213
<211> LENGTH: 62
<212> TYPE: DNA
<213> ORGANISM: Artificial Sequence
<220> FEATURE:
<223> OTHER INFORMATION: Diagnostic Oligonucleotide

<400> SEQUENCE: 213
cgcccgccgc gccccgcgcc cgcccgcccg ccccgcccg agttatgaaa ataggttgct    60
ac                                                                  62

<210> SEQ ID NO 214
<211> LENGTH: 58
<212> TYPE: DNA
<213> ORGANISM: Artificial Sequence
<220> FEATURE:
<223> OTHER INFORMATION: Diagnostic Oligonucleotide

<400> SEQUENCE: 214
cgcccgccgc gccccgcgcc cgcccgcccg ccccgcccg gggagaatga tgatgaag      58

<210> SEQ ID NO 215
<211> LENGTH: 21
<212> TYPE: DNA
<213> ORGANISM: Artificial Sequence
<220> FEATURE:
<223> OTHER INFORMATION: Diagnostic Oligonucleotide

<400> SEQUENCE: 215
acactgaaga tcactgttct a                                             21

<210> SEQ ID NO 216
<211> LENGTH: 18
<212> TYPE: DNA
<213> ORGANISM: Artificial Sequence
<220> FEATURE:
<223> OTHER INFORMATION: Diagnostic Oligonucleotide

<400> SEQUENCE: 216
ctccttttac ttgctttc                                                 18

<210> SEQ ID NO 217
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 217
gagcagtcct ggtttta                                                  17

<210> SEQ ID NO 218
<211> LENGTH: 480
<212> TYPE: DNA
<213> ORGANISM: Artificial Sequence
<220> FEATURE:
<223> OTHER INFORMATION: Diagnostic Oligonucleotide

<400> SEQUENCE: 218
atgagtctgt acagcgtctg gcacatagga ggcatttacc aaacagtagt tattattttt   60

```
gttaccatct atttgataat aaaataatgc ccatctgttg aataaaagaa atatgactta    120
aaaccttgag cagttcttaa tagataattt gacttgtttt tactattaga ttgattgatt    180
gattgattga ttgatttaca gagatcagag agctgggaag atcagtgaaa gacttgtgat    240
tacctcagaa atgattgaaa atatccaatc tgttaaggca tactgctggg aagaagcaat    300
ggaaaaaatg attgaaaact taagacagta agttgttcca ataatttcaa tattgttagt    360
aattctgtcc ttaattttt  aaaaatatgt ttatcatggt agacttccac ctcatatttg    420
atgtttgtga caatcaaatg attgcattta agttctgtca atattcatgc attagttgca    480

<210> SEQ ID NO 219
<211> LENGTH: 63
<212> TYPE: DNA
<213> ORGANISM: Artificial Sequence
<220> FEATURE:
<223> OTHER INFORMATION: Diagnostic Oligonucleotide

<400> SEQUENCE: 219
cgcccgccgc gccccgcgcc cgccccgccg ccccccgcccg ccttgagcag ttcttaatag    60
ata                                                                   63

<210> SEQ ID NO 220
<211> LENGTH: 21
<212> TYPE: DNA
<213> ORGANISM: Artificial Sequence
<220> FEATURE:
<223> OTHER INFORMATION: Diagnostic Oligonucleotide

<400> SEQUENCE: 220
atgccttaac agattggata t                                               21

<210> SEQ ID NO 221
<211> LENGTH: 21
<212> TYPE: DNA
<213> ORGANISM: Artificial Sequence
<220> FEATURE:
<223> OTHER INFORMATION: Diagnostic Oligonucleotide

<400> SEQUENCE: 221
gaaaatatcc aatctgttaa g                                               21

<210> SEQ ID NO 222
<211> LENGTH: 58
<212> TYPE: DNA
<213> ORGANISM: Artificial Sequence
<220> FEATURE:
<223> OTHER INFORMATION: Diagnostic Oligonucleotide

<400> SEQUENCE: 222
cgcccgccgc gccccgcgcc cgccccgccg ccccccgcccg tgaggtggaa gtctacca     58

<210> SEQ ID NO 223
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 223
aaaaccttga gcagtt                                                     16

<210> SEQ ID NO 224
```

```
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 224
ggtggaagtc taccatg                                                      17

<210> SEQ ID NO 225
<211> LENGTH: 752
<212> TYPE: DNA
<213> ORGANISM: Artificial Sequence
<220> FEATURE:
<223> OTHER INFORMATION: Diagnostic Oligonucleotide

<400> SEQUENCE: 225
tttacaagta ctacaagcaa aacactggta ctttcattgt tatcttttca tataaggtaa        60
ctgaggccca gagagattaa ataacatgcc caaggtcaca caggtcatat gatgtggagc       120
caggttaaaa atataggcag aaagactcta gagaccatgc tcagatcttc cattccaaga       180
tccctgatat ttgaaaaata aaataacatc ctgaatttta ttgttattgt tttttataga       240
acagaactga aactgactcg gaaggcagcc tatgtgagat acttcaatag ctcagccttc       300
ttcttctcag ggttctttgt ggtgttttta tctgtgcttc cctatgcact aatcaaagga       360
atcatcctcc ggaaaatatt caccaccatc tcattctgca ttgttctgcg catggcggtc       420
actcggcaat ttccctgggc tgtacaaaca tggtatgact ctcttggagc aataaacaaa       480
atacaggtaa tgtaccataa tgctgcatta tatactatga tttaaataat cagtcaatag       540
atcagttcta atgaactttg caaaaatgtg cgaaaagata gaaaagaaa tttccttcac        600 taggaagtta taaagttgc cagctaatac taggaatgtt caccttaaac ttttcctagc        660
atttctctgg acagtatgat ggatgagagt ggcatttatg caaattacct taaaatccca       720
ataatactga tgtagctagc agctttgaga aa                                     752

<210> SEQ ID NO 226
<211> LENGTH: 63
<212> TYPE: DNA
<213> ORGANISM: Artificial Sequence
<220> FEATURE:
<223> OTHER INFORMATION: Diagnostic Oligonucleotide

<400> SEQUENCE: 226
cgcccgccgc gccccgcgcc cgccccgccg ccccegcccg agaccatgct cagatcttcc        60
att                                                                     63

<210> SEQ ID NO 227
<211> LENGTH: 24
<212> TYPE: DNA
<213> ORGANISM: Artificial Sequence
<220> FEATURE:
<223> OTHER INFORMATION: Diagnostic Oligonucleotide

<400> SEQUENCE: 227
gctgccttcc gagtcagttt cagt                                              24

<210> SEQ ID NO 228
<211> LENGTH: 60
<212> TYPE: DNA
<213> ORGANISM: Artificial Sequence
<220> FEATURE:
<223> OTHER INFORMATION: Diagnostic Oligonucleotide
```

<400> SEQUENCE: 228
cgcccgccgc gccccgcgcc cgccccgccg ccccccgcccg actgaaactg actcggaagg    60

<210> SEQ ID NO 229
<211> LENGTH: 26
<212> TYPE: DNA
<213> ORGANISM: Artificial Sequence
<220> FEATURE:
<223> OTHER INFORMATION: Diagnostic Oligonucleotide

<400> SEQUENCE: 229
atggtacatt acctgtattt tgttta                                          26

<210> SEQ ID NO 230
<211> LENGTH: 26
<212> TYPE: DNA
<213> ORGANISM: Artificial Sequence
<220> FEATURE:
<223> OTHER INFORMATION: Diagnostic Oligonucleotide

<400> SEQUENCE: 230
ctgtacaaac atggtatgac tctctt                                          26

<210> SEQ ID NO 231
<211> LENGTH: 65
<212> TYPE: DNA
<213> ORGANISM: Artificial Sequence
<220> FEATURE:
<223> OTHER INFORMATION: Diagnostic Oligonucleotide

<400> SEQUENCE: 231
cgcccgccgc gccccgcgcc cgccccgccg ccccccgcccg gtgaaggaaa tttcttttttc    60 tatct                                                                 65

<210> SEQ ID NO 232
<211> LENGTH: 18
<212> TYPE: DNA
<213> ORGANISM: Artificial Sequence
<220> FEATURE:
<223> OTHER INFORMATION: Diagnostic Oligonucleotide

<400> SEQUENCE: 232
aatataggca gaaagact                                                   18

<210> SEQ ID NO 233
<211> LENGTH: 19
<212> TYPE: DNA
<213> ORGANISM: Artificial Sequence
<220> FEATURE:
<223> OTHER INFORMATION: Diagnostic Oligonucleotide

<400> SEQUENCE: 233
gaactgatct attgactga                                                  19

<210> SEQ ID NO 234
<211> LENGTH: 725
<212> TYPE: DNA
<213> ORGANISM: Artificial Sequence
<220> FEATURE:
<223> OTHER INFORMATION: Diagnostic Oligonucleotide

<400> SEQUENCE: 234
gcacattagt gggtaattca gggttgcttt gtaaattcat cactaaggtt agcatgtaat    60

-continued

```
agtacaagga agaatcagtt gtatgttaaa tctaatgtat aaaaagtttt ataaaatatc    120
atatgtttag agagtatatt tcaaatatga tgaatcctag tgcttggcaa attaacttta    180
gaacactaat aaaattattt tattaagaaa taattactat ttcattatta aaattcatat    240
ataagatgta gcacaatgag agtataaagt agatgtaata atgcattaat gctattctga    300
ttctataata tgttttttgct ctctttata ataggattt cttacaaaag caagaatata     360
agacattgga atataactta acgactacag aagtagtgat ggagaatgta acagccttct    420
gggaggaggt cagaattttt aaaaaattgt ttgctctaaa cacctaactg ttttcttctt    480
tgtgaatatg gatttcatcc taatggcgaa taaaattaga atgatgatat aactggtaga    540
actggaagga ggatcactca cttatttct agattaagaa gtagaggaat ggccaggtgc     600
tcatggttgt aatcccagca ctttcgggag accaaggcgg gtggatcacc tgaggtcagg    660
agttcaagac cagcctgcca acatggtaaa acccggtctc tactaaaaat acaaaaaatt    720
aactg                                                                725
```

<210> SEQ ID NO 235
<211> LENGTH: 61
<212> TYPE: DNA
<213> ORGANISM: Artificial Sequence
<220> FEATURE:
<223> OTHER INFORMATION: Diagnostic Oligonucleotide

<400> SEQUENCE: 235

```
cgcccgccgc gccccgcgcc cgcccgcccg ccccgcccg gcacaatgag agtataaagt    60
a                                                                      61
```

<210> SEQ ID NO 236
<211> LENGTH: 21
<212> TYPE: DNA
<213> ORGANISM: Artificial Sequence
<220> FEATURE:
<223> OTHER INFORMATION: Diagnostic Oligonucleotide

<400> SEQUENCE: 236

```
ccatcactac ttctgtagtc g                                               21
```

<210> SEQ ID NO 237
<211> LENGTH: 27
<212> TYPE: DNA
<213> ORGANISM: Artificial Sequence
<220> FEATURE:
<223> OTHER INFORMATION: Diagnostic Oligonucleotide

<400> SEQUENCE: 237

```
ctctctttta taaataggat ttcttac                                         27
```

<210> SEQ ID NO 238
<211> LENGTH: 65
<212> TYPE: DNA
<213> ORGANISM: Artificial Sequence
<220> FEATURE:
<223> OTHER INFORMATION: Diagnostic Oligonucleotide

<400> SEQUENCE: 238

```
cgcccgccgc gccccgcgcc cgcccgcccg ccccgcccg ttccagttct accagttata     60
tcatc                                                                  65
```

<210> SEQ ID NO 239
<211> LENGTH: 17

```
<212> TYPE: DNA
<213> ORGANISM: Artificial Sequence
<220> FEATURE:
<223> OTHER INFORMATION: Diagnostic Oligonucleotide

<400> SEQUENCE: 239
atgaatccta gtgcttg                                                      17

<210> SEQ ID NO 240
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 240
tccttccagt tctacc                                                       16

<210> SEQ ID NO 241
<211> LENGTH: 876
<212> TYPE: DNA
<213> ORGANISM: Artificial Sequence
<220> FEATURE:
<223> OTHER INFORMATION: Diagnostic Oligonucleotide

<400> SEQUENCE: 241
tgtatgtgta tgtatacatg tatgtattca gtctttactg aaattaaaaa atctttaact        60
tgataatggg caaatatctt agttttagat catgtcctct agaaaccgta tgctatataa       120
ttatgtacta taaagtaata atgtatacag tgtaatggat catgggccat gtgcttttca       180
aactaattgt acataaaaca agcatctatt gaaaatatct gacaaactca tcttttattt       240
ttgatgtgtg tgtgtgtgtg tgtgtgtgtt tttttaacag ggatttgggg aattatttga       300
gaaagcaaaa caaaacaata acaatagaaa aacttctaat ggtgatgaca gcctcttctt       360 cagtaattte tcacttcttg gtactcctgt cctgaaagat attaatttca agatagaaag       420
aggacagttg ttggcggttg ctggatccac tggagcaggc aaggtagttc ttttgttctt       480
cactattaag aacttaattt ggtgtccatg tctctttttt tttctagttt gtagtgctgg       540
aaggtatttt tggagaaatt cttacatgag cattaggaga atgtatgggt gtagtgtctt       600
gtataataga aattgttcca ctgataattt actctagttt tttatttcct catattattt       660
tcagtggctt tttcttccac atctttatat tttgcaccac attcaacact gtatcttgca       720
catggcgagc attcaataac tttattgaat aaacaaatca tccattttat ccattcttaa       780
ccagaacaga cattttttca gagctggtcc aggaaaatca tgacttacat tttgccttag       840
taaccacata aacaaaaagt ctccatttt gttgac                                 876

<210> SEQ ID NO 242
<211> LENGTH: 65
<212> TYPE: DNA
<213> ORGANISM: Artificial Sequence
<220> FEATURE:
<223> OTHER INFORMATION: Diagnostic Oligonucleotide

<400> SEQUENCE: 242
cgcccgccgc gccccgcgcc cgccccgccg ccccegcccg acaatagaaa aacttctaat        60
ggtga                                                                   65

<210> SEQ ID NO 243
<211> LENGTH: 22
<212> TYPE: DNA
```

```
<213> ORGANISM: Artificial Sequence
<220> FEATURE:
<223> OTHER INFORMATION: Diagnostic Oligonucleotide

<400> SEQUENCE: 243
aaaaaagaga catggacacc aa                                              22

<210> SEQ ID NO 244
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 244
agaaaccgta tgctat                                                     16

<210> SEQ ID NO 245
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 245
cccatacatt cttccta                                                    17

<210> SEQ ID NO 246
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 246
taaagatgtg gaagaaa                                                    17

<210> SEQ ID NO 247
<211> LENGTH: 831
<212> TYPE: DNA
<213> ORGANISM: Artificial Sequence
<220> FEATURE:
<223> OTHER INFORMATION: Diagnostic Oligonucleotide

<400> SEQUENCE: 247
cactgtagct gtactacctt ccatctcctc aacctattcc aactatctga atcatgtgcc      60
cttctctgtg aacctctatc ataatacttg tcacactgta ttgtaattgt ctcttttact     120
ttcccttgta tcttttgtgc atagcagagt acctgaaaca ggaagtattt taaatatttt     180
gaatcaaatg agttaataga atctttacaa ataagaaaat acacttctgc ttaggatgat     240
aattggaggc aagtgaatcc tgagcgtgat ttgataatga cctaataatg atgggtttta     300
tttccagact tcacttctaa tgatgattat gggagaactg gagccttcag agggtaaaat     360
taagcacagt ggaagaattt cattctgttc tcagtttttcc tggattatgc ctggcaccat     420
taaagaaaat atcatctttg gtgtttccta tgatgaatat agatacagaa gcgtcatcaa     480
agcatgccaa ctagaagagg taagaaacta tgtgaaaact ttttgattat gcatatgaac     540
ccttcacact acccaaatta tatatttggc tccatattca atcggttagt ctacatatat     600
ttatgtttcc tctatgggta agctactgtg aatggatcaa ttaataaaac acatgaccta     660
tgctttaaga agcttgcaaa cacatgaaat aaatgcaatt tattttttaa ataatgggtt     720
catttgatca caataaatgc attttatgaa atggtgagaa ttttgttcac tcattagtga     780
```

-continued

```
gacaaacgtc tcaatggtta tttatatggc atgcatatag tgatatgtgg t        831

<210> SEQ ID NO 248
<211> LENGTH: 18
<212> TYPE: DNA
<213> ORGANISM: Artificial Sequence
<220> FEATURE:
<223> OTHER INFORMATION: Diagnostic Oligonucleotide

<400> SEQUENCE: 248
cctgagcgtg atttgata                                              18

<210> SEQ ID NO 249
<211> LENGTH: 60
<212> TYPE: DNA
<213> ORGANISM: Artificial Sequence
<220> FEATURE:
<223> OTHER INFORMATION: Diagnostic Oligonucleotide

<400> SEQUENCE: 249
cgcccgccgc gccccgcgcc cgcccgcccg ccccgcccg atgtagacta accgattgaa  60

<210> SEQ ID NO 250
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 250
gggagaactg gagcct                                                16

<210> SEQ ID NO 251
<211> LENGTH: 58
<212> TYPE: DNA
<213> ORGANISM: Artificial Sequence
<220> FEATURE:
<223> OTHER INFORMATION: Diagnostic Oligonucleotide

<400> SEQUENCE: 251
cgcccgccgc gccccgcgcc cgcccgcccg ccccgcccg aaccgattga atatggag    58

<210> SEQ ID NO 252
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 252
ccttgtatct tttgtgc                                               17

<210> SEQ ID NO 253
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 253
ccgattgaat atggag                                                16

<210> SEQ ID NO 254
<211> LENGTH: 614
<212> TYPE: DNA
```

<213> ORGANISM: Artificial Sequence
<220> FEATURE:
<223> OTHER INFORMATION: Diagnostic Oligonucleotide

<400> SEQUENCE: 254

| atatacccat aaatatacac atattttaat ttttggtatt ttataattat tatttaatga | 60 |
| tcattcatga cattttaaaa attacaggaa aaatttacat ctaaaatttc agcaatgttg | 120 |
| tttttgacca actaaataaa ttgcatttga aataatggag atgcaatgtt caaaatttca | 180 |
| actgtggtta aagcaatagt gtgatatatg attacattag aaggaagatg tgcctttcaa | 240 |
| attcagattg agcatactaa aagtgactct ctaattttct attttggta ataggacatc | 300 |
| tccaagtttg cagagaaaga caatatagtt cttggagaag gtggaatcac actgagtgga | 360 |
| ggtcaacgag caagaatttc tttagcaagg tgaataacta attattggtc tagcaagcat | 420 |
| ttgctgtaaa tgtcattcat gtaaaaaaat tacagacatt tctctattgc tttatattct | 480 |
| gtttctggaa ttgaaaaaat cctggggttt tatggctagt gggttaagaa tcacatttaa | 540 |
| gaactataaa taatggtata gtatccagat ttggtagaga ttatggttac tcagaatctg | 600 |
| tgcccgtatc ttgg | 614 |

<210> SEQ ID NO 255
<211> LENGTH: 61
<212> TYPE: DNA
<213> ORGANISM: Artificial Sequence
<220> FEATURE:
<223> OTHER INFORMATION: Diagnostic Oligonucleotide

<400> SEQUENCE: 255

| cgcccgccgc gccccgcgcc cgcccgcccg ccccgcccg gatatatgat tacattagaa | 60 |
| g | 61 |

<210> SEQ ID NO 256
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 256

| accttctcca agaacta | 17 |

<210> SEQ ID NO 257
<211> LENGTH: 18
<212> TYPE: DNA
<213> ORGANISM: Artificial Sequence
<220> FEATURE:
<223> OTHER INFORMATION: Diagnostic Oligonucleotide

<400> SEQUENCE: 257

| ataggacatc tccaagtt | 18 |

<210> SEQ ID NO 258
<211> LENGTH: 59
<212> TYPE: DNA
<213> ORGANISM: Artificial Sequence
<220> FEATURE:
<223> OTHER INFORMATION: Diagnostic Oligonucleotide

<400> SEQUENCE: 258

| cgcccgccgc gccccgcgcc cgcccgcccg ccccgcccg gcaatagaga aatgtctgt | 59 |

```
<210> SEQ ID NO 259
<211> LENGTH: 20
<212> TYPE: DNA
<213> ORGANISM: Artificial Sequence
<220> FEATURE:
<223> OTHER INFORMATION: Diagnostic Oligonucleotide

<400> SEQUENCE: 259
cagattgagc atactaaaag                                                    20

<210> SEQ ID NO 260
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 260
aagatacggg cacaga                                                        16

<210> SEQ ID NO 261
<211> LENGTH: 676
<212> TYPE: DNA
<213> ORGANISM: Artificial Sequence
<220> FEATURE:
<223> OTHER INFORMATION: Diagnostic Oligonucleotide

<400> SEQUENCE: 261
cttacagtta gcaaaatcac ttcagcagtt cttggaatgt tgtgaaaagt gataaaaatc         60
ttctgcaact tattccttta ttcctcattt aaaataatct accatagtaa aaacatgtat        120
aaaagtgcta cttctgcacc acttttgaga atagtgttat ttcagtgaat cgatgtggtg        180
accatattgt aatgcatgta gtgaactgtt taaggcaaat catctacact agatgaccag        240
gaaatagaga ggaaatgtaa tttaatttcc attttctttt tagagcagta tacaaagatg        300
ctgatttgta tttattagac tctccttttg gatacctaga tgttttaaca gaaaaagaaa        360
tatttgaaag gtatgttctt tgaatacctt acttataatg ctcatgctaa aataaaagaa        420
agacagactg tcccatcata gattgcattt tacctcttga gaaatatgtt caccattgtt        480
ggtatggcag aatgtagcat ggtattaact caaatctgat ctgccctact gggccaggat        540
tcaagattac ttccattaaa accttttctc accgcctcat gctaaaccag tttctctcat        600
tgctatactg ttatagcaat tgctatctat gtagtttttg cagtatcatt gccttgtgat        660
atatattact ttaatt                                                       676

<210> SEQ ID NO 262
<211> LENGTH: 63
<212> TYPE: DNA
<213> ORGANISM: Artificial Sequence
<220> FEATURE:
<223> OTHER INFORMATION: Diagnostic Oligonucleotide

<400> SEQUENCE: 262
cgcccgccgc gccccgcgcc cgccccgccg ccccccgcccg gtgaactgtt taaggcaaat        60
cat                                                                      63

<210> SEQ ID NO 263
<211> LENGTH: 21
<212> TYPE: DNA
<213> ORGANISM: Artificial Sequence
<220> FEATURE:
<223> OTHER INFORMATION: Diagnostic Oligonucleotide
```

-continued

```
<400> SEQUENCE: 263
tgatgggaca gtctgtctttt c                                           21

<210> SEQ ID NO 264
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 264
tcacttcagc agttctt                                                 17

<210> SEQ ID NO 265
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 265
caatctatga tgggaca                                                 17

<210> SEQ ID NO 266
<211> LENGTH: 1200
<212> TYPE: DNA
<213> ORGANISM: Artificial Sequence
<220> FEATURE:
<223> OTHER INFORMATION: Diagnostic Oligonucleotide

<400> SEQUENCE: 266
gaattcacaa ggtaccaatt taattactac agagtactta tagaatcatt taaaatataa    60
taaaattgta tgatagagat tatatgcaat aaaacattaa caaaatgcta aaatacgaga   120
catattgcaa taaagtattt ataaaattga tatttatatg tttttatatc ttaaagctgt   180
gtctgtaaac tgatggctaa caaaactagg attttggtca cttctaaaat ggaacattta   240
aagaaagctg acaaaatatt aattttgcat gaaggtagca gctatttta tgggacattt    300 tcagaactcc aaaatctaca gccagacttt agctcaaaac tcatgggatg tgattctttc   360 gaccaatttta gtgcagaaag aagaaattca atcctaactg agaccttaca ccgtttctca   420
ttagaaggag atgctcctgt ctcctggaca gaaacaaaaa aacaatcttt taaacagact   480
ggagagtttg gggaaaaaag gaagaattct attctcaatc caatcaactc tatacgaaaa   540
ttttccattg tgcaaaagac tcccttacaa atgaatggca tcgaagagga ttctgatgag   600
cctttagaga gaaggctgtc cttagtacca gattctgagc agggagaggc gatactgcct   660
cgcatcagcg tgatcagcac tggccccacg cttcaggcac gaaggaggca gtctgtcctg   720
aacctgatga cacactcagt taaccaaggt cagaacattc accgaaagac aacagcatcc   780
acacgaaaag tgtcactggc ccctcaggca aacttgactg aactggatat atattcaaga   840
aggttatctc aagaaactgg cttggaaata agtgaagaaa ttaacgaaga agacttaaag   900
gtaggtatac atcgcttggg ggtatttcac cccacagaat gcaattgagt agaatgcaat   960
atgtagcatg taacaaaatt tactaaaatc ataggattag gataaggtgt atcttaaaac  1020
tcagaaagta tgaagttcat taattataca agcaacgtta aaatgtaaaa taacaaatga  1080 tttcttttg caatggacat atctcttccc ataaaatggg aaaggattta gttttggtc   1140 ctctactaag ccagtgataa ctgtgactat agttagaaag catttgcttt attaccatct  1200
```

```
<210> SEQ ID NO 267
<211> LENGTH: 25
<212> TYPE: DNA
<213> ORGANISM: Artificial Sequence
<220> FEATURE:
<223> OTHER INFORMATION: Diagnostic Oligonucleotide

<400> SEQUENCE: 267
aatacgagac atattgcaat aaagt                                          25

<210> SEQ ID NO 268
<211> LENGTH: 62
<212> TYPE: DNA
<213> ORGANISM: Artificial Sequence
<220> FEATURE:
<223> OTHER INFORMATION: Diagnostic Oligonucleotide

<400> SEQUENCE: 268
cgcccgccgc gccccgcgcc cgcccgcccg ccccgcccg ctggctgtag attttggagt    60
tc                                                                   62

<210> SEQ ID NO 269
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 269
aggtagcagc tattttt                                                   17

<210> SEQ ID NO 270
<211> LENGTH: 57
<212> TYPE: DNA
<213> ORGANISM: Artificial Sequence
<220> FEATURE:
<223> OTHER INFORMATION: Diagnostic Oligonucleotide

<400> SEQUENCE: 270
cgcccgccgc gccccgcgcc cgcccgcccg ccccgcccg ggacagcctt ctctcta       57

<210> SEQ ID NO 271
<211> LENGTH: 61
<212> TYPE: DNA
<213> ORGANISM: Artificial Sequence
<220> FEATURE:
<223> OTHER INFORMATION: Diagnostic Oligonucleotide

<400> SEQUENCE: 271
cgcccgccgc gccccgcgcc cgcccgcccg ccccgcccg atgggacatt ttcagaactc    60
c                                                                    61

<210> SEQ ID NO 272
<211> LENGTH: 19
<212> TYPE: DNA
<213> ORGANISM: Artificial Sequence
<220> FEATURE:
<223> OTHER INFORMATION: Diagnostic Oligonucleotide

<400> SEQUENCE: 272
cctcttcgat gccattcat                                                 19

<210> SEQ ID NO 273
<211> LENGTH: 63
<212> TYPE: DNA
```

```
<213> ORGANISM: Artificial Sequence
<220> FEATURE:
<223> OTHER INFORMATION: Diagnostic Oligonucleotide

<400> SEQUENCE: 273
cgcccgccgc gccccgcgcc cgcccgccg ccccgcccg caatccaatc aactctatac    60
gaa                                                                63

<210> SEQ ID NO 274
<211> LENGTH: 18
<212> TYPE: DNA
<213> ORGANISM: Artificial Sequence
<220> FEATURE:
<223> OTHER INFORMATION: Diagnostic Oligonucleotide

<400> SEQUENCE: 274
ctgatcacgc tgatgcga                                                18

<210> SEQ ID NO 275
<211> LENGTH: 60
<212> TYPE: DNA
<213> ORGANISM: Artificial Sequence
<220> FEATURE:
<223> OTHER INFORMATION: Diagnostic Oligonucleotide

<400> SEQUENCE: 275
cgcccgccgc gccccgcgcc cgcccgccg ccccgcccg tgatgagcct ttagagagaa    60

<210> SEQ ID NO 276
<211> LENGTH: 19
<212> TYPE: DNA
<213> ORGANISM: Artificial Sequence
<220> FEATURE:
<223> OTHER INFORMATION: Diagnostic Oligonucleotide

<400> SEQUENCE: 276
ccagttcagt caagtttgc                                               19

<210> SEQ ID NO 277
<211> LENGTH: 54
<212> TYPE: DNA
<213> ORGANISM: Artificial Sequence
<220> FEATURE:
<223> OTHER INFORMATION: Diagnostic Oligonucleotide

<400> SEQUENCE: 277
cgcccgccgc gccccgcgcc cgcccgccg ccccgcccg cagcgtgatc agca          54

<210> SEQ ID NO 278
<211> LENGTH: 18
<212> TYPE: DNA
<213> ORGANISM: Artificial Sequence
<220> FEATURE:
<223> OTHER INFORMATION: Diagnostic Oligonucleotide

<400> SEQUENCE: 278
tttgttacat gctacata                                                18

<210> SEQ ID NO 279
<211> LENGTH: 734
<212> TYPE: DNA
<213> ORGANISM: Artificial Sequence
<220> FEATURE:
<223> OTHER INFORMATION: Diagnostic Oligonucleotide

<400> SEQUENCE: 279
```

```
ggaaacttca tttagatggt atcattcatt tgataaaagg tatgccactg ttaagccttt      60
aatggtaaaa ttgtccaata ataatacagt tatataatca gtgatacatt tttagaattt     120
tgaaaaatta cgatgtttct catttttaat aaagctgtgt tgctccagta gacattattc     180
tggctataga atgacatcat acatggcatt taatgatt tatatttgtt aaaatacact       240
tagattcaag taatactatt cttttatttt catatattaa aaataaaacc acaatggtgg     300
catgaaactg tactgtctta ttgtaatagc cataattctt ttattcagga gtgcttttt     360 gatgatatgg agagcatacc agcagtgact acatggaaca catacctcg atatattact     420 gtccacaaga gcttaatttt tgtgctaatt tggtgcttag taatttttct ggcagaggta    480
agaatgttct attgtaaagt attactggat ttaaagttaa attaagatag tttggggatg    540
tatacatata tatgcacaca cataaatatg tatatataca catgtataca tgtataagta    600
tgcatatata cacacatata tcactatatg tatatatgta tatattacat atatttgtga    660
ttttacagta tataatggta tagattcata tagttcttag cttctgaaaa atcaacaagt   720
agaaccacta ctga                                                        734

<210> SEQ ID NO 280
<211> LENGTH: 62
<212> TYPE: DNA
<213> ORGANISM: Artificial Sequence
<220> FEATURE:
<223> OTHER INFORMATION: Diagnostic Oligonucleotide

<400> SEQUENCE: 280
cgcccgccgc gccccgcgcc cgccccgccg ccccgcccg ttcatatatt aaaaataaaa     60
cc                                                                    62

<210> SEQ ID NO 281
<211> LENGTH: 21
<212> TYPE: DNA
<213> ORGANISM: Artificial Sequence
<220> FEATURE:
<223> OTHER INFORMATION: Diagnostic Oligonucleotide

<400> SEQUENCE: 281
taatatatcg aaggtatgtg t                                               21

<210> SEQ ID NO 282
<211> LENGTH: 22
<212> TYPE: DNA
<213> ORGANISM: Artificial Sequence
<220> FEATURE:
<223> OTHER INFORMATION: Diagnostic Oligonucleotide

<400> SEQUENCE: 282
gagcatacca gcagtgacta ca                                              22

<210> SEQ ID NO 283
<211> LENGTH: 69
<212> TYPE: DNA
<213> ORGANISM: Artificial Sequence
<220> FEATURE:
<223> OTHER INFORMATION: Diagnostic Oligonucleotide

<400> SEQUENCE: 283
cgcccgccgc gccccgcgcc cgccccgccg ccccgcccg gtaatacttt acaatagaac     60
attcttacc                                                             69
```

```
<210> SEQ ID NO 284
<211> LENGTH: 20
<212> TYPE: DNA
<213> ORGANISM: Artificial Sequence
<220> FEATURE:
<223> OTHER INFORMATION: Diagnostic Oligonucleotide

<400> SEQUENCE: 284
accagcagtg actacatgga                                                    20

<210> SEQ ID NO 285
<211> LENGTH: 28
<212> TYPE: DNA
<213> ORGANISM: Artificial Sequence
<220> FEATURE:
<223> OTHER INFORMATION: Diagnostic Oligonucleotide

<400> SEQUENCE: 285
atatttatgt gtgtgcatat atatgtat                                           28

<210> SEQ ID NO 286
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 286
tgttgctcca gtagaca                                                       17

<210> SEQ ID NO 287
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 287
catccccaaa ctatct                                                        16

<210> SEQ ID NO 288
<211> LENGTH: 621
<212> TYPE: DNA
<213> ORGANISM: Artificial Sequence
<220> FEATURE:
<223> OTHER INFORMATION: Diagnostic Oligonucleotide

<400> SEQUENCE: 288
gaattccatt aacttaatgt ggtctcatca caaataatag tacttagaac acctagtaca         60
gctgctggac ccaggaacac aaagcaaagg aagatgaaat tgtgtgtacc ttgatattgg        120
tacacacatc aaatggtgtg atgtgaattt agatgtgggc atgggaggaa taggtgaaga        180
tgttagaaaa aaaatcaact gtgtcttgtt ccattccagg tggctgcttc tttggttgtg        240
ctgtggctcc ttggaaagtg agtattccat gtcctattgt gtagattgtg ttttatttct        300
gttgattaaa tattgtaatc cactatgttt gtatgtattg taatccactt tgtttcattt        360
ctcccaagca ttatggtagt ggaaagataa ggttttttgt ttaaatgatg accattagtt        420
gggtgaggtg acacattcct gtagtcctag ctcctccaca ggctgacgca ggaggatcac        480
ttgagcccag gagttcaggg ctgtagtgtt gtatcattgt gagtagccac caccgcactc        540
cagcctggac aatatagtga gatcctatat ctaaaataaa ataaaataaa atgaataaat        600
tgtgagcatg tgcagctcct g                                                 621
```

<210> SEQ ID NO 289
<211> LENGTH: 57
<212> TYPE: DNA
<213> ORGANISM: Artificial Sequence
<220> FEATURE:
<223> OTHER INFORMATION: Diagnostic Oligonucleotide

<400> SEQUENCE: 289
cgcccgccgc gccccgcgcc cgcccgcccg ccccgcccg gtgtaccttg atattgg    57

<210> SEQ ID NO 290
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 290
ctcactttcc aaggag    16

<210> SEQ ID NO 291
<211> LENGTH: 15
<212> TYPE: DNA
<213> ORGANISM: Artificial Sequence
<220> FEATURE:
<223> OTHER INFORMATION: Diagnostic Oligonucleotide

<400> SEQUENCE: 291
gctgtggctc cttgg    15

<210> SEQ ID NO 292
<211> LENGTH: 58
<212> TYPE: DNA
<213> ORGANISM: Artificial Sequence
<220> FEATURE:
<223> OTHER INFORMATION: Diagnostic Oligonucleotide

<400> SEQUENCE: 292
cgcccgccgc gccccgcgcc cgcccgcccg ccccgcccg actacagccc tgaactcc    58

<210> SEQ ID NO 293
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 293
ggaacacaaa gcaaag    16

<210> SEQ ID NO 294
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 294
tgggagaaat gaaaca    16

<210> SEQ ID NO 295
<211> LENGTH: 727
<212> TYPE: DNA
<213> ORGANISM: Artificial Sequence
<220> FEATURE:

<223> OTHER INFORMATION: Diagnostic Oligonucleotide

<400> SEQUENCE: 295

| | | | | | |
|---|---|---|---|---|---|
| tcctatatct | aaataaataa | ataaatgaat | aaattgtgag | catgtgcagc | tcctgcagtt | 60 |
| tctaaagaat | atagttctgt | tcagtttctg | tgaaacacaa | taaaaatatt | tgaaataaca | 120 |
| ttacatattt | agggttttct | tcaaatttt | taatttaata | agaacaact | caatctctat | 180 |
| caatagtgag | aaaacatatc | tatttcttg | caataatagt | atgattttga | ggttaagggt | 240 |
| gcatgctctt | ctaatgcaaa | atattgtatt | tatttagact | caagtttagt | tccatttaca | 300 |
| tgtattggaa | attcagtaag | taactttggc | tgccaaataa | cgattccta | tttgctttac | 360 |
| agcactcctc | ttcaagacaa | agggaatagt | actcatagta | gaaataacag | ctatgcagtg | 420 |
| attatcacca | gcaccagttc | gtattatgtg | ttttacattt | acgtgggagt | agccgacact | 480 |
| ttgcttgcta | tgggattctt | cagaggtcta | ccactggtgc | atactctaat | cacagtgtcg | 540 |
| aaaattttac | accacaaaat | gttacattct | gttcttcaag | cacctatgtc | aaccctcaac | 600 |
| acgttgaaag | caggtacttt | actaggtcta | agaaatgaaa | ctgctgatcc | accatcaata | 660 |
| gggcctgtgg | ttttgttggt | tttctaatgg | cagtgctggc | ttttgcacag | aggcatgtgc | 720 |
| ctttgtt | | | | | 727 |

<210> SEQ ID NO 296
<211> LENGTH: 66
<212> TYPE: DNA
<213> ORGANISM: Artificial Sequence
<220> FEATURE:
<223> OTHER INFORMATION: Diagnostic Oligonucleotide

<400> SEQUENCE: 296

| | | | | | |
|---|---|---|---|---|---|
| cgcccgccgc | gccccgcgcc | cgccccgccg | ccccgcccg | catgtattgg | aaattcagta | 60 |
| agtaac | | | | | 66 |

<210> SEQ ID NO 297
<211> LENGTH: 24
<212> TYPE: DNA
<213> ORGANISM: Artificial Sequence
<220> FEATURE:
<223> OTHER INFORMATION: Diagnostic Oligonucleotide

<400> SEQUENCE: 297

| | |
|---|---|
| ttcgacactg tgattagagt atgc | 24 |

<210> SEQ ID NO 298
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 298

| | |
|---|---|
| gtgggagtag ccgaca | 16 |

<210> SEQ ID NO 299
<211> LENGTH: 57
<212> TYPE: DNA
<213> ORGANISM: Artificial Sequence
<220> FEATURE:
<223> OTHER INFORMATION: Diagnostic Oligonucleotide

<400> SEQUENCE: 299

| | | | | | |
|---|---|---|---|---|---|
| cgcccgccgc | gccccgcgcc | cgccccgccg | ccccgcccg | caggccctat | tgatggt | 57 |

```
<210> SEQ ID NO 300
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 300
cgtgggagta gccgac                                                        16

<210> SEQ ID NO 301
<211> LENGTH: 58
<212> TYPE: DNA
<213> ORGANISM: Artificial Sequence
<220> FEATURE:
<223> OTHER INFORMATION: Diagnostic Oligonucleotide

<400> SEQUENCE: 301
cgcccgccgc gccccgcgcc cgcccgccg ccccgcccg cattagaaaa ccaacaaa            58

<210> SEQ ID NO 302
<211> LENGTH: 19
<212> TYPE: DNA
<213> ORGANISM: Artificial Sequence
<220> FEATURE:
<223> OTHER INFORMATION: Diagnostic Oligonucleotide

<400> SEQUENCE: 302
agactcaagt ttagttcca                                                     19

<210> SEQ ID NO 303
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 303
ccaacaaaac cacagg                                                        16

<210> SEQ ID NO 304
<211> LENGTH: 701
<212> TYPE: DNA
<213> ORGANISM: Artificial Sequence
<220> FEATURE:
<223> OTHER INFORMATION: Diagnostic Oligonucleotide

<400> SEQUENCE: 304
gtaagattgt aagcaggatg agtacccacc tattcctgac ataatttata gtaaaagcta        60
tttcagagaa attggtcgtt acttgaatct tacaagaatc tgaaactttt aaaaaggttt       120
aaaagtaaaa gacaataact tgaacacata attatttaga atgtttggaa agaaacaaaa       180
atttctaagt ctatctgatt ctatttgcta attcttattt gggttctgaa tgcgtctact       240
gtgatccaaa cttagtattg aatatattga tatatcttta aaaaattagt gttttttgag       300
gaatttgtca tcttgtatat tataggtggg attcttaata gattctccaa agatatagca       360
attttggatg accttctgcc tcttaccata tttgacttca tccaggtatg taaaaataag       420
taccgttaag tatgtctgta ttattaaaaa aacaataaca aaagcaaatg tgattttgtt       480
ttcatttttt atttgattga gggttgaagt cctgtctatt gcattaattt tgtaattatc       540
caaagccttc aaaatagaca taagtttagt aaattcaata ataagtcaga actgcttacc       600
```

```
tggcccaaac ctgaggcaat cccacattta gatgtaatag ctgtctactt gggagtgatt    660
tgagaggcac aaaggaccat ctttcccaaa atcactggca c                       701

<210> SEQ ID NO 305
<211> LENGTH: 56
<212> TYPE: DNA
<213> ORGANISM: Artificial Sequence
<220> FEATURE:
<223> OTHER INFORMATION: Diagnostic Oligonucleotide

<400> SEQUENCE: 305
cgcccgccgc gccccgcgcc cgccccgccg ccccgcccg ctgaatgcgt ctactg          56

<210> SEQ ID NO 306
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 306
catccaaaat tgctata                                                   17

<210> SEQ ID NO 307
<211> LENGTH: 23
<212> TYPE: DNA
<213> ORGANISM: Artificial Sequence
<220> FEATURE:
<223> OTHER INFORMATION: Diagnostic Oligonucleotide

<400> SEQUENCE: 307
ttgaggaatt tgtcatcttg tat                                            23

<210> SEQ ID NO 308
<211> LENGTH: 63
<212> TYPE: DNA
<213> ORGANISM: Artificial Sequence
<220> FEATURE:
<223> OTHER INFORMATION: Diagnostic Oligonucleotide

<400> SEQUENCE: 308
cgcccgccgc gccccgcgcc cgccccgccg ccccgcccg caaaatcaca tttgcttttg     60
tta                                                                  63

<210> SEQ ID NO 309
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 309
atgcgtctac tgtgatc                                                   17

<210> SEQ ID NO 310
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 310
cttcaaccct caatca                                                    16
```

```
<210> SEQ ID NO 311
<211> LENGTH: 637
<212> TYPE: DNA
<213> ORGANISM: Artificial Sequence
<220> FEATURE:
<223> OTHER INFORMATION: Diagnostic Oligonucleotide

<400> SEQUENCE: 311
agtgcaccag catggcacat gtatacatat gtaactaacc tcgacaatgt gcacatgtac    60
cctaaaactt aaagtataat aaaaaaaata aaaaaaagtt tgaggtgttt aaagtatgca   120
aaaaaaaaaa aagaaataaa tcactgacac actttgtcca ctttgcaatg tgaaaatgtt   180
tactcaccaa catgttttct ttgatcttac agttgttatt aattgtgatt ggagctatag   240
cagttgtcgc agttttacaa ccctacatct ttgttcaac agtgccagtg atagtggctt    300
ttattatgtt gagagcatat ttcctccaaa cctcacagca actcaaacaa ctggaatctg   360
aaggtatgac agtgaatgtg cgatactcat cttgtaaaaa agctataaga gctatttgag   420
attctttatt gttaatctac ttaaaaaaaa ttctgctttt aaactttac atcatataac     480 ataatttttt ttctacatgc atgtgtatat aaaaggaaac tatattacaa agtacacatg   540
gatttttttt cttaattaat gaccatgtga cttcattttg gttttaaaat aggtatatag   600
aatcttacca cagttggtgt acaggacatt catttat                             637

<210> SEQ ID NO 312
<211> LENGTH: 58
<212> TYPE: DNA
<213> ORGANISM: Artificial Sequence
<220> FEATURE:
<223> OTHER INFORMATION: Diagnostic Oligonucleotide

<400> SEQUENCE: 312
cgcccgccgc gccccgcgcc cgcccgccg ccccgcccg aaagaaataa atcactga       58

<210> SEQ ID NO 313
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 313
gtaaaactgc gacaac                                                    16

<210> SEQ ID NO 314
<211> LENGTH: 26
<212> TYPE: DNA
<213> ORGANISM: Artificial Sequence
<220> FEATURE:
<223> OTHER INFORMATION: Diagnostic Oligonucleotide

<400> SEQUENCE: 314
ccaacatgtt ttctttgatc ttacag                                         26

<210> SEQ ID NO 315
<211> LENGTH: 67
<212> TYPE: DNA
<213> ORGANISM: Artificial Sequence
<220> FEATURE:
<223> OTHER INFORMATION: Diagnostic Oligonucleotide

<400> SEQUENCE: 315
cgcccgccgc gccccgcgcc cgcccgccg ccccgcccg agaatctcaa atagctctta     60
``` tagcttt    67

<210> SEQ ID NO 316
<211> LENGTH: 19
<212> TYPE: DNA
<213> ORGANISM: Artificial Sequence
<220> FEATURE:
<223> OTHER INFORMATION: Diagnostic Oligonucleotide

<400> SEQUENCE: 316
aaataaatca ctgacacac    19

<210> SEQ ID NO 317
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 317
aatgaagtca catggtc    17

<210> SEQ ID NO 318
<211> LENGTH: 600
<212> TYPE: DNA
<213> ORGANISM: Artificial Sequence
<220> FEATURE:
<223> OTHER INFORMATION: Diagnostic Oligonucleotide

<400> SEQUENCE: 318
ttcaaagaat ggcaccagtg tgaaaaaaag cttttaacc aatgacattt gtgatatgat    60
tattctaatt tagtcttttt caggtacaag atattatgaa attacatttt gtgtttatg    120
ttatttgcaa tgttttctat ggaaatattt cacaggcagg agtccaattt tcactcatct    180
tgttacaagc ttaaaaggac tatggacact tcgtgccttc ggacggcagc cttactttga    240
aactctgttc cacaaagctc tgaatttaca tactgccaac tggttcttgt acctgtcaac    300
actgcgctgg ttccaaatga aatagaaat gattttgtc atcttcttca ttgctgttac    360
cttcatttcc attttaacaa caggtactat gaactcatta actttagcta agcatttaag    420
taaaaaattt tcaatgaata aaatgctgca ttctataggt tatcaatttt tgatatcttt    480
agagtttagt aattaacaaa tttgttggtt tattattgaa caagtgattt ctttgaaatt    540
tccattgttt tattgttaaa caataatttt ccttgaaatc ggtatatata tatatatagt    600

<210> SEQ ID NO 319
<211> LENGTH: 62
<212> TYPE: DNA
<213> ORGANISM: Artificial Sequence
<220> FEATURE:
<223> OTHER INFORMATION: Diagnostic Oligonucleotide

<400> SEQUENCE: 319
cgcccgccgc gccccgcgcc cgccccgccg ccccccgcccg ttaaccaatg acatttgtga    60
ta    62

<210> SEQ ID NO 320
<211> LENGTH: 21
<212> TYPE: DNA
<213> ORGANISM: Artificial Sequence
<220> FEATURE:
<223> OTHER INFORMATION: Diagnostic Oligonucleotide

<400> SEQUENCE: 320
gtgtccatag tcctttaag c                                             21

<210> SEQ ID NO 321
<211> LENGTH: 56
<212> TYPE: DNA
<213> ORGANISM: Artificial Sequence
<220> FEATURE:
<223> OTHER INFORMATION: Diagnostic Oligonucleotide

<400> SEQUENCE: 321
cgcccgccgc gccccgcgcc cgcccgcccg ccccgcccg aatatttcac aggcag        56

<210> SEQ ID NO 322
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 322
tgaaggtaac agcaat                                                   16

<210> SEQ ID NO 323
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 323
acttcgtgcc ttcggac                                                  17

<210> SEQ ID NO 324
<211> LENGTH: 62
<212> TYPE: DNA
<213> ORGANISM: Artificial Sequence
<220> FEATURE:
<223> OTHER INFORMATION: Diagnostic Oligonucleotide

<400> SEQUENCE: 324
cgcccgccgc gccccgcgcc cgcccgcccg ccccgcccg cagcaatgaa gaagatgaca    60
aa                                                                  62

<210> SEQ ID NO 325
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 325
ctggttccaa atgagaa                                                  17

<210> SEQ ID NO 326
<211> LENGTH: 59
<212> TYPE: DNA
<213> ORGANISM: Artificial Sequence
<220> FEATURE:
<223> OTHER INFORMATION: Diagnostic Oligonucleotide

<400> SEQUENCE: 326
cgcccgccgc gccccgcgcc cgcccgcccg ccccgcccg taacctatag aatgcagca     59

<210> SEQ ID NO 327

```
<211> LENGTH: 739
<212> TYPE: DNA
<213> ORGANISM: Artificial Sequence
<220> FEATURE:
<223> OTHER INFORMATION: Diagnostic Oligonucleotide

<400> SEQUENCE: 327
ttattactta tagaataata gtagaagaga caaatatggt acctacccat taccaacaac      60
acctccaata ccagtaacat tttttaaaaa gggcaacact ttcctaatat tcaatcgctc     120
tttgatttaa aatcctggtt gaatacttac tatatgcaga gcattattct attagtagat    180
gctgtgatga actgagattt aaaaattgtt aaaattagca taaaattgaa atgtaaattt     240
aatgtgatat gtgccctagg agaagtgtga ataaagtcgt tcacagaaga gagaaataac     300
atgaggttca tttacgtctt ttgtgcatct ataggagaag gagaaggaag agttggtatt     360
atcctgactt tagccatgaa tatcatgagt acattgcagt gggctgtaaa ctccagcata     420
gatgtggata gcttggtaag tcttatcatc tttttaactt ttatgaaaaa aattcagaca     480
agtaacaaag tatgagtaat agcatgagga agaactatat accgtatatt gagcttaaga     540
aataaaacat tacagataaa ttgagggtca ctgtgtatct gtcattaaat ccttatctct     600
tctttccttc tcatagatag ccactatgaa gatctaatac tgcagtgagc attctttcac     660
ctgtttcctt attcaggatt ttctaggaga aatacctagg ggttgtattg ctgggtcata     720
ggattcaccc atgcttaac                                                  739

<210> SEQ ID NO 328
<211> LENGTH: 60
<212> TYPE: DNA
<213> ORGANISM: Artificial Sequence
<220> FEATURE:
<223> OTHER INFORMATION: Diagnostic Oligonucleotide

<400> SEQUENCE: 328
cgcccgccgc gccccgcgcc cgccccgccg ccccccgcccg ttaatgtgat atgtgcccta    60

<210> SEQ ID NO 329
<211> LENGTH: 21
<212> TYPE: DNA
<213> ORGANISM: Artificial Sequence
<220> FEATURE:
<223> OTHER INFORMATION: Diagnostic Oligonucleotide

<400> SEQUENCE: 329
agatgataag acttaccaag c                                                21

<210> SEQ ID NO 330
<211> LENGTH: 21
<212> TYPE: DNA
<213> ORGANISM: Artificial Sequence
<220> FEATURE:
<223> OTHER INFORMATION: Diagnostic Oligonucleotide

<400> SEQUENCE: 330
gagaaggaga aggaagagtt g                                                21

<210> SEQ ID NO 331
<211> LENGTH: 63
<212> TYPE: DNA
<213> ORGANISM: Artificial Sequence
<220> FEATURE:
<223> OTHER INFORMATION: Diagnostic Oligonucleotide

<400> SEQUENCE: 331
```

```
cgcccgccgc gccccgcgcc cgcccgccg ccccccgcccg cttcctcatg ctattactca    60
tac                                                                 63

<210> SEQ ID NO 332
<211> LENGTH: 18
<212> TYPE: DNA
<213> ORGANISM: Artificial Sequence
<220> FEATURE:
<223> OTHER INFORMATION: Diagnostic Oligonucleotide

<400> SEQUENCE: 332
cctggttgaa tacttact                                                  18

<210> SEQ ID NO 333
<211> LENGTH: 20
<212> TYPE: DNA
<213> ORGANISM: Artificial Sequence
<220> FEATURE:
<223> OTHER INFORMATION: Diagnostic Oligonucleotide

<400> SEQUENCE: 333
ctcatacttt gttacttgtc                                                20

<210> SEQ ID NO 334
<211> LENGTH: 629
<212> TYPE: DNA
<213> ORGANISM: Artificial Sequence
<220> FEATURE:
<223> OTHER INFORMATION: Diagnostic Oligonucleotide

<400> SEQUENCE: 334
ttctcttcag ttaaactttt aattatatcc aattatttcc tgttagttca ttgaaaagcc    60
cgacaaataa ccaagtgaca aatagcaagt gttgcatttt acaagttatt ttttaggaag   120
catcaaacta attgtgaaat tgtctgccat tcttaaaaac aaaaatgttg ttatttttat   180
ttcagatgcg atctgtgagc cgagtctta agttcattga catgccaaca gaaggtaaac   240
ctaccaagtc aaccaaacca tacaagaatg gccaactctc gaaagttatg attattgaga   300
attcacacgt gaagaaagat gacatctggc cctcaggggg ccaaatgact gtcaaagatc   360
tcacagcaaa atacacagaa ggtggaaatg ccatattaga gaacatttcc ttctcaataa   420
gtcctggcca gagggtgaga tttgaacact gcttgctttg ttagactgtg ttcagtaagt   480
gaatcccagt agcctgaagc aatgtgttag cagaatctat ttgtaacatt attattgtac   540
agtagaatca atattaaaca cacatgtttt attatatgga gtcattattt ttaatatgaa   600
atttaatttg cagagtctga actatatat                                    629

<210> SEQ ID NO 335
<211> LENGTH: 61
<212> TYPE: DNA
<213> ORGANISM: Artificial Sequence
<220> FEATURE:
<223> OTHER INFORMATION: Diagnostic Oligonucleotide

<400> SEQUENCE: 335
cgcccgccgc gccccgcgcc cgcccgccg ccccccgcccg aagttatttt ttaggaagca    60
t                                                                   61

<210> SEQ ID NO 336
<211> LENGTH: 19
<212> TYPE: DNA
```

```
<213> ORGANISM: Artificial Sequence
<220> FEATURE:
<223> OTHER INFORMATION: Diagnostic Oligonucleotide

<400> SEQUENCE: 336
gaacttaaag actcggctc                                                    19

<210> SEQ ID NO 337
<211> LENGTH: 61
<212> TYPE: DNA
<213> ORGANISM: Artificial Sequence
<220> FEATURE:
<223> OTHER INFORMATION: Diagnostic Oligonucleotide

<400> SEQUENCE: 337
cgcccgccgc gccccgcgcc cgcccgccg ccccgcccg gaaattgtct gccattctta        60
a                                                                       61

<210> SEQ ID NO 338
<211> LENGTH: 21
<212> TYPE: DNA
<213> ORGANISM: Artificial Sequence
<220> FEATURE:
<223> OTHER INFORMATION: Diagnostic Oligonucleotide

<400> SEQUENCE: 338
gagttggcca ttctttgtat g                                                 21

<210> SEQ ID NO 339
<211> LENGTH: 56
<212> TYPE: DNA
<213> ORGANISM: Artificial Sequence
<220> FEATURE:
<223> OTHER INFORMATION: Diagnostic Oligonucleotide

<400> SEQUENCE: 339
cgcccgccgc gccccgcgcc cgcccgccg ccccgcccg tgtgagccga gtcttt            56

<210> SEQ ID NO 340
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 340
atggcatttc cacctt                                                       16

<210> SEQ ID NO 341
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 341
cgtgaagaaa gatgac                                                       16

<210> SEQ ID NO 342
<211> LENGTH: 59
<212> TYPE: DNA
<213> ORGANISM: Artificial Sequence
<220> FEATURE:
<223> OTHER INFORMATION: Diagnostic Oligonucleotide

<400> SEQUENCE: 342
```

```
cgcccgccgc gccccgcgcc cgcccgccgc ccccgcccg taatgttaca aatagattc    59
```

<210> SEQ ID NO 343
<211> LENGTH: 18
<212> TYPE: DNA
<213> ORGANISM: Artificial Sequence
<220> FEATURE:
<223> OTHER INFORMATION: Diagnostic Oligonucleotide

<400> SEQUENCE: 343

```
gacaaataac caagtgac                                                18
```

<210> SEQ ID NO 344
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 344

```
aacacattgc ttcagg                                                  16
```

<210> SEQ ID NO 345
<211> LENGTH: 720
<212> TYPE: DNA
<213> ORGANISM: Artificial Sequence
<220> FEATURE:
<223> OTHER INFORMATION: Diagnostic Oligonucleotide

<400> SEQUENCE: 345

```
acttaactgc tttctccatt tgtagtctct tgaaaataca gaaatttcag aaataattta    60
taagaatatc aaggattcaa atcatatcag cacaaacacc taaatacttg tttgctttgt   120
taaacacata tcccattttc tatcttgata acattggtg taaagtagtt gaatcattca   180
gtgggtataa gcagcatatt ctcaatacta tgtttcatta ataattaata gagatatatg   240
aacacataaa agattcaatt ataatcacct tgtggatcta aatttcagtt gacttgtcat   300
cttgatttct ggagaccaca aggtaatgaa aaataattac aagagtcttc catctgttgc   360
agtattaaaa tggcgagtaa gacaccctga aaggaaatgt tctattcatg gtacaatgca   420
attacagcta gcaccaaatt caacactgtt aactttcaa catattattt tgatttatct   480
tgatccaaca ttctcaggga ggaggtgcat tgaagttatt agaaaacact gacttagatt   540
tagggtatgt cttaaaagct tatttgcggg aagtactcta gccttattca acagatcact   600
gagaagcctg aaaaacaaa tcccggaaac taattattat gtgccagtta tataaacaag   660
aagactttgt tgggtacaaa ccagtgattc cttgcctttg aaaaatgtgt cagatatcat   720
```

<210> SEQ ID NO 346
<211> LENGTH: 56
<212> TYPE: DNA
<213> ORGANISM: Artificial Sequence
<220> FEATURE:
<223> OTHER INFORMATION: Diagnostic Oligonucleotide

<400> SEQUENCE: 346

```
cgcccgccgc gccccgcgcc cgcccgccg ccccgcccg cttgatttct ggagac        56
```

<210> SEQ ID NO 347
<211> LENGTH: 16
<212> TYPE: DNA
<213> ORGANISM: Artificial Sequence
<220> FEATURE:

<223> OTHER INFORMATION: Diagnostic Oligonucleotide

<400> SEQUENCE: 347
ctagctgtaa ttgcat                                                          16

<210> SEQ ID NO 348
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 348
agtgggtata agcagc                                                          16

<210> SEQ ID NO 349
<211> LENGTH: 19
<212> TYPE: DNA
<213> ORGANISM: Artificial Sequence
<220> FEATURE:
<223> OTHER INFORMATION: Diagnostic Oligonucleotide

<400> SEQUENCE: 349
gttgaataag gctagagta                                                       19

<210> SEQ ID NO 350
<211> LENGTH: 600
<212> TYPE: DNA
<213> ORGANISM: Artificial Sequence
<220> FEATURE:
<223> OTHER INFORMATION: Diagnostic Oligonucleotide

<400> SEQUENCE: 350
aaaggtcagt gataaaggaa gtctgcatca ggggtccaat tccttatggc cagtttctct          60
attctgttcc aaggttgttt gtctccatat atcaacattg gtcaggattg aaagtgtgca         120
acaaggtttg aatgaataag tgaaaatctt ccactggtga caggataaaa tattccaatg         180
gtttttattg aagtacaata ctgaattatg tttatggcat ggtacctata tgtcacagaa         240
gtgatcccat cactttttacc ttataggtgg gcctcttggg aagaactgga tcagggaaga        300
gtactttgtt atcagctttt tgagactac tgaacactga aggagaaatc cagatcgatg          360
gtgtgtcttg ggattcaata actttgcaac agtggaggaa agcctttgga gtgataccac         420
aggtgagcaa aaggacttag ccagaaaaaa ggcaactaaa ttatattttt tactgctatt         480
tgatacttgt actcaagaaa ttcatattac tctgcaaaat atatttgtta tgcattgctg         540 tcttttttt ctccagtgca gttttctcat aggcagaaaa gatgtctcta aaagtttggg         600

<210> SEQ ID NO 351
<211> LENGTH: 61
<212> TYPE: DNA
<213> ORGANISM: Artificial Sequence
<220> FEATURE:
<223> OTHER INFORMATION: Diagnostic Oligonucleotide

<400> SEQUENCE: 351
cgcccgccgc gccccgcgcc cgccccgccg ccccccgcccg gaattatgtt tatggcatgg         60
t                                                                          61

<210> SEQ ID NO 352
<211> LENGTH: 25
<212> TYPE: DNA
<213> ORGANISM: Artificial Sequence -continued

```
<220> FEATURE:
<223> OTHER INFORMATION: Diagnostic Oligonucleotide

<400> SEQUENCE: 352
gagtacaagt atcaaatagc agtaa                                          25

<210> SEQ ID NO 353
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 353
aaatcttcca ctggtga                                                   17

<210> SEQ ID NO 354
<211> LENGTH: 18
<212> TYPE: DNA
<213> ORGANISM: Artificial Sequence
<220> FEATURE:
<223> OTHER INFORMATION: Diagnostic Oligonucleotide

<400> SEQUENCE: 354
gacatctttt ctgcctat                                                  18

<210> SEQ ID NO 355
<211> LENGTH: 59
<212> TYPE: DNA
<213> ORGANISM: Artificial Sequence
<220> FEATURE:
<223> OTHER INFORMATION: Diagnostic Oligonucleotide

<400> SEQUENCE: 355
cgcccgccgc gccccgcgcc cgccccgccg ccccccgcccg ctgaattatg tttatggca    59

<210> SEQ ID NO 356
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 356
cttttttctg gctaagt                                                   17

<210> SEQ ID NO 357
<211> LENGTH: 716
<212> TYPE: DNA
<213> ORGANISM: Artificial Sequence
<220> FEATURE:
<223> OTHER INFORMATION: Diagnostic Oligonucleotide

<400> SEQUENCE: 357 ttttaatat tctacaatta acaattatct caatttcttt attctaaaga cattggatta    60
gaaaaatgtt cacaagggac tccaaatatt gctgtagtat tgtttcttta aaagaatgat   120
acaaagcaga catgataaaa tattaaaatt tgagagaact tgatggtaag tacatgggtg   180
tttcttattt taaataatt tttctacttg aaatatttta caatacaata agggaaaaat    240
aaaaagttat ttaagttatt catactttct tcttcttttc ttttttgcta tagaaagtat   300 ttatttttc tggaacattt agaaaaaact tggatcccta tgaacagtgg agtgatcaag    360
aaatatggaa agttgcagat gaggtaaggc tgctaactga aatgattttg aaggggtaa    420
```

| | |
|---|---|
| ctcataccaa cacaaatggc tgatatagct gacatcattc tacacacttt gtgtgcatgt | 480 |
| atgtgtgtgc acaactttaa aatggagtac cctaacatac ctggagcaac aggtactttt | 540 |
| gactggacct acccctaact gaaatgattt tgaaagaggt aactcatacc aacacaaatg | 600 |
| gttgatatgg ctaagatcat tctacacact ttgtgtgcat gtatttctgt gcacaacttc | 660 |
| aaaatggagt accctaaaat acctggcgcg acaagtactt ttgactgagc ctactt | 716 |

<210> SEQ ID NO 358
<211> LENGTH: 20
<212> TYPE: DNA
<213> ORGANISM: Artificial Sequence
<220> FEATURE:
<223> OTHER INFORMATION: Diagnostic Oligonucleotide

<400> SEQUENCE: 358
atggtaagta catgggtgtt    20

<210> SEQ ID NO 359
<211> LENGTH: 22
<212> TYPE: DNA
<213> ORGANISM: Artificial Sequence
<220> FEATURE:
<223> OTHER INFORMATION: Diagnostic Oligonucleotide

<400> SEQUENCE: 359
ccactgttca tagggatcca ag    22

<210> SEQ ID NO 360
<211> LENGTH: 56
<212> TYPE: DNA
<213> ORGANISM: Artificial Sequence
<220> FEATURE:
<223> OTHER INFORMATION: Diagnostic Oligonucleotide

<400> SEQUENCE: 360
cgcccgccgc gccccgcgcc cgccccgccg ccccccgcccg tttctggaac atttag    56

<210> SEQ ID NO 361
<211> LENGTH: 18
<212> TYPE: DNA
<213> ORGANISM: Artificial Sequence
<220> FEATURE:
<223> OTHER INFORMATION: Diagnostic Oligonucleotide

<400> SEQUENCE: 361
gaatgatgtc agctatat    18

<210> SEQ ID NO 362
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 362
tgttcacaag ggactc    16

<210> SEQ ID NO 363
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 363

```
cagttagggg taggtc                                                   16

<210> SEQ ID NO 364
<211> LENGTH: 60
<212> TYPE: DNA
<213> ORGANISM: Artificial Sequence
<220> FEATURE:
<223> OTHER INFORMATION: Diagnostic Oligonucleotide

<400> SEQUENCE: 364
cgcccgccgc gccccgcgcc cgccccgccg ccccccgcccg agttattcat actttcttct   60

<210> SEQ ID NO 365
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 365
agccttacct catctg                                                   16

<210> SEQ ID NO 366
<211> LENGTH: 910
<212> TYPE: DNA
<213> ORGANISM: Artificial Sequence
<220> FEATURE:
<223> OTHER INFORMATION: Diagnostic Oligonucleotide

<400> SEQUENCE: 366
cacagttgac tattttatgc tatcttttgt cctcagtcat gacagagtag aagatgggag   60
gtagcaccaa ggatgatgtc atacctccat cctttatgct acattctatc ttctgtctac  120
ataagatgtc atactagagg gcatatctgc aatgtataca tattatcttt ccagcatgc   180 attcagttgt gttggaataa tttatgtaca cctttataaa cgctgagcct cacaagagcc  240
atgtgccacg tattgtttct tactactttt ggatacctgg cacgtaatag acactcattg  300
aaagtttcct aatgaatgaa gtacaaagat aaaacaagtt atagactgat tcttttgagc  360
tgtcaaggtt gtaaatagac ttttgctcaa tcaattcaaa tggtggcagg tagtgggggt  420
agagggattg gtatgaaaaa cataagcttt cagaactcct gtgtttattt ttagaatgtc  480
aactgcttga gtgtttttaa ctctgtggta tctgaactat cttctctaac tgcaggttgg  540
gctcagatct gtgatagaac agtttcctgg gaagcttgac tttgtccttg tggatggggg  600
ctgtgtccta agccatggcc acaagcagtt gatgtgcttg gctagatctg ttctcagtaa  660
ggcgaagatc ttgctgcttg atgaacccag tgctcatttg gatccagtgt gagtttcaga  720
tgttctgtta cttaatagca cagtgggaac agaatcatta tgcctgcttc atggtgacac  780
atatttctat taggctgtca tgtctgcgtg tgggggtctc ccaagatatg aaataattgc  840
ccagtggaaa tgagcataaa tgcatatttc cttgctaaga gttcttgtgt tttcttccga  900
agatagtttt                                                         910

<210> SEQ ID NO 367
<211> LENGTH: 58
<212> TYPE: DNA
<213> ORGANISM: Artificial Sequence
<220> FEATURE:
<223> OTHER INFORMATION: Diagnostic Oligonucleotide

<400> SEQUENCE: 367
```

```
cgcccgccgc gccccgcgcc cgccccgccg ccccgcccg tgagctgtca aggttgta        58
```

<210> SEQ ID NO 368
<211> LENGTH: 19
<212> TYPE: DNA
<213> ORGANISM: Artificial Sequence
<220> FEATURE:
<223> OTHER INFORMATION: Diagnostic Oligonucleotide

<400> SEQUENCE: 368

```
caggaaactg ttctatcac                                                   19
```

<210> SEQ ID NO 369
<211> LENGTH: 64
<212> TYPE: DNA
<213> ORGANISM: Artificial Sequence
<220> FEATURE:
<223> OTHER INFORMATION: Diagnostic Oligonucleotide

<400> SEQUENCE: 369

```
cgcccgccgc gccccgcgcc cgccccgccg ccccgcccg gaatgtcaac tgcttgagtg      60
tttt                                                                   64
```

<210> SEQ ID NO 370
<211> LENGTH: 27
<212> TYPE: DNA
<213> ORGANISM: Artificial Sequence
<220> FEATURE:
<223> OTHER INFORMATION: Diagnostic Oligonucleotide

<400> SEQUENCE: 370

```
aagtaacaga acatctgaaa ctcacac                                          27
```

<210> SEQ ID NO 371
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 371

```
cttgctgctt gatgaac                                                     17
```

<210> SEQ ID NO 372
<211> LENGTH: 20
<212> TYPE: DNA
<213> ORGANISM: Artificial Sequence
<220> FEATURE:
<223> OTHER INFORMATION: Diagnostic Oligonucleotide

<400> SEQUENCE: 372

```
gcaattattt catatcttgg                                                  20
```

<210> SEQ ID NO 373
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 373

```
agggattggt atgaaaa                                                     17
```

<210> SEQ ID NO 374
<211> LENGTH: 18

```
<212> TYPE: DNA
<213> ORGANISM: Artificial Sequence
<220> FEATURE:
<223> OTHER INFORMATION: Diagnostic Oligonucleotide

<400> SEQUENCE: 374
ggaagaaaac acaagaac                                                       18

<210> SEQ ID NO 375
<211> LENGTH: 840
<212> TYPE: DNA
<213> ORGANISM: Artificial Sequence
<220> FEATURE:
<223> OTHER INFORMATION: Diagnostic Oligonucleotide

<400> SEQUENCE: 375
gcatgtttat agccccaaat aaaagaagta ctggtgattc tacataatga aaatgtactc          60
atttattaaa gtttctttga aatatttgtc ctgtttattt atggatactt agagtctacc        120
ccatggttga aaagctgatt gtgcgtaacg ctatatcaac attatgtgaa aagaacttaa        180
agaaataagt aatttaaaga gataatagaa caatagacat attatcaagg taaatacaga        240
tcattactgt tctgtgatat tatgtgtggt attttctttc ttttctagaa cataccaaat        300
aattagaaga actctaaaac aagcatttgc tgattgcaca gtaattctct gtgaacacag        360
gatagaagca atgctggaat gccaacaatt tttggtgagt ctttataact ttacttaaga        420
tctcattgcc cttgtaattc ttgataacaa tctcacatgt gatagttcct gcaaattgca        480
acaatgtaca agttcttttc aaaaatatgt atcatacagc catccagctt tactcaaaat        540
agctgcacaa gttttcact tgatctgag ccatgtggtg aggttgaaat atagtaaatc         600
taaaatggca gcatattact aagttatgtt tataaatagg atatatatac ttttgagccc        660
tttatttggg accaagtcat acaaaatact ctactgttta agattttaaa aaaggtccct        720
gtgattcttt caataactaa atgtcccatg gatgtggtct ggacaggcct agttgtctta        780
cagtctgatt tatggtatta atgacaaagt tgagaggcac atttcatttt tctagccatg        840

<210> SEQ ID NO 376
<211> LENGTH: 58
<212> TYPE: DNA
<213> ORGANISM: Artificial Sequence
<220> FEATURE:
<223> OTHER INFORMATION: Diagnostic Oligonucleotide

<400> SEQUENCE: 376
cgcccgccgc gccccgcgcc cgccccgccg ccccccgcccg tatcaaggta aatacaga          58

<210> SEQ ID NO 377
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 377
gcttctatcc tgtgttc                                                        17

<210> SEQ ID NO 378
<211> LENGTH: 21
<212> TYPE: DNA
<213> ORGANISM: Artificial Sequence
<220> FEATURE:
<223> OTHER INFORMATION: Diagnostic Oligonucleotide
```

<400> SEQUENCE: 378
gatattatgt gtggtatttt c                                         21

<210> SEQ ID NO 379
<211> LENGTH: 59
<212> TYPE: DNA
<213> ORGANISM: Artificial Sequence
<220> FEATURE:
<223> OTHER INFORMATION: Diagnostic Oligonucleotide

<400> SEQUENCE: 379
cgcccgccgc gccccgcgcc cgcccgccg ccccgcccg gaacttgtac attgttgca    59

<210> SEQ ID NO 380
<211> LENGTH: 720
<212> TYPE: DNA
<213> ORGANISM: Artificial Sequence
<220> FEATURE:
<223> OTHER INFORMATION: Diagnostic Oligonucleotide

<400> SEQUENCE: 380
agatggtaga acctccttag agcaaaagga cacagcagtt aaatgtgaca tacctgattg    60
ttcaaaatgc aaggctctgg acattgcatt ctttgacttt tattttcctt tgagcctgtg   120
ccagtttctg tccctgctct ggtctgacct gccttctgtc ccagatctca ctaacagcca   180
tttccctagg tcatagaaga gaacaaagtg cggcagtacg attccatcca gaaactgctg   240
aacgagagga gcctcttccg gcaagccatc agccctccg acagggtgaa gctctttccc   300
caccggaact caagcaagtg caagtctaag ccccagattg ctgctctgaa agaggagaca   360
gaagaagagg tgcaagatac aaggctttag agagcagcat aaatgttgac atgggacatt   420
tgctcatgga attggagctc gtgggacagt cacctcatgg aattggagct cgtggaacag   480
ttacctctgc ctcagaaaac aaggatgaat taagttttt tttaaaaaag aaacatttgg    540 taagggaat tgaggacact gatatgggtc ttgataaatg gcttcctggc aatagtcaaa    600
ttgtgtgaaa ggtacttcaa atccttgaag atttaccact tgtgttttgc aagccagatt    660
ttcctgaaaa cccttgccat gtgctagtaa ttggaaaggc agctctaaat gtcaatcagc    720

<210> SEQ ID NO 381
<211> LENGTH: 56
<212> TYPE: DNA
<213> ORGANISM: Artificial Sequence
<220> FEATURE:
<223> OTHER INFORMATION: Diagnostic Oligonucleotide

<400> SEQUENCE: 381
cgcccgccgc gccccgcgcc cgcccgccg ccccgcccg cctttgagcc tgtgcc         56

<210> SEQ ID NO 382
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 382
gcttgagttc cggtgg                                               16

<210> SEQ ID NO 383
<211> LENGTH: 16
<212> TYPE: DNA
<213> ORGANISM: Artificial Sequence

```
<220> FEATURE:
<223> OTHER INFORMATION: Diagnostic Oligonucleotide

<400> SEQUENCE: 383
catcagcccc tccgac                                                     16

<210> SEQ ID NO 384
<211> LENGTH: 57
<212> TYPE: DNA
<213> ORGANISM: Artificial Sequence
<220> FEATURE:
<223> OTHER INFORMATION: Diagnostic Oligonucleotide

<400> SEQUENCE: 384
cgcccgccgc gccccgcgcc cgccccgccg ccccgcccg tttctgaggc agaggta        57

<210> SEQ ID NO 385
<211> LENGTH: 20
<212> TYPE: DNA
<213> ORGANISM: Artificial Sequence
<220> FEATURE:
<223> OTHER INFORMATION: Diagnostic Oligonucleotide

<400> SEQUENCE: 385
gcagttaaat gtgacatacc                                                 20

<210> SEQ ID NO 386
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 386
tccttgtttt ctgaggc                                                    17

<210> SEQ ID NO 387
<211> LENGTH: 62
<212> TYPE: DNA
<213> ORGANISM: Artificial Sequence
<220> FEATURE:
<223> OTHER INFORMATION: Diagnostic Oligonucleotide

<400> SEQUENCE: 387
cgcccgccgc gccccgcgcc cgccccgccg ccccgcccg ggaagccaaa tgacatcaca     60
gc                                                                    62

<210> SEQ ID NO 388
<211> LENGTH: 21
<212> TYPE: DNA
<213> ORGANISM: Artificial Sequence
<220> FEATURE:
<223> OTHER INFORMATION: Diagnostic Oligonucleotide

<400> SEQUENCE: 388
tgaaaaaaag tttggagaca a                                               21

<210> SEQ ID NO 389
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 389
```

```
cccagcgccc agagacc                                              17
```

<210> SEQ ID NO 390
<211> LENGTH: 62
<212> TYPE: DNA
<213> ORGANISM: Artificial Sequence
<220> FEATURE:
<223> OTHER INFORMATION: Diagnostic Oligonucleotide

<400> SEQUENCE: 390

```
cgcccgccgc gccccgcgcc cgcccgcccg ccccgcccg actgcttatt cctttacccc    60
aa                                                                  62
```

<210> SEQ ID NO 391
<211> LENGTH: 63
<212> TYPE: DNA
<213> ORGANISM: Artificial Sequence
<220> FEATURE:
<223> OTHER INFORMATION: Diagnostic Oligonucleotide

<400> SEQUENCE: 391

```
cgcccgccgc gccccgcgcc cgcccgcccg ccccgcccg ccagaaaagt tgaatagtat    60
cag                                                                 63
```

<210> SEQ ID NO 392
<211> LENGTH: 19
<212> TYPE: DNA
<213> ORGANISM: Artificial Sequence
<220> FEATURE:
<223> OTHER INFORMATION: Diagnostic Oligonucleotide

<400> SEQUENCE: 392

```
agattgtcag cagaatcaa                                            19
```

<210> SEQ ID NO 393
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 393

```
ataccaaatc ccttcg                                               16
```

<210> SEQ ID NO 394
<211> LENGTH: 59
<212> TYPE: DNA
<213> ORGANISM: Artificial Sequence
<220> FEATURE:
<223> OTHER INFORMATION: Diagnostic Oligonucleotide

<400> SEQUENCE: 394

```
cgcccgccgc gccccgcgcc cgcccgcccg ccccgcccg tgctttctct tctctaaat     59
```

<210> SEQ ID NO 395
<211> LENGTH: 61
<212> TYPE: DNA
<213> ORGANISM: Artificial Sequence
<220> FEATURE:
<223> OTHER INFORMATION: Diagnostic Oligonucleotide

<400> SEQUENCE: 395

```
cgcccgccgc gccccgcgcc cgcccgcccg ccccgcccg tggaattgtc agacatatac    60
c                                                                   61
```

```
<210> SEQ ID NO 396
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 396
agccaccata cttggct                                                      17

<210> SEQ ID NO 397
<211> LENGTH: 56
<212> TYPE: DNA
<213> ORGANISM: Artificial Sequence
<220> FEATURE:
<223> OTHER INFORMATION: Diagnostic Oligonucleotide

<400> SEQUENCE: 397
cgcccgccgc gccccgcgcc cgcccgccg ccccgcccg tggtgttgta tggtct           56

<210> SEQ ID NO 398
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 398
aacataaatc tccagaa                                                      17

<210> SEQ ID NO 399
<211> LENGTH: 60
<212> TYPE: DNA
<213> ORGANISM: Artificial Sequence
<220> FEATURE:
<223> OTHER INFORMATION: Diagnostic Oligonucleotide

<400> SEQUENCE: 399
cgcccgccgc gccccgcgcc cgcccgccg ccccgcccg tgtctctata atacttgggt       60

<210> SEQ ID NO 400
<211> LENGTH: 22
<212> TYPE: DNA
<213> ORGANISM: Artificial Sequence
<220> FEATURE:
<223> OTHER INFORMATION: Diagnostic Oligonucleotide

<400> SEQUENCE: 400
atataaaaag attccataga ac                                                22

<210> SEQ ID NO 401
<211> LENGTH: 21
<212> TYPE: DNA
<213> ORGANISM: Artificial Sequence
<220> FEATURE:
<223> OTHER INFORMATION: Diagnostic Oligonucleotide

<400> SEQUENCE: 401
gctggcttca agaaaaatc c                                                  21

<210> SEQ ID NO 402
<211> LENGTH: 63
<212> TYPE: DNA
<213> ORGANISM: Artificial Sequence
<220> FEATURE:
```

<223> OTHER INFORMATION: Diagnostic Oligonucleotide

<400> SEQUENCE: 402
cgcccgccgc gccccgcgcc cgcccgcccg ccccgcccg caccagattt cgtagtcttt    60
tca                                                                63

<210> SEQ ID NO 403
<211> LENGTH: 61
<212> TYPE: DNA
<213> ORGANISM: Artificial Sequence
<220> FEATURE:
<223> OTHER INFORMATION: Diagnostic Oligonucleotide

<400> SEQUENCE: 403
cgcccgccgc gccccgcgcc cgcccgcccg ccccgcccg aatttctctg tttttcccct    60
t                                                                  61

<210> SEQ ID NO 404
<211> LENGTH: 23
<212> TYPE: DNA
<213> ORGANISM: Artificial Sequence
<220> FEATURE:
<223> OTHER INFORMATION: Diagnostic Oligonucleotide

<400> SEQUENCE: 404
agctattctt catctgcatt cca                                          23

<210> SEQ ID NO 405
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 405
gacactgctc ctacacc                                                 17

<210> SEQ ID NO 406
<211> LENGTH: 57
<212> TYPE: DNA
<213> ORGANISM: Artificial Sequence
<220> FEATURE:
<223> OTHER INFORMATION: Diagnostic Oligonucleotide

<400> SEQUENCE: 406
cgcccgccgc gccccgcgcc cgcccgcccg ccccgcccg tcagcattta tccctta      57

<210> SEQ ID NO 407
<211> LENGTH: 66
<212> TYPE: DNA
<213> ORGANISM: Artificial Sequence
<220> FEATURE:
<223> OTHER INFORMATION: Diagnostic Oligonucleotide

<400> SEQUENCE: 407
cgcccgccgc gccccgcgcc cgcccgcccg ccccgcccg ataatatatt tgtattttgt   60
ttgttg                                                             66

<210> SEQ ID NO 408
<211> LENGTH: 20
<212> TYPE: DNA
<213> ORGANISM: Artificial Sequence
<220> FEATURE:
<223> OTHER INFORMATION: Diagnostic Oligonucleotide

<400> SEQUENCE: 408
aatttgttca ggttgttgga                                          20

<210> SEQ ID NO 409
<211> LENGTH: 18
<212> TYPE: DNA
<213> ORGANISM: Artificial Sequence
<220> FEATURE:
<223> OTHER INFORMATION: Diagnostic Oligonucleotide

<400> SEQUENCE: 409
agctgtcaag ccgtgttc                                            18

<210> SEQ ID NO 410
<211> LENGTH: 59
<212> TYPE: DNA
<213> ORGANISM: Artificial Sequence
<220> FEATURE:
<223> OTHER INFORMATION: Diagnostic Oligonucleotide

<400> SEQUENCE: 410
cgcccgccgc gccccgcgcc cgcccgcgcg ccccgcccg atctgaccca ggaaaactc    59

<210> SEQ ID NO 411
<211> LENGTH: 60
<212> TYPE: DNA
<213> ORGANISM: Artificial Sequence
<220> FEATURE:
<223> OTHER INFORMATION: Diagnostic Oligonucleotide

<400> SEQUENCE: 411
cgcccgccgc gccccgcgcc cgcccgcgcg ccccgcccg ttgttagttt ctaggggtgg   60

<210> SEQ ID NO 412
<211> LENGTH: 21
<212> TYPE: DNA
<213> ORGANISM: Artificial Sequence
<220> FEATURE:
<223> OTHER INFORMATION: Diagnostic Oligonucleotide

<400> SEQUENCE: 412
aaggactatc aggaaaccaa g                                        21

<210> SEQ ID NO 413
<211> LENGTH: 20
<212> TYPE: DNA
<213> ORGANISM: Artificial Sequence
<220> FEATURE:
<223> OTHER INFORMATION: Diagnostic Oligonucleotide

<400> SEQUENCE: 413
gctaatctgg gagttgttac                                          20

<210> SEQ ID NO 414
<211> LENGTH: 62
<212> TYPE: DNA
<213> ORGANISM: Artificial Sequence
<220> FEATURE:
<223> OTHER INFORMATION: Diagnostic Oligonucleotide

<400> SEQUENCE: 414
cgcccgccgc gccccgcgcc cgcccgcccg ccccgcccg agttatgaaa ataggttgct   60
ac                                                             62

```
<210> SEQ ID NO 415
<211> LENGTH: 58
<212> TYPE: DNA
<213> ORGANISM: Artificial Sequence
<220> FEATURE:
<223> OTHER INFORMATION: Diagnostic Oligonucleotide

<400> SEQUENCE: 415
cgcccgccgc gccccgcgcc cgcccgccg ccccgcccg gggagaatga tgatgaag        58

<210> SEQ ID NO 416
<211> LENGTH: 21
<212> TYPE: DNA
<213> ORGANISM: Artificial Sequence
<220> FEATURE:
<223> OTHER INFORMATION: Diagnostic Oligonucleotide

<400> SEQUENCE: 416
acactgaaga tcactgttct a                                              21

<210> SEQ ID NO 417
<211> LENGTH: 18
<212> TYPE: DNA
<213> ORGANISM: Artificial Sequence
<220> FEATURE:
<223> OTHER INFORMATION: Diagnostic Oligonucleotide

<400> SEQUENCE: 417
tccttgccct ttttcagg                                                  18

<210> SEQ ID NO 418
<211> LENGTH: 65
<212> TYPE: DNA
<213> ORGANISM: Artificial Sequence
<220> FEATURE:
<223> OTHER INFORMATION: Diagnostic Oligonucleotide

<400> SEQUENCE: 418
cgcccgccgc gccccgcgcc cgcccgccg ccccgcccg tttaatgaca ctgaagatca      60
ctgtt                                                                65

<210> SEQ ID NO 419
<211> LENGTH: 63
<212> TYPE: DNA
<213> ORGANISM: Artificial Sequence
<220> FEATURE:
<223> OTHER INFORMATION: Diagnostic Oligonucleotide

<400> SEQUENCE: 419
cgcccgccgc gccccgcgcc cgcccgccg ccccgcccg ccttgagcag ttcttaatag      60
ata                                                                  63

<210> SEQ ID NO 420
<211> LENGTH: 21
<212> TYPE: DNA
<213> ORGANISM: Artificial Sequence
<220> FEATURE:
<223> OTHER INFORMATION: Diagnostic Oligonucleotide

<400> SEQUENCE: 420
atgccttaac agattggata t                                              21

<210> SEQ ID NO 421
<211> LENGTH: 21
```

```
<212> TYPE: DNA
<213> ORGANISM: Artificial Sequence
<220> FEATURE:
<223> OTHER INFORMATION: Diagnostic Oligonucleotide

<400> SEQUENCE: 421
gaaaatatcc aatctgttaa g                                              21

<210> SEQ ID NO 422
<211> LENGTH: 58
<212> TYPE: DNA
<213> ORGANISM: Artificial Sequence
<220> FEATURE:
<223> OTHER INFORMATION: Diagnostic Oligonucleotide

<400> SEQUENCE: 422
cgcccgccgc gccccgcgcc cgcccgccg ccccgcccg tgaggtggaa gtctacca       58

<210> SEQ ID NO 423
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 423
gaaaatatcc aatctg                                                    16

<210> SEQ ID NO 424
<211> LENGTH: 56
<212> TYPE: DNA
<213> ORGANISM: Artificial Sequence
<220> FEATURE:
<223> OTHER INFORMATION: Diagnostic Oligonucleotide

<400> SEQUENCE: 424
cgcccgccgc gccccgcgcc cgcccgccg ccccgcccg atgaggtgga agtcta          56

<210> SEQ ID NO 425
<211> LENGTH: 63
<212> TYPE: DNA
<213> ORGANISM: Artificial Sequence
<220> FEATURE:
<223> OTHER INFORMATION: Diagnostic Oligonucleotide

<400> SEQUENCE: 425
cgcccgccgc gccccgcgcc cgcccgccg ccccgcccg agaccatgct cagatcttcc     60
att                                                                  63

<210> SEQ ID NO 426
<211> LENGTH: 24
<212> TYPE: DNA
<213> ORGANISM: Artificial Sequence
<220> FEATURE:
<223> OTHER INFORMATION: Diagnostic Oligonucleotide

<400> SEQUENCE: 426
gctgccttcc gagtcagttt cagt                                           24

<210> SEQ ID NO 427
<211> LENGTH: 60
<212> TYPE: DNA
<213> ORGANISM: Artificial Sequence
<220> FEATURE:
<223> OTHER INFORMATION: Diagnostic Oligonucleotide
```

<400> SEQUENCE: 427
cgcccgccgc gccccgcgcc cgccccgccg ccccccgcccg actgaaactg actcggaagg    60

<210> SEQ ID NO 428
<211> LENGTH: 26
<212> TYPE: DNA
<213> ORGANISM: Artificial Sequence
<220> FEATURE:
<223> OTHER INFORMATION: Diagnostic Oligonucleotide

<400> SEQUENCE: 428
atggtacatt acctgtattt tgttta    26

<210> SEQ ID NO 429
<211> LENGTH: 26
<212> TYPE: DNA
<213> ORGANISM: Artificial Sequence
<220> FEATURE:
<223> OTHER INFORMATION: Diagnostic Oligonucleotide

<400> SEQUENCE: 429
ctgtacaaac atggtatgac tctctt    26

<210> SEQ ID NO 430
<211> LENGTH: 65
<212> TYPE: DNA
<213> ORGANISM: Artificial Sequence
<220> FEATURE:
<223> OTHER INFORMATION: Diagnostic Oligonucleotide

<400> SEQUENCE: 430
cgcccgccgc gccccgcgcc cgccccgccg ccccccgcccg gtgaaggaaa tttcttttc    60 tatct    65

<210> SEQ ID NO 431
<211> LENGTH: 24
<212> TYPE: DNA
<213> ORGANISM: Artificial Sequence
<220> FEATURE:
<223> OTHER INFORMATION: Diagnostic Oligonucleotide

<400> SEQUENCE: 431
agaccatgct cagatcttcc attc    24

<210> SEQ ID NO 432
<211> LENGTH: 62
<212> TYPE: DNA
<213> ORGANISM: Artificial Sequence
<220> FEATURE:
<223> OTHER INFORMATION: Diagnostic Oligonucleotide

<400> SEQUENCE: 432
cgcccgccgc gccccgcgcc cgccccgccg ccccccgcccg tgccttccga gtcagtttca    60
gt    62

<210> SEQ ID NO 433
<211> LENGTH: 62
<212> TYPE: DNA
<213> ORGANISM: Artificial Sequence
<220> FEATURE:
<223> OTHER INFORMATION: Diagnostic Oligonucleotide

<400> SEQUENCE: 433
cgcccgccgc gccccgcgcc cgccccgccg ccccccgcccg gcacaatgag agtataaagt    60
ag                                                                  62

<210> SEQ ID NO 434
<211> LENGTH: 21
<212> TYPE: DNA
<213> ORGANISM: Artificial Sequence
<220> FEATURE:
<223> OTHER INFORMATION: Diagnostic Oligonucleotide

<400> SEQUENCE: 434
ccatcactac ttctgtagtc g                                             21

<210> SEQ ID NO 435
<211> LENGTH: 27
<212> TYPE: DNA
<213> ORGANISM: Artificial Sequence
<220> FEATURE:
<223> OTHER INFORMATION: Diagnostic Oligonucleotide

<400> SEQUENCE: 435
ctctctttta taaataggat ttcttac                                       27

<210> SEQ ID NO 436
<211> LENGTH: 65
<212> TYPE: DNA
<213> ORGANISM: Artificial Sequence
<220> FEATURE:
<223> OTHER INFORMATION: Diagnostic Oligonucleotide

<400> SEQUENCE: 436
cgcccgccgc gccccgcgcc cgccccgccg ccccccgcccg ttccagttct accagttata   60
tcatc                                                               65

<210> SEQ ID NO 437
<211> LENGTH: 67
<212> TYPE: DNA
<213> ORGANISM: Artificial Sequence
<220> FEATURE:
<223> OTHER INFORMATION: Diagnostic Oligonucleotide

<400> SEQUENCE: 437
cgcccgccgc gccccgcgcc cgccccgccg ccccccgcccg ctctctttta taaataggat   60
ttcttac                                                             67

<210> SEQ ID NO 438
<211> LENGTH: 25
<212> TYPE: DNA
<213> ORGANISM: Artificial Sequence
<220> FEATURE:
<223> OTHER INFORMATION: Diagnostic Oligonucleotide

<400> SEQUENCE: 438
ttccagttct accagttata tcatc                                         25

<210> SEQ ID NO 439
<211> LENGTH: 65
<212> TYPE: DNA
<213> ORGANISM: Artificial Sequence
<220> FEATURE:
<223> OTHER INFORMATION: Diagnostic Oligonucleotide

<400> SEQUENCE: 439
cgcccgccgc gccccgcgcc cgccccgccg ccccccgcccg acaatagaaa aacttctaat   60

```
ggtga                                                           65

<210> SEQ ID NO 440
<211> LENGTH: 22
<212> TYPE: DNA
<213> ORGANISM: Artificial Sequence
<220> FEATURE:
<223> OTHER INFORMATION: Diagnostic Oligonucleotide

<400> SEQUENCE: 440
aaaaaagaga catggacacc aa                                        22

<210> SEQ ID NO 441
<211> LENGTH: 18
<212> TYPE: DNA
<213> ORGANISM: Artificial Sequence
<220> FEATURE:
<223> OTHER INFORMATION: Diagnostic Oligonucleotide

<400> SEQUENCE: 441
cctgagcgtg atttgata                                             18

<210> SEQ ID NO 442
<211> LENGTH: 60
<212> TYPE: DNA
<213> ORGANISM: Artificial Sequence
<220> FEATURE:
<223> OTHER INFORMATION: Diagnostic Oligonucleotide

<400> SEQUENCE: 442
cgcccgccgc gccccgcgcc cgcccgccg ccccgcccg atgtagacta accgattgaa  60

<210> SEQ ID NO 443
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 443
gggagaactg gagcct                                               16

<210> SEQ ID NO 444
<211> LENGTH: 58
<212> TYPE: DNA
<213> ORGANISM: Artificial Sequence
<220> FEATURE:
<223> OTHER INFORMATION: Diagnostic Oligonucleotide

<400> SEQUENCE: 444
cgcccgccgc gccccgcgcc cgcccgccg ccccgcccg aaccgattga atatggag    58

<210> SEQ ID NO 445
<211> LENGTH: 61
<212> TYPE: DNA
<213> ORGANISM: Artificial Sequence
<220> FEATURE:
<223> OTHER INFORMATION: Diagnostic Oligonucleotide

<400> SEQUENCE: 445
cgcccgccgc gccccgcgcc cgcccgccg ccccgcccg gatatatgat tacattagaa  60
g                                                               61

<210> SEQ ID NO 446
<211> LENGTH: 17
```

```
<212> TYPE: DNA
<213> ORGANISM: Artificial Sequence
<220> FEATURE:
<223> OTHER INFORMATION: Diagnostic Oligonucleotide

<400> SEQUENCE: 446
accttctcca agaacta                                                      17

<210> SEQ ID NO 447
<211> LENGTH: 18
<212> TYPE: DNA
<213> ORGANISM: Artificial Sequence
<220> FEATURE:
<223> OTHER INFORMATION: Diagnostic Oligonucleotide

<400> SEQUENCE: 447
ataggacatc tccaagtt                                                     18

<210> SEQ ID NO 448
<211> LENGTH: 59
<212> TYPE: DNA
<213> ORGANISM: Artificial Sequence
<220> FEATURE:
<223> OTHER INFORMATION: Diagnostic Oligonucleotide

<400> SEQUENCE: 448
cgcccgccgc gccccgcgcc cgcccgccg ccccgcccg gcaatagaga aatgtctgt         59

<210> SEQ ID NO 449
<211> LENGTH: 63
<212> TYPE: DNA
<213> ORGANISM: Artificial Sequence
<220> FEATURE:
<223> OTHER INFORMATION: Diagnostic Oligonucleotide

<400> SEQUENCE: 449
cgcccgccgc gccccgcgcc cgcccgccg ccccgcccg gtgaactgtt taaggcaaat        60
cat                                                                     63

<210> SEQ ID NO 450
<211> LENGTH: 21
<212> TYPE: DNA
<213> ORGANISM: Artificial Sequence
<220> FEATURE:
<223> OTHER INFORMATION: Diagnostic Oligonucleotide

<400> SEQUENCE: 450
tgatgggaca gtctgtcttt c                                                 21

<210> SEQ ID NO 451
<211> LENGTH: 25
<212> TYPE: DNA
<213> ORGANISM: Artificial Sequence
<220> FEATURE:
<223> OTHER INFORMATION: Diagnostic Oligonucleotide

<400> SEQUENCE: 451
aatacgagac atattgcaat aaagt                                             25

<210> SEQ ID NO 452
<211> LENGTH: 62
<212> TYPE: DNA
<213> ORGANISM: Artificial Sequence
<220> FEATURE:
<223> OTHER INFORMATION: Diagnostic Oligonucleotide
```

<400> SEQUENCE: 452
cgcccgccgc gccccgcgcc cgcccgccg ccccgcccg ctggctgtag attttggagt    60
tc    62

<210> SEQ ID NO 453
<211> LENGTH: 25
<212> TYPE: DNA
<213> ORGANISM: Artificial Sequence
<220> FEATURE:
<223> OTHER INFORMATION: Diagnostic Oligonucleotide

<400> SEQUENCE: 453
aatacgagac atattgcaat aaagt    25

<210> SEQ ID NO 454
<211> LENGTH: 21
<212> TYPE: DNA
<213> ORGANISM: Artificial Sequence
<220> FEATURE:
<223> OTHER INFORMATION: Diagnostic Oligonucleotide

<400> SEQUENCE: 454
ctggctgtag attttggagt t    21

<210> SEQ ID NO 455
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 455
aggtagcagc tattttt    17

<210> SEQ ID NO 456
<211> LENGTH: 57
<212> TYPE: DNA
<213> ORGANISM: Artificial Sequence
<220> FEATURE:
<223> OTHER INFORMATION: Diagnostic Oligonucleotide

<400> SEQUENCE: 456
cgcccgccgc gccccgcgcc cgcccgccg ccccgcccg ggacagcctt ctctcta    57

<210> SEQ ID NO 457
<211> LENGTH: 25
<212> TYPE: DNA
<213> ORGANISM: Artificial Sequence
<220> FEATURE:
<223> OTHER INFORMATION: Diagnostic Oligonucleotide

<400> SEQUENCE: 457
cacttctaaa atggaacatt taaag    25

<210> SEQ ID NO 458
<211> LENGTH: 58
<212> TYPE: DNA
<213> ORGANISM: Artificial Sequence
<220> FEATURE:
<223> OTHER INFORMATION: Diagnostic Oligonucleotide

<400> SEQUENCE: 458
cgcccgccgc gccccgcgcc cgcccgccg ccccgcccg gcagtatcgc ctctccct    58

<210> SEQ ID NO 459
<211> LENGTH: 61
<212> TYPE: DNA
<213> ORGANISM: Artificial Sequence
<220> FEATURE:
<223> OTHER INFORMATION: Diagnostic Oligonucleotide

<400> SEQUENCE: 459
cgcccgccgc gccccgcgcc cgccccgccg ccccgcccg atgggacatt ttcagaactc    60
c                                                                   61

<210> SEQ ID NO 460
<211> LENGTH: 19
<212> TYPE: DNA
<213> ORGANISM: Artificial Sequence
<220> FEATURE:
<223> OTHER INFORMATION: Diagnostic Oligonucleotide

<400> SEQUENCE: 460
cctcttcgat gccattcat                                                19

<210> SEQ ID NO 461
<211> LENGTH: 63
<212> TYPE: DNA
<213> ORGANISM: Artificial Sequence
<220> FEATURE:
<223> OTHER INFORMATION: Diagnostic Oligonucleotide

<400> SEQUENCE: 461
cgcccgccgc gccccgcgcc cgccccgccg ccccgcccg caatccaatc aactctatac    60
gaa                                                                 63

<210> SEQ ID NO 462
<211> LENGTH: 18
<212> TYPE: DNA
<213> ORGANISM: Artificial Sequence
<220> FEATURE:
<223> OTHER INFORMATION: Diagnostic Oligonucleotide

<400> SEQUENCE: 462
ctgatcacgc tgatgcga                                                 18

<210> SEQ ID NO 463
<211> LENGTH: 60
<212> TYPE: DNA
<213> ORGANISM: Artificial Sequence
<220> FEATURE:
<223> OTHER INFORMATION: Diagnostic Oligonucleotide

<400> SEQUENCE: 463
cgcccgccgc gccccgcgcc cgccccgccg ccccgcccg tgatgagcct ttagagagaa    60

<210> SEQ ID NO 464
<211> LENGTH: 19
<212> TYPE: DNA
<213> ORGANISM: Artificial Sequence
<220> FEATURE:
<223> OTHER INFORMATION: Diagnostic Oligonucleotide

<400> SEQUENCE: 464
ccagttcagt caagtttgc                                                19

<210> SEQ ID NO 465
<211> LENGTH: 54
<212> TYPE: DNA

<213> ORGANISM: Artificial Sequence
<220> FEATURE:
<223> OTHER INFORMATION: Diagnostic Oligonucleotide

<400> SEQUENCE: 465
cgcccgccgc gccccgcgcc cgcccgcccg ccccgcccg cagcgtgatc agca    54

<210> SEQ ID NO 466
<211> LENGTH: 18
<212> TYPE: DNA
<213> ORGANISM: Artificial Sequence
<220> FEATURE:
<223> OTHER INFORMATION: Diagnostic Oligonucleotide

<400> SEQUENCE: 466
tttgttacat gctacata    18

<210> SEQ ID NO 467
<211> LENGTH: 58
<212> TYPE: DNA
<213> ORGANISM: Artificial Sequence
<220> FEATURE:
<223> OTHER INFORMATION: Diagnostic Oligonucleotide

<400> SEQUENCE: 467
cgcccgccgc gccccgcgcc cgcccgcccg ccccgcccg catcagcgtg atcagcac    58

<210> SEQ ID NO 468
<211> LENGTH: 26
<212> TYPE: DNA
<213> ORGANISM: Artificial Sequence
<220> FEATURE:
<223> OTHER INFORMATION: Diagnostic Oligonucleotide

<400> SEQUENCE: 468
tagtaaattt tgttacatgc tacata    26

<210> SEQ ID NO 469
<211> LENGTH: 62
<212> TYPE: DNA
<213> ORGANISM: Artificial Sequence
<220> FEATURE:
<223> OTHER INFORMATION: Diagnostic Oligonucleotide

<400> SEQUENCE: 469
cgcccgccgc gccccgcgcc cgcccgcccg ccccgcccg ttcatatatt aaaaataaaa    60
cc    62

<210> SEQ ID NO 470
<211> LENGTH: 21
<212> TYPE: DNA
<213> ORGANISM: Artificial Sequence
<220> FEATURE:
<223> OTHER INFORMATION: Diagnostic Oligonucleotide

<400> SEQUENCE: 470
taatatatcg aaggtatgtg t    21

<210> SEQ ID NO 471
<211> LENGTH: 22
<212> TYPE: DNA
<213> ORGANISM: Artificial Sequence
<220> FEATURE:
<223> OTHER INFORMATION: Diagnostic Oligonucleotide

<400> SEQUENCE: 471

-continued

```
gagcatacca gcagtgacta ca                                              22

<210> SEQ ID NO 472
<211> LENGTH: 69
<212> TYPE: DNA
<213> ORGANISM: Artificial Sequence
<220> FEATURE:
<223> OTHER INFORMATION: Diagnostic Oligonucleotide

<400> SEQUENCE: 472
cgcccgccgc gccccgcgcc cgccccgccg ccccgcccg gtaatacttt acaatagaac      60
attcttacc                                                             69

<210> SEQ ID NO 473
<211> LENGTH: 20
<212> TYPE: DNA
<213> ORGANISM: Artificial Sequence
<220> FEATURE:
<223> OTHER INFORMATION: Diagnostic Oligonucleotide

<400> SEQUENCE: 473
accagcagtg actacatgga                                                 20

<210> SEQ ID NO 474
<211> LENGTH: 68
<212> TYPE: DNA
<213> ORGANISM: Artificial Sequence
<220> FEATURE:
<223> OTHER INFORMATION: Diagnostic Oligonucleotide

<400> SEQUENCE: 474
cgcccgccgc gccccgcgcc cgccccgccg ccccgcccg atatttatgt gtgtgcatat      60
atatgtat                                                              68

<210> SEQ ID NO 475
<211> LENGTH: 57
<212> TYPE: DNA
<213> ORGANISM: Artificial Sequence
<220> FEATURE:
<223> OTHER INFORMATION: Diagnostic Oligonucleotide

<400> SEQUENCE: 475
cgcccgccgc gccccgcgcc cgccccgccg ccccgcccg gtgtaccttg atattgg         57

<210> SEQ ID NO 476
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 476
ctcactttcc aaggag                                                     16

<210> SEQ ID NO 477
<211> LENGTH: 15
<212> TYPE: DNA
<213> ORGANISM: Artificial Sequence
<220> FEATURE:
<223> OTHER INFORMATION: Diagnostic Oligonucleotide

<400> SEQUENCE: 477
gctgtggctc cttgg                                                      15
```

<210> SEQ ID NO 478
<211> LENGTH: 57
<212> TYPE: DNA
<213> ORGANISM: Artificial Sequence
<220> FEATURE:
<223> OTHER INFORMATION: Diagnostic Oligonucleotide

<400> SEQUENCE: 478
cgcccgccgc gccccgcgcc cgcccgccg ccccgcccg actacagccc gaactcc        57

<210> SEQ ID NO 479
<211> LENGTH: 19
<212> TYPE: DNA
<213> ORGANISM: Artificial Sequence
<220> FEATURE:
<223> OTHER INFORMATION: Diagnostic Oligonucleotide

<400> SEQUENCE: 479
gtggctgctt ctttggttg                                                 19

<210> SEQ ID NO 480
<211> LENGTH: 69
<212> TYPE: DNA
<213> ORGANISM: Artificial Sequence
<220> FEATURE:
<223> OTHER INFORMATION: Diagnostic Oligonucleotide

<400> SEQUENCE: 480
cgcccgccgc gccccgcgcc cgcccgccg ccccgcccg tacaaacata gtggattaca     60
atatttaat                                                            69

<210> SEQ ID NO 481
<211> LENGTH: 66
<212> TYPE: DNA
<213> ORGANISM: Artificial Sequence
<220> FEATURE:
<223> OTHER INFORMATION: Diagnostic Oligonucleotide

<400> SEQUENCE: 481
cgcccgccgc gccccgcgcc cgcccgccg ccccgcccg catgtattgg aaattcagta    60
agtaac                                                               66

<210> SEQ ID NO 482
<211> LENGTH: 24
<212> TYPE: DNA
<213> ORGANISM: Artificial Sequence
<220> FEATURE:
<223> OTHER INFORMATION: Diagnostic Oligonucleotide

<400> SEQUENCE: 482
ttcgacactg tgattagagt atgc                                           24

<210> SEQ ID NO 483
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 483
gtgggagtag ccgaca                                                    16

<210> SEQ ID NO 484
<211> LENGTH: 57

```
<212> TYPE: DNA
<213> ORGANISM: Artificial Sequence
<220> FEATURE:
<223> OTHER INFORMATION: Diagnostic Oligonucleotide

<400> SEQUENCE: 484
cgcccgccgc gccccgcgcc cgcccgccg ccccgcccg caggccctat tgatggt        57

<210> SEQ ID NO 485
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 485
cgtgggagta gccgac                                                    16

<210> SEQ ID NO 486
<211> LENGTH: 58
<212> TYPE: DNA
<213> ORGANISM: Artificial Sequence
<220> FEATURE:
<223> OTHER INFORMATION: Diagnostic Oligonucleotide

<400> SEQUENCE: 486
cgcccgccgc gccccgcgcc cgcccgccg ccccgcccg cattagaaaa ccaacaaa       58

<210> SEQ ID NO 487
<211> LENGTH: 57
<212> TYPE: DNA
<213> ORGANISM: Artificial Sequence
<220> FEATURE:
<223> OTHER INFORMATION: Diagnostic Oligonucleotide

<400> SEQUENCE: 487
cgcccgccgc gccccgcgcc cgcccgccg ccccgcccg ctgaatgcgt cttactg        57

<210> SEQ ID NO 488
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 488
catccaaaat tgctata                                                   17

<210> SEQ ID NO 489
<211> LENGTH: 66
<212> TYPE: DNA
<213> ORGANISM: Artificial Sequence
<220> FEATURE:
<223> OTHER INFORMATION: Diagnostic Oligonucleotide

<400> SEQUENCE: 489
cgcccgccgc gccccgcgcc cgcccgccg ccccgcccg cgtctactgt gatccaaact    60
tagtat                                                               66

<210> SEQ ID NO 490
<211> LENGTH: 24
<212> TYPE: DNA
<213> ORGANISM: Artificial Sequence
<220> FEATURE:
<223> OTHER INFORMATION: Diagnostic Oligonucleotide
```

-continued

```
<400> SEQUENCE: 490
catacctgga tgaagtcaaa tatg                                          24

<210> SEQ ID NO 491
<211> LENGTH: 23
<212> TYPE: DNA
<213> ORGANISM: Artificial Sequence
<220> FEATURE:
<223> OTHER INFORMATION: Diagnostic Oligonucleotide

<400> SEQUENCE: 491
ttgaggaatt tgtcatcttg tat                                           23

<210> SEQ ID NO 492
<211> LENGTH: 63
<212> TYPE: DNA
<213> ORGANISM: Artificial Sequence
<220> FEATURE:
<223> OTHER INFORMATION: Diagnostic Oligonucleotide

<400> SEQUENCE: 492
cgcccgccgc gccccgcgcc cgcccgcccg ccccgcccg caaaatcaca tttgcttttg    60
tta                                                                 63

<210> SEQ ID NO 493
<211> LENGTH: 58
<212> TYPE: DNA
<213> ORGANISM: Artificial Sequence
<220> FEATURE:
<223> OTHER INFORMATION: Diagnostic Oligonucleotide

<400> SEQUENCE: 493
cgcccgccgc gccccgcgcc cgcccgcccg ccccgcccg aaagaaataa atcactga     58

<210> SEQ ID NO 494
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 494
gtaaaactgc gacaac                                                   16

<210> SEQ ID NO 495
<211> LENGTH: 26
<212> TYPE: DNA
<213> ORGANISM: Artificial Sequence
<220> FEATURE:
<223> OTHER INFORMATION: Diagnostic Oligonucleotide

<400> SEQUENCE: 495
ccaacatgtt ttctttgatc ttacag                                        26

<210> SEQ ID NO 496
<211> LENGTH: 67
<212> TYPE: DNA
<213> ORGANISM: Artificial Sequence
<220> FEATURE:
<223> OTHER INFORMATION: Diagnostic Oligonucleotide

<400> SEQUENCE: 496
cgcccgccgc gccccgcgcc cgcccgcccg ccccgcccg agaatctcaa atagctctta    60
tagcttt                                                             67
```

<210> SEQ ID NO 497
<211> LENGTH: 62
<212> TYPE: DNA
<213> ORGANISM: Artificial Sequence
<220> FEATURE:
<223> OTHER INFORMATION: Diagnostic Oligonucleotide

<400> SEQUENCE: 497
cgcccgccgc gccccgcgcc cgcccgcccg ccccgcccg ttaaccaatg acatttgtga    60
ta    62

<210> SEQ ID NO 498
<211> LENGTH: 21
<212> TYPE: DNA
<213> ORGANISM: Artificial Sequence
<220> FEATURE:
<223> OTHER INFORMATION: Diagnostic Oligonucleotide

<400> SEQUENCE: 498
gtgtccatag tccttttaag c    21

<210> SEQ ID NO 499
<211> LENGTH: 61
<212> TYPE: DNA
<213> ORGANISM: Artificial Sequence
<220> FEATURE:
<223> OTHER INFORMATION: Diagnostic Oligonucleotide

<400> SEQUENCE: 499
cgcccgccgc gccccgcgcc cgcccgcccg ccccgcccg atatttcaca ggcaggagtc    60
c    61

<210> SEQ ID NO 500
<211> LENGTH: 25
<212> TYPE: DNA
<213> ORGANISM: Artificial Sequence
<220> FEATURE:
<223> OTHER INFORMATION: Diagnostic Oligonucleotide

<400> SEQUENCE: 500
aaaatcattt ctattctcat ttgga    25

<210> SEQ ID NO 501
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 501
acttcgtgcc ttcggac    17

<210> SEQ ID NO 502
<211> LENGTH: 62
<212> TYPE: DNA
<213> ORGANISM: Artificial Sequence
<220> FEATURE:
<223> OTHER INFORMATION: Diagnostic Oligonucleotide

<400> SEQUENCE: 502
cgcccgccgc gccccgcgcc cgcccgcccg ccccgcccg cagcaatgaa gaagatgaca    60
aa    62

```
<210> SEQ ID NO 503
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 503
ctggttccaa atgagaa                                                17

<210> SEQ ID NO 504
<211> LENGTH: 59
<212> TYPE: DNA
<213> ORGANISM: Artificial Sequence
<220> FEATURE:
<223> OTHER INFORMATION: Diagnostic Oligonucleotide

<400> SEQUENCE: 504
cgcccgccgc gccccgcgcc cgcccgcccg ccccgcccg taacctatag aatgcagca    59

<210> SEQ ID NO 505
<211> LENGTH: 60
<212> TYPE: DNA
<213> ORGANISM: Artificial Sequence
<220> FEATURE:
<223> OTHER INFORMATION: Diagnostic Oligonucleotide

<400> SEQUENCE: 505
cgcccgccgc gccccgcgcc cgcccgcccg ccccgcccg ttaatgtgat atgtgcccta   60

<210> SEQ ID NO 506
<211> LENGTH: 21
<212> TYPE: DNA
<213> ORGANISM: Artificial Sequence
<220> FEATURE:
<223> OTHER INFORMATION: Diagnostic Oligonucleotide

<400> SEQUENCE: 506
agatgataag acttaccaag c                                           21

<210> SEQ ID NO 507
<211> LENGTH: 21
<212> TYPE: DNA
<213> ORGANISM: Artificial Sequence
<220> FEATURE:
<223> OTHER INFORMATION: Diagnostic Oligonucleotide

<400> SEQUENCE: 507
gagaaggaga aggaagagtt g                                           21

<210> SEQ ID NO 508
<211> LENGTH: 63
<212> TYPE: DNA
<213> ORGANISM: Artificial Sequence
<220> FEATURE:
<223> OTHER INFORMATION: Diagnostic Oligonucleotide

<400> SEQUENCE: 508
cgcccgccgc gccccgcgcc cgcccgcccg ccccgcccg cttcctcatg ctattactca   60
tac                                                               63

<210> SEQ ID NO 509
<211> LENGTH: 61
<212> TYPE: DNA
<213> ORGANISM: Artificial Sequence
```

```
<220> FEATURE:
<223> OTHER INFORMATION: Diagnostic Oligonucleotide

<400> SEQUENCE: 509
cgcccgccgc gccccgcgcc cgcccgcccg ccccgcccg aagttatttt ttaggaagca    60
t                                                                   61

<210> SEQ ID NO 510
<211> LENGTH: 19
<212> TYPE: DNA
<213> ORGANISM: Artificial Sequence
<220> FEATURE:
<223> OTHER INFORMATION: Diagnostic Oligonucleotide

<400> SEQUENCE: 510
gaacttaaag actcggctc                                                19

<210> SEQ ID NO 511
<211> LENGTH: 61
<212> TYPE: DNA
<213> ORGANISM: Artificial Sequence
<220> FEATURE:
<223> OTHER INFORMATION: Diagnostic Oligonucleotide

<400> SEQUENCE: 511
cgcccgccgc gccccgcgcc cgcccgcccg ccccgcccg gaaattgtct gccattctta    60
a                                                                   61

<210> SEQ ID NO 512
<211> LENGTH: 20
<212> TYPE: DNA
<213> ORGANISM: Artificial Sequence
<220> FEATURE:
<223> OTHER INFORMATION: Diagnostic Oligonucleotide

<400> SEQUENCE: 512
gagttggcca ttcttgtatg                                               20

<210> SEQ ID NO 513
<211> LENGTH: 56
<212> TYPE: DNA
<213> ORGANISM: Artificial Sequence
<220> FEATURE:
<223> OTHER INFORMATION: Diagnostic Oligonucleotide

<400> SEQUENCE: 513
cgcccgccgc gccccgcgcc cgcccgcccg ccccgcccg tgtgagccga gtcttt        56

<210> SEQ ID NO 514
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 514
atggcatttc cacctt                                                   16

<210> SEQ ID NO 515
<211> LENGTH: 61
<212> TYPE: DNA
<213> ORGANISM: Artificial Sequence
<220> FEATURE:
<223> OTHER INFORMATION: Diagnostic Oligonucleotide
```

-continued

```
<400> SEQUENCE: 515
cgcccgccgc gccccgcgcc cgcccgccg ccccgcccg tgttattttt atttcagatg    60
c                                                                  61

<210> SEQ ID NO 516
<211> LENGTH: 19
<212> TYPE: DNA
<213> ORGANISM: Artificial Sequence
<220> FEATURE:
<223> OTHER INFORMATION: Diagnostic Oligonucleotide

<400> SEQUENCE: 516
taatatggca tttccacct                                               19

<210> SEQ ID NO 517
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 517
cgtgaagaaa gatgac                                                  16

<210> SEQ ID NO 518
<211> LENGTH: 59
<212> TYPE: DNA
<213> ORGANISM: Artificial Sequence
<220> FEATURE:
<223> OTHER INFORMATION: Diagnostic Oligonucleotide

<400> SEQUENCE: 518
cgcccgccgc gccccgcgcc cgcccgccg ccccgcccg taatgttaca aatagattc     59

<210> SEQ ID NO 519
<211> LENGTH: 21
<212> TYPE: DNA
<213> ORGANISM: Artificial Sequence
<220> FEATURE:
<223> OTHER INFORMATION: Diagnostic Oligonucleotide

<400> SEQUENCE: 519
cacacgtgaa gaaagatgac a                                            21

<210> SEQ ID NO 520
<211> LENGTH: 66
<212> TYPE: DNA
<213> ORGANISM: Artificial Sequence
<220> FEATURE:
<223> OTHER INFORMATION: Diagnostic Oligonucleotide

<400> SEQUENCE: 520
cgcccgccgc gccccgcgcc cgcccgccg ccccgcccg taatgttaca aatagattct    60
gctaac                                                             66

<210> SEQ ID NO 521
<211> LENGTH: 56
<212> TYPE: DNA
<213> ORGANISM: Artificial Sequence
<220> FEATURE:
<223> OTHER INFORMATION: Diagnostic Oligonucleotide

<400> SEQUENCE: 521
cgcccgccgc gccccgcgcc cgcccgccg ccccgcccg cttgatttct ggagac        56
```

<210> SEQ ID NO 522
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 522
ctagctgtaa ttgcat                                              16

<210> SEQ ID NO 523
<211> LENGTH: 61
<212> TYPE: DNA
<213> ORGANISM: Artificial Sequence
<220> FEATURE:
<223> OTHER INFORMATION: Diagnostic Oligonucleotide

<400> SEQUENCE: 523
cgcccgccgc gccccgcgcc cgccccgccg ccccccgcccg gaattatgtt tatggcatgg    60
t                                                              61

<210> SEQ ID NO 524
<211> LENGTH: 25
<212> TYPE: DNA
<213> ORGANISM: Artificial Sequence
<220> FEATURE:
<223> OTHER INFORMATION: Diagnostic Oligonucleotide

<400> SEQUENCE: 524
gagtacaagt atcaaatagc agtaa                                    25

<210> SEQ ID NO 525
<211> LENGTH: 59
<212> TYPE: DNA
<213> ORGANISM: Artificial Sequence
<220> FEATURE:
<223> OTHER INFORMATION: Diagnostic Oligonucleotide

<400> SEQUENCE: 525
cgcccgccgc gccccgcgcc cgccccgccg ccccccgccg ctgaattatg tttatggca     59

<210> SEQ ID NO 526
<211> LENGTH: 18
<212> TYPE: DNA
<213> ORGANISM: Artificial Sequence
<220> FEATURE:
<223> OTHER INFORMATION: Diagnostic Oligonucleotide

<400> SEQUENCE: 526
ccttttttct ggctaagt                                            18

<210> SEQ ID NO 527
<211> LENGTH: 61
<212> TYPE: DNA
<213> ORGANISM: Artificial Sequence
<220> FEATURE:
<223> OTHER INFORMATION: Diagnostic Oligonucleotide

<400> SEQUENCE: 527
cgcccgccgc gccccgcgcc cgccccgccg ccccccgccg gatggtaagt acatgggtgt    60
t                                                              61

<210> SEQ ID NO 528

```
<211> LENGTH: 21
<212> TYPE: DNA
<213> ORGANISM: Artificial Sequence
<220> FEATURE:
<223> OTHER INFORMATION: Diagnostic Oligonucleotide

<400> SEQUENCE: 528
actccactgt tcatagggat c                                       21

<210> SEQ ID NO 529
<211> LENGTH: 60
<212> TYPE: DNA
<213> ORGANISM: Artificial Sequence
<220> FEATURE:
<223> OTHER INFORMATION: Diagnostic Oligonucleotide

<400> SEQUENCE: 529
cgcccgccgc gccccgcgcc cgccccgccg ccccgcccg agttattcat actttcttct    60

<210> SEQ ID NO 530
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 530
agccttacct catctg                                             16

<210> SEQ ID NO 531
<211> LENGTH: 56
<212> TYPE: DNA
<213> ORGANISM: Artificial Sequence
<220> FEATURE:
<223> OTHER INFORMATION: Diagnostic Oligonucleotide

<400> SEQUENCE: 531
cgcccgccgc gccccgcgcc cgccccgccg ccccgcccg tttctggaac atttag        56

<210> SEQ ID NO 532
<211> LENGTH: 18
<212> TYPE: DNA
<213> ORGANISM: Artificial Sequence
<220> FEATURE:
<223> OTHER INFORMATION: Diagnostic Oligonucleotide

<400> SEQUENCE: 532
gaatgatgtc agctatat                                           18

<210> SEQ ID NO 533
<211> LENGTH: 63
<212> TYPE: DNA
<213> ORGANISM: Artificial Sequence
<220> FEATURE:
<223> OTHER INFORMATION: Diagnostic Oligonucleotide

<400> SEQUENCE: 533
cgcccgccgc gccccgcgcc cgccccgccg ccccgcccg tttctggaac atttagaaaa    60
aac                                                           63

<210> SEQ ID NO 534
<211> LENGTH: 19
<212> TYPE: DNA
<213> ORGANISM: Artificial Sequence
<220> FEATURE:
<223> OTHER INFORMATION: Diagnostic Oligonucleotide
```

<400> SEQUENCE: 534
tcagttaggg gtaggtcca					19

<210> SEQ ID NO 535
<211> LENGTH: 58
<212> TYPE: DNA
<213> ORGANISM: Artificial Sequence
<220> FEATURE:
<223> OTHER INFORMATION: Diagnostic Oligonucleotide

<400> SEQUENCE: 535
cgcccgccgc gccccgcgcc cgccccgccg ccccgcccg tgagctgtca aggttgta					58

<210> SEQ ID NO 536
<211> LENGTH: 19
<212> TYPE: DNA
<213> ORGANISM: Artificial Sequence
<220> FEATURE:
<223> OTHER INFORMATION: Diagnostic Oligonucleotide

<400> SEQUENCE: 536
caggaaactg ttctatcac					19

<210> SEQ ID NO 537
<211> LENGTH: 64
<212> TYPE: DNA
<213> ORGANISM: Artificial Sequence
<220> FEATURE:
<223> OTHER INFORMATION: Diagnostic Oligonucleotide

<400> SEQUENCE: 537
cgcccgccgc gccccgcgcc cgccccgccg ccccgcccg gaatgtcaac tgcttgagtg					60 tttt					64

<210> SEQ ID NO 538
<211> LENGTH: 27
<212> TYPE: DNA
<213> ORGANISM: Artificial Sequence
<220> FEATURE:
<223> OTHER INFORMATION: Diagnostic Oligonucleotide

<400> SEQUENCE: 538
aagtaacaga acatctgaaa ctcacac					27

<210> SEQ ID NO 539
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 539
cttgcgcttg atgaac					16

<210> SEQ ID NO 540
<211> LENGTH: 63
<212> TYPE: DNA
<213> ORGANISM: Artificial Sequence
<220> FEATURE:
<223> OTHER INFORMATION: Diagnostic Oligonucleotide

<400> SEQUENCE: 540
cgcccgccgc gccccgcgcc cgccccgccg ccccgcccg tgggcaatta tttcatatct					60

-continued

```
tgg                                                                63

<210> SEQ ID NO 541
<211> LENGTH: 58
<212> TYPE: DNA
<213> ORGANISM: Artificial Sequence
<220> FEATURE:
<223> OTHER INFORMATION: Diagnostic Oligonucleotide

<400> SEQUENCE: 541
cgcccgccgc gccccgcgcc cgccccgccg ccccccgcccg tatcaaggta aatacaga    58

<210> SEQ ID NO 542
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 542
gcttctatcc tgtgttc                                                 17

<210> SEQ ID NO 543
<211> LENGTH: 21
<212> TYPE: DNA
<213> ORGANISM: Artificial Sequence
<220> FEATURE:
<223> OTHER INFORMATION: Diagnostic Oligonucleotide

<400> SEQUENCE: 543
gatattatgt gtggtatttt c                                            21

<210> SEQ ID NO 544
<211> LENGTH: 59
<212> TYPE: DNA
<213> ORGANISM: Artificial Sequence
<220> FEATURE:
<223> OTHER INFORMATION: Diagnostic Oligonucleotide

<400> SEQUENCE: 544
cgcccgccgc gccccgcgcc cgccccgccg ccccccgcccg gaacttgtac attgttgca   59

<210> SEQ ID NO 545
<211> LENGTH: 67
<212> TYPE: DNA
<213> ORGANISM: Artificial Sequence
<220> FEATURE:
<223> OTHER INFORMATION: Diagnostic Oligonucleotide

<400> SEQUENCE: 545
cgcccgccgc gccccgcgcc cgccccgccg ccccccgcccg catattatca aggtaaatac   60
agatcat                                                            67

<210> SEQ ID NO 546
<211> LENGTH: 25
<212> TYPE: DNA
<213> ORGANISM: Artificial Sequence
<220> FEATURE:
<223> OTHER INFORMATION: Diagnostic Oligonucleotide

<400> SEQUENCE: 546
ggaactatca catgtgagat tgtta                                        25

<210> SEQ ID NO 547
<211> LENGTH: 56
```

```
<212> TYPE: DNA
<213> ORGANISM: Artificial Sequence
<220> FEATURE:
<223> OTHER INFORMATION: Diagnostic Oligonucleotide

<400> SEQUENCE: 547
cgcccgccgc gccccgcgcc cgcccgccg ccccgcccg cctttgagcc tgtgcc        56

<210> SEQ ID NO 548
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 548
gcttgagttc cggtgg                                                  16

<210> SEQ ID NO 549
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 549
catcagcccc tccgac                                                  16

<210> SEQ ID NO 550
<211> LENGTH: 57
<212> TYPE: DNA
<213> ORGANISM: Artificial Sequence
<220> FEATURE:
<223> OTHER INFORMATION: Diagnostic Oligonucleotide

<400> SEQUENCE: 550
cgcccgccgc gccccgcgcc cgcccgccg ccccgcccg tttctgaggc agaggta       57

<210> SEQ ID NO 551
<211> LENGTH: 58
<212> TYPE: DNA
<213> ORGANISM: Artificial Sequence
<220> FEATURE:
<223> OTHER INFORMATION: Diagnostic Oligonucleotide

<400> SEQUENCE: 551
cgcccgccgc gccccgcgcc cgcccgccg ccccgcccg cattgcattc tttgactt      58

<210> SEQ ID NO 552
<211> LENGTH: 16
<212> TYPE: DNA
<213> ORGANISM: Artificial Sequence
<220> FEATURE:
<223> OTHER INFORMATION: Diagnostic Oligonucleotide

<400> SEQUENCE: 552
aagagctcac cctgtc                                                  16

<210> SEQ ID NO 553
<211> LENGTH: 17
<212> TYPE: DNA
<213> ORGANISM: Artificial Sequence
<220> FEATURE:
<223> OTHER INFORMATION: Diagnostic Oligonucleotide

<400> SEQUENCE: 553
```

-continued

```
gcagtacgat tccatcc                                          17

<210> SEQ ID NO 554
<211> LENGTH: 56
<212> TYPE: DNA
<213> ORGANISM: Artificial Sequence
<220> FEATURE:
<223> OTHER INFORMATION: Diagnostic Oligonucleotide

<400> SEQUENCE: 554
cgcccgccgc gcccgcgcc cgcccgccg ccccgcccg ccttgttttc tgaggc         56
```

METHODS OF IDENTIFYING GENETIC MARKERS IN THE HUMAN CYSTIC FIBROSIS TRANSMEMBRANE CONDUCTANCE REGULATOR (CFTR) GENE

CROSS REFERENCE TO RELATED APPLICATIONS

This application is a continuation-in-part of U.S. Patent Application No. 10/142,722, filed May 8, 2002, now abandoned, which is a continuation of International Patent Application No. PCT/US00/30493, designating the Untied States of America and published in English, having an international filing date of Nov. 3, 2000, now expired, and claiming the benefit of priority to U.S. Provisional Application No. 60/165,301, filed Nov. 12, 1999. This application is also a continuation-in-part of U.S. patent application No. 09/851,501, filed May 8, 2001, now abandoned. This application claims priority to U.S. Provisional Application No. 60/333,351, filed November 19, 2001, the disclosure of which hereby expressly incorporated by reference in its entirety.

FIELD OF THE INVENTION

The present invention relates to the field of genetic screening. More specifically, the described embodiments concern methods to screen multiple samples, in a single assay, for the presence or absence of mutations or polymorphisms in a plurality of genes. Approaches to screen for the presence or absence of mutations that are associated with cystic fibrosis and approaches to design primers that generate extension products that facilitate the resolution of multiple extension products in a single lane of a gel or in a single run on a column are also provided.

BACKGROUND OF THE INVENTION

Despite the tremendous progress in molecular biology and the identification of genes, mutations, and polymorphisms responsible for disease, the ability to rapidly screen a subject for the presence of multiple disorders has been technically difficult and cost prohibitive. Current DNA-based diagnostics allow for the identification of a single mutation or polymorphism or gene per analysis. Although high-throughput methods and gene chip technology have enabled the ability to screen multiple samples or multiple loci within the same sample, these approaches require several independent reactions, which increases the time required to process clinical samples and drastically increases the cost. Further, because of time and expense, conventional diagnostic approaches focus on the identification of the presence of DNA fragments that are associated with a high frequency of mutation, leaving out analysis of other loci that may be critical to diagnose a disease. The need for a better way to diagnose genetic disease is manifest.

With the advent of multiplex Polymerase Chain Reaction (PCR), the ability to use multiple primer sets to generate multiple extension products from a single gene is at hand. By hybridizing isolated DNA with multiple sets of primers that flank loci of interest on a single gene, it is possible to generate a plurality of extension products in a single PCR reaction corresponding to fragments of the gene. As the number of primers increases, however, the complexity of the reaction increases and the ability to resolve the extension products using conventional techniques fails. Further, since many diseases are caused by changes of a single nucleotide, the rapid detection of the presence or absence of these mutations or polymorphisms is frustrated by the fact that the PCR products that indicate both the diseased and non-diseased state are of the same size.

Developments in gel electrophoresis and high performance liquid chromatography (HPLC), however, have enabled the separation of double-stranded DNAs based upon differences in their melting behaviors, which has allowed investigators to resolve DNA fragments having a single mutation or single polymorphism. Techniques such as temporal temperature gradient gel electrophoresis (TTGE) and denaturing high performance liquid chromatography (DHPLC) have been used to screen for small changes or point mutations in DNA fragments.

The separation principle of TTGE, for example, is based on the melting behavior of DNA molecules. In a denaturing polyacrylamide gel, double-stranded DNA is subject to conditions that will cause it to melt in discrete segments called "melting domains." The melting temperature $T_m$ of these domains is sequence-specific. When the $T_m$ of the lowest melting domain is reached, the DNA will become partially melted, creating branched molecules. Partial melting of the DNA reduces its mobility in a polyacrylamide gel.

Since the $T_m$ of a particular melting domain is sequence-specific, the presence of a mutation or polymorphism will alter the melting profile of that DNA in comparison to the wild-type or non-polymorphic DNA. That is, a heteroduplex DNA consisting of a wild-type or non-polymorphic strand annealed to mutant or polymorphic strand, will melt at a lower temperature than a homoduplex DNA strand consisting of two wild-type or non-polymorphic strands. Accordingly, the DNA containing the mutation or polymorphism will have a different mobility compared to the wild-type or non-polymorphic DNA. The TTGE approach has been used as a method for screening for mutations in the cystic fibrosis gene, for example. (Bio-Rad U.S./E.G. Bulletin 2103, herein expressly incorporated by reference in its entirety).

Similarly, the separation principle of DHPLC is based on the melting or denaturing behavior of DNA molecules. As the use and understanding of HPLC developed, it became apparent that when HPLC analyses were carried out at a partially denaturing temperature, i.e., a temperature sufficient to denature a heteroduplex at the site of base pair mismatch, homoduplexes could be separated from heteroduplexes having the same base pair length. (See e.g., Hayward-Lester, et al., *Genome Research* 5:494 (1995); Underhill, et al., *Proc. Natl. Acad. Sci. USA* 93:193 (1996); Oefner, et al., *DHPLC Workshop*, Stanford University, Palo Alto, Calif., (Mar. 17, 1997); Underhill, et al., *Genome Research* 7:996 (1997); Liu, et al., *Nucleic Acid Res.*, 26:1396 (1998), all of which and the references contained therein are hereby expressly incorporated by reference in their entireties). Techniques such as Matched Ion Polynucleotide Chromatography (MIPC) and Denaturing Matched Ion Polynucleotide Chromatography (DMIPC) have also been employed to increase the sensitivity of detection. It was soon realized that DHPLC, which for the purposes of this disclosure includes but is not limited to, MIPC, DMIPC, and ion-pair reverse phase high-performance liquid chromatography, could be used to separate heteroduplexes from homoduplexes that differed by as little as one base pair. Various DHPLC techniques have been described in U.S. Pat. Nos. 5,795,976; 5,585,236; 6,024,878; 6,210,885; Huber, et al., *Chromatographia* 37:653 (1993); Huber, et al., *Anal. Biochem*. 212:351 (1993); Huber, et al., *Anal. Chem*. 67:578 (1995); O'Donovan et al., *Genomics* 52:44 (1998), *Am J Hum Genet*. December;67(6):1428-36 (2000); *Ann Hum Genet*. September:63 (Pt 5):383-91 (1999); *Biotechniques*, April;28 (4):740-5 (2000); *Biotechniques*. November;29(5):1084-90, 1092 (2000); *Clin Chem*. August;45(8 Pt 1):1133-40 (1999); *Clin Chem*. April;47(4):635-44 (2001); *Genomics*. August 15;52(1):44-9 (1998); *Genomics*. March 15;56(3):247-53 (1999); *Genet Test*.;1(4):237-42 (1997-98); *Genet Test*.:4(2): 125-9 (2000); *Hum Genet*. June;106(6):663-8(2000); *Hum Genet*. November;107(5):483-7 (2000); *Hum Genet*. November;107(5):488-93 (2000); *Hum Mutat*. December;16(6): 518-26 (2000); *Hum Mutat*. 15(6):556-64 (2000); *Hum Mutat*. March;17(3):210-9 (2001); *J Biochem Biophys Methods*. November 20;46(1-2):83-93 (2000); *J Biochem Biophys Methods*. January 30;47(1-2):5-19 (2001); *Mutat Res*. November 29;430(1):13-21(1999); *Nucleic Acids Res*. March 1;28(5):E13 (2000); and *Nucleic Acids Res*. October 15;28 (20):E89 (2000), all of which, including the references contained therein, are hereby expressly incorporated by reference in their entireties. Despite the efforts of many, there remains a need for a better approach to screen for mutations and/or polymorphisms.

BRIEF SUMMARY OF THE INVENTION

Aspects of the invention concern rapid and inexpensive but efficient approaches to determine the presence or absence of genetic markers associated with cystic fibrosis. Several oligonucleotide primers specific for the human cystic fibrosis transmembrane conductance regulator (CFTR) gene have been developed (e.g., TABLE A and TABLE 2). These primers and oligonucleotides that are any number between 1-75 nucleotides upstream or downstream of said primers are unique in sequence and in their ability to generate extension products that melt evenly over vast stretches of nucleotides, which greatly improves the sensitivity of detection (e.g., single base mutations). It was then realized that by grouping extension products with similar melting behaviors, one can rapidly and efficiently separate multiple extension products on the basis of melting behavior on the same lane of a TTGE gel or in the same run on a DHPLC. Accordingly, a rapid, inexpensive and efficient approach to diagnose a subject suffering from cystic fibrosis or a carrier of the disease was discovered, whereby extension products are generated from a subject's DNA using the primers described herein, the extension products are grouped or mixed according to their melting behavior, and the grouped or mixed extension products are separated on the basis of melting behavior (e.g., one group per lane of TTGE gel). Not only does the pooling of extension products reduce cost and the time to perform the analysis but, because the extension products are optimized for melting behavior, the sensitivity of detection remains very high.

By one approach, for example, a method of identifying the presence or absence of a genetic marker in the human cystic fibrosis transmembrane conductance regulator (CFTR) gene of a subject is conducted by providing a DNA sample from said subject; providing at least one primer set from TABLE A; contacting said DNA and said at least one primer set; generating an extension product from said at least one primer set that comprises a region of DNA that includes the location of said genetic marker; separating said extension product on the basis of melting behavior; and identifying the presence or absence of said genetic marker in said subject by analyzing the melting behavior of said extension product. In related embodiments, at least 2, 3, 4, 5, 6, 7, or 8 primer sets from TABLE A are contacted with said DNA. In more related embodiments, the extension products generated from said 2, 3, 4, 5, 6, 7, or 8 primer sets are grouped according to TABLE E and separated on the basis of melting behavior.

By another approach, a method of identifying the presence or absence of a genetic marker in the human cystic fibrosis transmembrane conductance regulator (CFTR) gene of a subject is conducted by providing a DNA sample from said subject; providing at least one primer set from TABLE 2; contacting said DNA and said at least one primer set; generating an extension product from said at least one primer set that comprises a region of DNA that includes the location of said genetic marker; separating said extension product on the basis of melting behavior; and identifying the presence or absence of said genetic marker in said subject by analyzing the melting behavior of said extension product. In related embodiments, at least 2, 3, 4, 5, 6, 7, or 8 primer sets from TABLE 2 are contacted with said DNA. In more related embodiments, the extension products generated from said 2, 3, 4, 5, 6, 7, or 8 primer sets are grouped according to TABLE 3 and separated on the basis of melting behavior.

In another set of embodiments, a method of identifying the presence or absence of a genetic marker in the human cystic fibrosis transmembrane conductance regulator (CFTR) gene of a subject is conducted by providing a DNA sample from said subject; providing at least one primer set that is any number between 1-75 nucleotides upstream or downstream of a primer set from TABLE A; contacting said DNA and said at least one primer set; generating an extension product from said at least one primer set that comprises a region of DNA that includes the location of said genetic marker; separating said extension product on the basis of melting behavior; and identifying the presence or absence of said genetic marker in said subject by analyzing the melting behavior of said extension product. In related embodiments, at least 2, 3, 4, 5, 6, 7, or 8 primer sets from TABLE A are contacted with said DNA. In more related embodiments, the extension products generated from said 2, 3, 4, 5, 6, 7, or 8 primer sets are grouped according to TABLE E and separated on the basis of melting behavior.

DETAILED DESCRIPTION OF THE INVENTION

Figure 1:
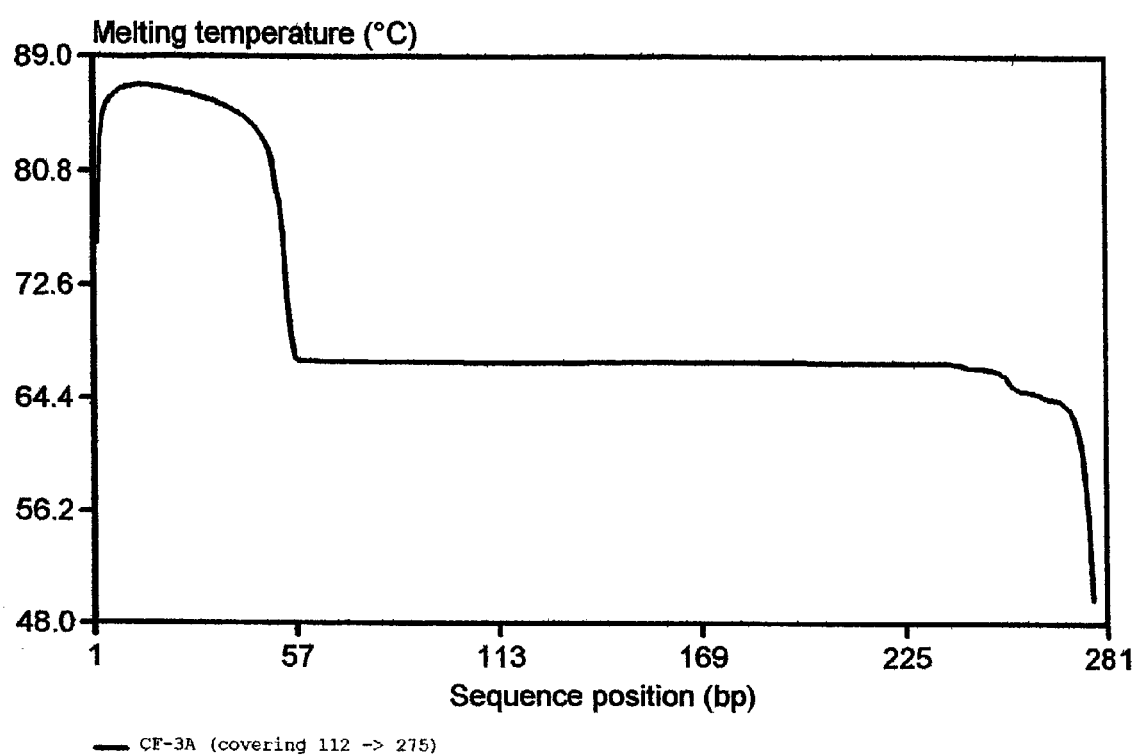
FIG. 1 shows a melting curve for the extension product CF3A spanning nucleotides 112-275 of the human cystic fibrosis transmembrane conductance regulator (CFTR) gene. The x axis shows the number of nucleotides and the y axis shows the temperature.

Embodiments described herein concern a novel approach to screen for the presence or absence of multiple mutations or polymorphisms in a plurality of genes, thus, improving the speed and lowering the cost to diagnose genetic diseases. Particularly preferred embodiments concern approaches to screen multiple loci in the human cystic fibrosis transmembrane conductance regulator (CFTR) gene so as to determine a cystic fibrosis carrier status or diagnose the disease. Several embodiments also permit very sensitive detection of single base mutations, single base mismatches, and small nuclear polymorphisms (SNPs), as well as, larger alterations in DNA at multiple loci, in a plurality of genes, in multiple samples. Further, by employing a DNA standard or by screening a plurality of DNA samples in the same assay, improved sensitivity of detection can be obtained. A novel approach to designing primers and extension products generated therefrom is described in the context of an assay that was performed to detect the presence or absence of genetic markers, polymorphisms, or mutations on the Cystic Fibrosis Transmembrane Conductance Regulator gene (CFTR).

Embodiments include methods of identifying the presence or absence of a plurality of genetic markers in a subject in the same gene or separate genes. One method is practiced, for example, by providing a DNA sample from said subject, providing a plurality of nucleic acid primer sets that hybridize to said DNA at regions that flank said plurality of genetic markers, wherein each primer set has a first and a second primer and, wherein said plurality of genetic markers exist on the same gene or a plurality of genes, contacting said DNA and said plurality of nucleic acid primer sets in a single reaction vessel or multiple reaction vessels, generating, in said reaction vessel(s), a plurality of extension products that comprise regions of DNA that include the location of said plurality of genetic markers, separating said plurality of extension products on the basis of melting behavior in a single lane or multiple lanes of a gel or a single run or multiple runs on a column, and identifying the presence or absence of said plurality of genetic markers in said subject by analyzing the melting behavior of said plurality of extension products. In some aspects of this method the separation on the basis of melting behavior is accomplished by TTGE and in other embodiments the separation on the basis of melting behavior is accomplished by DHPLC. In some embodiments, said extension products are first separated by size for a period sufficient to separate populations of extension products and then separated by melting behavior. The size separation can be accomplished on the TTGE gel or DHPLC column prior to separating on the basis of melting behavior.

Preferably, after generating the extension products by an amplification technique (e.g., Polymerase Chain Reaction or PCR), the extension products are grouped and pooled according to their predicted and/or actual melting behavior. In this way, multiple extension products, which correspond to different regions on the same gene or different regions on a plurality of genes can be separated on the same lane of a TTGE gel or in the same run on a DHPLC column. By carefully designing the primers, such that the extension products generated therefrom melt over large stretches of DNA (approximately 25, 50, 75, 100, 125, or 150 nucleotides) at roughly the same temperature (within up to 1.5° C. of one another), it was unexpectedly discovered that multiple extension products (2, 3, 4, 5, 6 or more) can be separated on the same lane of a TTGE gel or in the same run on an DHPLC column, thereby substantially reducing the cost of conducting the analysis.

In some embodiments, the subject is selected from the group consisting of a plant, virus, bacteria, mold, yeast, animal, and human and either the first or the second primer comprise a GC clamp. In other aspects of the invention, either the first or the second primer hybridize to a sequence within an intron. Preferably, at least one of the plurality of genetic markers is indicative of a disease selected from the group consisting of familial hypercholesterolemia (FH), cystic fibrosis, Tay-sachs, thalassemia, sickle cell disease, phenylketonuria, galactosemia, fragile X syndrome, hemophilia A, myotonic dystrophy, medium-chain acyl CoA dehydrogenase, maturity onset diabetes, cystinuria, methylmolonic acidemia, urea cycle disorders, hereditary fructose intolerance, hereditary hemachromatosis, neonatal thrombocytopenia, Gaucher's disease, tyrosinemia, Wilson's disease, alcaptonuria, hypolactasia, Baker's disease, argininemia Adenomatous polyposis coli (APC), Adult Polycystic Kidney disease, a-1-antitrypsin deficiency, Duchenne Muscular Dystrophy, Hemophilia A, Hereditary Nonpolyposis colorectal cancer, Huntingtons disease, Marfans syndrome, Myotonic dystrophy, Neurofibromatosis, Osteogenesis imperfecta, Retinoblastoma, Sickle cell disease, Freidrichs ataxia, Hemoglobinopathies, Leber's hereditary optic neuropathy, MCAD, Canavan's disease, Retintitus Pigmentosa, Bloom Syndrome, Fanconi anemia, and Neimann Pick disease.

In other embodiments, the plurality of primer sets consist of at least 3, 4, 5, 6, or 7 primer sets. Additionally, in some embodiments, the plurality of genes consist of at least 2, 3, 4, 5, 6, or 7 genes. The method above preferably generates the extension products using the Polymerase Chain Reaction (PCR) and the method can be supplemented by a step in which a control DNA is added.

Another embodiment concerns a method of identifying the presence or absence of a plurality of genetic markers in a plurality of subjects. This method is practiced by: providing a DNA sample from said plurality of subjects, providing a plurality of nucleic acid primer sets that hybridize to said DNA at regions that flank said plurality of genetic markers, wherein each primer set has a first and a second primer and, wherein said plurality of genetic markers exist on the same gene or on a plurality of genes, contacting said DNA and said plurality of nucleic acid primer sets in a single reaction vessel or multiple vessels, generating, in said reaction vessel(s), a plurality of extension products that comprise regions of DNA that include the location of said plurality of genetic markers, separating said plurality of extension products on the basis of melting behavior in a single lane or multiple lanes of a gel or a single run or multiple runs on a column, and identifying the presence or absence of said plurality of genetic markers in said plurality of subjects by analyzing the melting behavior of said plurality of extension products. In some aspects of this embodiment, the separation on the basis of melting behavior is accomplished by TTGE and in other embodiments the separation on the basis of melting behavior is accomplished by DHPLC.

As above, preferably, after generating the extension products by the amplification technique (e.g., PCR) from the plurality of subjects, the extension products are grouped and pooled according to their predicted and/or actual melting behavior. By separating multiple extension products generated from a plurality of subjects in the same lane of a TTGE gel or in the same run on a DHPLC column, the cost of analysis is substantially reduced. Because the incidence of polymorphism or mutation in the population as a whole is small, the large scale screening, described above, can be performed. When a polymorphism and/or mutation is detected in this type of assay, single subject assays can be performed, as described above, to identify the subject(s) that have the polymorphism and/or mutation.

In other embodiments, the subject is selected from the group consisting of a plant, virus, bacteria, mold, yeast, animal, and human and either the first or the second primer comprise a GC clamp. In other aspects of this embodiment, either the first or the second primer hybridize to a sequence within an intron. Preferably, at least one of the plurality of genetic markers is indicative of a disease selected from the group consisting of familial hypercholesterolemia (FH), cystic fibrosis, Tay-sachs, thalassemia, sickle cell disease, phenylketonuria, galactosemia, fragile X syndrome, hemophilia A, myotonic dystrophy, medium-chain acyl CoA dehydrogenase, maturity onset diabetes, cystinuria, methylmolonic acidemia, urea cycle disorders, hereditary fructose intolerance, hereditary hemachromatosis, neonatal thrombocytopenia, Gaucher's disease, tyrosinemia, Wilson's disease, alcaptonuria, hypolactasia, Baker's disease, argininemia Adenomatous polyposis coli (APC), Adult Polycystic Kidney disease, a-1-antitrypsin deficiency, Duchenne Muscular Dystrophy, Hemophilia A, Hereditary Nonpolyposis colorectal cancer, Huntingtons disease, Marfans syndrome, Myotonic dystrophy, Neurofibromatosis, Osteogenesis imperfecta, Retinoblastoma, Sickle cell disease, Freidrichs ataxia, Hemoglobinopathies, Leber's hereditary optic neuropathy, MCAD, Canavan's disease, Retintitus Pigmentosa, Bloom Syndrome, Fanconi anemia, and Neimann Pick disease.

In more embodiments, the plurality of subjects consist of at least 2, 3, 4, 5, 6, or 7 subjects. In more aspects of this embodiment, the plurality of primer sets consist of at least 3, 4, 5, 6, or 7 primer sets. Additionally, in some embodiments, the plurality of genes consist of at least 2, 3, 4, 5, 6, or 7 genes. The method above preferably generates the extension products using PCR and the method can be supplemented by a step in which a control DNA is added.

Still another embodiment involves a method of identifying the presence or absence of a mutation or polymorphism in a subject. This method is practiced by: providing a DNA sample from said subject, generating a population of extension products from said sample, wherein said extension products comprise a region of said DNA that corresponds to the location of said mutation or polymorphism, providing at least one control DNA, wherein said control DNA corresponds to the extension product but lacks said mutation or polymorphism, contacting said control DNA and said population of extension products in a single reaction vessel, thereby forming a mixed DNA sample, heating said mixed DNA sample to a temperature sufficient to denature said control DNA and said DNA sample, cooling said mixed DNA sample to a temperature sufficient to anneal said control DNA and said DNA sample, separating said mixed sample on the basis of melting behavior in a single lane or multiple lanes of a gel or a single run or multiple runs on a column, and identifying the presence or absence of said mutation or polymorphism by analyzing the melting behavior of said mixed DNA sample. By this approach, the addition of the control DNA followed by the heating and cooling steps, forces heteroduplex formation, if a polymorphism or mutation is present, which facilitates identification. In some aspects of this embodiment, the control DNA is DNA obtained or amplified from a second subject and the presence or absence of a mutation or polymorphism is known. In other aspects of the invention, heteroduplex formation can be forced by pooling the extension products generated from a plurality of subjects and denaturing and annealing, as above. Because the predominant genotype in a plurality of subjects lacks polymorphisms or mutations in the gene(s) analyzed, the majority of the DNA will force heteroduplex formation with any polymorphic or mutant DNA in the pool. Accordingly, the identification of mutant and/or polymorphic DNA is facilitated and the cost of the analysis is reduced. In some aspects of this embodiment, the separation on the basis of melting behavior is accomplished by TTGE and in other embodiments the separation on the basis of melting behavior is accomplished by DHPLC.

Still more embodiments concern the primers or groups of primers disclosed herein (preferably CFTR specific primers), kits containing said nucleic acids, and methods of using these primers or groups of primers to diagnose a carrier status or the presence of disease (e.g., cystic fibrosis). These nucleic acid primers can be used to efficiently determine the presence or absence of a polymorphism or mutation in a multiplex PCR reaction that screens a plurality of genes and a plurality of subjects in a single reaction vessel or multiple reaction vessels. Additionally, reaction vessels comprising a DNA sample, and a plurality of nucleic acid primer sets that hybridize to said DNA sample at regions that flank a plurality of genetic markers, wherein said plurality of genetic markers exist on a single gene or a plurality of genes are embodiments. Further, a reaction vessel comprising a plurality of DNA samples obtained from a plurality of subjects and a plurality of nucleic acid primer sets that hybridize to said plurality of DNA samples at regions that flank a plurality of genetic markers, wherein said plurality of genetic markers exist on a plurality of genes or on a single gene are embodiments. Still more aspects of the invention include a reaction vessel containing a plurality of extension products (2, 3, 4, 5, 6, 7, 8, 9, or 10 or more), which melt at approximately the same temperature (e.g., 0° C.-1.5° C. from one another).

Other embodiments concern a gel having lanes and adapted to separate different DNAs comprising a plurality of extension products, in a single lane of said gel, wherein said plurality of extension products melt at approximately the same temperature but are resolvable on said gel and, which correspond to regions of DNA located on a plurality of genes or on a single gene and, wherein said regions of DNA comprise loci that indicate a genetic trait and a gel having lanes and adapted to separate different DNAs comprising a plurality of extension products, in a single lane of said gel, wherein said plurality of extension products correspond to regions of DNA located on a plurality of genes or on a single gene in a single individual or a plurality of subjects and, wherein said regions of DNA comprise loci that indicate a genetic trait.

Additional embodiments include a DHPLC column adapted to separate different DNAs comprising a plurality of extension products, wherein said plurality of extension products melt at approximately the same temperature but are resolvable on said column and, which correspond to regions of DNA located on a plurality of genes or a single gene or and, wherein said regions of DNA comprise loci that indicate a genetic trait and a DHPLC column adapted to separate different DNAs comprising a plurality of extension products, wherein said plurality of extension products correspond to regions of DNA located on a plurality of genes or on a single gene in a single individual or a plurality of subjects and, wherein said regions of DNA comprise loci that indicate a genetic trait. More description of the compositions and methods described above is provided in the in the following sections.

Approaches to Facilitate and Reduce the Cost of Genetic Analysis

Aspects of the invention described herein concern approaches to analyze DNA samples for the presence or absence of a plurality of genetic markers that reside on a plurality of genes in a single assay. Some embodiments allow one to rapidly distinguish a plurality of DNA fragments in a single sample that differ only slightly in size and/or composition (e.g., a single base change, mutation, or polymorphism). Other embodiments concern methods to screen multiple genes from a subject, in a single assay, for the presence or absence of a mutation or polymorphism. An approach to achieve greater sensitivity of detection of mutations or polymorphisms present in a DNA sample is also provided. Preferred embodiments, however, include methods to screen multiple genes, in a plurality of DNA samples, in a single assay, for the presence or absence of mutations or polymorphisms.

It was discovered that multiple extension products that have slight differences in length and/or composition can be resolved by separating the DNA on the basis of melting temperature. By one approach, a plurality of varying lengths of double-stranded DNA are applied to a denaturing gel and the double-stranded DNAs are separated by applying an electrical current while the temperature of the gel is raised gradually. By slowly increasing the temperature while the DNA is electrically separated on a polyacrylamide gel containing a denaturant (e.g., urea), the dsDNA eventually denatures to partially single stranded (branched molecules) DNA. Because branched or heteroduplex DNA migrates more rapidly or more slowly than dsDNA or homoduplex DNA, one can quickly determine the differences in melting behavior between DNA fragments, compare this melting temperature to a standard DNA (e.g., a wild-type DNA or non-polymorphic DNA), and identify the presence or absence of a mutation or polymorphism in the screened DNA. This technique efficiently separates multiple DNA fragments, generated by a single multiplex PCR reaction on a plurality of loci from different genes (e.g., in one experiment, 10 different loci were analyzed in the same reaction and each of the extension products, some that differed by only a single mutation, were efficiently resolved).

It was also discovered that multiple extension products that have slight differences in length and/or composition can be resolved by separating the DNA by DHPLC. By one approach, a plurality of varying lengths of double-stranded DNA are applied to a ion-pair reverse phase HPLC column (e.g., alkylated non-porous poly(styrene-divinylbenzene)) that has been equilibrated to an appropriate denaturing temperature, depending on the size and composition of the DNA to be separated (e.g., 53° C. to 63° C.) in an appropriate buffer (e.g., 0.1 mM triethylamine acetate (TEAA) pH 7.0). Once applied to the column, the double stranded DNA binds to the matrix. By slowly increasing the presence of a denaturant (e.g., acetonitrile in TEAA), the dsDNA eventually denatures to partially single stranded (branched molecules) DNA and elutes from the column. Preferably a linear gradient is used to slowly elute the bound DNA. Detection can be accomplished using a U.V. detector, radioactivity, dyes, or fluoresence. In some embodiments, the extension products are first separated on the basis of size using a shallow gradient of denaturant for a time sufficient to separate individual populations of extension products and then on the basis of melting behavior using a deeper gradient of denaturant. The techniques described in the following references can also be modified for use with aspects of the invention: U.S. Pat. Nos. 5,795,976; 5,585,236; 6,024,878; 6,210,885; Huber, et al., *Chromatographia* 37:653 (1993); Huber, et al., *Anal. Biochem.* 212:351 (1993); Huber, et al., *Anal. Chem.* 67:578 (1995); O'Donovan et al., *Genomics* 52:44 (1998), *Am J Hum Genet*. December;67(6): 1428-36 (2000); *Ann Hum Genet*. September:63 (Pt 5):383-91 (1999); *Biotechniques*, April;28(4):740-5 (2000); *Biotechniques*. November;29(5):1084-90, 1092 (2000); *Clin Chem*. August;45(8 Pt 1):1133-40 (1999); *Clin Chem*. April; 47(4):635-44 (2001); *Genomics*. August 15;52(1):44-9 (1998); *Genomics*. March 15;56(3):247-53 (1999); *Genet Test*.; 1(4):237-42 (1997-98); *Genet Test*.:4(2):125-9 (2000); *Hum Genet*. Jun;106(6):663-8 (2000); *Hum Genet*. November;107(5):483-7 (2000); *Hum Genet*. November;107(5): 488-93 (2000); *Hum Mutat*. December;16(6):518-26 (2000); *Hum Mutat*. 15(6):556-64 (2000); *Hum Mutat*. March;17(3): 210-9 (2001); *J Biochem Biophys Methods*. November 20;46 (1-2):83-93 (2000); *J Biochem Biophys Methods*. January 30;47(1-2):5-19 (2001); *Mutat Res*. November 29;430(l):13-21(1999); *Nucleic Acids Res*. March 1;28(5):E13 (2000); and *Nucleic Acids Res*. October 15;28(20):E89 (2000), all of which are hereby expressly incorporated by reference in their entireties including the references cited therein, Because branched or heteroduplex DNA elutes either more rapidly or more slowly than homoduplex DNA, one can quickly determine the differences in melting behavior between DNA fragments, compare this melting temperature to a standard DNA (e.g., a wild-type or non-polymorphic homoduplex DNA), and identify the presence or absence of a mutation or polymorphism in the screened DNA. This technique efficiently separates multiple DNA fragments, generated by a single multiplex PCR reaction on a plurality of loci from different genes.

Some of the embodiments described herein have adapted the DNA separation techniques described above to allow for high-throughput genetic screening of organisms (e.g., plant, virus, bacteria, mold, yeast, and animals including humans). Typically, multiple primers that flank genetic markers (e.g., mutations or polymorphisms that indicate a congenital disease or a trait) on different genes are employed in a single amplification reaction and the multiple extension products are separated on a denaturing gel or by DHPLC according to their melting behavior. The presence or absence of mutations or polymorphisms, also referred to as "genetic markers", in the subject's DNA are then detected by identifying an aberrant melting behavior in the extension products (e.g., migration on a gel that is too fast or too slow or elution from a DHPLC column that is too fast or too slow). Advantageously, some embodiments provide a greater understanding of a subject's health because more loci that are indicative of disease, for example, are analyzed in a single assay. Further, some embodiments drastically reduce the cost of performing such diagnostic assays because many different genes and markers for disease can be screened simultaneously in a single assay.

By one approach, for example, a biological sample from the subject (e.g., blood) is obtained by conventional means and the DNA is isolated. Next, the DNA is hybridized with a plurality of nucleic acid primers that flank regions of a plurality of genetic loci or markers that are associated with or linked to the plurality of traits to be analyzed. Although 10 different loci have been detected in a single assay (requiring 20 primers), more or less loci can be screened in a single assay depending on the needs of the user. Preferably, each assay has sufficient primers to screen at least three different loci, which may be located on three different genes. That is, the embodied assays can employ sufficient primers to screen at least 3, 4, 5, 6, 7, 8, 9, 10, 11, 12, 13, 14, 15, 16, 17, 18, 19, 20, 24 or more, independent loci or markers that are indicative of a disease in a single assay and these loci can be on different genes. Because more than one loci or marker can be detected by a single set of primers, the detection of 20 different markers, for example, can be accomplished with less than 40 primers. However, in many assays, a different set of primers is needed to detect each different loci. Thus, in several embodiments, at least 6, 8, 10, 12, 14, 16, 18, 20, 22, 24, 26, 28, 30, 32, 34, 36, 38, 40, or more primers are used.

Desirably, the primers hybridize to regions of human DNA that flank markers or loci associated with or linked to human diseases such as: familial hypercholesterolemia (FH), cystic fibrosis, Tay-sachs, thalassemia, sickle cell disease, phenylketonuria, galactosemia, fragile X syndrome, hemophilia A, myotonic dystrophy, medium-chain acyl CoA dehydrogenase, maturity onset diabetes, cystinuria, methylmolonic acidemia, urea cycle disorders, hereditary fructose intolerance, hereditary hemachromatosis, neonatal thrombocytopenia, Gaucher's disease, tyrosinemia, Wilson's disease, alcaptonuria, hypolactasia, Baker's disease, argininemia Adenomatous polyposis coli (APC), Adult Polycystic Kidney disease, a-1-antitrypsin deficiency, Duchenne Muscular Dystrophy, Hemophilia A, Hereditary Nonpolyposis colorectal cancer, Huntingtons disease, Marfans syndrome, Myotonic dystrophy, Neurofibromatosis, Osteogenesis imperfecta, Retinoblastoma, Sickle cell disease, Freidrichs ataxia, Hemoglobinopathies, Leber's hereditary optic neuropathy, MCAD, Canavan's disease, Retintitus Pigmentosa, Bloom Syndrome, Fanconi anemia, and Neimann Pick disease. It should be understood, however, that the list above is not intended to limit the invention in any way and the techniques described herein can be used to detect and identify any gene or mutation or polymorphism desired (e.g., polymorphisms or mutations associated with alcohol dependence, obesity, and cancer).

Once the primers are hybridized to the subject's DNA; a plurality of extension products having the marker or loci indicative of the trait are generated. Preferably, the extension products are generated through a polymerase-driven amplification reaction, such as multiplex PCR or multiplex Ligase Chain Reaction (LCR). Then the extension products are separated on the basis of melting behavior (e.g., TTGE or DHPLC).

In some approaches, for example, the extension products are isolated from the reactants in the amplification reaction, suspended in a non-denaturing loading buffer, and are loaded on a TTGE denaturing gel (e.g., an 8%, 7M urea polyacrylamide gel). The sample can be heated to a temperature sufficient to denature a DNA duplex and then cooled to a temperature that allows reannealing, prior to suspending the DNA in the non-denaturing loading buffer. The extension products are then loaded into a single lane or multiple lanes, as desired. Next, an electrical current is applied to the gel and extension products.

Subsequently, the temperature of the denaturing gel is gradually raised, while maintaining the electrical current, so as to separate the extension products on the basis of their melting behaviors. Once the fragments have been separated by size and melting behavior, one can identify the presence or absence of mutations or polymorphisms at the screened loci by analyzing the migration behavior of the extension products.

In other approaches, the extension products are isolated from the reactants and suspended in a DHPLC buffer (e.g., 0.1M TEAA pH 7.0). The extension products are then injected onto a DHPLC column (e.g., an ion-pair reverse phase HPLC column composed of alkylated non-porous poly (styrene-divinylbenzene)) that has been equilibrated to an appropriate denaturing temperature, depending on the size and composition of the DNA to be separated (e.g., 53° C. to 63° C.) in an appropriate buffer (e.g., 0.1 mM triethylamine acetate (TEAA) pH 7.0) and the extension products are allowed to bind. The presence of a denaturant (e.g., acetonitrile in TEAA) on the column is gradually raised over time so as to slowly elute the extension products from the column. Preferably a linear gradient is used. Presence of the extension products in the eluant is preferably accomplished using a UV detector (e.g., at 260 and/or 280 nm), however, greater sensitivity may be obtained using radioactivity, binding dyes, fluorescence or the techniques described in U.S. Pat. Nos. 5,795,976; 5,585,236; 6,024,878; 6,210,885; Huber, et al., *Chromatographia* 37:653 (1993); Huber, et al., *Anal. Biochem.* 212:351 (1993); Huber, et al., *Anal. Chem.* 67:578 (1995); and O'Donovan et al., *Genomics* 52:44 (1998), which are all hereby incorporated by reference in their entireties including the references cited therein.

The appearance of a slower or faster migrating band at a temperature below or above the predicted melting point for the particular extension product in the TTGE approach, for example, indicates the presence of a mutation or polymorphism in the subject's DNA. Similarly, the appearance of a slower or faster eluting peak at a concentration of denaturant predicted to elute a wild-type or non-polymorphic homoduplex extension product in the DHPLC approach indicates the presence of a mutation or polymorphism in the subject's DNA. A heterozygous sample will display both homoduplex bands (wild-type homoduplexes and mutant homoduplexes), as well as, two heteroduplex bands that are the product of mutant/wild-type annealing. Because of base pair mismatches in these fragments, they melt significantly sooner than the two homoduplex bands. Accordingly, a user can rapidly identify the presence or absence of a mutation or polymorphism at the screened loci by either the TTGE or DHPLC approach and determine whether the tested subject has a predilection for a disease.

In a related embodiment, greater sensitivity is obtained by adding a "standard" DNA or "control" DNA to the DNA to be screened prior to amplification or after amplification, prior to separation of the DNA on the TTGE gel or DHPLC column. This insures the presence of heteroduplexes in the case of either a homozygous mutant, which normally would not display heteroduplexes, or a heterozygous mutant. Desired DNA standards include, but are not limited to, DNA that is wild-type for at least one of the traits that are being screened. Preferred standards include, but are not limited to, DNA that is wild-type for all of the traits that are being screened. A DNA standard can also be a mutant or polymorphic DNA. In some embodiments, particularly when the control DNA is added after amplification, the DNA standard is an extension product generated from a wild-type genomic DNA or a mutant genomic DNA. By this approach, the amplification phase of the method is performed as described above. That is, DNA from the subject to be screened and the DNA standard are hybridized with nucleic acid primers that flank regions of the genetic loci or markers that are associated with or linked to the traits being tested.

Extension products are then generated. If the subject being tested has at least one trait that is detected by the assay (e.g., a congenital disorder), then two populations of extension products are generated, a first population that corresponds to the standard DNA and a second population that corresponds to the subject's DNA having at least one mutation or polymorphism. Next, preferably, the two populations of extension products are isolated from the amplification reactants and are denatured by heat (e.g., 95° C. for 5 minutes), then are allowed to anneal by cooling (e.g., ice for 5 minutes). This ensures the formation of the heteroduplex bands in the presence of any relatively small mutation (e.g., point mutation, small insertion, or small deletion). The isolation and denaturing/annealing steps are not practiced with some embodiments, however.

Subsequently, by the TTGE approach, the two populations of extension products are suspended in a non-denaturing loading buffer and loaded on a denaturing polyacrylamide gel and separated on the basis of melting behavior, as described above. By the DHPLC approach, the two populations of extension products are suspended in a suitable buffer (e.g., 0.1M TEAA pH 7.0), loaded onto a buffer and temperature equilibrated DHPLC column and a linear gradient of denaturant is applied, as described above. Because the two populations of extension products are not perfectly complementary, they form heteroduplexes. Heteroduplexes are less stable than homoduplexes, have a lower melting temperature, and are easily differentiated from homoduplexes using the DNA separation techniques described above. One can identify the presence or absence of mutations or polymorphisms at the screened loci, for example, by comparing the migration behavior or elution behavior of the extension products generated from the screened DNA with the migration behavior or elution behavior of the DNA standard. If heteroduplexes are present, generally, two additional bands that correspond to the single extension product will appear on the gel or the extension products will elute from the column more rapidly than the control or standard DNA alerting the user to the presence of a mutation or polymorphism. Accordingly, a significant increase in sensitivity is obtained and a user can rapidly identify the presence or absence of a mutation or polymorphism in the tested DNA sample and, thereby, determine whether the screened subject has a predilection for a particular trait (e.g., a congenital disease).

Similarly, an increase in sensitivity can be obtained by mixing DNA from a plurality of subjects prior to amplification. Because the frequency of mutations or polymorphisms for most disorders are very low in the population, most of the extension products generated are wild-type DNA. Thus, most of the pool of DNA behaves as a DNA standard. That is, the predominant structure formed upon annealing after denaturation is a homoduplex, which can be rapidly distinguished from any heteroduplex that would appear if a subject were to have a polymorphism or mutation. Of course, extension products previously generated from multiple subjects can be used as control DNA by mixing the previously generated extension products with the extension products generated from the DNA that is being screened prior to electrophoresis. In several embodiments, the DNA from at least 2 subjects is mixed. Desirably, the DNA from at least 3 subjects is mixed. Preferably, the DNA from at least 4 subjects is mixed. It should be understood, however, that the DNA from at least 2, 3, 4, 5, 6, 7, 8, 9, 10, 11, 12, 13, 14, 15, 16, 17, 18, 19, 20, or more subjects can be mixed prior to amplification or prior to separation on the basis of melting behavior, in accordance with some of the described embodiments.

In one embodiment, for example, DNA from a plurality of subjects to be tested is obtained by conventional methods, pooled, and hybridized with the desired nucleic acid primers. Extension products are then generated, as before. If at least one of the subjects being tested has at least one congenital disorder that is detected by the screen then two populations of extension products will be generated, a first population that corresponds to DNA from subjects that have the wild-type gene and a second population that corresponds to DNA from subjects having at least one mutant or polymorphic gene.

By one approach, the two populations of extension products are then isolated from the amplification reactants, suspended in a non-denaturing loading buffer, denatured by heat, annealed by cooling, and are separated by TTGE, as described above. By another approach, the two populations of extension products are isolated from the amplification reactants, suspended in a DHPLC loading buffer (0.1M TEAA pH 7.0), denatured by heat, annealed by cooling, and are separated on a DHPLC column, as described above. The presence of a subject in the DNA pool having at least one mutation or polymorphism is identified by analyzing the migration behavior of the DNA on the gel or the elution behavior from the column. The appearance of a slower or faster migrating band at a temperature below or above the predicted melting point for a particular extension product on the gel indicates the presence of a mutation or polymorphism in the DNA from one of the subjects. Similarly, the appearance of a slower or faster eluting extension product from the DHPLC column indicates the presence of a mutation or polymorphism in the DNA from one of the subjects. By repeating the analysis with smaller and smaller pools of samples, one can identify the individual(s) in the pool that has the mutation or polymorphism. Additionally, DNA standards can be used, as described above, to facilitate identification of the individual(s) having the mutation or polymorphism. Advantageously, some embodiments can be used to screen multiple samples at multiple loci that are on found on a plurality of genes in a single assay, thus, increasing sample throughput. The analysis of a plurality of DNA samples in the same assay also unexpectedly provides greater sensitivity. The section below describes a DNA separation technique that can be used with the embodiments described herein.

Multiple Extension Products of Similar Composition can be Separated on the Same Lane of a Denaturing Gel or in the Same Run on a DHPLC Column It was discovered that multiple fragments of DNA, which vary slightly in length and/or composition, can be rapidly and efficiently resolved on the basis of melting behavior. Although the preferred methods for differentiating multiple fragments of DNA on the basis of melting behavior involve TTGE gel electrophoresis and DHPLC, it is contemplated that other conventional techniques that are amenable to DNA separation on the basis of melting behavior can be equivalently employed (e.g., size exclusion chromatography, ion exchange chromatography, and reverse phase chromatography on high pressure (e.g., HPLC), low pressure (e.g., FPLC), gravity-flow, or spin-columns, as well as, thin layer chromatography).

By one approach, a polyacrylamide gel having a porosity sufficient to resolve the DNA fragments on the basis of size (e.g., 4-20% acrylamide/bis acrylamide gel having a set concentration of denaturant) is used. The amount of denaturant in the gel (e.g., urea or formamide) can vary according to the length and composition of the DNA to be resolved. The concentration of urea in a polyacrylamide gel, for example, can be 3M, 3.5M, 4M, 4.5M, 5M, 5.5M, 6M, 6.5M, 7M, 7.5M, or 8M. In preferred embodiments, an 8% polyacrylamide gel with 7M urea is used. It should be emphasized, however, that other types of polyacrylamide gels, equivalents thereof, and agarose gels can be used.

The DNA samples to be resolved are placed in a non-denaturing buffer and can be loaded directly to the gel. In some embodiments, for example, when heteroduplex formation is desired to increase the sensitivity of the assay, it is desirable to heat the double stranded DNA to a temperature that permits denaturation (e.g., 95° C. for 5-10 minutes) and then slowly cool the DNA to a temperature that allows annealing (e.g., ice for 5-10 minutes) prior to mixing with the loading buffer. Preferably, the DNA is loaded onto the gel in a total volume of 10-20 µl. Preferably, a Temporal Temperature Gradient Gel Electrophoresis (TTGE) apparatus is used. A commercially available system that is suitable for this technique can be obtained from BioRad. The gel can be run at 120, 130, 140, 150, 175, 200, 220, 250, 275, or 300 V for 1.5-10 hours, for example.

Once the DNA has been loaded, an electrical current is applied to begin separating the fragments on the bass of size and the temperature of the gel is raised gradually. In one embodiment, for example, the melting behavior separation is performed by raising the temperature beyond 60° C., 61° C., 62° C., 63° C., 64° C., 65° C., 66° C., 67° C., 68° C., 69° C., 70° C., 71° C., 72° C., 73° C., 74° C., or 75° C. at approximately 5.0° C./hour-0.5° C./hour in 0.1° C. increments.

Once the extension products have been separated by melting behavior, the gel can be stained to reveal the separated DNA. Many conventional stains are suitable for this purpose including, but not limited to, ethidium bromide stain (e.g., 1% ethidium bromide in a 1.25×Tris Acetate EDTA pH 8.0 (TAE) solution), fluorescent stains, silver stains, and colloidal gold stains. In some embodiments, it is desirable to destain the gel (e.g., 20 minutes in a 1.25×TAE solution). After staining, the gel can be analyzed visually (e.g., under a U.V. lamp) and/or with a digital camera and computer software such as, the Eagle Eye System by Stratagene or the Gel Documentation System (BioRad).

Mutations or polymorphisms are easily identified by comparing the migration behavior of the DNA to be screened with the migration behavior of a control DNA and/or by monitoring the melting temperature of the extension products generated from the screened DNA. Desirable "control" DNA or "standard" DNA includes a DNA that is wild-type or non-polymorphic for at least one loci that is screened and preferred standard DNA is wild-type or non-polymorphic for all of the loci that are being screened. Because this DNA separation technique is sufficiently sensitive to identify a single base pair substitution in a DNA fragment up to 600 base pairs in length, small changes in the melting behaviors and migration of the extension products can be rapidly identified.

By another approach, DHPLC is used to resolve heteroduplex and homoduplex molecules of several PCR extension products in a single assay. Preferably, the heteroduplex and homoduplex extension products are separated from each other by ion-pair reverse phase high performance liquid chromatography. In one embodiment, a DHPLC column that contains alkylated non-porous poly(styrene-divinylbenzene) is used. Preferably, the DHPLC column is equilibrated in an appropriate degassed buffer, referred to as Buffer "A" (e.g., 0.1M TEAA pH 7.0) and is kept at a constant temperature somewhat below the predicted melting temperature of the extension products (e.g., 53° C.-60° C., preferably 50° C.). A plurality of extension products that may be generated from a plurality of different loci, as described herein, are suspended in Buffer A and are injected onto the DHPLC column. The Buffer A is then allowed to run through the column for a time sufficient to insure that the extension products have adequately bound to the column. Preferably, flow rate and the amount of gas (e.g., argon or helium) are adjusted and kept constant so that the pressure on the column does not exceed the recommended level. Gradually, degassed denaturing buffer, referred to as Buffer "B", (e.g., 0.1M TEAA pH 7.0 and 25% acetonitrile) is applied to the column. Although an isocratic gradient can be used, a gradual linear gradient is preferred. By one approach, to separate fragments that range in size from 200-450 bp, for example, a gradient of 50%-65% Buffer B (0.1M TEAA pH 7.0 and 25% acetonitrile) is used. Of course, as the size of extension products to be separated on the DHPLC column decreases, the gradient and/or the amount of denaturant in Buffer B can be reduced, whereas, as the size of extension products to be separated on the DHPLC column increases, the gradient and/or the amount of denaturant in Buffer B can be increased.

The DHPLC column is designed such that double stranded DNA binds well but as the extension products become partially denatured the affinity to the column is reduced until a point is reached at which the particular extension product can no longer adhere to the column matrix. Typically, heteroduplexes denature before homoduplexes, thus, they would be expected to elute more rapidly from the column than homoduplexes.

In some embodiments, particularly embodiments concerning the separation of a plurality of different extension products (e.g., extension products generated from a plurality of loci), the choice of primers and, thus, the extension products generated therefrom, requires careful design. For example, a GC-clamp or other artificial sequence can be used to adjust the melting characteristics and increase the length of a particular DNA fragment, if needed, to facilitate separation on the DHPLC or improve resolution of the extension products. By one approach, each set of primers in a multiplex reaction are designed and selected to generate an extension product that has a unique homoduplex and heteroduplex elution behavior. In this manner, each species can be easily identified.

By another approach, each set of primers are designed to generate extension products that have homoduplexes with very similar melting characteristics. By this strategy, all of the homoduplexes will elute at the same or very similar concentration of denaturant, which is different than the concentration of denaturant required to elute the heteroduplexes. Accordingly, the elution of a species of extension product outside of the expected range for the homoduplexes indicates the presence of a mutation or polymorphism.

In the case that the extension products happen to have overlapping retention times/elution behaviors, the DHPLC conditions can be adjusted to include a primary separation on the basis of size prior to increasing the concentration of the denaturant on the column to improve resolution. The techniques described in Huber, et al., *Anal. Chem.* 67:578 (1995), hereby expressly incorporated by reference in its entirety, can be adapted for use with the novel DHPLC separation approach described herein. In one embodiment, for example, the alkylated non-porous poly(styrene-divinylbenzene) DHPLC column can be used to separate the extension products on the basis of size for a time sufficient to group the various populations of extension products (i.e., the homoduplexes and heteroduplexes generated from a single independent set of primers constitute a single population of extension products) prior to separating on the basis of melting behavior.

By one approach, the extension products are applied to the column, as above, in Buffer A and a shallow linear gradient of Buffer B (e.g., 30%-50% of a solution of 0.1M TEAA pH 7.0 and 25% acetonitrile for 200-450 bp extension products) is applied so as to resolve the various populations of extension products. Then, a deeper linear gradient of Buffer B (e.g., 50%-65% of a solution of 0.1M TEAA pH 7.0 and 25% acetonitrile for 200-450 bp extension products) is applied to resolve the homoduplexes from the heteroduplexes within each individual population of extension product. In this manner, the homoduplexes and heteroduplexes from each population of extension product can be resolved despite having overlapping elution behaviors.

It should be understood that the separation based on size can be performed at virtually any temperature as long as the extension products do not denature on the column, however, the amount of denaturant in Buffer B and the type of gradient may have to be adjusted. For example, the size separation can be accomplished at 4° C.-23° C., or 23° C.-40° C., or 40°-50° C., or 50° C.-60° C. Additionally, the size separation can be accomplished while the column is being gradually equilibrated to the temperature that is going to be used for the DHPLC. It should also be understood that the size separation can be performed on the same column with the appropriate gradient (shallow for a time sufficient to separate on the basis of size followed by a deeper gradient to separate on the basis of melting behavior). Additionally, columns in series can be used to separate extension products that have overlapping retention times/elution behaviors. For example, a first DHPLC column can be used to separate on the basis of size and a second DHPLC column can be used to separate on the basis melting behavior.

Mutations or polymorphisms are easily identified using the DHPLC techniques above by comparing the elution behavior of the DNA to be screened with the elution behavior of a control DNA. As above, desirable "control" DNA or "standard" DNA includes a DNA that is wild-type or non-polymorphic for at least one loci that is screened and preferred standard DNA is wild-type or non-polymorphic for all of the loci that are being screened. Control or standard DNA can also include extension products that are homoduplexes by virtue of a mutation or polymorphism or plurality of mutations or polymorphisms. Since the elution behavior of the wild type or non-polymorphic DNA or a homozygous mutant or polymorphism, represents the elution behavior of a homoduplex, one can use DHPLC values obtained from separating these controls, such as the retention time, elution time, or amount of denaturant required to elute the homoduplex as a basis for comparison to a screened sample to identify the presence of homoduplexes. Similarly, a control DNA can be a known heteroduplex and the elution behavior values described above can be used to identify the presence of a heteroduplex in a screened sample.

Additionally, the separated extension products can be collected after passing through the DHPLC column or TTGE gel or reamplified and sequenced to verify the existence of the mutation or polymorphism. Further, the identified products can be isolated from the gel and sequenced. Sequencing can be performed using the conventional dideoxy approach (e.g., Sequenase kit) or an automated sequencer. Preferably, all possible mutant fragments are sequenced using the CEQ 2000 automated sequencer from Beckman/Coulter and the accompanying analysis software. The mutations or polymorphisms identified by sequencing can be compiled along with the respective melting behaviors and the sizes of extension products. This data can be recorded in a database so as to generate a profile for each loci.

Additionally, this profile information can be recorded with other subject-specific information, for example family or medical history, so as to generate a subject profile. By creating such databases, individual mutations can be better characterized. Mutation analysis hardware and software can also be employed to aid in the identification of mutations or polymorphisms. For example, the "ALFexpress II DNA Analysis System", available from Amersham Pharmacia Biotech and the "Mutation Analyser 1.01", also available from Amersham Pharmacia Biotech, can be used. Mutation Analyser automatically detects mutations in sample sequence data, generated by the ALFexpress II DNA analysis instrument. The section below describes embodiments that allow for the identification of a mutation or polymorphism at multiple loci in a plurality of genes in a single assay.

Identification of the Presence or Absence of a Mutation or Polymorphism at Multiple Loci in a Plurality of Genes in a Single Assay The DNA separation techniques described herein can be used to rapidly identify the presence or absence of a mutation or polymorphism at multiple loci in a plurality of genes in a single assay. Accordingly, a biological sample containing DNA is obtained from a subject and the DNA is isolated by conventional means. For some applications, it may be desired to screen the RNA of a subject for the presence of a genetic disorder (e.g., a congenital disease that arises through a splicing defect). In this case, a biological sample containing RNA is obtained, the RNA is isolated, and then is converted to cDNA by methods well known to those of skill in the art. DNA from a subject or cDNA synthesized from the mRNA obtained from a subject can be easily and efficiently isolated by various techniques known in the art. Also known in the art is the ability to amplify DNA fragments from whole cells, which can also be used with the embodiments described herein. Thus, the DNA sample for use with the embodiments described herein need only be isolated in the sense that the DNA is in a form that allows for PCR amplification.

In some embodiments, genomic DNA is isolated from a biological sample by using the Amersham Pharmacia Biotech "GenomicPrep Blood DNA Isolation Kit". The isolation procedure involves four steps: (1) cell lysis (cells are lysed using an anionic detergent in the presence of a DNA preservative, which limits the activity of endogenous and exogenous Dnases); (2) RNAse treatment (contaminating RNA is removed by treatment with RNase A); (3) protein removal (cytoplasmic and nuclear proteins are removed by salt precipitation); and (4) DNA precipitation (genomic DNA is isolated by alcohol precipitation). EXAMPLE 1 also describes an approach that was used to isolate DNA from human blood.

Once the sample DNA has been obtained, primers that flank the desired loci to be screened are designed and manufactured. Preferably, optimal primers and optimal primer concentrations are used. Desirably, the concentrations of reagents, as well as, the parameters of the thermal cycling are optimized by performing routine amplifications using control templates. Primers can be made by any conventional DNA synthesizer or are commercially available. Optimal primers desirably reduce non-specific annealing during amplification and also generate extension products that resolve reproducibly on the basis of size or melting behavior and, preferably, both. Preferably, the primers are designed to hybridize to sample DNA at regions that flank loci that can be used to diagnose a trait, such as a congenital disease (e.g., loci that have mutations or polymorphisms that indicate a human disease).

Desirably, the primers are designed to detect loci that diagnose conditions selected from the group consisting of familial hypercholesterolemia (FH), cystic fibrosis, Tay-sachs, thalassemia, sickle cell disease, phenylketonuria, galactosemia, fragile X syndrome, hemophilia A, myotonic dystrophy, medium-chain acyl CoA dehydrogenase, maturity onset diabetes, cystinuria, methylmolonic acidemia, urea cycle disorders, hereditary fructose intolerance, hereditary hemachromatosis, neonatal thrombocytopenia, Gaucher's disease, tyrosinemia, Wilson's disease, alcaptonuria, hypolactasia, Baker's disease, argininemia Adenomatous polyposis coli (APC), Adult Polycystic Kidney disease, a-1-antitrypsin deficiency, Duchenne Muscular Dystrophy, Hemophilia A, Hereditary Nonpolyposis colorectal cancer, Huntingtons disease, Marfans syndrome, Myotonic dystrophy, Neurofibromatosis, Osteogenesis imperfecta, Retinoblastoma, Sickle cell disease, Freidrichs ataxia, Hemoglobinopathies, Leber's hereditary optic neuropathy, MCAD, Canavan's disease, Retintitus Pigmentosa, Bloom Syndrome, Fanconi anemia, and Neimann Pick disease. Primers can be designed to amplify any region of DNA, however, including those regions known to be associated with diseases such as alcohol dependence, obesity, and cancer. It should be understood that the embodiments described herein can be used to detect any gene, mutation, or polymorphism found in plants, virus, molds, yeast, bacteria, and animals.

Preferred primers are designed and manufactured to have a GC rich "clamp" at one end of a primer, which allows the dsDNA to denature in a "zipper-like" fashion. As one of skill will appreciate, PCR requires a "primer set", which includes a first and a second primer, only one of which has the GC clamp so as to allow for separation of the double stranded molecule from one end only. Since the GC clamp is significantly stable, the rest of the fragment melts but does not completely separate until a point after the inflection point of the DNA, which contains the mutation or polymorphism of interest. The denaturant in the gel or on the column allows the temperature of melting to be lower and allows the inflection point of the melt to be longer in terms of temperature and, thus, the sensitivity to temperature at the inflection point is less (i.e., increment temperature=less increment melting), which increases the resolution.

Additionally, desirable primers are designed with a properly placed GC-clamp so that extension products that contain a single melting domain are produced. Preferably, the primers are selected to complement regions of introns that flank exons containing the genetic markers of interest so that polymorphisms or mutations that reside within the early portions of exons are not masked by the GC clamp. For example, it was discovered that GC clamps significantly perturb melting behavior and can prevent the detection of a polymorphism or mutation by melting behavior if the mutation or polymorphism resides too close to the GC clamp (e.g., within 40 nucleotides). By performing amplification reactions with control templates, optimal primer design and optimal concentration can be determined. The use of computer software, including, but not limited to, WinMelt or MacMelt (Bio-Rad) and Primer Premire 5.0 can aid in the creation and optimization of primers and proper positioning of the GC-clamp. Accordingly, many of the primers and groupings of primers described herein, as used in a particular assay (e.g., to screen for cystic fibrosis) are embodiments of the invention. EXAMPLE 2 further describes the design and optimization of primers that allowed for the high-throughput multiplex PCR technique described herein.

Once optimal primers are designed and selected, the DNA sample is screened using the inventive multiplex PCR technique. In some embodiments, for example, approximately 25 ng-500 ng of template DNA (preferably, 200 ng for human genomic DNA) is suspended in a buffer comprising: 10 mM Tris (pH 8.4), 50 mM KCl, 1.5 mM $MgCl_2$, 200 µM dNTPs, 50 pmol of each primer, and 1 unit Taq polymerase per primer set in a total volume of 50 µl. Preferably, amplification is performed under the same conditions that were used to design the primers. In some embodiments, for example, amplification is performed on a conventional thermal cycler for 30 cycles, wherein each cycle is: 1 minute @ 95° C., 58° C. for 1 minute, 72° C. for 1 minute. Final extension is performed at 72° C. for 5 minutes. When the primers have a GC clamp, it was found that conditions often favor an amplification reaction having over 40 cycles, wherein each cycle is: 35 seconds @ 95° C., 120 seconds @ 50-57° C., and 60 seconds+3 seconds/cycle @ 72° C. Thermal cyclers are available from a number of scientific suppliers and most are suitable for the embodiments described herein.

Once the PCR reaction is complete, the extension products are desirably isolated by centrifugal microfiltration using a standard PCR cleanup cartridge, for example, Qiagen's QIAquick 96 PCR Purification Kit, according to manufacture's instructions. Isolation or purification of the extension products is not necessary to practice the invention, however. The isolated extension products can then be suspended in a non-denaturing loading buffer and either loaded directly on a DHPLC column or TTGE denaturing gel. The sample can also be denatured by heating (e.g., 95° C. for 5-10 minutes) and annealed by cooling (e.g., ice for 5-10 minutes) prior to loading onto the DHPLC column or TTGE denaturing gel. The various extension products are then separated on a TTGE denaturing gel or DHPLC column on the basis of melting behavior, as described above and, after separation, the extension products can be analyzed for the presence or absence of polymorphisms or mutations. EXAMPLES 3 and 4 describe experiments that verified that multiple loci on a plurality of genes can be screened in a single assay. The section below describes a method of genetic analysis, wherein improved sensitivity of detection was obtained by adding a DNA standard to the screened DNA.

Improved Sensitivity was Obtained When a DNA Standard was Mixed With the Screened DNA It was also discovered that greater sensitivity in the inventive multiplex PCR reactions described herein can be obtained by mixing a DNA standard with the DNA to be tested prior to conducting amplification or after amplification but prior to separation on the basis of melting behavior. Desired DNA standards include, but are not limited to, DNA that is wild-type for at least one of the traits that are being screened and preferred DNA standards include, but are not limited to, DNA that is wild-type for all of the traits that are being screened. DNA standards can also be mutant or polymorphic DNA. In some embodiments, particularly when the control DNA is added after amplification, the DNA standard is an extension product generated from a wild-type genomic DNA or a mutant genomic DNA.

By one approach, the DNA from the subject to be screened and the DNA standard are pooled and then the amplification reaction, as described above, is performed. Accordingly, optimal primers are designed and selected and approximately 25 ng-500 ng of template DNA (preferably, 200 ng for human genomic DNA) is suspended in a buffer comprising: 10 mM Tris (pH 8.4), 50 mM KCl, 1.5 mM $MgCl_2$, 200 µM dNTPs, 50 pmol of each primer, and 1 unit Taq polymerase per primer set in a total volume of 50 µl. Preferably, amplification is performed under the same conditions that were used to design the primers. In some embodiments, amplification is performed on a conventional thermal cycler for 30 cycles, wherein each cycle is: 1 minute @ 95° C., 58° C. for 1 minute, 72° C. for 1 minute. Final extension is performed at 72° C. for 5 minutes. When the primers have a GC clamp, however, conditions often favor an amplification reaction having over 40 cycles, wherein each cycle is: 35 seconds @ 95° C., 120 seconds @ 50-57° C., and 60 seconds+3 seconds/cycle @ 72° C.

If the subject being tested has at least one disorder that is detected by the assay then two populations of extension products are generated, a first population that corresponds to the standard DNA and a second population that corresponds to the subject's DNA having at least one mutation or polymorphism. The pool of extension products are desirably isolated from the amplification reactants, as above, and are suspended in a non-denaturing loading buffer. Preferably, the extension products are then denatured by heat (e.g., 95° C. for 5 minutes), and are allowed to anneal by cooling (e.g., ice for 5 minutes) prior to loading on the TTGE denaturing gel or DHPLC column. In this manner, the formation of heteroduplexes will be favored if the subject has a mutation or polymorphism because the two populations of extension products are not perfectly complementary. However, the isolation and denaturing/annealing steps are not necessary for some embodiments.

By another approach, the DNA standard is added to the extension products generated from the tested subject's DNA after the amplification reaction. As above, the pooled DNA sample is preferably denatured by heat (e.g., 95° C. for 5 minutes), and allowed to anneal by cooling (e.g., ice for 5 minutes). This second approach also produces heteroduplexes if the extension product and the DNA standard are not perfectly complementary.

Next, the TTGE denaturing gel or DHPLC column is loaded and the extension products are separated on the basis of melting behavior, as described above. Since heteroduplexes are less stable than homoduplexes and have a lower melting temperature, the presence or absence of a mutation or polymorphism in the tested DNA sample is easily determined. By comparing the migration behavior or elution behavior of the extension products generated from the screened DNA with the migration behavior of the DNA standard, a user can rapidly determine the presence or absence of a mutation or polymorphism (e.g., two additional bands that correspond to the single extension product will appear on the gel when a mutation or polymorphism is present in the tested DNA or a population of extension products will elute from the DHPLC column earlier than homoduplex controls or the majority of homoduplexes present in the sample). The section below describes a method of genetic analysis, wherein improved efficiency and sensitivity of detection was obtained by screening multiple DNA samples in the same assay.

Improved Sensitivity was Obtained When Multiple DNA Samples Were Screened in the Same Assay It was also discovered that an improved sensitivity of detection and increased throughput could be obtained by mixing DNA from a plurality of subjects prior to amplification. Because the frequency of mutations or polymorphisms for most disorders are very low in the population, most of the extension products generated correspond to wild-type or non-polymorphic DNA. Accordingly, most of the DNA in a reaction comprising DNA from a plurality of subjects behave similar to a DNA standard. That is, the predominant structure formed upon annealing after denaturation is a homoduplex, which can be rapidly distinguished from any heteroduplex that would appear if a subject were to have a mutation or polymorphism. Although the reaction is "dirty" from the perspective that the identity of each subject's DNA is not known initially, the identity of any polymorphic or mutant DNA can be determined through a process of elimination. For example, by repeating the analysis with smaller and smaller pools of samples, one can identify the individual(s) in the pool that have the mutation or polymorphism. Additionally, DNA standards can be used, as described above, to facilitate identification of the individual(s) having the mutation or polymorphism.

By one approach, DNA from a plurality of subjects to be tested is obtained by conventional methods, pooled, and hybridized with the desired nucleic acid primers. Accordingly, optimal primers are designed and selected and approximately 25 ng-500 ng of template DNA (preferably, 200 ng for human genomic DNA) is suspended in a buffer comprising: 10 mM Tris (pH 8.4), 50 mM KCl, 1.5 mM $MgCl_2$, 200µM dNTPs, 50 pmol of each primer, and 1 unit Taq polymerase per primer set in a total volume of 50 µl. Preferably, amplification is performed under the same conditions that were used to design the primers. In some embodiments, amplification is performed on a conventional thermal cycler for 30 cycles, wherein each cycle is: 1 minute @ 95° C., 58° C. for 1 minute, 72° C. for 1 minute. Final extension is performed at 72° C. for 5 minutes. When the primers have a GC clamp, however, conditions often favor an amplification reaction having over 40 cycles, wherein each cycle is: 35 seconds @ 95° C., 120 seconds @ 50-57° C., and 60 seconds+3 seconds/cycle @ 72° C.

The pool of extension products are preferably isolated from the amplification reactants, as above, and are suspended in a non-denaturing loading buffer. Preferably, the extension products are then denatured by heat (e.g., 95° C. for 5 minutes), and are allowed to anneal by cooling (e.g., ice for 5 minutes). In this manner, the formation of heteroduplexes will be favored if the subject has a mutation or polymorphism because the two types of extension products are not perfectly complementary. Again, the isolation and denaturing/annealing steps are not performed in some embodiments.

Next, the TTGE denaturing gel or DHPLC column is loaded and the extension products are separated on the basis of melting behavior, as described above. When one of the subjects being tested has at least one trait that is detected by the screen, heteroduplexes are detected on the gel or eluting from the DHPLC column. The assay can be then repeated with smaller pools of samples and assays with a DNA standard can be conducted with individual samples to confirm the identity of the subject having the mutation or polymorphism. EXAMPLE 5 describes an experiment that verified that an improved sensitivity can be obtained by mixing a plurality of DNA samples. EXAMPLE 6 describes an experiment that verified that multiple genes and multiple loci therein can be screened in a plurality of subjects, in a single assay. EXAMPLE 7 describes the screening of multiple genes and multiple loci therein, in a plurality of subjects, in a single assay using a DHPLC approach. The section below describes the optimization of primer design in the context of an approach that was used to detect mutations and/or polymorphisms in the CFTR gene.

Optimization of Primer Design and Extension Product Design Facilitates Identification of Genetic Markers Associated With Cystic Fibrosis A preferred embodiment concerns the identification of the presence or absence of genetic markers, mutations, or polymorphisms in one or more subjects that are associated with cystic fibrosis. By one approach, almost the entire CFTR gene was scanned for the presence or absence of genetic markers, mutations, or polymorphisms that contribute to cystic fibrosis. (See EXAMPLE 8). TABLE A provides the sequences of exons of the CFTR gene and several oligonucleotide primers that have been used to screen regions of the CFTR gene for the presence or absence of genetic markers, polymorphisms, and mutations that are associated with cystic fibrosis. Where indicated, the notation (GC) refers to a GC clamp. TABLE B also lists many oligonucleotide primers that have been used to screen regions of the CFTR gene for the presence or absence of genetic markers, polymorphisms, and mutations that are associated with cystic fibrosis. TABLE B also shows starting and ending point for each primer as it relates to the publicly available gene sequence for the CFTR gene (GenBank Accession No. AH006034, the contents of which are expressly incorporated by reference in its entirety, also provided in SEQ. ID No. 45). It is contemplated that primers that are any number between 5, 10, 15, 20, 25, 30, 35, 40, 45, 50, 55, 60, 65, 70, 75, 80, 85, 90, 95, 100 or more nucleotides upstream or down stream of the primers identified in TABLE A or B can be used with embodiments of the invention so long as these primers produce extension products that melt over long stretches of DNA (approximately 25, 50, 75, 100, 125, or 150 nucleotides) at approximately the same temperature (within 0° C.-1.5° C.) and are resolvable on a TTGE gel or DHPLC column. TABLE B further provides the nucleotide positions on the CFTR gene (GenBank Accession No. AH006034) that are 50 nucleotides upstream or down stream of the listed oligonucleotides. In some embodiments, the primers CF9T-s: (5'TAATGGATCATGGGCCATGT 3' (SEQ. ID. NO. 46)) and CF9T-as: 5' CGCCCGCCGCGCCCCGCGCCCGC-CCCGCCGCCCCGCCCGAAGAGACATG GACAC-CAAAT 3' (SEQ. ID. NO. 47)) are also used.

The sequence of the CFTR gene sequence can also be obtained from GenBank entries AC000061, or AC000111, all of which are herein expressly incorporated by reference in their entireties. Accordingly, embodiments include methods of diagnosing cystic fibrosis with primers that are any number from 1-75 nucleotides upstream or down stream from the beginning or ending of the primers listed in TABLE A or B, preferably using the approaches described herein. It is also preferred that said methods use primers that produce extension products that melt over long stretches of DNA (approximately 25, 50, 75, 100, 125, or 150 nucleotides) at approximately the same temperature (within 0° C.-1.5° C.) and are resolvable on a TTGE gel or DHPLC column. Preferably, these extension products are obtained, grouped, and separated as described below.

By one approach, samples of DNA were obtained from several subjects to be screened using the approaches described herein and were disposed in a plurality of 96-well micro-titer plates such that a single row of each plate corresponded to a single tested subject. In some cases, 7 total plates were used per assay, wherein each plate has 7 sample lanes (i.e., 7 subjects analyzed) and an eighth lane was used for positive control sample DNA. Amplification buffer, amplification enzyme (e.g., Taq polymerase), and DNTPs were added to the sample DNA in each well, as described above, and a plurality of primer sets that encompass the most of the gene (e.g., 61 primer sets) were to yield a final volume of 10 μl. The primer sets that were employed in a first set of tests are identified in TABLE A. TABLE C describes the plate setup for these amplification reactions, whereas TABLE D describes the conditions for the TTGE separation for these tests, whereas TABLE E describes the groupings for the various fragments for TTGE separation. Preferred methods of diagnosing cystic fibrosis employ the primers of TABLE A to generate extension products that are grouped according to TABLE E and separated by melting behavior (e.g., TTGE). By using this approach, a rapid, inexpensive, and efficient diagnosis of the presence or absence of a marker associated with cystic fibrosis can be ascertained. The names of the extension products, "fragments" in TABLE C, TABLE D, and TABLE E correspond to the names of the primer sets used throughout. The "position" refers to the location of the well on the 96 well plate and the "Multi G" refers to the grouping pool of the extension products prior to TTGE.

Although multiplex PCR reactions can be employed, preferably, each primer set is run in an individual reaction. Conditions for PCR were, in one case for example: 5 minutes at 96° C. for initial denaturing followed by 35 total cycles of: 30 seconds at 94° C. and 30 seconds at the annealing temperature or at a gradient of 49° C. to 63° C. and a final 10 minutes at 72° C. to complete synthesis of any partial products. Most preferred are primers that have an annealing temperature between 49° C. and 63° C., though many of the primer sets have annealing temperatures that are at 49° C., 52° C., 59° C., and 62.4° C. (See Appendix H). An approximately 3° C. window is allowed for each plate (e.g., primers having annealing temperatures that are within 3° C. of one another are grouped on a single plate). Programs such as WINMELT were used to determine whether the primers could be grouped into various primer sets that have similar annealing temperatures so that individual groups of primers can be amplified by Polymerase Chain Reaction (PCR) on the same plate.

Once the extension products had been generated they were grouped, pooled, and mixed with loading dye. Thirteen Multi G groups were used and the extension products "fragments" generated by the various primer sets, which belong to one of the thirteen groups are identified in TABLE C and TABLE E. After grouping and pooling, the samples were loaded onto a TTGE gel. TABLE C also lists the start and stop temperatures for the TTGE, for each Multi G group. Preferably, the TTGE is run with a very shallow temperature gradient, e.g., about 1.0° C./hour for a total of three hours, at high voltage, e.g., 150 volts. Once the separation was complete, the gels were grouped, stained with ethidum bromide, and analyzed by the Decode system. The analysis above was rapid, inexpensive, and very effective at detecting mutations and/or polymorphisms, many of which go undetected or are not analyzed by others in the field.

Figure 2:
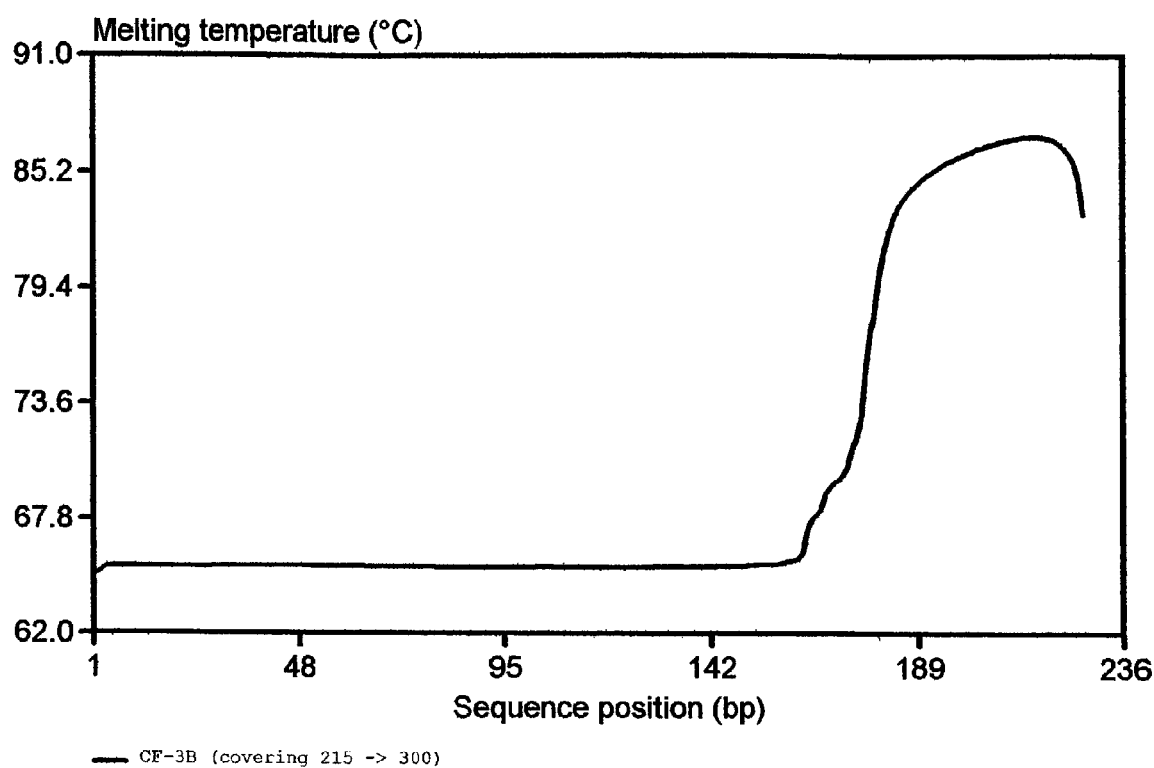
FIG. 2 shows a melting curve for the extension product CF3B spanning nucleotides 215-300 of the CFTR gene. The x axis shows the number of nucleotides and the y axis shows the temperature.
Figure 3:
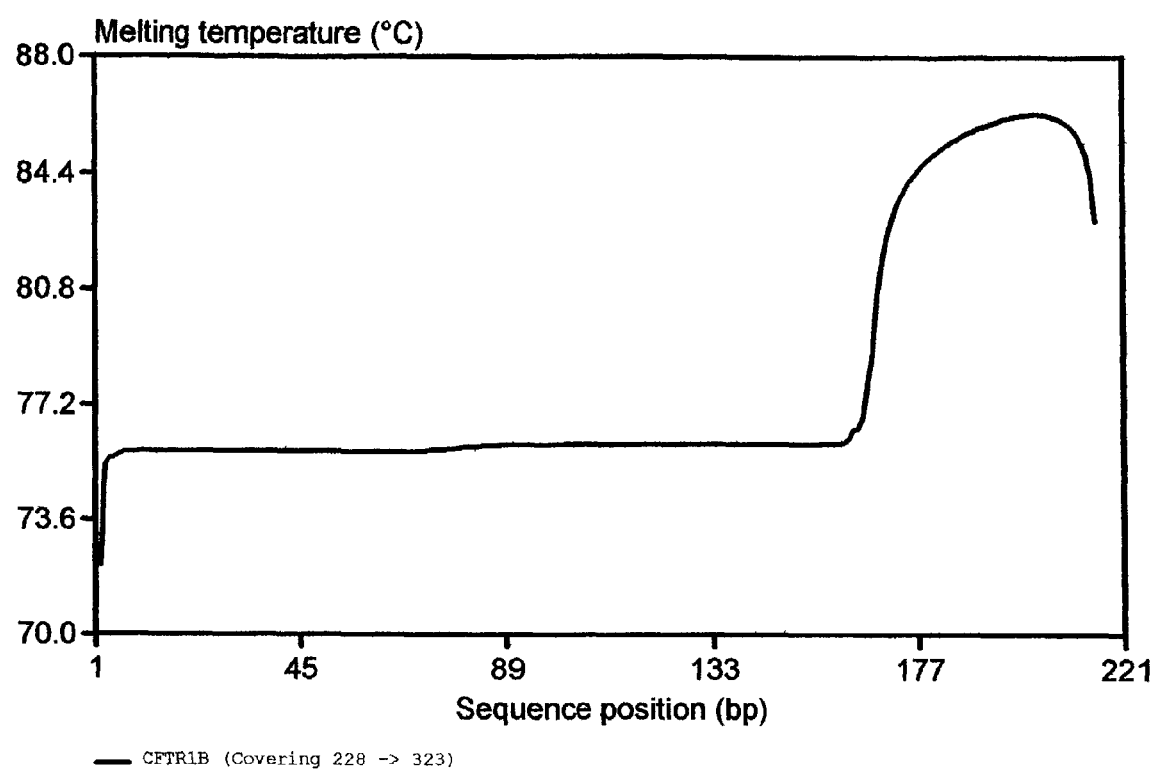
FIG. 3 shows a melting curve for the extension product CFTR1B spanning nucleotides 228-323 of the CFTR gene. The x axis shows the number of nucleotides and the y axis shows the temperature.
Figure 4:
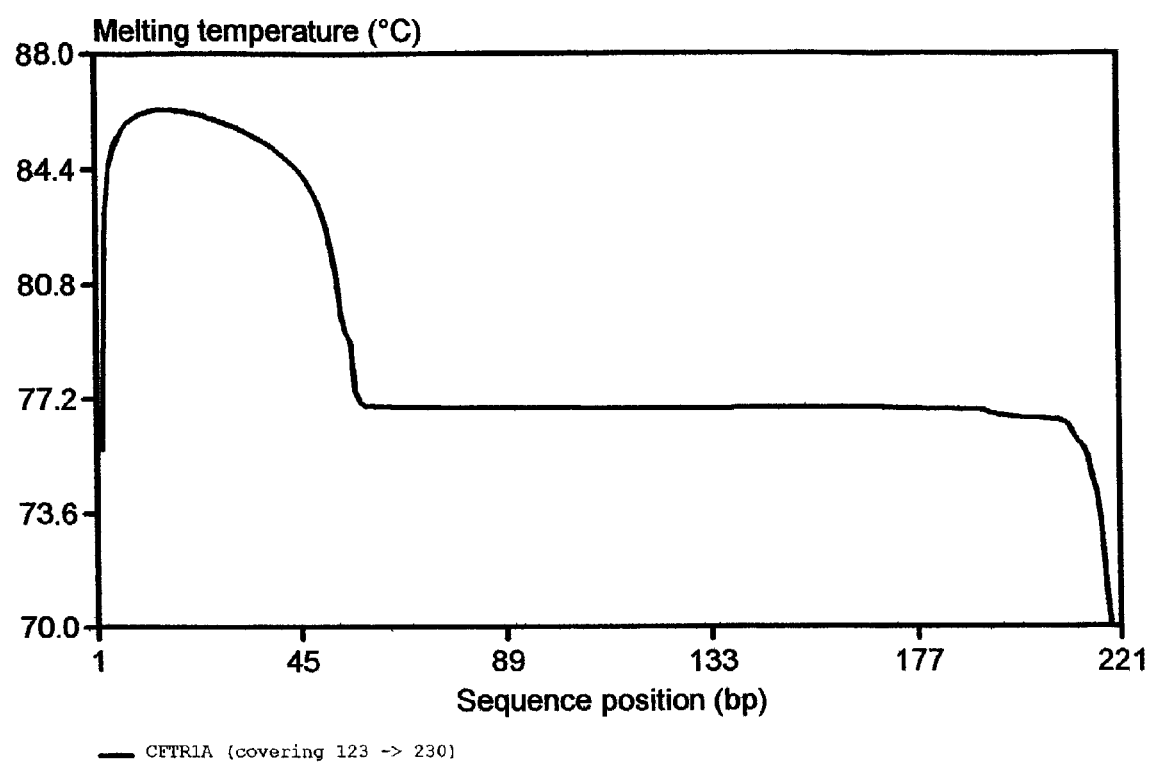
FIG. 4 shows a melting curve for the extension product CFTR1A spanning nucleotides 123-230 of the CFTR gene. The x axis shows the number of nucleotides and the y axis shows the temperature.

Whereas many in the field seek to design primers that optimally anneal with a template DNA, it has been discovered that primers can also be designed to produce an optimal extension product (e.g., a fragment of short length with a reliable and rapid melting point). Preferably, primers are designed to generate extension products that are approximately 100-300 nucleotides in length and that have long stretches of DNA that melt at approximately the same temperature (e.g., DNA stretches that are 25, 35, 45, 55, 65, 75, 85, 95, 100, 125, 15, 175, or 200 nucleotides that melt at the same temperature or within about a 0° C. to about a 1.5° C. temperature difference). Programs such as WINMELT were used to evaluate the melting behavior of extension products generated from the various primer sets and test TTGE separation of the extension products generated by the various primer sets were also performed to ensure that the predicted melting behavior was represented on the gel. FIGS. 1-4 show graphs of four extension products produced by two of the primer sets, described herein. The flat melting curve is preferred for the applications described herein because the extension products melt rapidly and are quickly retarded in the gel, which improves resolution and allows multiple different extension products to be separated in the same lane on a TTGE gel. That is, by grouping extension products that have flat melting profiles, which are within approximately 1.5° C. of one another, it allows a shallow TTGE temperature ramp (e.g., 1° C. change per hour for 3 hours) or shallow DHPLC temperature ramp, which increases the sensitivity, allowing multiple extension products to be separated in the same lane, which increases throughput and reduces the cost of the analysis.

TABLE E shows several of the characteristics of the extension products generated by the primers described herein. In particular, the PCR annealing temperature for the primer set used to generate the extension product ("PCR temp.") and a subjective rating of performance is provided. The approximate melting temperature ("App Tm") of the extension product and its length with and without the GC clamp is provided. A range for the predicted annealing temperature for the PCR and the range for the actual annealing temperature for PCR is provided. The TTGE melting temperature range is also given. Further, the Multi G group is also listed. The following examples describe the foregoing methodologies in greater detail. The first example describes an approach that was used to isolate DNA from human blood.

EXAMPLE 1

A sample of blood was obtained from a subject to be tested by phlebotomy. A portion of the sample (e.g., approximately 1.0 ml) was added to approximately three times the sample volume or 3.0 ml of a lysis solution (10 mM $KHCO_3$, 155 mM $NH_4Cl$, 0.1 mM EDTA) and was mixed gently. The lysis solution and blood were allowed to react for approximately five minutes. Next, the sample was centrifuged (×500 g) for approximately 2 minutes and the supernatant was removed. Some of the supernatant was left (e.g., on the walls of the vessel) to facilitate suspension. The pellet was then vortexed for approximately 5-10 seconds. An extraction solution, which contains chaotropc and detergent (Qiagen), was then added (e.g., 500 μl), the sample was vortexed again for approximately 5-10 seconds, and the solution was allowed to react for five minutes at room temperature.

Next, a GFX column, which are pre-packed columns containing a glass fiber matrix, was placed under vacuum (e.g., a Microplex 24 vacuum system) and the extracted solution containing the DNA was transferred to the column (e.g., in 500 µl aliquots). Once all of the sample has been passed through the column, the vacuum was allowed to continue for approximately 5 minutes. Subsequently, a wash solution (Tris-EDTA buffer in 80% ethanol) was added (e.g., approximately 500 µl) under vacuum. Once the wash solution had been drained from the column, the vacuum was allowed to continue for approximately 15 minutes. The GFX columns containing the DNA were then placed into sterile microfuge tubes but the lids were kept open.

Elution buffer (10 mM Tris-HCl, 1 mM EDTA, pH 8.0) was then added to the column (e.g., approximately 100 µl of buffer that was heated to approximately 70° C.) and the buffer was allowed to react with the column for approximately 2 minutes. Then, the tubes containing the columns were centrifuged at ×5000 g for approximately 1.5 minutes. After centrifugation, the column was discarded and the microfuge tube containing the isolated DNA was stored at −20° C. The example below describes the design and optimization of primers that allowed for the inventive high-throughput multiplex PCR technique, described herein.

EXAMPLE 2

Sets of primers for PCR amplification were designed for every exon of the following genes: Cystic Fibrosis Transmembrane Reductase (CFTR), Beta-hexosaminidase alpha chain (HEXA), PAH, Alpha globin-2 (HBA2), Beta globin (HBB), Glucocerebrosidase (GBA), Galactose-1-phosphae uridyl transferase (GALT), Medium chain acyl-CoA dehydrogenase (MCAD), Protease inhibitor 1 (PI), Factor VIII, FMR1, and Aspartoacylase (ASPA). The primers were designed from sequence information that was available from GenBank or from sequence information obtained from Ambry Genetics Corporation. Information regarding mutations or polymorphisms was obtained from The Human Gene Mutation Database.

One of the primers in each primer set contained a GC-clamp. It was discovered that the addition of a GC-clamp significantly altered the melting profile of the DNA extension product. Further, proper positioning of the GC-clamp served to level the melting profile. It was desired to position the GC-clamp so that a single melting domain across the fragment was created. Proper positioning of the GC-clamp was oftentimes needed to prevent the GC-clamp from masking the presence of a mutation or polymorphism (e.g., if the mutation or polymorphism is too close to the GC-clamp). Software was also used to optimize primer design. For example, many primers were designed with the aid of Primer Premiere 4.0 and 5.0 and appropriate positioning of the GC-clamps was determined using WinMelt software from BioRad. To maintain sensitivity of the test, the primers were designed to anneal at a minimum of 40 base pairs either upstream or downstream of the nearest known mutation in the intronic region of the genes.

Although multiplex PCR can be technically difficult when using the quantity of primers described herein, it was discovered that almost all of the PCR artifacts disappeared when salt concentration, temperature, primer selection, and primer concentration were carefully optimized. Optimization was determined for each primer set alone and in combination with other primer sets. Optimization experiments were conducted using Master Mix from Qiagen and a Thermocyler from MJ Research. The conditions for thermal cycling were 5 minutes @ 95° C. for the initial denaturation, then 30 cycles of: 30 seconds @ 94° C., 45 seconds @ 48-68° C., and 1 minute @ 72° C. A final extension was performed at 72° C. for 10 minutes.

In addition to primer compatibility, primers were selected to facilitate identification of extension products by electrophoresis. To optimize primer design in this regard, separate PCR reactions were conducted for each individual set of primers and the extension products were separated by the inventive DNA separation technique, described above. Identical parameters were maintained for each assay and the migration behavior for each extension product was analyzed (e.g., compared to a standard to determine a $R_f$ value for each fragment). An $R_f$ value is a unit less value that characterizes a fragment's mobility relative to a standard under set conditions. In many primer optimization experiments, for example, the generated extension products were compared to a standard extension product obtained from amplification of the first exon of the PAH (phenylalanine hydroxylase) gene. A measurement of the distance of migration of each band in comparison to the distance of migration of the first exon of PAH was recorded and the $R_f$ value was calculated according to the following:

$$R_f = \frac{\text{(migration distance of fragment) cm}}{\text{(migration distance of PAH exon 1) cm}}$$

By conducting these experiments, it was verified that the selected primers did not produce extension products that overlapped on the gel. Optimal primer selection was obtained when optimal PCR parameters were maintained and the extension products produced dissimilar $R_f$ values. Finally, the multiplex PCR was tested with all sets of primers and it was verified that few artifacts were created during amplification. Embodiments of the invention include the primers provided in the tables and sequence listing provided herein and methods of using said primers and/or groups of primers. The example below describes an experiment that verified that the embodiments described herein effectively screen multiple loci present on a plurality of genes in a single assay.

EXAMPLE 3

Two independent PCR reactions were conducted to demonstrate that multiple loci on a plurality of genes can be screened in a single assay using an embodiment of the invention. In a first reaction, seven different loci from four different genes were screened and, in the second reaction, eight different loci from four different genes were screened. The primers used in each multiplex reaction are provided in TABLE 1.

TABLE 1*

| Multiplex #1 | Multiplex #2 |
| --- | --- |
| Factor VIII 4 | CFTR 23 |
| (SEQ. ID. Nos. 7 and 25) | (SEQ. ID. Nos. 3 and 21) |
| Factor VIII 11 | CFTR 18 |
| (SEQ. ID. Nos. 9 and 27) | (SEQ. ID. Nos. 2 and 20) |
| Factor VIII 24 | Factor VIII 11 |
| (SEQ. ID. Nos. 10 and 28) | (SEQ. ID. Nos. 9 and 27) |
| PAH 9 | Factor VIII 3 |
| (SEQ. ID. Nos. 18 and 36) | (SEQ. ID. Nos. 6 and 24) |
| GBA 6 | CFTR 24 |
| (SEQ. ID. Nos. 15 and 33) | (SEQ. ID. Nos. 37 and 38) |

TABLE 1*-continued

| Multiplex #1 | Multiplex #2 |
|---|---|
| Factor VIII 1 (SEQ. ID. Nos. 4 and 22) | GBA 4 (SEQ. ID. Nos. 14 and 32) |
| GALT 9 (SEQ. ID. Nos. 17 and 35) | GALT 9 (SEQ. ID. Nos. 17 and 35) |
| | GBA 3 (SEQ. ID. Nos. 13 and 31) |

*Primers are stored in a 50 μM storage stock and a 12.5 μM working stock. Abbreviations are: Phenyl alanine hydroxylase (PAH), Glucocerebrosidase (GBA), Galactose-1-phosphate uridyl transferase (GALT), and cystic fibrosis transmembrane reductase (CFTR). The numbers following the abbreviations represent the exons probed.

The amplification was carried out in 25 μl reactions using a 2× Hot Start Master Mix, which contains Hot Start Taq DNA Polymerase, and a final concentration of 1.5 mM $MgCl_2$ and 200 μM of each dNTP (commercially available from Qiagen). In each reaction, 12.5 μl of Hot Start Master Mix was mixed with 1 μl of genomic DNA (approximately 200 ng genomic DNA), which was purified from blood using a commercially available blood purification kit (Pharmacia or Amersham). Primers were then added to the mixture (0.5 μM final concentration of each primer). Then, $ddH_2O$ was added to bring the final volume to 25 μl.

Thermal cycling for the Multiplex #1 reaction was performed using the following parameters: 15 minutes @ 95° C. for 1 cycle; 30 seconds @ 94° C., 1 minute @ 53° C., 1 minute and 30 seconds @ 72° C. for 35 cycles; and 10 minutes @ 72° C. for 1 cycle. Thermal cycling for the Multiplex #2 reaction was performed using the following parameters: 15 minutes @ 95° C. for 1 cycle; 30 seconds @ 94° C., 1 minute @ 49° C., 1 minute and 30 seconds @ 72° C. for 35 cycles; and 10 minutes @ 72° C. for 1 cycle.

After the amplification was finished, approximately 5 μl of each PCR product was mixed with 5 μl of non-denaturing gel loading dye (70% glycerol, 0.05% bromophenol blue, 0.05% xylene cyanol, 2 mM EDTA). The DNA in the two reactions was then separated on the basis of melting behavior on separate denaturing gels. Each gel was a 16×16 cm, 1 mm thick, 7M urea, 8% acrylamidelbis (37.5:1) gel composed in 1.25× TAE (50 mM Tris, 25 mM acetic acid, 1.25 mM EDTA). Separation was conducted for 4 hours at 150 V on the Dcode system (BioRad) and the temperature ranged from 51° C. to 63° C. with a temperature ramp rate of 3° C./hour. Subsequently, the gels were stained in 1 μg/ml ethidium bromide in 1.25×TAE for 3 minutes and destained in 1.25×TAE buffer for 20 minutes. The gels were then photographed using the Gel Doc 1000 system from BioRad.

The primers in TABLE 1 were selected and manufactured because they produced extension products with very different $R_f$ values and the extension products were clearly resolved by separation on the basis of melting behavior. Although some bands were more visible than others on the gel, seven distinct bands were observed on the gel loaded with extension products generated from the Multiplex 1 reaction and eight distinct bands were observed on the gel loaded with extension products generated from the Multiplex 2 reaction. These results verified that the described method effectively screened multiple loci on a plurality of genes in a single assay. The example below describes another experiment that verified that the embodiments described herein can be used to effectively screen multiple loci present on a plurality of genes in a single assay.

EXAMPLE 4

Experiments were conducted to differentiate extension products generated from wild-type DNA and extension products generated from mutant DNA. Samples of genomic DNA that had been previously identified to contain mutations or polymorphisms were purchased from Coriell Cell Repositories. The mutation or polymorphism that was analyzed in this experiment was the delta-F508 mutation of the CFTR gene. This mutation is a 3 bp deletion in exon 10 of the CFTR gene. Other loci analyzed in these experiments included the Fragile X gene, exon 17; Fragile X gene, exon 3; Factor VIII gene exon 2; and the Factor VIII gene, exon 7. Both the known mutant and a control wild-type for CFTR exon 10 were amplified within a multiplex reaction and individually.

PCR amplification was conducted as described in EXAMPLE 3; however, 0.25 μM (final concentration) of each primer was used. The primers used in these experiments were CFTR 10 (SEQ. ID. Nos. 1 and 19), FragX 17 (SEQ. ID. Nos. 12 and 30), FragX 3 (SEQ. ID. Nos. 11 and 29), Factor VIII 7 (SEQ. ID. Nos. 8 and 26) and Factor VIII 2 (SEQ. ID. Nos. 5 and 23). The numbers following the abbreviations represent the exons probed.

The DNA templates that were analyzed included known wild-type genomic DNA, known mutant genomic DNA, mixed wild-type genomic DNA from various subjects, and mixed wild-type and mutant genomic DNA. Approximately 200 ng of genomic DNA was added to each reaction. The mixed wild-type and mutant DNA sample had approximately 100 ng of each DNA type. Thermal cycling was carried out with a 15-minute. step at 95° C. to activate the Hot Start Polymerase, followed by 30 cycles of 30 seconds at @ 94° C., 1 minute at @ 53° C., 1 minute and 30 seconds at @ 72° C.; and 72° C. for 10 minutes.

After amplification, approximately 5 μl of the PCR product was mixed with 51 μl of non-denaturing gel loading dye (70% glycerol, 0.05% bromophenol blue, 0.05% xylene cyanol, 2 mM EDTA). The samples were then separated on a 16×16 cm, 1 mm thick, 6M urea, 6% acrylamide/bis (37.5:1) gel in 1.25×TAE (50 mM Tris, 25 mM acetic acid, 1.25 mM EDTA) for 5 hours at 130 V using the Dcode system (BioRad). The temperature ranged from 40° C. to 50° C. at a temperature ramp rate of 2° C./hour. The gels were then stained in 1 μg/ml ethidium bromide in 1.25×TAE for 3 minutes and destained in 1.25×TAE buffer for 20 minutes. The gels were then photographed using the Gel Doc 1000 system from BioRad.

The resulting gel revealed that the lane containing the extension products generated from the wild-type DNA using the CFTR10 primers had a mobility commensurate to the wild-type DNA standard, as did the extension products generated from the other primers and the wild-type DNA. That is, a single band appeared on the gel in these lanes. The lane containing the extension products generated from the template having the F508 mutant, on the other hand, showed 2 bands. One of the bands had the same mobility as the extension products generated from the wild-type or DNA standard and the other band migrated slightly faster. These two populations of bands represent the two populations of homoduplexes (i.e., wild-type/wild-type and mutant/mutant). The top band is the wild-type homoduplex and the lower band is the mutant F508 homoduplex. Similarly, the lane that contained the wild-type/mutant DNA mix exhibited two populations of extension products, one representing the wild-type homoduplex population and the other representing the mutant homoduplex. Since F508 is a 3 bp deletion it failed to form heteroduplex bands in sufficient quantity to be visible on the gel. Thus, this experiment demonstrated that the described method effectively screened multiple genes, in a single assay, and detected the presence of a polymorphism in one of the screened genes. The example below describes an experiment that demonstrated that an improved sensitivity can be obtained by mixing a plurality of DNA samples.

EXAMPLE 5

This example describes two experiments that verified that an improved sensitivity of detection can be obtained by (1) mixing the DNA samples from a plurality of subjects prior to amplification or by (2) mixing amplification products before separation on the basis of melting behavior. In these experiments, PCR amplifications of exon 9 of the GBA gene (Glucocerebrosidase gene) were used. DNA samples known to contain a mutation in exon 9 of the GBA gene were purchased from Coriell Cell Repositories. These DNA samples contain a homozygous mutation in exon 9 of the GBA gene (the N370S mutation).

In a first experiment, single amplification of exon 9 was performed in a 25 µl reaction. A Taq PCR Master Mix (containing Taq DNA Polymerase and a final concentration of 1.5 mM $MgCl_2$ and 200 µM dNTPs)(Qiagen) was mixed with 0.5 µM (final concentration) of primers (SEQ. ID. Nos. 16 and 34). The template genomic DNAs analyzed in this experiment included wild-type DNA, mutant DNA, and various mixtures of wild-type and mutant DNA. For the single non-mixed reactions, approximately 200 ng of genomic DNA was used for amplification. In the mixed samples, approximately 200 ng of DNA was again used, however, the percentage of wild-type to mutant genomic DNA varied. Thermal cycling was performed according to the following parameters: 10 minutes @ 94° C.; 30 cycles of 30 seconds @ 94° C., 1 minute @ 44.5° C., and 1 minutes and 30 seconds @ 72° C.; and 10 minutes @ 72° C.

In the second experiment, the amplification products were mixed prior to separation on the basis of melting behavior. Amplification of both wild-type and mutant (N370S) exon 9 of the GBA gene was performed using 25 µl reactions, as before. The Taq Master Mix obtained from Qiagen was mixed with 200 ng of genomic DNA and 0.5 µM final concentration of both primers (SEQ. ID. Nos. 16-34). PCR was carried out for 30 cycles with an annealing temperature of 56° C. for 1 minute. The denaturation and elongation steps were 94° C. for 30 seconds and 72° C. for 1 minute and 30 seconds. Final elongation was carried out at 72° C. for 10 minutes. The extension products obtained from the single amplification of wild-type GBA exon 9 was then mixed with the extension products obtained from the single amplification of the mutant GBA exon 9. Next, the pooled DNA was subjected to denaturation at 95° C. for 10 minutes and cooled on ice for 5 minutes, then heated to 65° C. for 5 minutes and cooled to 4° C. This denaturation and annealing procedure was performed to facilitate the formation of heteroduplex DNA.

Once the extension products from both experiments were in hand, approximately 5 µl of both the prior to PCR mixture and post PCR mixture were loaded on 16×16 cm, 1 mm thick gels (7M Urea/8% acrylamide (37.5:1) gel in 1.25×TAE) using the gel loading dye and the Dcode system (BioRad), described above. The DNA on the gel was then separated at 150V for 5 hours and the temperature was uniformly raised 2° C./hour throughout the run starting at 50° C. and ending at 60° C. The gel was stained in 1 µg/ml ethidium bromide in 1.25× TAE buffer for 3 minutes and destained in buffer for 20 minutes.

It should be noted that the GBA gene has a pseudo gene, which was co-amplified by the procedure above. An extension product generated from this psuedo gene migrated slightly faster than the extension product generated from the true expressed gene on the gel. In all lanes, the band representing the extension product generated from the psuedo gene was present. Then next fastest band on the gel was the extension product generated from the GBA exon 9 wild-type allele. The extension product generated from the mutant GBA exon 9 allele comigrated with the wild-type allele and was virtually indistinguishable on the basis of melting behavior due to the single base difference.

The heteroduplexes formed in the mixed samples were easily differentiated from the homoduplexes. The samples mixed prior to PCR showed both homoduplexes (wild-type and mutant) along with heteroduplexes, which appeared higher on the gel. Thus, by mixing samples, either prior to amplification or prior to separation on the basis of melting behavior an improved sensitivity of detection was obtained. Since homoduplex bands no longer need to be resolved to identify a mutation or polymorphism, only the heteroduplex bands need to be resolved, the throughput of diagnostic analysis was greatly improved. The example below describes experiments that verified that the embodiments taught herein can be used to effectively screen multiple genes in a plurality of subjects, in a single assay, for the presence or absence of a polymorphism or mutation.

EXAMPLE 6

Two experiments were conducted to verify that multiple genes from a plurality of subjects can be screened in a single assay for the presence or absence of a genetic marker (e.g. a polymorphism or mutation) that is indicative of disease. These experiments also demonstrated that an improved sensitivity of detection could be obtained by mixing DNA samples either prior to generation of extension products or prior to separation on the basis of melting behavior.

In both experiments, five different extension products were generated from three different genes in a single reaction vessel. The five different extension products were generated using the following primers: Factor VIII 1 (SEQ. ID. Nos. 4 and 22); GBA 9 (SEQ. ID. Nos. 16 and 34); GBA 11 (SEQ. ID. Nos. 39 and 40); GALT 5 (SEQ. ID. Nos. 41 and 42), and GALT 8 (SEQ. ID. Nos. 43 and 44). Abbreviations are: Glucocerebrosidase (GBA) and Galactose-1-phosphate uridyl transferase (GALT). The numbers following the abbreviations represent the exons probed.

Extension products were generated for each experiment in 25µl amplification reactions using Qiagen's 2× Hot Start Master Mix (Contains Hot Start Taq DNA Polymerase, and a final concentration of 1.5 mM $MgCl_2$ and 200 µM of each dNTP). To each reaction, 12.5 µl of Hot Start Master Mix was added to 1 µl of genomic DNA (approximately 200 ng genomic DNA for the mutant DNA sample and the wild-type DNA sample), which was purified from human blood using Pharmacia Amersham Blood purification kits. For the experiment in which the DNA samples from a plurality of subjects were mixed prior to generation of the extension products, approximately 100 ng of wild-type genomic DNA was mixed with approximately 100 ng of mutant N370S genomic DNA. In both experiments, primers were added to achieve a final concentration of 0.5 µM for each primer and a final volume of 25 µl was obtained by adjusting the volume with $ddH_2O$.

Thermal cycling for both experiments was performed using the following parameters: 15 minutes @ 95° C. for 1 cycle; 30 seconds @ 94° C., one minute @ 57° C., and one minute 30 seconds @ 72° C. for 35 cycles; and 10 minutes @ 72° C. for 1 cycle. After amplification, the extension products generated from the wild-type and mutant templates (the unmixed samples) were separated from the PCR reactants using a PCR Clean Up kit (Qiagen). Then, approximately 10 μL of the wild-type and mutant DNA were removed from each tube and gently mixed in a single reaction vessel. This preparation was then denatured at 95° C. for 1 minute and rapidly cooled to 4° C. for 5 minutes. Finally, the preparation was brought to 65° C. for an additional 1.5 minutes. The extension products generated from the mixed sample (wild-type DNA and mutant DNA mixed prior to amplification) were stored until loaded onto a denaturing gel.

Next, approximately 10 μl of the unmixed sample was combined with 10 μl of loading dye and approximately 5 μl of the mixed sample was combined with 5 μl of loading dye. The loading dye was composed of 70% glycerol, 0.05% bromophenol blue, 0.05% xylene cyanol, and 2 mM EDTA). The samples in loading dye were then loaded on separate 16×16 cm, 1 mm thick, 7M urea, 8% acrylamidelbis (37.5:1) gels in 1.25×TAE (50 mM Tris, 25 mM acetic acid, 1.25 mM EDTA). The DNA was separated on the basis of melting behavior for 5 hours at 150 V on the Dcode system (BioRad). The temperature ranged from 56° C. to 68° C. at a temperature ramp rate of 2° C./hr. The gels were then stained in 1 μg/ml ethidium bromide in 1.25×TAE for 3 minutes and destained in 1.25×TAE buffer for 20 minutes. The gels were photographed using the Gel Doc 1000 system (BioRad).

In all lanes of the gel, 5 extension products generated from three different genes were visible in the following order from top to bottom: Factor VIII 1, GBA 9, GBA 11, GALT 8, and GALT 5. Two different extension products were generated from the GBA 9 primers, as described above. The less intense band below the homoduplex bands corresponded to an extension product generated from the pseudogene. In the lanes loaded with extension products generated from only the wild-type or mutant DNA template, it was difficult to distinguish the wild type homoduplex from the N370S mutant homoduplex. In the lane loaded with the extension products generated from the mixed DNA templates (wild-type and mutant DNA mixed prior to amplification) and the lane loaded with extension products (generated from wild type and mutant DNA separately) that were mixed after amplification, heteroduplex bands were easily visualized. These experiments verified that multiple genes can be screened in a plurality of individuals in a single assay and that a single nucleotide mutation or polymorphism can be detected. Further, these experiments demonstrate that screening a plurality of DNA samples in a single reaction vessel or adding a control DNA before or after amplification greatly improves the sensitivity of detection. By practicing the methods taught in this example, the throughput of diagnostic screening can be drastically improved and the cost of identifying genetic traits can be significantly reduced. The example below describes approaches to screen multiple genes in a plurality of subjects, in a single assay, for the presence or absence of a polymorphism or mutation using DRPLC.

EXAMPLE 7

Multiple genes in a plurality of subjects, in a single assay, can be screened for the presence or absence of a polymorphism or mutation using a DHPLC separation approach. For example, five different extension products can be generated using the following primers: Factor VIII 1 (SEQ. ID. Nos. 4 and 22); GBA 9 (SEQ. ID. Nos. 16 and 34); GBA 11 (SEQ. ID. Nos. 39 and 40); GALT 5 (SEQ. ID. Nos. 41 and 42), and GALT 8 (SEQ. ID. Nos. 43 and 44). Abbreviations are: Glucocerebrosidase (GBA) and Galactose-1-phosphate uridyl transferase (GALT). The numbers following the abbreviations represent the exons probed. The extension products can be generated in 25 μl amplification reactions using Qiagen's 2× Hot Start Master Mix (Contains Hot Start Taq DNA Polymerase, and a final concentration of 1.5 mM $MgCl_2$ and 200 μM of each dNTP).

To each reaction, 12.5 μl of Hot Start Master Mix is added to 1 μl of genomic DNA (approximately 200 ng genomic DNA for the mutant DNA sample and the wild-type DNA sample), which is purified from human blood using Pharmacia Amersham Blood purification kits. By another approach, the DNA samples from a plurality of subjects can be mixed prior to generation of the extension products. In this case, approximately 100 ng of wild-type genomic DNA is mixed with approximately 100 ng of mutant N370S genomic DNA. Primers are added to achieve a final concentration of 0.5 μM for each primer and a final volume of 25 μl is obtained by adjusting the volume with $ddH_2O$.

Thermal cycling is performed using the following parameters: 15 minutes @ 95° C. for 1 cycle; 30 seconds @ 94° C., one minute @ 57° C., and one minute 30 seconds @ 72° C. for 35 cycles; and 10 minutes @ 72° C. for 1 cycle. After amplification, the extension products generated from the wild-type and mutant templates (if un-mixed samples) are separated from the PCR reactants using a PCR Clean Up kit (Qiagen). Then, approximately 10 μL of the wild-type and mutant DNA are removed from each tube and gently mixed in a single reaction vessel. This preparation is then denatured at 95° C. for 1 minute and rapidly cooled to 4° C. for 5 minutes. Finally, the preparation is brought to 65 ° C. for an additional 1.5 minutes. The extension products generated from the mixed sample (wild-type DNA and mutant DNA mixed prior to amplification) can be stored until loaded onto a DHPLC column.

Next, the extension products are loaded on to a 50×4.6 mm ion pair reverse phase HPLC column that is equilibrated in degassed Buffer A (0.1 M triethylamine acetate (TEAA) pH 7.0) at 56° C. A linear gradient of 40%-50% of degassed Buffer B (0.1 M triethylamine acetate (TEAA) pH 7.0 and 25% acetonitrile) is then performed over 2.5 minutes at a flow rate of 0.9 ml/min at 56° C., followed by a linear gradient of 50%-55.3% Buffer B over 0.5 minutes, and finally a linear gradient of 55.3%-61% Buffer B over 4 minutes. U.V. absorption is monitored at 260 nm, recorded and plotted against retention time.

When the loaded sample is un-mixed extension products, the extension products generated from only the wild-type or mutant DNA template, it is difficult to distinguish the wild type homoduplex from the N370S mutant homoduplex. When the loaded sample is the mixed extension products, the extension products generated from the mixed DNA templates (wild-type and mutant DNA mixed prior to amplification), or the extension products (generated from wild type and mutant DNA separately) that were mixed after amplification, heteroduplex elution behavior is detected. By practicing the methods taught in this example, the throughput of diagnostic screening can be drastically improved and the cost of identifying genetic traits can be significantly reduced. The example below describes an approach that was used to diagnostically screen patient samples for cystic fibrosis.

EXAMPLE 8

Sets of primers for PCR amplification were designed for every exon and one deep intronic region of the CFTR gene. The primers were designed from sequence information that was available from GenBank or from sequence information obtained from Ambry Genetics Corporation. Information regarding mutations or polymorphisms was obtained from The Human Gene Mutation Database.

Primer sets and PCR stacking groups were designed for optimal sensitivity for TTGE, as described above. DNA from one individual was amplified with each primer set in a separate reaction, then stacked in average groups of three fragments/gel for gel analysis. Preferably, one of the primers in each primer set contained a GC-clamp. It was discovered that the addition of a GC-clamp significantly altered the melting profile of the DNA extension product. Further, proper positioning of the GC-clamp served to level the melting profile. It was desired to position the GC-clamp so that a tight single melting domain across the fragment was created. Proper positioning of the GC-clamp was often times needed to prevent the GC-clamp from masking the presence of a mutation or polymorphism (e.g., if the mutation or polymorphism is too close to the GC-clamp). Software was also used to optimize primer design. For example, many primers were designed with the aid of Primer Premiere 4.0 and 5.0 and appropriate positioning of the GC-clamps was determined using WinMelt software from BioRad. To maintain sensitivity of the test, the primers were designed to anneal at a minimum of 40 base pairs either upstream or downstream of the nearest known mutation in the intronic region of the genes.

Optimization was determined for each primer set. Optimization experiments were conducted using Hotstart Master Mix from Qiagen and a Thermocyler from MJ Research. Resulting PCR conditions for all fragments were 15 minutes @ 95° C. for the initial denaturation, then 35 cycles of: 30 seconds @ 94° C., 30 seconds @ 46-62° C., and 30 seconds @ 72° C. A final extension was performed at 72° C. for 10 minutes. Approximately 15 µl PCR reactions contained 7.5 µl Qiagen 2× Hotstart Master Mix, 50-200 ng genomic DNA, sense and antisense primer for each fragment at a final concentration of 0.5-1 µM. Prior to gel loading and stacking of gel groups PCR samples were heated and re-annealed to provide best heteroduplex formation. PCR product was heated to 95° C. for 5 min, 50° C. for 10 min, then brought to 4° C.

On occasion, diagnostic patient samples may contain mutations that are homozygous in nature, and sporadically homozygous mutation band may settle in line with the wild-type band. The most common mutation for CF (allele frequency ~70% known as dF508) has this situation. Therefore, wild-type gDNA was always mixed with the diagnostic sample for exon 10 (primer set 10C) and heteroduplex formation was performed. This creates heteroduplex bands which will predict a dF508, either homozygous or heterozygous for the patient. Approximately 4 µl of the 10C-amplified PCR sample from each patient was removed from the PCR plate, transferred into 200 µl strip tubes, mixed with 4 µl of 10C amplified wild type DNA, heated to 95° C. for 5 min, 50° C. for 10 min, 4° C. and added back to the assay.

PCR products (approximately 4-8 µl each depending on signal strength) were then assembled for groups of equal melting characteristics and mixed with loading dye consisting of 70% glycerol, 0.05% bromophenol blue, 0.05% xylene cyanol, 2 mM EDTA). DNA was separated on denaturing gels (7 M urea, 8% acrylamide/bis (37.5:1) in 50 mM Tris, 25 mM acetic acid, 1.25 mM EDTA) for 3-5 hours at 125 V or 150 V on the Dcode system. (Biorad). Temperature ranged from 45.5° C. to 64° C. with ramp rates of 1.0-1.5° C./hr depending on gel groups. The gels were stained in 1 µg/ml ethidium bromide in 1.25×TAE for 3 minutes and destained in 1.25× TAE buffer for 20 minutes. The gels were photographed using the Gel Doc 1000 system (BioRad). TABLE 2 lists the primers used in this assay. TABLE 3 shows the TTGE gel grouping and temperatures used for TTGE separation. TABLE 3 also names the extension products generated from the various primer sets employed and the positions of each fragment on the gel after separation. Previous experiments, described above, have demonstrated that extension products generated from primers that are any number between 1-75 nucleotides upstream or downstream from the primers listed in TABLE A (e.g., the primer sets listed in TABLE 2) can be grouped and efficiently separated in accordance with rules set forth herein. Preferably, the primers listed in TABLE 2 are used to generate extension products that are grouped according to TABLE 3 and are separated on the basis of melting behavior (e.g., TTGE).

TABLE 2

| | |
|---|---|
| CFTR1A-s | CGCCCGCCGCGCCCCGCGCGCCCGCCCCGCCGCCCCCGCCCGGGAAGCCAAATGA CATCACAGC (SEQ. ID. No. 48) |
| CFTR1A-as | TGAAAAAAAGTTTGGAGACAACGC (SEQ. ID. No. 49) |
| CFTR1B-s | CCCAGCGCCCAGAGACC (SEQ. ID. No. 50) |
| CFTR1B-as | CGCCCGCCGCGCCCCGCGCCCGCCCCGCCGCCCCCGCCCGACTGCTTATTCCTTTA CCCCAA (SEQ. ID. No. 51) |
| CFTR2A-s2 | CGCCCGCCGCGCCCCGCGCCCGCCCCGCCGCCCCCGCCCGCCAGAAAAGTTGAAT AGTATCAG (SEQ. ID. No. 52) |
| CFTR2A-as2 | AGATTGTCAGCAGAATCAA (SEQ. ID. No. 53) |
| CF2B-s5 | ATACCAAATCCCTTCTG (SEQ. ID. No. 54) |
| CF2B-as5 | CGCCCGCCGCGCCCCGCGCCCGCCCCGCCGCCCCCGCCCGTGCTTTCTCTTCTCTA AAT (SEQ. ID. No. 55) |
| CF3A-s2 | CGCCCGCCGCGCCCCGCGCCCGCCCCGCCGCCCCCGCCCGTGGTGTTGTATGGTCT (SEQ. ID. No. 56) |
| CF3A-as2 | AACATAAATCTCCAGAA (SEQ. ID. No. 57) |
| CFTR3B-s | GCTGGCTTCAAAGAAAAATCC (SEQ. ID. No. 58) |
| CFTR3B-as | CGCCCGCCGGGCCCCGCGCCCGCCCCGCCGCCCCCGCCCGCACCAGATTTCGTAGTCT TTTCA (SEQ. ID. No. 59) |

TABLE 2-continued

| | |
|---|---|
| CFTR4A-s | CGCCCGCCGCGCCCCGCGCCCGCCCCGCCGCCCCGCCCGAATTTCTCTGTTTTTCCCCTT (SEQ. ID. No. 60) |
| CFTR4A-as | AGCTATTCTCATCTGCATTCCA (SEQ. ID. No. 61) |
| CFTR4B-s | GACACTGCTCCTACACC (SEQ. ID. No. 62) |
| CFTR4A-s | CGCCCGCCGCGCCCCGCGCCCGCCCCGCCGCCCCGCCCGTCAGCATTTATCCCTTA (SEQ. ID. No. 63) |
| CFTR5A-s | CGCCCGCCGCGCCCCGCGCCCGCCCCGCCGCCCCGCCCGATAATATATTTGTATTTTGTTTGTTG (SEQ. ID. No. 64) |
| CFTR5A-as | AATTTGTTCAGGTTGTTGGA (SEQ. ID. No. 65) |
| CFTR5B-s | AGCTGTCAAGCCGTGTTC (SEQ. ID. No. 66) |
| CFTR5B-as | CGCCCGCCGCGCCCCGCGCCCGCCCCGCCGCCCCGCCCGATCTGACCCAGGAAAACTC (SEQ. ID. No. 67) |
| CFTR6A-1-s | CGCCCGCCGCGCCCCGCGCCCGCCCCGCCGCCCCGCCCGTTGTTAGTTTCTAGGGGTGG (SEQ. ID. No. 68) |
| CFTR6A-1-as | AAGGACTATCAGGAAACCAAG (SEQ. ID. No. 69) |
| CFTR6A-2-s | GCTAATCTGGGAGTTGTTAC (SEQ. ID. No. 70) |
| CFTR6A-2-as | CGCCCGCCGCGCCCCGCGCCCGCCCCGCCGCCCCGCCCGAGTTATGAAAATAGGTTGCAC (SEQ. ID. No. 71) |
| CF6A-3-s2 | CGCCCGCCGCGCCCCGCGCCCGCCCCGCCGCCCCGCCCGGGGAGAATGATGATGAAG (SEQ. ID. No. 72) |
| CF6A-3-as2 | ACACTGAAGATCACTGTTCTA (SEQ. ID. No. 73) |
| CFTR6B-1-s2 | CGCCCGCCGCGCCCCGCGCCCGCCCCGCCGCCCCGCCCGCCTTGAGCAGTTCTTAATAGATA (SEQ. ID. No. 74) |
| CFTR6B-1-as2 | ATGCCTTAACAGATTGGATAT (SEQ. ID. No. 75) |
| CFTR6B-2-s2 | GAAAATATCCAATCTGTTAAG (SEQ. ID. No. 76) |
| CFTR6B-2-as2 | CGCCCGCCGCGCCCCGCGCCCGCCCCGCCGCCCCGCCCGTGAGGTGGAAGTCTACCA (SEQ. ID. No. 77) |
| CFTR7A-s | CGCCCGCCGCGCCCCGCGCCCGCCCCGCCGCCCCGCCCGAGACCATGCTCAGATCTTCCATT (SEQ. ID. No. 78) |
| CFTR7A-as | GCTGCCTTCCGAGTCAGTTTCAGT (SEQ. ID. No. 79) |
| CFTR7C-s | CGCCCGCCGCGCCCCGCGCCCGCCCCGCCGCCCCGCCCGACTGAAACTGACTCGGAAGG (SEQ. ID. No. 80) |
| CFTR7C-as | ATGGTACATTACCTGTATTTTGTTTA (SEQ. ID. No. 81) |
| CFTR7D-s | CTGTACAAAGATGGTATGACTCTCTT (SEQ. ID. No. 82) |
| CFTR7D-as | CGCCCGCCGCGCCCCGCGCCCGCCCCGCCGCCCCGCCCGGTGAAGGAAATTTCTTTTTCTATCT (SEQ. ID. No. 83) |
| CFTR8A-s | CGCCCGCCGCGCCCCGCGCCCGCCCCGCCGCCCCGCCCGGCAGAATGAGAGTATAAAGTAG (SEQ. ID. No. 84) |
| CFTR8A-as | CCATCACTACTTCTGTAGTCG (SEQ. ID. No. 85) |
| CF8B-s2: | CTCTCTTTTATAAATAGGATTTCTTAC (SEQ. ID. No. 86) |
| CF8B-as2: | CGCCCGCCGCGCCCCGCGCCCGCCCCGCCGCCCCGCCCGTTCCAGTTCTACCAGTTATATCATC (SEQ. ID. No. 87) |
| CFTR9C-s | CGCCCGCCGCGCCCCGCGCCCGCCCCGCCGCCCCGCCCGACAATAGAAAAACTTCTAATGGTGA (SEQ. ID. No. 88) |
| CFTR9C-as | AAAAAAGAGACATGGACACCAA (SEQ. ID. No. 89) |
| CFTR10-s | CCTGAGCGTGATTTGATA (SEQ. ID. No. 90) |
| CFTR10-as | CGCCCGCCGCGCCCCGCGCCCGCCCCGCCGCCCCGCCCGATGTAGACTAACCGATTGAA (SEQ. ID. No. 91) |
| CF10C-s3 | GGGAGAACTGGAGCCT (SEQ. ID. No. 92) |
| CF10C-as3 | CGCCCGCCGCGCCCCGCGCCCGCCCCGCCGCCCCGCCCGAACCGATTGAATATGGAG (SEQ. ID. No. 93) |
| CFTR11A-s2 | CGCCCGCCGCGCCCCGCGCCCGCCCCGCCGCCCCGCCCGGATATATGATTACATTAGAAG (SEQ. ID. No. 94) |
| CFTR11A-as2 | ACCTTCTCCAAGAACTA (SEQ. ID. No. 95) |
| CFTR11B-s | ATAGGACATCTCCAAGTT (SEQ. ID. No. 96) |
| CFTR11B-as | CGCCCGCCGCGCCCCGCGCCCGCCCCGCCGCCCCGCCCGGCAATAGAGAAATGTCTGT (SEQ. ID. No. 97) |
| CFTR12-s | CGCCCGCCGCGCCCCGCGCCCGCCCCGCCGCCCCGCCCGGTGAACTGTTTAAGGCAAATCAT (SEQ. ID. No. 98) |
| CFTR12-as | TGATGGGACAGTCTGTCTTTC (SEQ. ID. No. 99) |

TABLE 2-continued

```
CFTR13A-s      AATACGAGACATATTGCAATAAAGT (SEQ. ID. No. 100)
CFTR13A-as     CGCCCGCCGCGCCCCGCGCCCGCCCCGCCGCCCCGCCCGCTGGCTGTAGATTT
               TGGAGTTC (SEQ. ID. No. 101)

CF13B-s3       AGGTAGCAGCTATTTTT (SEQ. ID. No. 102)
CF13B-as3      CGCCCGCCGCGCCCCGCGCCCGCCCCGCCGCCCCGCCCGGGACAGCCT
               TCTCTCTA (SEQ. ID. No. 103)

CFTR13C-s      CGCCCGCCGCGCCCCGCGCCCGCCCCGCCGCCCCGCCCGATGGGACATTT
               TCAGAACTCC (SEQ. ID. No. 104)
CFTR13C-as     CCTCTTCGATGCCATTCAT (SEQ. ID. No. 105)

CFTR13E-s      CGCCCGCCGCGCCCCGCGCCCGCCCCGCCGCCCCGCCCGTGATGAGCCT
               TTAGAGAGAA (SEQ. ID. No. 106)
CFTR13E-as     CCAGTTCAGTCAAGTTTGC (SEQ. ID. No. 107)

CF13F-s2       CGCCCGCCGCGCCCCGCGCCCGCCCCGCCGCCCCGCCCGCAGCGTGA
               TCAGCA (SEQ. ID. No. 108)
CF13F-as2      TTTGTTTACATGCTACATA (SEQ. ID. No. 109)

CFTR14A-1-s    CGCCCGCCGCGCCCCGCGCCCGCCCCGCCGCCCCGCCCGTTCATATATTA
               AAAATAAAACC (SEQ. ID. No. 110)
CFTR14A-1-as   TAATATATCGAAGGTATGTGT (SEQ. ID. No. 111)

CFTR14A-2-s    GAGCATACCAGCAGTGACTACA (SEQ. ID. No. 112)
CFTR14A-2-as   CGCCCGCCGCGCCCCGCGCCCGCCCCGCCGCCCCGCCCGGTAATACTTTA
               CAATAGAACATTCTTACC (SEQ. ID. No. 113)

CFTR14A-3-s    ACCAGCAGTGACTACATGGA (SEQ. ID. No. 114)
CFTR14A-3-as   CGCCCGCCGCGCCCCGCGCCCGCCCCGCCGCCCCGCCCGATATTTATGTGTG
               TGCATATATATGTAT (SEQ. ID. No. 115)

CFTR14B-1-s    CGCCCGCCGCGCCCCGCGCCCGCCCCGCCGCCCCGCCCGGTGTACCTTG
               ATATTGG (SEQ. ID. No. 116)
CFTR14B-1-as   CTCACTTTCCAAGGAG (SEQ. ID. No. 117)

CF14B-3-s      GGTGTGGCTCCTTGG (SEQ. ID. No. 118)
CF14B-3-as     CGCCCGCCGCGCCCCGCGCCCGCCCCGCCGCCCCGCCCGACTACAGC
               CCTGAACTCC (SEQ. ID. No. 119)

CFTR15A-s      CGCCCGCCGCGCCCCGCGCCCGCCCCGCCGCCCCGCCCGCATGTATTGGAA
               ATTCAGTAAGTAAC (SEQ. ID. No. 120)
CFTR15A-as     TTCGACACTGTGATTAGAGTATGC (SEQ. ID. No. 121)
``` alternate 15B:

```
CF15B-s2       CGTGGGAGTAGCCGAC (SEQ. ID. No. 122)
CF15B-as2      CGCCCGCCGCGCCCCGCGCCCGCCCCGCCGCCCCGCCCGCATTAGAAA
               ACCAACAAA (SEQ. ID. No. 123)

CF16A-s5       CGCCCGCCGCGCCCCGCGCCCGCCCCGCCGCCCCGCCCGCTGAATG
               CGTCTACTG (SEQ. ID. No. 124)
CF16A-as5      CATCCAAAATTGCTATA (SEQ. ID. No. 125)

CFTR16B-s      TTGAGGAATTTGTCATCTTGTAT (SEQ. ID. No. 126)
CFTR16B-as     CGCCCGCCGCGCCCCGCGCCCGCCCCGCCGCCCCGCCCGCAAAATCACA
               TTTGCTTTTGTTA (SEQ. ID. No. 127)

CF17A-1-s6     CGCCCGCCGCGCCCCGCGCCCGCCCCGCCGCCCCGCCCGAAAGAAATA
               AATCACTGA (SEQ. ID. No. 128)
CF17A-1-as6    GTAAAACTGCGACAAC (SEQ. ID. No. 129)

CFTR17A-2-s    CCAACATGTTTTCTTTGATCTTACAG (SEQ. ID. No. 130)
CFTR17A-2-as   CGCCCGCCGCGCCCCGCGCCCGCCCCGCCGCCCCGCCCGAGAATCTC
               AAATAGCTCTTATAGCTTT (SEQ. ID. No. 131)

CFTR17B-1-s    CGCCCGCCGCGCCCCGCGCCCGCCCCGCCGCCCCGCCCGTTAACCAATGA
               CATTTGTGATA (SEQ. ID. No. 132)
CFTR17B-1-as   GTGTCCATAGTCCTTTTAAGC (SEQ. ID. No. 133)

CFTR17B-2-s    CGCCCGCCGCGCCCCGCGCCCGCCCCGCCGCCCCGCCCGATATTTCACAGG
               CAGGAGTCC (SEQ. ID. No. 134)
CFTR17B-2-as   AAAATCATTTCTATTCTCATTTGGA (SEQ. ID. No. 135)

CFTR17B-3-s    ACTTCGTGCCTTCGGAC (SEQ. ID. No. 136)
CFTR17B-3-as   CGCCCGCCGCGCCCCGCGCCCGCCCCGCCGCCCCGCCCGCAGCAATGAAG
               AAGATGACAAA (SEQ. ID. No. 137)
```

TABLE 2-continued

| | |
|---|---|
| CFTR17B-4-s | CTGGTTCCAAATGAGAA (SEQ. ID. No. 138) |
| CFTR17B-4-as | CGCCCGCCGCGCCCCGCGCCCGCCCCGCCGCCCCGCCCGTAACCTATAGAATGCAGCA (SEQ. ID. No. 139) |
| CFTR18A-s | CGCCCGCCGCGCCCCGCGCCCGCCCCGCCGCCCCGCCCGTTAATGTGATATGTGCCCTA (SEQ. ID. No. 140) |
| CFTR18A-as | AGATGATAAGACTTACCAAGC (SEQ. ID. No. 141) |
| CFTR18B-s | GAGAAGGAGAAGGAAGAGTTG (SEQ. ID. No. 142) |
| CFTR18B-as | CGCCCGCCGCGCCCCGCGCCCGCCCCGCCGCCCCGCCCGCTTCCTCATGCTATTACTCATAC (SEQ. ID. No. 143) |
| CFTR19A-s2 | CGCCCGCCGCGCCCCGCGCCCGCCCCGCCGCCCCGCCCGAAGTTATTTTTAGGAAGCAT (SEQ. ID. No. 144) |
| CFTR19A-as | GAACTTAAAGACTCGGCTC (SEQ. ID. No. 145) |
| CFTR19B-s | CGCCCGCCGCGCCCCGCGCCCGCCCCGCCGCCCCGGCCCGGAAATTGTCTGCCATTCTTAA (SEQ. ID. No. 146) |
| CFTR19B-as | GAGTTGGCCATTCTTGTATG (SEQ. ID. No. 147) |
| CF19C-s3 | CGCCCGCCGCGCCCCGCGCCCGCCCCGCCGCCCCGCCCGTGTGAGCCGAGTCTTT (SEQ. ID. No. 148) |
| CF19C-as2 | ATGGCATTTCCACCTT (SEQ. ID. No. 149) |
| CF19D-s2 | CGTGAAGAAAGATGAC (SEQ. ID. No. 150) |
| CF19D-as2 | CGCCCGCCGCGCCCCGCGCCCGCCCCGCCGCCCCGCCCGTAATGTTACAAATAGATTC (SEQ. ID. No. 151) |
| CF19i-s2 | CGCCCGCCGCGCCCCGCGCCCGCCCCGCCGCCCCGCCCGCTTGATTTCTGGAGAC (SEQ. ID. No. 152) |
| CF19i-as2 | CTAGCTGTAATTGCAT (SEQ. ID. No. 153) |
| new 20-s: | CGCCCGCCGCGCCCCGCGCCCGCCCCGCCGCCCCGCCCGCTGAATTATGTTTATGGCA (SEQ. ID. No. 154) |
| new 20-as | CCTTTTTTCTGGCTAAGT (SEQ. ID. No. 155) |
| alternate 21A | |
| CF 21A-s3 | CGCCCGCCGCGCCCCGCGCCCGCCCCGCCGCCCCGCCCGAGTTATTCATACTTTCTTCT (SEQ. ID. No. 156) |
| CF21A-as3 | AGCCTTACCTCATCTG (SEQ. ID. No. 157) |
| CF21B-s3 | CGCCCGCCGCGCCCCGCGCCCGCCCCGCCGCCCCGCCCGTTTCTGGAACATTTAG (SEQ. ID. No. 158) |
| CF21B-as3 | GAATGATGTCAGCTATAT (SEQ. ID. No. 159) |
| CFTR22A-s2 | CGCCCGCCGCGCCCCGCGCCCGCCCCGCCGCCCCGCCCGTGAGCTGTCAAGGTTGTA (SEQ. ID. No. 160) |
| CFTR22A-as2 | CAGGAAACTGTTCTATAC (SEQ. ID. No. 161) |
| CFTR22B-s | CGCCCGCCGCGCCCCGCGCCCGCCCCGCCGCCCCGCCCGGAATGTCAACTGCTTGAGTGTTTT (SEQ. ID. No. 162) |
| CFTR22B-as | AAGTAACAGAACATCTGAAACTCACAC (SEQ. ID. No. 163) |
| CFTR22C-s2 | CTTGCTGCTTGATGAAC (SEQ. ID. No. 164) |
| CFTR22C-as | CGCCCGCCGCGCCCCGCGCCCGCCCCGCCGCCCCGCCCGTGGGCAATTATTTCATATCTTGG (SEQ. ID. No. 165) |
| CF23A-s3 | CGCCCGCCGCGCCCCGCGCCCGCCCCGCCGCCCCGCCCGTATCAAGGTAAATACAGA (SEQ. ID. No. 166) |
| CF23A-as3 | GCTTCTATCCTGTGTTC (SEQ. ID. No. 167) |
| CF23B-s2 | GATATTATGTGTGGTATTTC (SEQ. ID. No. 168) |
| CF24A-s2 | CGCCCGCCGCGCCCCGCGCCCGCCCCGCCGCCCCGCCCGGAACTTGTACATTGTTGCA (SEQ. ID. No. 169) |
| CF24A-s2 | CGCCCGCCGCGCCCCGCGCCCGCCCCGCCGCCCCGCCCGCTTTGAGCCTGTGCC (SEQ. ID. No. 170) |
| CF24A-as2 | GCTTGAGTTCCGGTGG (SEQ. ID. No. 171) |
| CF24B-s2 | CATCAGCCCCTCCGAC (SEQ. ID. No. 172) |
| CF24B-s2 | CGCCCGCCGCGCCCCGCGCCCGCCCCGCCGCCCCGCCCGTTTCTGAGGCAGAGGTA (SEQ. ID. No. 173) |

TABLE 3

TTGE Group Listing for CFTR Gene

| Gene | Fragment | Group | Position | run group | PCR temp |
|---|---|---|---|---|---|
| CFTR | 16A-5 | 1 | A | 45.5-52.5 | 49 |
| CFTR | 6B2 | 1 | B | 125 V | 49 |
| CFTR | 17B1 | 1 | C | 1.5 rr | 52 |
| CFTR | 21A3 | 1 | D | run time 4.67 hours | 52 |
| CFTR | 12 | 2 | A | | 60 |
| CFTR | 5A | 2 | B | | 52 |
| CFTR | 7A | 2 | C | | 62 |
| CFTR | 16B | 3 | A | | 49 |
| CFTR | 7D | 3 | B | | 60 |
| CFTR | 5B | 3 | C | | 62 |
| CFTR | 17B4 | 4 | A | | 49 |
| CFTR | 6B1 | 4 | B | | 54 |
| CFTR | 6A3-2 | 4 | C | | 52 |
| CFTR | 8B2 | 5 | A | 47.5-53 | 52 |
| CFTR | 2B5 | 5 | B | 150 V | 49 |
| CFTR | 13A | 6 | A | 1 rr | 59 |
| CFTR | 8A | 6 | B | run time 5.5 hours | 60 |
| CFTR | 11A | 7 | A | 50.5-56.5 | 49 |
| CFTR | 19A | 7 | B | 125 V | 54 |
| CFTR | 19B | 7 | C | 1.5 rr | 59 |
| CFTR | 14B2-3 | 8 | A | run time 4 hours | 60 |
| CFTR | 13B3 | 8 | B | | 49 |
| CFTR | 21B3 | 8 | C | | 46 |
| CFTR | 14A3 | 9 | A | | 54 |
| CFTR | 17A2 | 9 | B | | 60 |
| CFTR | 4B | 9 | C | | 52 |
| CFTR | 13F2 | 10 | A | | 46 |
| CFTR | 23A3 | 10 | B | | 46 |
| CFTR | 19in | 10 | C | | 49 |
| CFTR | 14A2 | 10 | D | | 62 |
| CFTR | 3A2 | 11 | A | 50.5-56.5 | 46 |
| CFTR | 18A | 11 | B | 125 V | 60 |
| CFTR | 2A | 11 | C | 1.2 rr | 54 |
| CFTR | 10 | 12 | A | run time 5 hours | 59 |
| CFTR | 14A1 | 12 | B | | 46 |
| CFTR | 22A2 | 12 | C | | 52 |
| CFTR | 10C3 | 13 | A | 50.5-56.5 | 54 |
| CFTR | 11B | 13 | B | 125 V | 52 |
| CFTR | 3B | 14 | A | 1.5 rr | 54 |
| CFTR | 18B | 14 | B | run time 4 hours | 60 |
| CFTR | 17A16 | 14 | C | | 52 |
| CFTR | 9Ts | 15 | A | 50.5-56.5 | 59 |
| CFTR | 9C | 15 | B | 150 V prerun 30 min | 59 |
| CFTR | 23B2 | 16 | A | 1.2 rr | 49 |
| CFTR | 13C | 16 | B | run time 5 hours | 60 |
| CFTR | 22C | 17 | A | 54.5-61 | 59 |
| CFTR | 22B | 17 | B | 125 V | 59 |
| CFTR | 6A2 | 17 | C | 1.5 rr | 49 |
| CFTR | 15A | 18 | A | run time 4 hours | 54 |
| CFTR | 19D2 | 18 | B | | 46 |
| CFTR | 4A | 18 | C | | 60 |
| CFTR | 14B1 | 18 | D | | 54 |
| CFTR | 15B2 | 19 | A | | 54 |
| CFTR | 17B3 | 19 | B | | 60 |
| CFTR | 6A1 | 19 | C | | 62 |
| CFTR | 17B2 | 20 | A | | 49 |
| CFTR | 19C3 | 20 | B | | 52 |
| CFTR | 24B2 | 20 | C | | 52 |
| CFTR | 20 | 21 | A | 55-60 | 49 |
| CFTR | 7C | 21 | B | 150 V, 1 rr, run time 5 hours | 60 |
| CFTR | 13E | 22 | A | 59-64 | 59 |
| CFTR | 1A | 22 | B | 125 V | 59 |
| CFTR | 24A2 | 23 | A | 1.5 rr | 62 |
| CFTR | 1B | 23 | B | run time 3.3 hours | 59 |

Although the invention has been described with reference to embodiments and examples, it should be understood that various modifications can be made without departing from the spirit of the invention. Accordingly, the invention is limited only by the following claims.

TABLE A

CF exon 1

```
 541  gggaggggtg ctggcggggg tgcgtagtgg gtggagaaag ccgctagagc aaatttgggg   (SEQ. ID. NO. 174)

601  ccggaccagg cagcactcgg cttttaacct gggcagtgaa ggcgggggaa agagcaaaag 661  gaaggggtgg tgtgcggagt aggggtgggt ggggggaatt ggaagccaaa tgacatcaca 721  gcaggtcaga gaaaagggt tgagcggcag gcacccagag tagtaggtct ttggcattag 781  gagcttgagc ccagacggcc ctagcaggga ccccagcgcc cagagaccAT GCAGAGGTCG 841  CCTCTGGAAA AGGCCAGCGT TGTCTCCAAA CTTTTTTTCA Ggtgagaagg tggccaaccg 901  agcttcggaa agacacgtgc ccacgaaaga ggagggcgtg tgtatgggtt gggtttgggg 961  taaaggaata agcagttttt aaaaagatgc gctatcattc attgttttga aagaaaatgt 1021  gggtattgta gaataaaaca gaaagcatta agaagagatg gaagaatgaa ctgaagctga 1081  ttgaatagag agccacatct acttgcaact gaaaagttag aatctcaaga ctcaagtacg 1141  ctactatgca cttgttttat ttcatttttc taagaaacta aaaatacttg ttaataagta CFTR1A-s:     5' CGCCCCCCGCGCCCCGCGCCCGCCCCGCCGCCCCCGCCCG-         (SEQ. ID. NO. 175)
                 GGAAGCCAAATGACATCACAGC 3'
CFTR1A-as:    5' TGAAAAAAACTTTGGAGACAACGC 3'                         (SEQ. ID. NO. 176)

CFTR1B-s:     5' CCCAGCGCCCAGAGACC 3'                                 (SEQ. ID. NO. 177)
CFTR1B-as:    5' CGCCCGCCGCGCCCCGCGCCCGCCCCGCCGCCCCCGCCCG-         (SEQ. ID. NO. 178)
                 ACTGCTTATTCCTTTACCCCAA 3'
```

TABLE A-continued

```
CFTR1-s-tag:     5' GGGTGGTGTGCGGAGTA 3'                              (SEQ. ID. NO. 179)
CFTR1-as-tag:    5' CAAAACAATGAATGATAGCG 3'                           (SEQ. ID. NO. 180)
```

CF exon 2

```
  1  aaaccatact attattccct cccaatccct tgacaaagt gacagtcaca ttagttcaga  (SEQ. ID. NO. 181)
 61  gatattgatg ttttatacag gtgtagcctg taagagatga agcctggtat ttatagaaat
121  tgacttattt tattctcata tttacatgtg cataattttc catatgccag aaaagttgaa
181  tagtatcaga ttccaaatct gtatggagac caaatcaagt gaatatctgt tcctcctctc
241  tttattttag CTGGACCAGA CCAATTTTGA GGAAAGCATA CAGACAGCGC CTGGAATTGT
301  CAGACATATA CCAAATCCCT TCTGTTCATT CTGCTCACAA TCTATCTGAA AAATTGGAAA
361  Ggtatgttca tgtacattgt ttagttgaag agagaaattc atattattaa ttatttagag
421  aagagaaagc aaacatatta taagtttaat tcttatattt aaaaatagga gccaagtatg
481  gtggctaatg cctgtaatcc caactatttg ggaggccaag atgagaggat tgcttgagac
541  caggagtttg ataccagcct gggcaacata gcaagatgtt atctctacac aaaataaaaa
601  gttagctggg aatggtagtg catgcttgta
```

```
CF2A-s:          5' CGCCCGCCGCGCCCCGCGCCCGCCCCGCCGCCCCCGCCCG-         (SEQ. ID. NO. 182)
                    CCAGAAAAGTTGAATAGTATCAG 3'
CF2A-as:         5' AGATTGTCAGCAGAATCAA 3'                            (SEQ. ID. NO. 183)
CFTR2-s-tag:     5' GACAGTCACATTAGTTCAG 3'                            (SEQ. ID. NO. 184)
CFTR2-as-tag:    5' TGTTTGCTTTCTCTTCT 3'                              (SEQ. ID. NO. 185)
CF2B-s5:         5' ATACCAAATCCCTTCTG 3'                              (SEQ. ID. NO. 186)
CF2B-as5:        5' CGCCCGCCGCGCCCCGCGCCCGCCCCGCCGCCCCCGCCCG-         (SEQ. ID. NO. 187)
                    TGCTTTCTCTTCTCTAAAT 3'
```

CF exon 3

```
  1  aggaatctgc cagatatctg gctgagtgtt tggtgttgta tggtctccat gagattttgt  (SEQ. ID. NO. 188)
 61  ctctataata cttgggttaa tctccttgga tatacttgtg tgaatcaaac tatgttaagg
121  gaaataggac aactaaaata tttgcacatg caacttattg gtcccacttt ttattctttt
181  gcagAGAATG GGATAGAGAG CTGGCTTCAA AGAAAAATCC TAAACTCATT AATGCCCTTC
241  GGCGATGTTT TTTCTGGAGA TTTATGTTCT ATGGAATCTT TTTATATTTA GGGtaagga
301  tctcattgt acattcatta tgtatcacat aactatatgc attttgtga ttatgaaaag
361  actacgaaat ctggtgaata ggtgtaaaaa tataaggat gaatccaact ccaaacacta
421  agaaaccacc taaaactcta gtaaggataa gtaa
```

```
CF3A-s:          5' CGCCCGCCGCGCCCCGCGCCCGCCCCGCCGCCCCCGCCCG-         (SEQ. ID. NO. 189)
                    TGGTGTTGTATGGTCT 3'
CF3A-as:         5' AACATAAATCTCCAGAA 3'                              (SEQ. ID. NO. 190)
CF3B-s:          5' GCTGGCTTCAAAGAAAAATCC 3'                          (SEQ. ID. NO. 191)
CF3B-as:         5' CGCCCGCCGCGCCCCGCGCCCGCCCCGCCCCCCGCCCCCGCCCG-     (SEQ. ID. NO. 192)
                    CACCAGATTTCGTAGTCTTTTCA 3'
CFTR-3-s-tag:    5' TGGTGTTGTATGGTCTC 3'                              (SEQ. ID. NO. 193)
CFTR-3-as-tag:   5' TTAGGTCCTTTCTTAGTG 3'                             (SEQ. ID. NO. 194)
```

CF exon 4

```
  1  ccactattca ctgtttaact taaaataccct catatgtaaa cttgtctccc actgttgcta  (SEQ. ID. NO. 195)
 61  taacaaatcc caagtcttat ttcaaagtac caagatattg aaaatagtgc taagagtttc
121  acatatggta tgaccctcta tataaactca ttttaagtct cctctaaaga tgaaaagtct
181  tgtgttgaaa ttctcagggt attttatgag aaataaatga aatttaattt ctctgttttt
241  ccccttttgt agGAAGTCAC CAAAGCAGTA CAGCCTCTCT TACTCCCAAG AATCATAGCT
```

TABLE A-continued

```
301  TCCTATGACC CGGATAACAA GGAGGAACGC TCTATCCCGA TTTATCTAGG CATAGGCTTA
361  TGCCTTCTCT TTATTGTGAG GACACTGCTC CTACACCCAG CCATTTTTGG CCTTCATCAC
421  ATTGGAATGC AGATGAGAAT AGCTATCTTT AGTTTGATTT ATAAGAAGgt aatacttcct
481  tgcacaggcc ccatggcaca tatattctgt atcgtacatg ttttaatgtc ataaattagg
541  tagtgagctg gtacaagtaa gggataaatg ctgaaattaa tttaatatgc ctattaaata
601  aatggcagga ataattaatg ctcttaatta tccttgataa tttaattgac ttaaactgat
661  aattattgag tatc
```

| | | |
|---|---|---|
| CF4A-s: | 5' CGCCCGCCGCGCCCCGCGCCCGCCCCGCCGCCCCGCCCG-AATTTCTCTGTTTTTCCCCTT 3' | (SEQ. ID. NO. 196) |
| CF4A-as: | 5' AGCTATTCTCATCTGCATTCCA 3' | (SEQ. ID. NO. 197) |
| CF4B-s: | 5' GACACTCCTCCTACACC 3' | (SEQ. ID. NO. 198) |
| CF4B-as: | 5' CGCCCGCCGCGCCCCCCCCCGCCCCGCCGCCCCGCCCG-TCAGCATTTATCCCTTA 3' | (SEQ. ID. NO. 199) |
| CF4-s-tag: | 5' ATAACAAATCCCAAGTC 3' | (SEQ. ID. NO. 200) |
| CF4-as-tag: | 5' TGTACCAGCTCACTACC 3' | (SEQ. ID. NO. 201) |

CF exon 5

```
  1  taattatttc tgcctagatg ctgggaaata aacaactag aagcatgcca gtataatatt  (SEQ. ID. NO. 202)
 61  gactgttgaa agaaacattt atgaacctga gaagatagta agctagatga atagaatata
121  attttcatta cctttactta ataatgaatg cataataact gaattagtca tattataatt
181  ttacttataa tatatttgta ttttgtttgt tgaaattatc taactttcca ttttttcttt
241  agACTTTAAA GCTGTCAAGC CCTGTTCTAG ATAAAATAAC TATTGGACAA CTTGTTAGTC
301  TCCTTTCCAA CAACCTCAAC AAATTTGATG AAgtatgtac ctattgattt aatcttttag
361  gcactattgt tataaattat acaactggaa aggcggagtt ttcctgggtc agataatagt
421  aattagtggt taagtcttgc tcagctctag cttccctatt ctggaaacta agaaaggtca
481  attgtatagc agagcaccat tctggggtct ggtagaacca cccaactcaa aggcaccta
541  gcctgttgtt aataagattt tcaaaactt aattcttatc agaccttgct tcttttaaac
```

| | | |
|---|---|---|
| CF5A-s: | 5' CGCCCGCCGCGCCCCGCGCCCGCCCCGCCGCCCCGCCCG-ATAATATATTTGTATTTTGTTTGTTG 3' | (SEQ. ID. NO. 203) |
| CF5A-as: | 5' AATTTGTTCAGGTTGTTGGA 3' | (SEQ. ID. NO. 204) |
| CF5B-s: | 5' AGCTGTCAAGCCGTGTTC 3' | (SEQ. ID. NO. 205) |
| CF5B-as: | 5' CGCCCGCCGCGCCCCGCGCCCGCCCCGCCGCCCCGCCCG-ATCTGACCCAGGAAAACTC 3' | (SEQ. ID. NO. 206) |
| CF5-s-tag: | 5' TGCTGGGAAATAAAAC 3' | (SEQ. ID. NO. 207) |
| CF5-as-tag: | 5' AGAATGGTGCTCTGCT 3' | (SEQ. ID. NO. 208) |

CF exon 6A

```
  1  gacatgatac ttaagatgtc caatcttgat tccactgaat aaaaatatgc ttaaaaatgc  (SEQ. ID. NO. 209)
 61  actgacttga aatttgtttt tgggaaaac cgattctatg tgtagaatgt ttaagcacat
121  tgctatgtgc tccatgtaat gattacctag attttagtgt gctcagaacc acgaagtgtt
181  tgatcatata agctcctttt acttgctttc tttcatatat gattgttagt ttctagggt
241  ggaagataca atgcacctg ttttttgctgt gcttttattt tccagGGACT TGCATTGGCA
301  CATTTCGTGT GGATCGCTCC TTTGCAACTC GCACTCCTCA TGGGCTAAT CTGGGAGTTG
361  TTACAGGCGT CTGCCTTCTG TGGACTTGGT TTCCTGATAG TCCTTGCCCT TTTTCAGGCT
421  GGGCTAGGGA GAATGATGAT GAAGTACAGg tagcaaccta ttttcataac ttgaaagttt
481  taaaaattat gttttcaaaa agcccacttt agtaaaacca ggactgctct atgcatagaa
541  cagtgatctt cagtgtcatt aaatttttt ttttttttt tttgagacag agtctagatc
```

TABLE A-continued

```
601 tgtcacccag gctggagtgc agtggcacga tcttggctca ctgcactgca acttctgcct 661 cccaggctca agcaattctc ctgcctcagc ctccggagta gctgggatta gaggcgcatg
```

| | | |
|---|---|---|
| CF6A-1-s: | 5' CGCCCGCCGCGCCCCGCGCCCGCCCCGCCGCCCCGCCCG-<br>TTGTTAGTTTCTAGGGGTGG 3' | (SEQ. ID. NO. 210) |
| CF6A-1-as: | 5' AAGGACTATCAGGAAACCAAG 3' | (SEQ. ID. NO. 211) |
| CF6A-2-s: | 5' GCTAATCTGGGAGTTGTTAC 3' | (SEQ. ID. NO. 212) |
| CF6A-2-as: | 5' CGCCCGCCGCGCCCCGCGCCCGCCCCGCCGCCCCGCCG-<br>AGTTATGAAAATAGGTTGCTAC 3' | (SEQ. ID. NO. 213) |
| CF6A-3-s2: | 5'CGCCCGCCGCGCCCCGCGCCCGCCCCGCCGCCCCGCCCGGGGAGAATGAT-<br>GATGAAG 3' | (SEQ. ID. NO. 214) |
| CF6A-3-as2: | 5'ACACTGAAGATCACTGTTCTA 3' | (SEQ. ID. NO. 215) |
| CF6a-s-tag: | 5' CTCCTTTTACTTGCTTTC 3' | (SEQ. ID. NO. 216) |
| CF6a-as-tag: | 5' GAGCACTCCTGGTTTTA 3' | (SEQ. ID. NO. 217) |

CF exon 6B

```
atgagtctgtacagcgtctggcacataggaggcatttaccaaacagtagttattattttttgttaccatcta   (SEQ. ID. NO. 218)

tttgataataaaataatgcccatctgttgaataaaagaaatatgacttaaaaccttgagcagttcttaata gataatttgacttgttttttactattagattgattgattgattgattgattgatttacagAGATCAGAGAGC

TGGGAAGATCAGTGAAAGACTTGTGATTACCTCAGAAATGATTGAAAATATCCAATCTGTTAAGGCATACT

GCTGGGAAGAAGCAATGGAAAAAATGATTGAAAACTTAAGACAgtaagttgttccaataatttcaatattg ttagtaattctgtccttaatttttttaaaaatatgtttatcatggtagacttccacctcatatttgatgttt gtgacaatcaaatgattgcatttaagttctgtcaatattcatgcattagttgca
```

| | | |
|---|---|---|
| CF6B-1-s: | 5' CGCCCGCCGCGCCCCGCGCCCGCCCCGCCGCCCCGCCCG-<br>CCTTGAGCAGTTCTTAATAGATA 3' | (SEQ. ID. NO. 219) |
| CF6B-1-as: | 5' ATGCCTTAACAGATTGGATAT 3' | (SEQ. ID. NO. 220) |
| CF6B-2-s: | 5' GAAAATATCCAATCTGTTAAG 3' | (SEQ. ID. NO. 221) |
| CF6B-2-as: | 5' CGCCCGCCGCGCCCCGCGCCCGCCCCGCCGCCCCGCCCG-<br>TGAGGTGGAAGTCTACCA 3' | (SEQ. ID. NO. 222) |
| CF6b-s-tag: | 5' AAAACCTTGAGCAGTT 3' | (SEQ. ID. NO. 223) |
| CF6b-as-tag: | 5' GGTGGAAGTCTACCATG 3' | (SEQ. ID. NO. 224) |

CF exon 7

```
  1 tttacaagta ctacaagcaa acactggta ctttcattgt tatctttca tataaggtaa   (SEQ. ID. NO. 225)

61 ctgaggccca gagagattaa ataacatgcc caaggtcaca caggtcatat gatgtggagc 121 caggttaaaa atataggcag aaagactcta gagaccatgc tcagatcttc cattccaaga 181 tccctgatat ttgaaaaata aaataacatc ctgaatttta ttgttattgt tttttatagA

241 ACAGAACTGA AACTGACTCG GAAGGCAGCC TATGTGAGAT ACTTCAATAG CTCAGCCTTC

301 TTCTTCTCAG GGTTCTTTGT GGTGTTTTTA TCTGTGCTTC CCTATGCACT AATCAAAGGA

361 ATCATCCTCC GGAAAATATT CACCACCATC TCATTCTCCA TTGTTCTGCG CATGGCGGTC

421 ACTCGGCAAT TCCCTGGGC TGTACAAACA TGGTATGACT CTCTTGGAGC AATAAACAAA

481 ATACAGgtaa tgtaccataa tgctgcatta tatactatga tttaaataat cagtcaatag 541 atcagttcta atgaactttg caaaaatgtg cgaaaagata gaaaagaaa tttccttcac 601 taggaagtta taaaagttgc cagctaatac taggaatgtt caccttaaac ttttcctagc 661 atttctctgg acagtatgat ggatgagagt ggcatttatg caaattacct taaaatccca 721 ataatactga tgtagctagc agctttgaga aa
```

| | | |
|---|---|---|
| CF7A-s: | 5' CGCCCGCCGCGCCCCGCGCCCGCCCCGCCGCCCCGCCCG-<br>AGACCATGCTCAGATCTTCCATT 3' | (SEQ. ID. NO. 226) |
| CF7A-as: | 5' GCTGCCTTCCGAGTCAGTTTCAGT 3' | (SEQ. ID. NO. 227) |

TABLE A-continued

| | | |
|---|---|---|
| CF7C-s: | 5' CGCCCGCCGCGCCCCGCGCCCGCCCCGCCGCCCCGCCCG-<br>ACTGAAACTGACTCGGAAGG 3' | (SEQ. ID. NO. 228) |
| CF7C-as: | 5' ATGGTACATTACCTGTATTTTGTTTA 3' | (SEQ. ID. NO. 229) |
| CF7D-s: | 5' CTGTACAAACATGGTATGACTCTCTT 3' | (SEQ. ID. NO. 230) |
| CF7D-as: | 5' CGCCCGCCGCGCCCCGCGCCCGCCCCGCCGCCCCGCCCG-<br>GTGAAGGAAATTTCTTTTTCTATCT 3' | (SEQ. ID. NO. 231) |
| CF7-s-tag: | 5' AATATAGGCAGAAAGACT 3' | (SEQ. ID. NO. 232) |
| CF7-as-tag: | 5' GAACTGATCTATTGACTGA 3' | (SEQ. ID. NO. 233) |

CF exon 8

```
  1 gcacattagt gggtaattca gggttgcttt gtaaattcat cactaaggtt agcatgtaat    (SEQ. ID. NO. 234)

61 agtacaagga agaatcagtt gtatgttaaa tctaatgtat aaaaagtttt ataaaatatc 121 atatgtttag agagtatatt tcaaatatga tgaatcctag tgcttggcaa attaacttta 181 gaacactaat aaaattattt tattaagaaa taattactat ttcattatta aaattcatat 241 ataagatgta gcacaatgag agtataaagt agatgtaata atgcattaat gctattctga 301 ttctataata tgttttttgct ctcttttata aatagGATTT CTTACAAAAG CAAGAATATA

361 AGACATTGGA ATATAACTTA ACGACTACAG AAGTAGTGAT GGAGAATGTA ACAGCCTTCT

421 GGGAGGAGgt cagaattttt aaaaaattgt tgctctaaa cacctaactg ttttcttctt 481 tgtgaatatg gatttcatcc taatggcgaa taaaattaga atgatgatat aactggtaga 541 actggaagga ggatcactca cttattttct agattaagaa gtagaggaat ggccaggtgc 601 tcatggttgt aatcccagca ctttcgggag accaaggcgg gtggatcacc tgaggtcagg 661 agttcaagac cagcctgcca acatggtaaa acccggtctc tactaaaaat acaaaaaatt 721 aactg
```

| | | |
|---|---|---|
| CF8A-s: | 5' CGCCCGCCGCGCCCCGCGCCCGCCCCGCCGCCCCGCCCG-<br>GCACAATGAGAGTATAAAGTAG 3' | (SEQ. ID. NO. 235) |
| CF8A-as: | 5' CCATCACTACTTCTGTAGTCG 3' | (SEQ. ID. NO. 236) |
| CF8B-s2: | 5' CTCTCTTTTATAAATAGGATTTCTTAC 3' | (SEQ. ID. NO. 237) |
| CF8B-as2: | 5' CGCCCGCCGCGCCCCGCGCCCGCCCCGCCGCCCCGCCCG-<br>TTCCAGTTCTACCAGTTATATCATC 3' | (SEQ. ID. NO. 238) |
| CF8-s-tag: | 5' ATGAATCCTAGTGCTTG 3' | (SEQ. ID. NO. 239) |
| CF8-as-tag: | 5' TCCTTCCAGTTCTACC 3' | (SEQ. ID. NO. 240) |

CF exon 9

```
181 tgtatgtgta tgtatacatg tatgtattca gtctttactg aaattaaaaa atctttaact    (SEQ. ID. NO. 241)

241 tgataatggg caaatatctt agttttagat catgtcctct agaaaccgta tgctatataa 301 ttatgtacta taaagtaata atgtatacag tgtaatggat catgggccat gtgcttttca 361 aactaattgt acataaaaca agcatctatt gaaaatatct gacaaactca tcttttattt 421 ttgatgtgtg tgtgtgtgtg tgtgtgtgtt tttttaacag GGATTTGGGG AATTATTTGA

481 GAAAGCAAAA CAAAACAATA ACAATAGAAA AACTTCTAAT GGTGATGACA GCCTCTTCTT

541 CAGTAATTTC TCACTTCTTG GTACTCCTGT CCTGAAAGAT ATTAATTTCA AGATAGAAAG

601 AGGACAGTTG TTGGCGGTTG CTGGATCCAC TGGAGCAGGC AAGgtagttc tttgttctt 661 cactattaag aacttaattt ggtgtccatg tctcttttttt tttctagttt gtagtgctgg 721 aaggtatttt tggagaaatt cttacatgag cattaggaga atgtatgggt gtagtgtctt 781 gtataatagg aattgttcca ctgataattt actctagttt tttatttcct catattattt 841 tcagtggctt tttcttccac atctttatat tttgcaccac attcaacact gtatcttgca 901 catggcgagc attcaataac tttattgaat aaacaaatca tccatttttat ccattcttaa
```

TABLE A-continued

```
 961 ccagaacaga catttttca gagctggtcc aggaaaatca tgacttacat tttgccttag 1021 taaccacata aacaaaaagt ctccattttt gttgac
```

| | | |
|---|---|---|
| CF9C-s: | 5' CGCCCGCCGCGCCCCGCGCCCGCCCCGCCGCCCCGCCCG-<br>ACAATAGAAAAACTTCTAATGGTGA 3' | (SEQ. ID. NO. 242) |
| CF9C-as: | 5' AAAAAAGAGACATGGACACCAA 3' | (SEQ. ID. NO. 243) |
| CF9-s-tag: | 5' AGAAACCGTATGCTAT 3' | (SEQ. ID. NO. 244) |
| CF9-as-tag: | 5' CCCATACATTCTCCTA 3' | (SEQ. ID. NO. 245) |
| CF9-as2-tag: | 5' TAAAGATGTGGAAGAAA 3' | (SEQ. ID. NO. 246) |

CF exon 10

```
   1 cactgtagct gtactacctt ccatctcctc aacctattcc aactatctga atcatgtgcc    (SEQ. ID. NO. 247)

61 cttctctgtg aacctctatc ataatacttg tcacactgta ttgtaattgt ctcttttact 121 ttcccttgta tcttttgtgc atagcagagt acctgaaaca ggaagtattt taaatatttt 181 gaatcaaatg agttaataga atcttacaa ataagaatat acacttctgc ttaggatgat 241 aattggaggc aagtgaatcc tgagcgtgat ttgataatga cctaataatg atgggtttta 301 tttccagACT TCACTTCTAA TGATGATTAT GGGAGAACTG GAGCCTTCAG AGGGTAAAAT

361 TAAGCACAGT GGAAGAATTT CATTCTGTTC TCAGTTTTCC TGGATTATGC CTGGCACCAT

421 TAAAGAAAAT ATCATCTTTG GTGTTTCCTA TGATGAATAT AGATACAGAA GCGTCATCAA

481 AGCATGCCAA CTAGAAGAGg taagaaaacta tgtgaaaact ttttgattat gcatatgaac 541 ccttcacact acccaaatta tatatttggc tccatattca atcggttagt ctacatatat 601 ttatgtttcc tctatgggta agctactgtg aatggatcaa ttaataaaac acatgaccta 661 tgctttaaga agcttgcaaa cacatgaaat aaatgcaatt tatttttaa ataatgggtt 721 catttgatca caataaatgc attttatgaa atggtgagaa ttttgttcac tcattagtga 781 gacaaacgtc tcaatggtta tttatatggc atgcatatag tgatatgtgg t
```

| | | |
|---|---|---|
| CF10-s: | 5' CCTGAGCGTGATTTGATA 3' | (SEQ. ID. NO. 248) |
| CF10-as: | 5' CGCCCGCCGCGCCCCGCGCCCGCCCCGCCGCCCCGCCCG-<br>ATGTAGACTAACCGATTGAA 3' | (SEQ. ID. NO. 249) |
| CF10C-s: | 5' GGGAGAACTGGAGCCT 3' | (SEQ. ID. NO. 250) |
| CF10C-as: | 5' CGCCCGCCGCGCCCCGCGCCCGCCCCGCCGCCCCGCCCG-<br>AACCGATTGAATATGGAG 3' | (SEQ. ID. NO. 251) |
| CF10-s2-tag: | 5' CCTTGTATCTTTTGTGC 3' | (SEQ. ID. NO. 252) |
| CF10-as2-tag: | 5' CCGATTGAATATGGAG 3' | (SEQ. ID. NO. 253) |

CF exon 11

```
   1 atatacccat aaatatacac atattttaat ttttggtatt ttataattat tatttaatga    (SEQ. ID. NO. 254)

61 tcattcatga catttttaaaa attacaggaa aaatttacat ctaaaatttc agcaatgttg 121 ttttgacca actaaataaa ttgcatttga aataatggag atgcaatgtt caaaatttca 181 actgtggtta aagcaatagt gtgatatatg attacattag aaggaagatg tgcctttcaa 241 attcagattg agcatactaa aagtgactct ctaattttct attttggta atagGACATC

301 TCCAAGTTTG CAGAGAAAGA CAATATAGTT CTTGGAGAAG GTGGAATCAC ACTGAGTGGA

361 GGTCAACGAG CAAGAATTTC TTTAGCAAGg tgaataacta attattggtc tagcaagcat 421 ttgctgtaaa tgtcattcat gtaaaaaaat tacagacatt tctctattgc tttatattct 481 gtttctgaa ttgaaaaaat cctgggggttt tatggctagt gggttaagaa tcacatttaa 541 gaactataaa taatggtata gtatccagat ttggtagaga ttatggttac tcagaatctg
```

TABLE A-continued

```
601 tgcccgtatc ttgg
```

| | | |
|---|---|---|
| CF11A-s: | 5' CGCCCCCGCGCCCCGCGCCCGCCCCGCCGCCCCGCCCG-<br>GATATATGATTACATTAGAAG 3' | (SEQ. ID. NO. 255) |
| CF11A-as: | 5' ACCTTCTCCAAGAACTA 3' | (SEQ. ID. NO. 256) |
| CF11B-s: | 5' ATAGGACATCTCCAAGTT 3' | (SEQ. ID. NO. 257) |
| CF11B-as: | 5' CGCCCCGCCGCGCCCCGCGCCCGCCCCGCCGCCCCGCCCG-<br>GCAATAGAGAAATGTCTGT 3' | (SEQ. ID. NO. 258) |
| CF11-s-tag: | 5' CAGATTGAGCATACTAAAAG 3' | (SEQ. ID. NO. 259) |
| CF11-as-tag: | 5' AAGATACGGGCACAGA 3' | (SEQ. ID. NO. 260) |

CF exon 12

```
  1 cttacagtta gcaaaatcac ttcagcagtt cttggaatgt tgtgaaaagt gataaaaatc    (SEQ. ID. NO. 261)
 61 ttctgcaact tattccttta ttcctcattt aaaataatct accatagtaa aacatgtat
121 aaaagtgcta cttctgcacc acttttgaga atagtgttat ttcagtgaat cgatgtggtg
181 accatattgt aatgcatgta gtgaactgtt taaggcaaat catctacact agatgaccag
241 gaaatagaga ggaaatgtaa tttaatttcc attttctttt tagAGCAGTA TACAAAGATG
301 CTGATTTGTA TTTATTAGAC TCTCCTTTTG GATACCTAGA TGTTTTAACA GAAAAGAAA
361 TATTTGAAAG gtatgttctt tgaataccct acttataatg ctcatgctaa aataaaagaa
421 agacagactg tcccatcata gattgcattt tacctcttga gaaatatgtt caccattgtt
481 ggtatggcag aatgtagcat ggtattaact caaatctgat ctgccctact gggccaggat
541 tcaagattac ttccattaaa accttttctc accgcctcat gctaaaccag tttctctcat
601 tgctatactg ttatagcaat tgctatctat gtagttttg cagtatcatt gccttgtgat
661 atatattact ttaatt
```

| | | |
|---|---|---|
| CF12-s: | 5' CGCCCCGCCGCGCCCCGCGCCCGCCCCGCCGCCCCGCCCG-<br>GTGAACTGTTTAAGGCAAATCAT 3' | (SEQ. ID. NO. 262) |
| CF12-as: | 5' TGATGGGACAGTCTGTCTTTC 3' | (SEQ. ID. NO. 263) |
| CF12-s-tag: | 5' TCACTTCAGCAGTTCTT 3' | (SEQ. ID. NO. 264) |
| CF12-as-tag: | 5' CAATCTATGATGGGACA 3' | (SEQ. ID. NO. 265) |

CF exon 13

```
  1 gaattcacaa ggtaccaatt taattactac agagtactta tagaatcatt taaaatataa   (SEQ. ID. NO. 266)
 61 taaaattgta tgatagagat tatatgcaat aaaacattaa caaaatgcta aaatacgaga
121 catattgcaa taaagtattt ataaaattga tatttatatg tttttatatc ttaaagCTGT
181 GTCTGTAAAC TGATGGCTAA CAAAACTAGG ATTTTGGTCA CTTCTAAAAT GGAACATTTA
241 AAGAAAGCTG ACAAAATATT AATTTTGCAT GAAGGTAGCA GCTATTTTTA TGGGACATTT
301 TCAGAACTCC AAAATCTACA GCCAGACTTT AGCTCAAAAC TCATGGGATG TGATTCTTTC
361 GACCAATTTA GTGCAGAAAG AAGAAATTCA ATCCTAACTG AGACCTTACA CCGTTTCTCA
421 TTAGAAGGAG ATGCTCCTCT CTCCTGGACA GAAACAAAAA AACAATCTTT TAAACAGACT
481 GGAGAGTTTG GGGAAAAAAG GAAGAATTCT ATTCTCAATC CAATCAACTC TATACGAAAA
541 TTTTCCATTG TGCAAAAGAC TCCCTTACAA ATGAATGGCA TCGAAGAGGA TTCTGATGAG
601 CCTTTAGAGA GAAGGCTGTC CTTAGTACCA GATTCTGAGC AGGGAGAGGC GATACTGCCT
661 CGCATCAGCG TGATACAGCA CTGGCCCCACG CTTCAGGCAC GAAGGAGGCA GTCTGTCCTG
721 AACCTGATGA CACACTCAGT TAACCAAGGT CAGAACATTC ACCGAAAGAC AACAGCATCC
781 ACACGAAAAG TGTCACTGGC CCCTCAGGCA AACTTGACTG AACTGGATAT ATATTCAAGA
```

TABLE A-continued

```
 841 AGGTTATCTC AAGAAACTGG CTTCGAAATA AGTGAAGAAA TTAACCAAGA AGACTTAAAG 901 gtaggtatac atcgcttggg ggtatttcac cccacagaat gcaattgagt agaatgcaat 961 atgtagcatg taacaaaatt tactaaaatc ataggattag gataaggtgt atcttaaaac 1021 tcagaaagta tgaagttcat taattataca agcaacgtta aaatgtaaaa taacaaatga 1081 tttcttttg caatggacat atctcttccc ataaaatggg aaggattta gttttggtc 1141 ctctactaag ccagtgataa ctgtgactat agttagaaag catttgcttt attaccatct
```

| | | |
|---|---|---|
| CFTR13A-s: | 5' AATACGAGACATATTGCAATAAAGT 3' | (SEQ. ID. NO. 267) |
| CFTR13A-as: | 5' CGCCCGCCGCGCCCCGCGCCCGCCCCGCCGCCCCCGCCCG-<br>CTGGCTGTAGATTTTGGAGTTC 3' | (SEQ. ID. NO. 268) |
| CF13B-s3: | 5' AGGTAGCAGCTATTTTT 3' | (SEQ. ID. NO. 269) |
| CF13B-as3: | 5' CGCCCGCCGCGCCCCGCGCCCGCCCCGCCGCCCCCGCCCG-<br>GGACAGCCTTCTCTCTA 3' | (SEQ. ID. NO. 270) |
| CFTR13C-s: | 5' CGCCCGCCGCGCCCCGCGCCCGCCCCGCCGCCCCCGCCCGATGGGACATTTTC-<br>AGAACTCC 3' | (SEQ. ID. NO. 271) |
| CFTR13C-as: | 5' CCTCTTCGATGCCATTCAT 3' | (SEQ. ID. NO. 272) |
| CFTR13D-s: | 5' CGCCCGCCGCGCCCCGCGCCCGCCCCGCCGCCCCCGCCCGCAATCCAATCAAC-<br>TCTATACGAA 3' | (SEQ. ID. NO. 273) |
| CFTR13D-as: | 5' CTGATCACGCTGATGCGA 3' | (SEQ. ID. NO. 274) |
| CFTR13E-s: | 5' CGCCCGCCGCGCCCCGCGCCCGCCCCGCCGCCCCCGCCCGTGATGAGCC<br>TTTAGAGAGAA 3' | (SEQ. ID. NO. 275) |
| CFTR13E-as: | 5' CCAGTTCAGTCAAGTTTGC 3' | (SEQ. ID. NO. 276) |
| CF13F-s2: | 5' CGCCCGCCGCGCCCCGCGCCCGCCCCGCCGCCCCCGCCCGCAGCGTGAT-<br>CAGCA 3' | (SEQ. ID. NO. 277) |
| CF13F-as2: | 5' TTTGTTACATGCTACATA 3' | (SEQ. ID. NO. 278) |

CF exon 14A

```
  1 ggaaacttca tttagatggt atcattcatt tgataaaagg tatgccactg ttaagccttt    (SEQ. ID. NO. 279)

61 aatggtaaaa ttgtccaata ataatacagt tatataatca gtgatacatt tttagaattt 121 tgaaaaatta cgatgtttct catttttaat aaagctgtgt tgctccagta gacattattc 181 tggctataga atgacatcat acatggcatt tataatgatt tatatttgtt aaaatacact 241 tagattcaag taatactatt cttttatttt catatattaa aaataaaacc acaatggtgg 301 catgaaactg tactgtctta ttgtaatagc cataattctt TTATTCAGGA GTGCTTTTTT

361 GATGATATGG AGAGCATACC AGCAGTGACT ACATGGAACA CATACCTTCG ATATATTACT

421 GTCCACAAGA GCTTAATTTT TGTGCTAATT TGGTGCTTAG TAATTTTTCT GGCAGAGgta 481 agaatgttct attgtaaagt attactggat ttaaagttaa attaagatag tttggggatg 541 tatacatata tatgcacaca cataaatatg tatatataca catgtataca tgtataagta 601 tgcatatata cacacatata tcactatatg tatatatgta tatattacat atatttgtga 661 ttttacagta tataatggta tagattcata tagttcttag cttctgaaaa atcaacaagt 721 agaaccacta ctga
```

| | | |
|---|---|---|
| CFTR14A-1-s: | 5' CGCCCGCCGCGCCCCGCGCCCGCCCCGCCGCCCCCGCCCG-<br>TTCATATATTAAAAATAAAACC 3' | (SEQ. ID. NO. 280) |
| CFTR14A-1-as: | 5' TAATATATCGAAGGTATGTGT 3' | (SEQ. ID. NO. 281) |
| CFTR14A-2-s: | 5' GAGCATACCAGCAGTGACTACA 3' | (SEQ. ID. NO. 282) |
| CFTR14A-2-as: | 5' CGCCCGCCGCGCCCCGCGCCCGCCCCGCCGCCCCCGCCCG-<br>GTAATACTTTACAATAGAACATTCTTACC 3' | (SEQ. ID. NO. 283) |
| CFTR14A-3-s: | 5' ACCAGCAGTGACTACATGGA 3' | (SEQ. ID. NO. 284) |
| CFTR14A-3-as: | 5' ATATTTATGTGTGTGCATATATATGTAT 3' | (SEQ. ID. NO. 285) |

TABLE A-continued

```
CF14A-s-tag:     5' TGTTGCTCCAGTAGACA 3'                            (SEQ. ID. NO. 286)
CF14A-as-tag:    5' CATCCCCAAACTATCT 3'                             (SEQ. ID. NO. 287)
```

CF exon 14B

```
  1  gaattccatt aacttaatgt ggtctcatca caaataatag tacttagaac acctagtaca  (SEQ. ID. NO. 288)
 61  gctgctggac ccaggaacac aaagcaaagg aagatgaaat tgtgtgtacc ttgatattgg
121  tacacacatc aaatggtgtg atgtgaattt agatgtgggc atgggaggaa taggtgaaga
181  tgttagaaaa aaaatcaact gtgtcttgtt ccattccagG TGGCTGCTTC TTTGGTTGTG
241  CTGTGGCTCC TTGGAAAgtg agtattccat gtcctattgt gtagattgtg ttttatttct
301  gttgattaaa tattgtaatc cactatgttt gtatgtattg taatccactt tgtttcattt
361  ctcccaagca ttatggtagt ggaaagataa ggttttttgt ttaaatgatg accattagtt
421  gggtgaggtg acacattcct gtagtcctag ctcctccaca ggctgacgca ggaggatcac
481  ttgagcccag gagttcaggg ctgtagtgtt gtatcattgt gagtagccac caccgcactc
541  cagcctggac aatatagtga gatcctatat ctaaaataaa ataaaataaa atgaataaat
601  tgtgagcatg tgcagctcct g
```

```
CFTR14B-1-s:     5' CGCCCGCCGCGCCCCGCGCCCGCCCCGCCGCCCCCGCCCG-         (SEQ. ID. NO. 289)
                    GTGTACCTTGATATTGG 3'
CFTR14B-1-as:    5' CTCACTTTCCAAGGAG 3'                              (SEQ. ID. NO. 290)

CF14B-3-s:       5' GCTGTGGCTCCTTGG 3'                               (SEQ. ID. NO. 291)
CF14B-3-as:      5' CGCCCGCCGCGCCCCGCGCCCGCCCCGCCGCCCCCGCCCG-         (SEQ. ID. NO. 292)
                    ACTACAGCCCTGAACTCC 3'

CF14B-s-tag:     5' GGAACACAAAGCAAAG 3'                              (SEQ. ID. NO. 293)
CF14B-as-tag:    5' TGGGAGAAATGAAACA 3'                              (SEQ. ID. NO. 294)
```

CF exon 15

```
  1  tcctatatct aaataaataa ataaatgaat aaattgtgag catgtgcagc tcctgcagtt  (SEQ. ID. NO. 295)
 61  tctaaagaat atagttctgt tcagtttctg tgaaacacaa taaaaatatt tgaaataaca
121  ttacatattt agggttttct tcaattttt taatttaata agaacaact caatctctat
181  caatagtgag aaaacatatc tattttcttg caataatagt atgattttga ggttaagggt
241  gcatgctctt ctaatgcaaa atattgtatt tatttagact caagttagt tccatttaca
301  tgtattggaa attcagtaag taactttggc tgccaaataa cgatttccta tttgctttac
361  agCACTCCTC TTCAAGACAA AGGGAATAGT ACTCATAGTA GAAATAACAG CTATGCACTG
421  ATTATCACCA GCACCAGTTC GTATTATGTG TTTTACATTT ACGTGGGAGT AGCCGACACT
481  TGCTTGCTA TGGGATTCTT CAGACGTCTA CCACTGGTGC ATACTCTAAT CACAGTGTCG
541  AAAATTTTAC ACCACAAAAT GTTACATTCT GTTCTTCAAG CACCTATGTC AACCCTCAAC
601  ACGTTGAAAG CAGgtacttt actaggtcta agaaatgaaa ctgctgatcc accatcaata
661  gggcctgtgg ttttgttggt tttctaatgg cagtgctggc ttttgcacag aggcatgtgc
721  ctttgtt
```

```
CFTR15A-s:       5' CGCCCGCCGCGCCCCGCGCCCGCCCCGCCGCCCCCGCCCGCATGTATTGGAA  (SEQ. ID. NO. 296)
                    ATTCAGTAAGTAAC 3'
CFTR15A-as:      5' TTCGACACTGTGATTAGAGTATGC 3'                           (SEQ. ID. NO. 297)

CFTR15B-s:       5' GTGGGAGTAGCCGACA 3'                                   (SEQ. ID. NO. 298)
CFTR15B-as:      5' CGCCCGCCGCGCCCCGCGCCCGCCCCGCCGCCCCCGCCCG-             (SEQ. ID. NO. 299)
                    CAGGCCCTATTGATGGT 3'
```

TABLE A-continued

| | | |
|---|---|---|
| CF15B-s2: | 5' CGTGGGAGTAGCCGAC 3' | (SEQ. ID. NO. 300) |
| CF15B-as2: | 5' CGCCCGCCGCGCCCCGCGCCCGCCCCGCCGCCCCGCCCG-<br>CATTAGAAAACCAACAAA 3' | (SEQ. ID. NO. 301) |
| CF15-s-tag: | 5' AGACTCAAGTTTAGTTCCA 3' | (SEQ. ID. NO. 302) |
| CF15-as-tag: | 5' CCAACAAAACCACAGG 3' | (SEQ. ID. NO. 303) |

CF exon 16

```
  1  gtaagattgt aagcaggatg agtacccacc tattcctgac ataatttata gtaaaagcta   (SEQ. ID. NO. 304)

61  tttcagagaa attggtcgtt acttgaatct tacaagaatc tgaaactttt aaaaaggttt 121  aaaagtaaaa gacaataact tgaacacata attatttaga atgtttggaa agaaacaaaa 181  atttctaagt ctatctgatt ctatttgcta attcttattt gggttctgaa tgcgtctact 241  gtgatccaaa cttagtattg aatatattga tatatcttta aaaaattagt gtttttgag 301  gaatttgtca tcttgtatat tatagGTGGG ATTCTTAATA GATTCTCCAA AGATATAGCA 361  ATTTTGGATG ACCTTCTGCC TCTTACCATA TTTGACTTCA TCCAGgtatg taaaaataag 421  taccgttaag tatgtctgta ttattaaaaa aacaataaca aaagcaaatg tgattttgtt 481  ttcatttttt atttgattga gggttgaagt cctgtctatt gcattaattt tgtaattatc 541  caaagccttc aaaatagaca taagtttagt aaattcaata ataagtcaga actgcttacc 601  tggcccaaac ctgaggcaat cccacattta gatgtaatag ctgtctactt gggagtgatt 661  tgagaggcac aaaggaccat ctttcccaaa atcactggca c
```

| | | |
|---|---|---|
| CF16A-s5 | 5'CGCCCGCCGCGCCCCGCGCCCGCCCCGCCGCCCCGCCCGCTGAATGCGTCT-<br>ACTG 3' | (SEQ. ID. NO. 305) |
| CF16A-as5 | 5'CATCCAAAATTGCTATA 3' | (SEQ. ID. NO. 306) |
| CFTR16B-s: | 5' TTGAGGAATTTGTCATCTTGTAT 3' | (SEQ. ID. NO. 307) |
| CFTR16B-as: | 5' CGCCCGCCGCGCCCCGCGCCCGCCCCGCCGCCCCGCCCG-<br>CAAAATCACATTTGCTTTTGTTA 3' | (SEQ. ID. NO. 308) |
| CF16-s-tag: | 5' ATGCGTCTACTGTGATC 3' | (SEQ. ID. NO. 309) |
| CF16-as-tag: | 5' CTTCAACCCTCAATCA 3' | (SEQ. ID. NO. 310) |

CF exon 17A

```
  1  agtgcaccag catggcacat gtatacatat gtaactaacc tcgacaatgt gcacatgtac   (SEQ. ID. NO. 311)

61  cctaaaactt aaagtataat aaaaaaaata aaaaaaagtt tgaggtgttt aaagtatgca 121  aaaaaaaaaa aagaaataaa tcactgacac actttgtcca ctttgcaatg tgaaaatgtt 181  tactccaccaa catgttttct ttgatcttac agTTGTTATT AATTGTGATT GGAGCTATAG

241  CAGTTGTCGC AGTTTTACAA CCCTACATCT TGTTGCAAC AGTGCCAGTG ATAGTGGCTT

301  TTATTATGTT GAGAGCATAT TTCCTCCAAA CCTCACAGCA ACTCAAACAA CTGGAATCTG

361  AAGgtatgac agtgaatgtg cgatactcat cttgtaaaaa agctataaga gctatttgag 421  attcttattt gttaatctac ttaaaaaaaa ttctgctttt aaacttttac atcatataac 481  ataattttt ttctacatgc atgtgtatat aaaaggaaac tatattacaa agtacacatg 541  gattttttt cttaattaat gaccatgtga cttcattttg gttttaaaat aggtatatag 601  aatcttacca cagttggtgt acaggacatt catttat
```

| | | |
|---|---|---|
| CF17A-1-s6: | 5' CGCCCGCCGCGCCCCGCGCCCGCCCCGCCGCCCCGCCCG-<br>AAAGAAATAAATCACTGA 3' | (SEQ. ID. NO. 312) |
| CF17A-1-as6: | 5' GTAAAACTGCGACAAC 3' | (SEQ. ID. NO. 313) |
| CFTR17A-2-s: | 5' CCAACATGTTTTCTTTGATCTTACAG 3' | (SEQ. ID. NO. 314) |
| CFTR17A-2-as: | 5' CGCCCGCCGCGCCCCGCGCCCGCCCCGCCGCCCCGCCCG-<br>AGAATCTCAAATAGCTCTTATAGCTTT 3' | (SEQ. ID. NO. 315) |

TABLE A-continued

```
CF17A-s-tag:    5' AAATAAATCACTGACACAC 3'                          (SEQ. ID. NO. 316)
CF17A-as-tag:   5' AATGAAGTCACATGGTC 3'                            (SEQ. ID. NO. 317)
```

CF exon 17B

```
  1 ttcaaagaat ggcaccagtg tgaaaaaaag cttttttaacc aatgacattt gtgatatgat  (SEQ. ID. NO. 318)

61 tattctaatt tagtctttttt caggtacaag atattatgaa aattacattt tgtgtttatg 121 ttatttgcaa tgttttctat ggaaatattt cacagGCAGG AGTCCAATTT TCACTCATCT

181 TGTTACAAGC TTAAAAGGAC TATGGACACT TCGTGCCTTC GGACGGCAGC CTTACTTTGA

241 AACTCTGTTC CACAAAGCTC TGAATTTACA TACTGCCAAC TGGTTCTTGT ACCTGTCAAC

301 ACTGCGCTGG TTCCAAATGA GAATAGAAAT GATTTTTGTC ATCTTCTTCA TTGCTGTTAC

361 CTTCATTTCC ATTTTAACAA CAGgtactat gaactcatta actttagcta agcatttaag 421 taaaaaattt tcaatgaata aaatgctgca ttctataggt tatcaattt tgatatcttt 481 agagtttagt aattaacaaa tttgttggtt tattattgaa caagtgattt cttttgaaatt 541 tccattgttt tattgttaaa caaataattt ccttgaaatc ggtatatata tatatatagt
```

```
CFTR17B-1-s:    5' CGCCCGCCGCGCCCCGCGCCCGCCCCGCCGCCCCGCCCG-         (SEQ. ID. NO. 319)
                   TTAACCAATGACATTTGTGATA 3'
CFTR17B-1-as:   5' GTGTCCATAGTCCTTTTAAGC 3'                        (SEQ. ID. NO. 320)
CF17B-2-s2:     5' CGCCCGCCGCGCCCCGCGCCCGCCCCGCCGCCCCGCCCG-         (SEQ. ID. NO. 321)
                   AATATTTCACAGGCAG 3'
CF17B-2-as2:    5' TGAAGGTAACAGCAAT 3'                              (SEQ. ID. NO. 322)
CFTR17B-3-s:    5' ACTTCGTGCCTTCGGAC 3'                             (SEQ. ID. NO. 323)
CFTR17B-3-as:   5' CGCCCGCCGCGCCCCGCGCCCGCCCCGCCGCCCCGCCCG-         (SEQ. ID. NO. 324)
                   CAGCAATGAAGAAGATGACAAA 3'
CFTR17B-4-s:    5' CTGGTTCCAAATGAGAA 3'                             (SEQ. ID. NO. 325)
CFTR17B-4-as:   5' CGCCCGCCGCGCCCCGCGCCCGCCCCGCCGCCCCGCCCG-         (SEQ. ID. NO. 326)
                   TAACCTATAGAATGCAGCA 3'
```

CF exon 18

```
  1 ttattactta tagaataata gtagaagaga caaatatggt acctacccat taccaacaac  (SEQ. ID. NO. 327)

61 acctccaata ccagtaacat ttttttaaaaa gggcaacact ttcctaatat tcaatcgctc 121 tttgatttaa aatcctggtt gaatacttac tatatgcaga gcattattct attagtagat 181 gctgtgatga actgagattt aaaaattgtt aaaattagca taaaattgaa atgtaaattt 241 aatgtgatat gtgccctagg agaagtgtga ataaagtcgt tcacagaaga gagaaataac 301 atgaggttca tttacgtctt ttgtgcatct atagGAGAAG GAGAAGGAAG AGTTGGTATT

361 ATCCTGACTT TAGCCATGAA TATCATGAGT ACATTGCAGT GGGCTGTAAA CTCCAGCATA

421 GATGTGGATA GCTTGgtaag tcttatcatc ttttttaactt ttatgaaaaa aattcagaca 481 agtaacaaag tatgagtaat agcatgagga agaactatat accgtatatt gagcttaaga 541 aataaaacat tacagataaa ttgagggtca ctgtgtatct gtcattaaat ccttatctct 601 tctttccttc tcatagatag ccactatgaa gatcaatac tgcagtgagc attctttcac 661 ctgtttcctt attcaggatt ttctaggaga aatacctagg ggttgtattg ctgggtcata 721 ggattcaccc atgcttaac
```

```
CFTR18A-s:      5' CGCCCGCCGCGCCCCGCGCCCGCCCCGCCGCCCCGCCCG-         (SEQ. ID. NO. 328)
                   TTAATGTGATATGTGCCCTA 3'
CFTR18A-as:     5' AGATGATAAGACTTACCAAGC 3'                         (SEQ. ID. NO. 329)
CFTR18B-s:      5' GAGAAGGAGAAGGAAGAGTTG 3'                         (SEQ. ID. NO. 330)
CFTR18B-as:     5' CGCCCGCCGCGCCCCGCGCCCGCCCCGCCGCCCCGCCCG-         (SEQ. ID. NO. 331)
                   CTTCCTCATGCTATTACTCATAC 3'
```

TABLE A-continued

| | | |
|---|---|---|
| CF18-s-tag: | 5' CCTGGTTGAATACTTACT 3' | (SEQ. ID. NO. 332) |
| CF18-as-tag: | 5' CTCATACTTTGTTACTTGTC 3' | (SEQ. ID. NO. 333) |

CF exon 19

```
  1 ttctcttcag ttaaactttt aattatatcc aattatttcc tgttagttca ttgaaaagcc   (SEQ. ID. NO. 334)
 61 cgacaaataa ccaagtgaca aatagcaagt gttgcatttt acaagttatt ttttaggaag
121 catcaaacta attgtgaaat tgtctgccat tcttaaaaac aaaaatgttg ttatttttat
181 ttcagATGCG ATCTGTGAGC CGAGTCTTTA AGTTCATTGA CATGCCAACA GAAGGTAAAC
241 CTACCAAGTC AACCAAACCA TACAAGAATG CCAACTCTC GAAAGTTATG ATTATTGAGA
301 ATTCACACGT GAAGAAAGAT GACATCTGGC CCTCAGGGGG CCAAATGACT GTCAAAGATC
361 TCACAGCAAA ATACACAGAA GCTGGAAATG CCATATTAGA GAACATTTCC TTCTCAATAA
421 GTCCTGGCCA GAGGgtgaga tttgaacact gcttgctttg ttagactgtg ttcagtaagt
481 gaatcccagt agcctgaagc aatgtgttag cagaatctat ttgtaacatt attattgtac
541 agtagaatca atattaaaca cacatgtttt attatatgga gtcattattt ttaatatgaa
601 atttaatttg cagagtctga actatatat
```

| | | |
|---|---|---|
| CF19A-s2: | 5' CGCCCGCCGCGCCCCGCGCCCGCCCCGCCGCCCCGCCCG-<br>AAGTTATTTTTTAGGAAGCAT 3' | (SEQ. ID. NO. 335) |
| CF19A-as: | 5' GAACTTAAAGACTCGGCTC 3' | (SEQ. ID. NO. 336) |
| CF19B-s: | 5' CGCCCGCCGCGCCCCGCGCCCGCCCCGCCGCCCCGCCCG-<br>GAAATTGTCTGCCATTCTTAA 3' | (SEQ. ID. NO. 337) |
| CF19B-as: | 5' GAGTTGGCCATTCTTGTATG 3' | (SEQ. ID. NO. 338) |
| CF19C-s3: | 5' CGCCCGCCGCGCCCCGCGCCCGCCCCGCCGCCCCGCCCG-<br>TGTGAGCCGAGTCTTT 3' | (SEQ. ID. NO. 339) |
| CF19C-as2: | 5' ATGGCATTTCCACCTT 3' | (SEQ. ID. NO. 340) |
| CF19D-s2: | 5' CGTGAAGAAAGATGAC 3' | (SEQ. ID. NO. 341) |
| CF19D-as2: | 5' CGCCCGCCGCGCCCCGCGCCCGCCCCGCCGCCCCGCCCG-<br>TAATGTTACAAATAGATTC 3' | (SEQ. ID. NO. 342) |
| CF19-s-tag: | 5' GACAAATAACCAAGTGAC 3' | (SEQ. ID. NO. 343) |
| CF19-as-tag: | 5' AACACATTGCTTCAGG 3' | (SEQ. ID. NO. 344) |

CF intron 19

```
29941 acttaactgc tttctccatt tgtagtctct tgaaaataca gaaatttcag aaataattta   (SEQ. ID. NO. 345)
30001 taagaatatc aaggattcaa atcatatcag cacaaacacc taaatacttg tttgctttgt
30061 taaacacata tcccattttc tatcttgata aacattggtg taaagtagtt gaatcattca
30121 gtgggtataa gcagcatatt ctcaatacta tgtttcatta ataattaata gagatatatg
30181 aacacataaa agattcaatt ataatcacct tgtggatcta aatttcagtt gacttgtcat
30241 cttgatttct ggagaccaca aggtaatgaa aaataattac aagagtcttc catctgttgc
30301 agtattaaaa tggCgagtaa gacaccctga aggaaatgt tctattcatg gtacaatgca
30361 attacagcta gcaccaaatt caacactgtt taactttcaa catattattt tgatttatct
30421 tgatccaaca ttctcaggga ggaggtgcat tgaagttatt agaaaacact gacttagatt
30481 tagggtatgt cttaaaagct tatttgcggg aagtactcta gccttattca acagateact
30541 gagaagcctg gaaaaacaaa tcccggaaac taattattat gtgccagtta tataaacaag
30601 aagacttgt tgggtacaaa ccagtgattc cttgccttg aaaaatgtgt cagatatcat
```

| | | |
|---|---|---|
| CF19i-s2: | 5'CGCCCGCCGCGCCCCGCGCCCGCCCCGCCGCCCCGCCCGCTTGATTTCTG- | (SEQ. ID. NO. 346) |
| CF19i-as2: | 5'CTAGCTGTAATTGCAT 3' | (SEQ. ID. NO. 347) |
| CF19i-s1 tag: | 5'tagAGTGGGTATAAGCAGC 3' | (SEQ. ID. NO. 348) |
| CF19i-as1 tag: | 5'tagGTTGAATAAGGCTAGAGTA 3' | (SEQ. ID. NO. 349) |

TABLE A-continued

CF exon 20

```
  1  aaaggtcagt gataaaggaa gtctgcatca ggggtccaat tccttatggc cagtttctct  (SEQ. ID. NO. 350)
 61  attctgttcc aaggttgttt gtctccatat atcaacattg gtcaggattg aaagtgtgca
121  acaaggtttg aatgaataag tgaaaatctt ccactggtga caggataaaa tattccaatg
181  gttttattg aagtacaata ctgaattatg tttatggcat ggtacctata tgtcacagaa
241  gtgatcccat cactttttacc ttatagGTGG GCCTCTTGGG AAGAACTGGA TCAGGGAAGA
301  GTACTTTGTT ATCAGCTTTT TTGAGACTAC TGAACACTGA AGGAGAAATC CAGATCGATG
361  GTGTGTCTTG GGATTCAATA ACTTTGCAAC AGTGGAGGAA AGCCTTTGGA GTGATACCAC
421  AGgtgagcaa aaggacttag ccagaaaaaa ggcaactaaa ttatatttt tactgctatt
481  tgatacttgt actcaagaaa ttcatattac tctgcaaaat atatttgtta tgcattgctg
541  tcttttttt ctccagtgca gttttctcat aggcagaaaa gatgtctcta aaagtttggg
```

| | | |
|---|---|---|
| CFTR20-s: | 5' CGCCCGCCGCGCCCCGCGCCCGCCCCGCCGCCCCGCCCG-GAATTATGTTTATGGCATGGT 3' | (SEQ. ID. NO. 351) |
| CFTR20-as: | 5' GAGTACAAGTATCAAATAGCAGTAA 3' | (SEQ. ID. NO. 352) |
| CF20-s-tag: | 5' AAATCTTCCACTGGTGA 3' | (SEQ. ID. NO. 353) |
| CF20-as-tag: | 5' GACATCTTTTCTGCCTAT 3' | (SEQ. ID. NO. 354) |
| new 20-s: | 5'CGCCCGCCGCGCCCCGCGCCCGCCCCGCCGCCCCGCCCGCTGAATTAT-GTTTATGGCA3' | (SEQ. ID. NO. 355) |
| new 20-as: | 5'CCTTTTTTCTGGCTAAGT3' | (SEQ. ID. NO. 356) |

CF exon 21

```
  1  tttttaatat tctacaatta acaattatct caatttctt attctaaaga cattggatta  (SEQ. ID. NO. 357)
 61  gaaaaatgtt cacaagggac tccaaatatt gctgtagtat ttgtttctta aaagaatgat
121  acaaagcaga catgataaaa tattaaaatt tgagagaact tgatggtaag tacatgggtg
181  tttcttattt taaaataatt tttctacttg aaatatttta caatacaata agggaaaaat
241  aaaaagttat ttaagttatt catactttct tcttcttttc ttttttgcta tagAAAGTAT
301  TTATTTTTC TGGAACATTT AGAAAAAACT TGGATCCCTA TGAACAGTGG AGTGATCAAG
361  AAATATGGAA AGTTGCAGAT GAGgtaaggc tgctaactga aatgattttg aaaggggtaa
421  ctcataccaa cacaaatggc tgatatagct gacatcattc tacacactt tgtgtgcatgt
481  atgtgtgtgc acaactttaa aatggagtac cctaacatac ctggagcaac aggtacttt
541  gactggacct accccctaact gaaatgattt tgaaagaggt aactcatacc aacacaaatg
601  gttgatatagg ctaagatcat tctacacact tgtgtgcat gtatttctgt gcacaacttc
661  aaaatggagt accctaaaat acctggcgcg acaagtactt ttgactgagc ctactt
```

| | | |
|---|---|---|
| CF21A-s2: | 5' ATGGTAAGTACATGGGTGTT 3' | (SEQ. ID. NO. 358) |
| CF21A-as2: | 5' CCACTGTTCATAGGGATCCAAG 3' | (SEQ. ID. NO. 359) |
| CF21B-s3: | 5' CGCCCGCCGCGCCCCGCGCCCGCCCCGCCGCCCCGCCCG-TTTCTGGAACATTTAG 3' | (SEQ. ID. NO. 360) |
| CF21B-as3: | 5' GAATGATGTCAGCTATAT 3' | (SEQ. ID. NO. 361) |
| CF21-s-tag: | 5' TGTTCACAAGGGACTC 3' | (SEQ. ID. NO. 362) |
| CF21-as-tag: | 5' CAGTTAGGGGTAGGTC 3' | (SEQ. ID. NO. 363) |
| CF 21A-s3: | 5' CGCCCGCCGCGCCCCGCGCCCGCCCCGCCGCCCCGCCCG-AGTTATTCATACTTTCTTCT 3' | (SEQ. ID. NO. 364) |
| CF21A-as3: | 5' AGCCTTACCTCATCTG 3' | (SEQ. ID. NO. 365) |

CF exon 22

```
  1  cacagttgac tattttatgc tatctttgt cctcagtcat gacagagtag aagatgggag  (SEQ. ID. NO. 366)
 61  gtagcaccaa ggatgatgtc atacctccat cctttatgct acattctatc ttctgtctac
```

TABLE A-continued

```
 121   ataagatgtc atactagagg gcatatctgc aatgtataca tattatcttt tccagcatgc
 181   attcagttgt gttggaataa tttatgtaca cctttataaa cgctgagcct cacaagagcc
 241   atgtgccacg tattgtttct tactactttt ggatacctgg cacgtaatag acactcattg
 301   aaagtttcct aatgaatgaa gtacaaagat aaaacaagtt atagactgat tcttttgagc
 361   tgtcaaggtt gtaaatagac ttttgctcaa tcaattcaaa tggtggcagg tagtgggggt
 421   agagggattg gtatgaaaaa cataagcttt cagaactcct gtgtttattt ttagaatgtc
 481   aactgcttga gtgttttttaa ctctgtggta tctgaactat cttctctaac tgcagGTTGG
 541   GCTCAGATCT GTGATAGAAC AGTTTCCTGG GAAGCTTGAC TTTGTCCTTG TGGATGGGGG
 601   CTGTGTCCTA AGCCATGGCC ACAAGCAGTT GATGTGCTTG CTAGATCTG TTCTCAGTAA
 661   GGCGAAGATC TTGCTGCTTG ATGAACCCAG TGCTCATTTG GATCCAGTgt gagtttcaga
 721   tgttctgtta cttaatagca cagtggggaac agaatcatta tgcctgcttc atggtgacac
 781   atatttctat taggctgtca tgtctgcgtg tgggggtctc ccaagatatg aaataattgc
 841   ccagtggaaa tgagcataaa tgcatatttc cttgctaaga gttcttgtgt tttcttccga
 901   agatagtttt
```

| | | | |
|---|---|---|---|
| CFTR22A-s2: | 5' CGCCCGCCGCGCCCCGCGCCCGCCCCGCCGCCCCGCCCG-<br>TGAGCTGTCAAGGTTGTA 3' | | (SEQ. ID. NO. 367) |
| CFTR22A-as2: | 5' CAGGAAACTGTTCTATCAC 3' | | (SEQ. ID. NO. 368) |
| CFTR22B-s: | 5' CGCCCGCCGCGCCCCGCGCCCGCCCCGCCGCCCCGCCCG-<br>GAATGTCAACTGCTTGAGTGTTTT 3' | | (SEQ. ID. NO. 369) |
| CFTR22B-as: | 5' AAGTAACAGAACATCTGAAACTCACAC 3' | | (SEQ. ID. NO. 370) |
| CF22C-s: | 5' CTTGCTGCTTGATGAAC 3' | | (SEQ. ID. NO. 371) |
| CF22C-as: | 5' GCAATTATTTCATATCTTGG 3' | | (SEQ. ID. NO. 372) |
| CF22-s-tag: | 5' AGGGATTGGTATGAAAA 3' | | (SEQ. ID. NO. 373) |
| CF22-as-tag: | 5' GGAAGAAAACACAAGAAC 3' | | (SEQ. ID. NO. 374) |

CF exon 23

```
   1   gcatgtttat agccccaaat aaaagaagta ctggtgattc tacataatga aaatgtactc   (SEQ. ID. NO. 375)
  61   atttattaaa gtttctttga atatttgtc ctgtttattt atggatactt agagtctacc
 121   ccatggttga aaagctgatt gtgcgtaacg ctatatcaac attatgtgaa aagaacttaa
 181   agaaataagt aatttaaaga gataatagaa caatagacat attatcaagg taaatacaga
 241   tcattactgt tctgtgatat tatgtgtggt attttctttc ttttctagAA CATACCAAAT
 301   AATTAGAAGA ACTCTAAAAC AAGCATTTGC TGATTGCACA GTAATTCTCT GTGAACACAG
 361   GATAGAAGCA ATGTGGAAT GCCAACAATT TTTGgtgagt ctttataact ttacttaaga
 421   tctcattgcc cttgtaattc ttgataacaa tctcacatgt gatagttcct gcaaattgca
 481   acaatgtaca agttcttttc aaaaatatgt atcatacagc catccagctt tactcaaaat
 541   agctgcacaa gttttttcact ttgatctgag ccatgtggtg aggttgaaat atagtaaatc
 601   taaaatggca gcatattact aagttatgtt tataaatagg atatatatac ttttgagccc
 661   tttatttggg accaagtcat acaaaatact ctactgttta agattttaaa aaaggtccct
 721   gtgattcttt caataactaa atgtcccatg gatgtggtct ggacaggcct agttgtctta
 781   cagtctgatt tatggtatta atgacaaagt tgagaggcac atttcatttt tctagccatg
```

| | | | |
|---|---|---|---|
| CF23A-s3: | 5' CGCCCGCCGCGCCCCGCGCCCGCCCCGCCGCCCCGCCCG-<br>TATCAAGGTAAATACAGA 3' | | (SEQ. ID. NO. 376) |
| CF23A-as3: | 5' GCTTCTATCCTGTGTTC 3' | | (SEQ. ID. NO. 377) |

TABLE A-continued

| | | |
|---|---|---|
| CF23B-s2: | 5' GATATTATGTGTGGTATTTTC 3' | (SEQ. ID. NO. 378) |
| CF23B-as2: | 5'CGCCCGCCGCGCCCCGCGCCCGCCCCGCCGCCCCGCCCGGAACTTGTACATTGTTGCA 3' | (SEQ. ID. NO. 379) |

CF exon 24

```
  1 agatggtaga acctccttag agcaaaagga cacagcagtt aaatgtgaca tacctgattg     (SEQ. ID. NO. 380)

61 ttcaaaatgc aaggctctgg acattgcatt ctttgacttt tattttcctt tgagcctgtg 121 ccagtttctg tccctgctct ggtctgacct gccttctgtc ccagatctca ctaacagcca 181 tttccctagG TCATAGAAGA GAACAAAGTG CGGCAGTACG ATTCCATCCA GAAACTGCTG

241 AACGAGAGGA GCCTCTTCCG GCAAGCCATC AGCCCCTCCG ACAGGGTGAA GCTCTTTCCC

301 CACCGGAACT CAAGCAAGTG CAAGTCTAAG CCCCAGATTG CTGCTCTGAA AGAGGAGACA

361 GAAGAAGAGG TGCAAGATAC AAGGCTTTAG agagcagcat aaatgttgac atgggacatt 421 tgctcatgga attggagctc gtgggacagt cacctcatgg aattggagct cgtggaacag 481 ttacctctgc ctcagaaaac aaggatgaat taagttttt tttaaaaaag aaacatttgg 541 taaggggaat tgaggacact gatatgggtc ttgataaatg gcttcctggc aatagtcaaa 601 ttgtgtgaaa ggtacttcaa atccttgaag atttaccact tgtgttttgc aagccagatt 661 ttcctgaaaa cccttgccat gtgctagtaa ttggaaaggc agctctaaat gtcaatcagc
```

| | | |
|---|---|---|
| CF24A-s2: | 5' CGCCCGCCGCGCCCCGCGCCCGCCCCGCCGCCCCGCCCG-CCTTTGAGCCTGTGCC 3' | (SEQ. ID. NO. 381) |
| CF24A-as2: | 5' GCTTGAGTTCCGGTGG 3' | (SEQ. ID. NO. 382) |
| CF24B-s2: | 5' CATCAGCCCCTCCGAC 3' | (SEQ. ID. NO. 383) |
| CF24B-s2: | 5' CGCCCGCCGCGCCCCGCGCCCGCCCCGCCGCCCCGCCCG-TTTCTGAGGCAGAGGTA 3' | (SEQ. ID. NO. 384) |
| CF24-s-tag: | 5' GCAGTTAAATGTGACATACC 3' | (SEQ. ID. NO. 385) |
| CF24-as-tag: | 5' TCCTTGTTTTCTGAGGC 3' | (SEQ. ID. NO. 386) |

TABLE B

| locus on AH006034 | primer name | primer alignment start | end | upstre 50 bp | downstr. 50 bp | Alignment to GemBank Accession Number AH006034 Primer sequences 5'-3' | |
|---|---|---|---|---|---|---|---|
| HUMCFTRA1 | CFTR1A-s | 701 | 722 | 651 | 772 | CGCCCCCGCGCCCCGCCCCGCCCCGGGAAGCAAATGACATCACAGC | (Seq Id No. 387) |
| | CFTR1A-as | 857 | 880 | 807 | 903 | TGAAAAAAAGTTTTGGAGCACAF | (Seq Id No. 388) |
| | CFTR1B-s | 782 | 828 | 732 | 878 | CCAGCGCCAGAGACC | (Seq Id No. 389) |
| | CFTR1B-as | 955 | 976 | 905 | 1026 | CGCCCCCGCGCCCCGCCCCGCCCCGACTGCTTATTCCTTTACCCAA | (Seq Id No. 390) |
| HUMCFTRA2 | CRTR2A-sa | 167 | 189 | 117 | 239 | GGCCCCGCGCGCCCCGCCCCGCCCCAGAAAAGTTGAAATAGTATCAG | (Seq Id No. 391) |
| | CFTR2A-as2 | 325 | 343 | 275 | 393 | AGATTGTCAGCAGAATCAA | (Seq Id No. 392) |
| | CF2B-s5: | 308 | 324 | 258 | 374 | ATACCAAATCCTTCTG | (Seq Id No. 393) |
| | CF2B-as5: | 413 | 431 | 363 | 481 | CGCCCCCGCGCCCCGCCCCGCCCCGTGCTTTCTTCTTTCTCTAAT | (Seq Id No. 394) |
| | CFTR2B-s2 | 292 | 312 | 242 | 362 | CGCCCCCGCGCCCCGCCCCGCCCCGTGGAATTGTCAGACATATACC | (Seq Id No. 395) |
| | CFTR2B-as2 | 470 | 486 | 420 | 536 | AGCCACCATACTTGGCT | (Seq Id No. 396) |
| HUMCFTRA3 | CF3A-s2 | 31 | 46 | -19 | 96 | CGCCCCCGCGCCCCGCCCCGCCCCGTGGTGTTGTATGGTCT | (Seq Id No. 397) |
| | CF3A-as2 | 252 | 268 | 202 | 318 | AACATAAATCTCCAGAA | (Seq Id No. 398) |
| | CFTR3A-s | 58 | 77 | 8 | 127 | CGCCCCCGCGCCCCGCCCCGCCCCGTGTCTCTATAATACTTGGGT | (Seq Id No. 399) |
| | CFTR3A-as | 266 | 287 | 216 | 337 | ATATAAAAGATTCCATAGAAC | (Seq Id No. 400) |
| | CFTR3B-s | 200 | 220 | 150 | 270 | GCTGGCTTCAAAGAAAAATCC | (Seq Id No. 401) |
| | CFTR3B-as | 354 | 376 | 304 | 426 | CGCCCCCGCGCCCCGCCCCGCCCCGACCAGATTTCGTAGTCTTTTCA | (Seq Id No. 402) |
| HUMCFTRA4 | CFTR4A-s | 226 | 246 | 176 | 296 | CGCCCCCGCGCCCCGCCCCGCCCCGAATTTCTCTGTTTTTCCCCTT | (Seq Id No. 403) |
| | CFTR4A-as | 423 | 444 | 373 | 494 | AGCTATTCTCATCTGCATTCCA | (Seq Id No. 404) |
| | CFTR4B-s | 381 | 397 | 331 | 447 | GACACTGCTCTCACACC | (Seq Id No. 405) |
| | CFTR4B-as | 557 | 574 | 507 | 624 | CGCCCCCGCGCCCCGCCCCGCCCCGTCAGCATTTATCCCTTA | (Seq Id No. 406) |
| HUMCFTRA5 | CFTR5A-s | 187 | 212 | 137 | 262 | CGCCCCCGCGCCCCGCCCCGCCCCGATAATATATTTGTATTTGTTGTTG | (Seq Id No. 407) |
| | CFTR5A-as | 306 | 325 | 256 | 375 | AATTTGTTCAGGTTGTTGGA | (Seq Id No. 408) |
| | CFTR5B-a | 250 | 267 | 200 | 317 | AGCTGTCAASCCGTGTTC | (Seq Id No. 409) |
| | CFTR5B-as | 396 | 414 | 346 | 464 | CGCCCCGCGCCCCGCCCCGCCCCGATCTGACCCAGCAAAACTC | (Seq Id No. 410) |
| HUMCFTRA6 | CFTR6A-1-a | 223 | 242 | 173 | 292 | CGCCCCCGCGCCCCGCCCCGCCCCGTTGTTAGTTTCTAGGGTGG | (Seq Id No. 411) |
| | CFTR6A-1-as | 385 | 405 | 335 | 455 | AAGGACTATCACGAAACCAAG | (Seq Id No. 412) |
| | CFTR6A-2-s | 345 | 364 | 295 | 414 | GCTAATCTCCGAGTTGTTAC | (Seq Id No. 413) |
| | CFTR6A-2-as | 450 | 471 | 400 | 521 | CGCCCCCGCGCCCCGCCCCGCCCCGAGTTATGAAAATAGGTTGCTAC | (Seq Id No. 414) |
| | CF6A-3-s | 427 | 444 | 377 | 494 | CGCCCCCGCGCCCCGCCCCGCCCCGGGAGAATGATGATGAAG | (Seq Id No. 415) |
| | CF6A-3-as | 536 | 556 | 486 | 606 | ACACTGAAGATCACTGTTCTA | (Seq Id No. 416) |

TABLE B-continued

Alignment to GemBank Accession Number AH006034

| locus on AH006034 | primer name | primer alignment start | end | upstre 50 bp | downstr. 50 bp | Primer sequences 5'-3' | |
|---|---|---|---|---|---|---|---|
| | CFTR6A-3-s | 401 | 418 | 351 | 468 | TCCTTGCCCTTTTTCAGG | (Seq Id No. 417) |
| | CFTR6A-3-as | 539 | 553 | 489 | 613 | CGCCCGGCGCGCCCGGCCCCGCCCCGCCCCGCCCCTTTAATGACACTGAAGATCACTGTT | (SEQ Id No. 418) |
| | CFTR6B-1-s2 | 1504 | 1526 | 1454 | 1576 | CGCCCCGCGCCCCGCCCCGCCCCGCCCCGCCCCCTTGAGCAGTTCTTAATAGATA | (Seq Id No. 419) |
| | CFTR6B-1-as2 | 1641 | 1661 | 1591 | 1711 | ATGCCTTAACAGATTGGATAT | (Seq Id No. 420) |
| | CFTR6B-2-s2 | 1637 | 1657 | 1567 | 1707 | GAAAATATCCAATCTGTTAAG | (Seq Id No. 421) |
| | CFTR6B-2-as2 | 1777 | 1794 | 1727 | 1844 | CGCCCCGCGCCCCGCCCCGCCCCGCCCCGTGAGGTGGAGTCTACCA | (Seq Id No. 422) |
| | CFTR6B-2-s | 1637 | 1652 | 1587 | 1702 | GAAAATATCCAATCTG | (Seq Id No. 423) |
| | CFTR6B-2-as | 1780 | 1795 | 1730 | 1845 | CGCCCCGCGCCCCGCCCCGCC--CCCCCGCCCCGCCCCGATGAGGTGGAAGTCTA | (Seq Id No. 424) |
| HUMCFTRA7 | CFTR7A-s | 152 | 174 | 102 | 224 | GCTGCCTTCCGAGTCAGTTTCAGT | (Seq Id No. 425) |
| | CFTR7A-as | 246 | 269 | 196 | 319 | CGCCCCGCGCCCCGCCCCGCCCCGCCCCGACTCCGAAGG | (Seq Id No. 426) |
| | CFTR7C-s | 246 | 265 | 196 | 315 | ATGGTACATTACCTGTATTTTGTTTA | (Seq Id No. 427) |
| | CFTR7C-as | 476 | 498 | 426 | 548 | CGCCCCGCGCCCCGCCCCGCCCCGCCCCGACTCCGAAGG (partial) | (Seq Id No. 428) |
| | CFTR7D-s | 440 | 465 | 390 | 515 | CTGTACAAACATGGTATGACTCTCTT | (Seq Id No. 429) |
| | CFTR7D-as | 576 | 600 | 526 | 650 | CGCCCCGCGCCCCGCCCCGCCCCGCCCCGGTGAAGGAAATTTCTTTTTCTATCT | (Seq Id No. 430) |
| | CFTR7B-s | 152 | 175 | 102 | 225 | AGACCATGCTCAGATCTTCCATTC | (Seq Id No. 431) |
| | CFTR7B-as | 246 | 267 | 196 | 317 | CGCCCCGCGCCCCGCCCCGCCCCGCCCCGTGCCTTCCGAGTCAGTTTCAGT | (Seq Id No. 432) |
| HUMCFTRA8 | CFTR8A-s | 251 | 272 | 201 | 322 | CGCCCCGCGCCCCGCCCCGCCCCGCCCCGGCACAATGAGAGTATAAAGTAG | (Seq Id No. 433) |
| | CFTR8A-as | 382 | 402 | 332 | 452 | CCATCACTACTTCTGTAGTCG | (Seq Id No. 434) |
| | CF8B-S2: | 319 | 345 | 269 | 395 | CTCTCTTTTATAAATAGGATTTCTTAC | (Seq Id No. 435) |
| | CF8B-as2 | 523 | 547 | 473 | 597 | CGCCCCGCGCCCCGCCCCGCCCCGCCCCGTTCCAGTTCTTCCAGTTATATCATC | (Seq Id No. 436) |
| | CFTR8B-s | 319 | 345 | 269 | 395 | CGCCCCGCGCCCCGCCCCGCCCCGCCCCGCTCTCTTTTATAAATAGGATTTCTTAC | (Seq Id No. 437) |
| | CSTR8B-as | 523 | 547 | 473 | 597 | TTCCAGTTCTACCAGTTATATCATC | (Seq Id No. 438) |
| HUMCFTRA9 | CFTR9C-s | 501 | 525 | 451 | 575 | CGCCCCGCGCCCCGCCCCGCCCCGCCCCGACAATAGAAAAACTTCTAATGGTGA | (Seq Id No. 439) |
| | CFTR9C-as | 679 | 700 | 629 | 750 | AAAAAAGAGACATGGACACCA | (Seq Id No. 440) |
| HUMCFTRA10 | CFTR10-s | 259 | 276 | 209 | 326 | CCTGAGCGTGATTTGATA | (Seq Id No. 441) |
| | CFTR10-ae | 331 | 346 | 281 | 396 | CGCCCCGCGCCCCGCCCCGCCCCGCCCCGATGTAGACTAACCGATTGAA | (Seq Id No. 442) |
| | CF10C-e3 | 333 | 346 | 283 | 396 | GGGAGAACTGGAGCCT | (Seq Id No. 443) |
| | CF10C-as3 | 357 | 587 | 520 | 637 | CGCCCCGCGCCCCGCCCCGCCCCGCCCCGCCCGATTGAATATGGAG | (Seq Id No. 444) |
| HUMCFTRA11 | CFTR11A-s2 | 203 | 223 | 153 | 273 | CGCCCCGCGCCCCGCCCCGCCCCGCCCCGGATATATGATTACATTAGAAG | (Seq Id No. 445) |
| | CFTR11A-as2 | 326 | 342 | 276 | 392 | ACCTTCTCCAAGAACTA | (Seq Id No. 446) |

TABLE B-continued

| locus on AH006034 | primer name | Alignment to GemBank Accession Number AH006034 | | | | | |
|---|---|---|---|---|---|---|---|
| | | primer alignment | | upstre 50 bp | downstr. 50 bp | Primer sequences 5'-3' | |
| | | start | end | | | | |
| HUMCFTRA12 | CFTR11B-s | 291 | 308 | 241 | 358 | ATAGGACATCTCCAAGTT | (Seq Id No. 447) |
| | CFTR11B-as | 452 | 470 | 402 | 520 | CGCCCCGCGCGCCCGGCCCCGGCAATAGAGAGAAATGTCTGT | (Seq Id No. 448) |
| | CFTR12-s | 201 | 223 | 151 | 273 | CGCCCCGCGCGCGCCCGCGCCCCGGCCCCGGCCCCGGTGTTTAAGGCAATCAT | (Seq Id No. 449) |
| | CFTR12-as | 418 | 438 | 368 | 488 | TGATGGGACAGTCTGTCTTTC | (Seq Id No. 450) |
| HUMCFTRA13 | CFTR13A-s | 112 | 136 | 62 | 186 | AATACGAGACATATTGCAATAAGT | (Seq Id No. 451) |
| | CFTR13A-as | 304 | 325 | 254 | 375 | CGCCCCGCGCGCCCGCGCCCGCTGGCTGTAGATTTTGGAGTTC | (Seq Id No. 452) |
| | CF13B-s | 273 | 289 | 223 | 339 | AGGTAGCAGCTATTTT | (Seq Id No. 455) |
| | CF13B-as | 360 | 621 | 555 | 671 | CGCCCCGCGCGCCCGCGCCCCGGGACAGCCTTCTCTCTA | (Seq Id No. 456) |
| | CFTR13B-s | 291 | 243 | 169 | 293 | CACTTCTAAAATGGAACATTTAAAG | (Seq Id No. 457) |
| | CFTR13B-as | 641 | 658 | 591 | 708 | CGCCCCGCGCGCCCGCGCCCCGGCCCCGGCAGTATCGCCTCTCCCT | (Seq Id No. 458) |
| | CFTR13C-s | 290 | 310 | 240 | 360 | CGCCCCGCGCGCCCGCGCCCCGGCCCCGCCGATGGGACATTTTCAGAACTCC | (Seq Id No. 459) |
| | CFTR13C-as | 571 | 589 | 521 | 639 | CCTCTTCGATGCCATTCAT | (Seq Id No. 460) |
| | CFTR13D-s | 516 | 538 | 466 | 588 | CGCCCCGCGCGCCCGCGCCCCGCCCCGCAATCAATCAACTCTATACGAA | (Seq Id No. 461) |
| | CFTR13D-as | 660 | 677 | 610 | 727 | CTGATCACGCTGATGCCA | (Seq Id No. 462) |
| | CFTR13E-s | 594 | 613 | 544 | 663 | CGCCCCGCGCGCCCGCGCCCCGCCCCGTGATGAGCCTTTAGAGAGAA | (Seq Id No. 463) |
| | CFTR13E-as | 808 | 826 | 758 | 876 | CCAGTTCAGTCAAGTTTGC | (Seq Id No. 464) |
| | CF13F-s2 | 666 | 679 | 616 | 729 | CGCCCCGCGCGCCCGCGCCCCGCCCCGCCAGCGTGATCAGCA | (Seq Id No. 465) |
| | CF13F-as2 | 960 | 977 | 910 | 1027 | TTTGTTACATGCTACATA | (Seq Id No. 466) |
| HUMCFTRA14 | CFTR13F-s | 663 | 680 | 613 | 730 | CGCCCCGCGCGCCCGCGCCCCGGCCATCAGCGTGATCAGCAC | (Seq Id No. 467) |
| | CFTR13F-as | 960 | 985 | 910 | 1035 | TAGTAAATTTTGTTACATGCTACATA | (Seq Id No. 468) |
| | CFTR14A-1-s | 260 | 290 | 210 | 340 | CGCCCCGCGCGCCCGCGCCCCGCCCCGTTCATATATTAAAATAAAACC | (Seq Id No. 469) |
| | CFTR14A-1-as | 398 | 418 | 348 | 468 | TAATATATCGAAGGTATGTGT | (Seq Id No. 470) |
| | CFTR14A-2-s | 372 | 393 | 322 | 443 | GAGCATACCAGCAGTGACTACA | (Seq Id No. 471) |
| | CFTR14A-2-as | 477 | 505 | 427 | 555 | GCCCCCGCGCGCCCGCGCCCCGGTAATACTTTACAATAGAACATTCTTACC | (Seq Id No. 472) |
| | CFTR14A-3-s | 379 | 397 | 329 | 447 | ACCAGCAGTGACTACATGGA | (Seq Id No. 473) |
| | CFTR14A-3-as | 542 | 569 | 492 | 619 | CGCCCCGCGCGCCCGCGCCCCGCCCCGATATTTATGTGTGCATATATATGTAT | (Seq Id No. 474) |
| HUMCFTRA15 | CFTR14B-1-s | 104 | 120 | 54 | 170 | CGCCCCGCGCGCCCGCGCCCCGCCGCCGGTGTACCTGATATTTGG | (Seq Id No. 475) |
| | CFTR14B-1-as | 247 | 262 | 197 | 312 | CTCACTTTCCAAGGAG | (Seq Id No. 476) |
| | CF14B-3-s | 240 | 254 | 190 | 304 | GCTGTGGCTCCTTGG | (Seq Id No. 477) |
| | CF14B-3-as | 490 | 507 | 440 | 557 | CGCCCCGCGCGCCCGCGCCCCGCCCCGACTACAGCCCTGAACTCC | (Seq Id No. 478) |

TABLE B-continued

| locus on AH006034 | primer name | primer alignment start | end | upstre 50 bp | downstr. 50 bp | Primer sequences 5'-3' | |
|---|---|---|---|---|---|---|---|
| | CFTR14B-2-s | 220 | 238 | 170 | 288 | GTGGCTGCTCTTCTTTGGTTG | (Seq Id No. 479) |
| | CFTR14B-2-as | 305 | 333 | 255 | 383 | CGCCCGCGCGCCCGCCCGCTGCCCCGCCCCGCCCGCTACTAGTGGATTACATATATTAAT | (Seq Id No. 480) |
| HUMCFTRA16 | CFTR15A-s | 299 | 324 | 249 | 374 | CGCCCCGCCGCGCCCCCGCCCCGCCCGCCCGCCCGCATGTATTGGAAATTCAGTAAGTAAC | (Seq Id No. 481) |
| | CFTR15A-as | 519 | 542 | 469 | 592 | TTCGACACTGTGATTAGAGTATGC | (Seq Id No. 482) |
| | | 50 | | | | | |
| | CFTR15B-s | 463 | 478 | 413 | 528 | GTGGGAGTAGCCGACA | (Seq Id No. 483) |
| | CFTR15B-as | 651 | 667 | 601 | 717 | CGCCCCGCCGCGCCCCCGCCCCCGCGCCCCGCCCCGCAGGCCCTATTGATGGT | (Seq Id No. 484) |
| | CF15B-s2: | 462 | 477 | 412 | 527 | CGTGGGAGTAGCCGAC | (Seq Id No. 485) |
| | CF15B-as2: | 672 | 689 | 622 | 739 | GGCCCCGCCGCGCCCCCGCCCCGCCCGCCCGCATTAGAAAACCAACAA | (Seq Id No. 486) |
| HUMCFTRA17 | CF16A-s5 | 226 | 241 | 176 | 291 | CCCCCGCCGCGCCCCCGCCCCCGCCCCGCCCGCCCGCTGAATGCTCTACTG | (Seq Id No. 487) |
| | CF16A-as5 | 354 | 370 | 304 | 420 | CATCCAAAATTGCTATA | (Seq Id No. 488) |
| | CFTR16A-s | 233 | 258 | 183 | 308 | CGCCCCGCCGCGCCCCCGCCCCCGCCCCCGCTCTACTGTGATCCAAACTTAGTAT | (Seq Id No. 489) |
| | CFTR16A-as | 387 | 410 | 337 | 460 | CATACCTGGATGAAGTCAAATATG | (Seq Id No. 490) |
| | CFTR16B-s | 296 | 318 | 246 | 368 | TTGAGGAATTTGTCATCTTGTAT | (Seq Id No. 491) |
| | CFTR16B-as | 456 | 478 | 406 | 528 | CGCCCCGCCGCGCCCCCGCCCCCGCCCCGCCCGAAAATCACATTTGCTTTTGTTA | (Seq Id No. 492) |
| HUMCFTRA18 | CF17A-1-s | 130 | 147 | 80 | 197 | CGCCCCGCCGCGCCCCCGCCCCCGCCCGCCCAAAGAAATAAATCACTGA | (Seq Id No. 493) |
| | CF17A-1-as6 | 243 | 258 | 193 | 308 | GTAAAACTGCGACAAC | (Seq Id No. 494) |
| | CFTR17A-2-s | 187 | 212 | 137 | 262 | CCAACATGTTTTCTTTTGATCTTACAG | (Seq Id No. 495) |
| | CFTR17A-2-as | 399 | 425 | 349 | 475 | CGCCCCGCCGCGCCCCCGCCCCCGCCCGCCCGAGAATCTCAAATAGCTCTTATAGCTTT | (Seq Id No. 496) |
| HUMCFTRA19 | CFTR18A-1-s | 35 | 56 | -15 | 106 | CGCCCCGCCGCGCCCCCGCCCCCGCCCCGCCCGCCCCGTTAACCAATGACATTTGTGATA | (Seq Id No. 497) |
| | CFTR17B-1-As | 189 | 209 | 139 | 259 | GTGTCCATAGTCCTTTTAAGC | (Seq Id No. 498) |
| | CFTR17B-2-s | 145 | 165 | 95 | 215 | CGCCCCGCCGCGCCCCCGCCCCCGCCCCGCCCCGATATTTCACAGGCAGGAGTCC | (Seq Id No. 499) |
| | CFTR17B-2-as | 312 | 336 | 262 | 386 | AAAATCATTTCTATTCTCATTTGGA | (Seq Id No. 500) |
| | CFTR17B-3-s | 208 | 224 | 158 | 274 | ACTTCGTGCCTTCGGAC | (Seq Id No. 501) |
| | CFTR17B-3-as | 335 | 356 | 285 | 406 | CGCCCCGCCGCGCCCCCGCCCCCGCCCCGCCAGAATGAAGAAGATGACAAA | (Seq Id No. 502) |
| | CFTR17B-4-s | 307 | 323 | 257 | 373 | CTGGTTCCAAATGAGAA | (Seq Id No. 503) |
| | CFTR7B-4-as | 444 | 462 | 394 | 512 | CGCCCCGCCGCGCCCCCGCCCCCGCCCCGCTAACCTATAGAATGCAGCA | (Seq Id No. 504) |
| HUMCFTRA20 | CFTR18A-s | 239 | 258 | 189 | 308 | CGCCCCGCCGCGCCCCCGCCCCCGCCCCGCCCGTTAATGTGATATGTGCCCTA | (Seq Id No. 505) |
| | CFTR18A-as | 431 | 451 | 381 | 501 | AGATGATAAGACTTACCAAGC | (Seq Id No. 506) |
| | CFTR18B-s | 335 | 355 | 285 | 405 | GAGAAGGAGGAAGAAGAGTTG | (Seq Id No. 507) |

TABLE B-continued

Alignment to GemBank Accession Number AH006034

| locus on AH006034 | primer name | primer alignment start | end | upstre 50 bp | downstr. 50 bp | Primer sequences 5'-3' | |
|---|---|---|---|---|---|---|---|
| HUMCFTRA21 | CFTR18B-as | 490 | 512 | 440 | 562 | CGCCCCGCGCCCCGGCCCCGGCCCCGGCCCCGCCTTCCTTCATGCTATTACTCATAC | (Seq Id No. 508) |
| | CFTR19A-s2 | 103 | 123 | 53 | 173 | CGCCCCGCGCCCCGGCCCCGGCCCCGGCCCCGCCGAAGTTATTTTTAGGAAGCAT | (Seq Id No. 509) |
| | CFTR19A-as | 197 | 215 | 147 | 265 | GAACTTAAAGACTCGGCTC | (Seq Id No. 510) |
| | CFTR19B-s | 136 | 156 | 86 | 206 | CGCCCCGCGCCCCGGCCCCGGCCCCGGCCCCGCCGAAATTGTCTGCCATTCTTAA | (Seq Id No. 511) |
| | CFTR19b-as | 259 | 278 | 209 | 328 | GAGTTGGCCATTCTTGTATG | (Seq Id No. 512) |
| | CF19C-s3 | 194 | 209 | 144 | 259 | CGCCCCGCGCCCCGGCCCCGGCCCCGGCCCCGCCGTGTGAGCCGAGTCTTT | (Seq Id No. 513) |
| | CF19C-as2 | 379 | 394 | 329 | 444 | ATGGCATTTCCACCTT | (Seq Id No. 514) |
| | CF19C-s2 | 169 | 189 | 119 | 239 | CGCCCCGCGCCCCGGCCCCGGCCCCGGCCCCGCCGTGTTATTTTTTATTCAGATGC | (Seq Id No. 515) |
| | CF19C-as2 | 380 | 398 | 330 | 448 | TAATATGGCATTTCCACCT | (Seq Id No. 516) |
| | CF19D-s2 | 308 | 323 | 258 | 373 | CGTGAAGAAAGATGAC | (Seq Id No. 517) |
| | CF19D-as2 | 513 | 531 | 463 | 581 | CGCCCCGCGCCCCGGCCCCGGCCCCGGCCCCGCCGTAATGTTACAAATAGATT | (Seq Id No. 518) |
| | CFTR19D-s | 304 | 324 | 254 | 374 | CACACGTGAAGAAAGATCACA | (Seq Id No. 519) |
| | CFTR19D-as | 506 | 531 | 456 | 581 | CGCCCCGCGCCCCGGCCCCGGCCCCGGCCCCGCCGTAATGTTAATAGATTCTGCTAAAC | (Seq Id No. 520) |
| dssp intronic: no alignment to AH006034 | CF19l-s2 | | | | | CGCCCCGCGCCCCGGCCCCGGCCCCGGCCCCGCCGCTTGATTTCTGGAGAC | (Seq Id No. 521) |
| | CF19l-as2 | | | | | CTAGCTGTAATTGCAT | (Seq Id No. 522) |
| HUMCFTRA22 | CFTR20-s | 203 | 223 | 153 | 273 | CGCCCCGCGCCCCGGCCCCGGCCCCGGCCCCGCCCAATTATGTTTATGGCATGGT | (Seq Id No. 523) |
| | CFTR20-as | 470 | 494 | 420 | 544 | GAGTACAASTATCAAATAGCAGTAA | (Seq Id No. 524) |
| | new 20-s: | 201 | 219 | 151 | 269 | CGCCCCGCGCCCCGGCCCCGGCCCCGGCCCCGCCGCTGAATTATGTTTATGGCA | (Seq Id No. 525) |
| | new 20-as | 435 | 452 | 385 | 502 | CCTTTTTTCTGGCTAAGT | (Seq Id No. 526) |
| HUMCFTRA23 | CFTR21A-s | 162 | 182 | 112 | 232 | CGCCCCGCGCCCCGGCCCCGGCCCCGGCCCCGCCCCGATGGTAAGTACATGGGTGTT | (Seq Id No. 527) |
| | CFTR21A-as | 333 | 353 | 283 | 403 | ACTCCACTGTTCATAGGGATC | (Seq Id No. 528) |
| | CF 21A-s3: | 254 | 273 | 204 | 323 | CGCCCCGCGCCCCGGCCCCGGCCCCGGCCCCGCCCCAGAGTTATTCATACTTTCTTCT | (Seq Id No. 529) |
| | CF 21A-as3: | 376 | 391 | 326 | 441 | AGCCTTACCTCATCTG | (Seq Id No. 530) |
| | CF21B-s3 | 307 | 322 | 257 | 372 | CGCCCCGCGCCCCGGCCCCGGCCCCGGCCCCGCCGTTTCTGAACATTAG | (Seq Id No. 531) |
| | CF21B-as3 | 443 | 460 | 393 | 510 | GAATGATGTCAGCTATAT | (Seq Id No. 532) |
| | CFTR21B-s2 | 307 | 329 | 257 | 379 | CGCCCCGCGCCCCGGCCCCGGCCCCGGCCCCGCCGTTTCTGGAACATTTAGAAAAAC | (Seq Id No. 533) |
| | CFTR21B-as2 | 544 | 562 | 494 | 612 | TCAGTTAGGGGTAGTTCCA | (Seq Id No. 534) |
| HUMCFTRA24 | CFTR22A-s2 | 356 | 373 | 306 | 423 | CGCCCCGCGCCCCGGCCCCGGCCCCGGCCCCGCCGTGAGCTGTCAAGGTTGTA | (Seq Id No. 535) |
| | CFTR22A-as2 | 551 | 569 | 501 | 619 | CAGGAAACTGTTCTTATCAC | (Seq Id No. 536) |

TABLE B-continued

| locus on AH006034 | primer name | primer alignment start | end | upstre 50 bp | downstr. 50 bp | Primer sequences 5'-3' | |
|---|---|---|---|---|---|---|---|
| | CFTR22B-s | 474 | 497 | 424 | 547 | CGCCCCCCGCGCCCCCGCGCCCCCCGGAATGTCAACTGCTTGAGTGTTTT | (Seq Id No. 537) |
| | CFTR22B-as | 707 | 733 | 657 | 783 | AAGTAACAGAACATCTGAAACTCACAC | (Seq Id No. 538) |
| | CFTR22C-s2 | 570 | 686 | 620 | 736 | CTTGCTTGATGAAC | (Seq Id No. 539) |
| | CFTR22C-as | 821 | 843 | 771 | 893 | CGCCCCCCGCGCCCCCGCGCCCCCCGTGGGCAATTATTTCATATCTTGG | (Seq Id No. 540) |
| HUMCFTRA25 | CF23A-s3 | 223 | 240 | 173 | 290 | CGCCCCCCGCGCCCCCGCGCCCCCCGTATCAAGGTAAATACAGA | (Seq Id No. 541) |
| | CF23A-as3 | 353 | 369 | 303 | 419 | GCTTCTATCCTGTGTTC | (Seq Id No. 542) |
| | CF233-s2 | 256 | 276 | 206 | 326 | GATATTATGTGGTATTTC | (Seq Id No. 543) |
| | CF235-as2 | 477 | 495 | 427 | 545 | GCCCGCCCCGCGCCCCCGCGCCCCCCTTGTACATTGTTGCA | (Seq Id No. 544) |
| | CFTR23-s | 218 | 244 | 168 | 294 | CGCCCCCCGCGCCCCCGCGCCCCCCGCATATTATCAAGGTAAATACAGATCAT | (Seq Id No. 545) |
| | CFTR23-as | 445 | 469 | 395 | 519 | GGAACTATCACATGTGAGATTGTTA | (Seq Id No. 546) |
| HUMCFTRA26 | CF24A-s2 | 107 | 122 | 57 | 172 | CGCCCCCCGCGCCCCCGCGCCCCCCGCCTTTGAGCCTGTGCC | (Seq Id No. 547) |
| | CF24A-as2 | 300 | 315 | 250 | 365 | GCTTGAGTTCCGGTGG | (Seq Id No. 548) |
| | CF24B-s | 267 | 282 | 217 | 332 | CATCAGCCCCTCCGAC | (Seq Id No. 549) |
| | CF24B-s2 | 482 | 498 | 432 | 548 | CGCCCCCCGCGCCCCCGCGCCCCCCGTTTCTGATGAAGGCAGAGGTA | (Seq Id No. 550) |
| | CFTR24A-s | 82 | 99 | 32 | 149 | CGCCCCCCGCGCCCCCGCGCCCCCCGCATTGCATTCTTTGACTT | (Seq Id No. 551) |
| | CFTR24A-as | 280 | 296 | 23 | 346 | AAGAGCTTCACCCTGTC | (Seq Id No. 552) |
| | CFTR24B-s | 213 | 229 | 163 | 279 | GCAGTACGATTCCATCC | (Seq Id No. 553) |
| | CFTR24B-as | 489 | 504 | 439 | 554 | CGCCCCCCGCGCCCCCGCGCCCCCCGCCTTGTTTTCTGACGC | (Seq Id No. 554) |

TABLE C

PCR Plate Set Up

| | | | | | Position | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Plate 49 | | | | | | | | | | | | |
| Fragment | 16B | 6B2 | 17B4 | 14A1 | 6A2 | 11A | | | | | | |
| Multi G | 3A | 3B1 | 3B2 | 5A2 | 10B2 | 5F | | | | | | |
| Plate 52 | | | | | | | | | | | | |
| Fragment | 17B1 | 14A3 | 3A | 11B | 7B | 21B | 22C | 22A | | | | |
| Multi G | 3A3 | 4B3 | 5D1 | 6A2 | 8A1 | 7B | 8A | 7B | | | | |
| Plate 54 | | | | | | | | | | | | |
| Fragment | 5A | 3B | 19A | 4B | 2A | 19C | 14B1 | 22B | 17B2 | 6B1 | | |
| Multi G | 4A | 4B2 | 5B2 | 6A3 | 7B | 8B2 | 8B4 | 10A1 | 10A2 | 4C | | |
| Plate 59 A | | | | | | | | | | | | |
| Fragment | 8B | 13F | 10 | 18B | 19B | 18A | 14B2 | | | | | |
| Multi G | 5B | 5C | 5E | 5F | 6A | 7A | 8A | | | | | |
| Plate 59 B | | | | | | | | | | | | |
| Fragment | 15B | 13D | 24B | 24A | 13E | 1A | 1B | | | | | |
| Multi G | 8B | 9A | 11A | 11A | 12A | 13A | 13A | | | | | |
| Plate 62.4 A | | | | | | | | | | | | |
| Fragment | 21A | 8A | 13A | 7D | 23 | 14A2 | 13B | 13C | 15A | 9C | 2B | 5B |
| Multi G | 1A | 2A | 4A | 4B | 5A | 5D | 6A | 7A | 7A | 7B | 1B | 4C |
| Plate 62.4 B | | | | | | | | | | | | |
| Fragment | 12 | 6A3 | 17A2 | 19D | 20 | 4A | 17B3 | 7C | 6A1 | 16A | 7A | |

61 total fragments

TABLE D

| Group | TTGE Start | TTGE End | Gels/Group | Dcodes |
|---|---|---|---|---|
| 1 | 44.5 | 48.0 | 2 | 1 |
| 2 | 48.0 | 50.5 | 1 | 1 |
| 3 | 48.0 | 51.0 | 2 | 1 |
| 4 | 49.0 | 52.5 | 3 | 2 |
| 5 | 50.5 | 53.5 | 6 | 3 |
| 6 | 52.5 | 55.5 | 1 | 1 |
| 7 | 53.5 | 56.5 | 2 | 1 |
| 8 | 55.0 | 58.0 | 2 | 1 |
| 9 | 56.0 | 58.5 | 2 | 1 |
| 10 | 57.0 | 59.5 | 2 | 1 |
| 11 | 58.5 | 62.0 | 1 | 1 |
| 12 | 58.5 | 62.0 | 1 | 1 |
| 13 | 62.0 | 64.0 | 1 | 1 |
| Totals: | | | 26 | 16 |

TABLE E

| Gene | Fragment | PCR Temp | Rating | App Tm | Length | Length_GC | Min PCR | Max PCR | Min Melt | Max Melt | Min Actual | Max Actual | Group | Position |
|---|---|---|---|---|---|---|---|---|---|---|---|---|---|---|
| CFTR | 21A | 55 | 81 | 52 | 192 | 242 | 45 | 65 | 60 | 62 | 46 | 48 | 1 | A1 |
| CFTR | 2B | 60 | 60 | 57 | 199 | 249 | 45 | 56.7 | 61 | 62 | 47 | 48 | 1 | B1 |
| CFTR | 8A | 55 | 60 | 48 | 152 | 202 | 50 | 62 | 62 | 64 | 48 | 50 | 2 | A1 |
| CFTR | 16A | 55 | 80 | 56 | 178 | 228 | 45 | 65 | 62 | 64 | 48 | 50 | 2 | A2 |
| CFTR | 7A | 55 | 78 | 63 | 118 | 168 | 50 | 65 | 62 | 64 | 48 | 50 | 2 | A3 |
| CFTR | 12 | 50 | 80 | 55 | 238 | 288 | 45 | 65 | 63 | 65 | 49 | 51 | 3 | A1 |
| CFTR | 18B | 50 | 78 | 54 | 183 | 233 | 45 | 65 | 63 | 65 | 49 | 51 | 3 | A2 |
| CFTR | 17B-1 | 53 | 83 | 51 | 175 | 225 | 45 | 59.6 | 63 | 65 | 49 | 51 | 3 | A3 |
| CFTR | 6B-2 | 50 | 86 | 36 | 159 | 209 | 48 | 59 | 63 | 65 | 49 | 51 | 3 | B1 |
| CFTR | 17B-4 | 50 | 78 | 45 | 156 | 206 | 45 | 56.7 | 63 | 65 | 49 | 51 | 3 | B2 |
| CFTR | 13A | 50 | 73 | 38.5 | 209 | 259 | 45 | 65 | 63.5 | 66.5 | 49.5 | 52.5 | 4 | A1 |
| CFTR | 5A | 53 | 77 | 52 | 139 | 189 | 45 | 59.6 | 65 | 66 | 51 | 52 | 4 | A2 |
| CFTR | 7D | 62 | 64 | 56 | 161 | 211 | 45 | 65 | 64 | 66 | 50 | 52 | 4 | B1 |
| CFTR | 3B | 55 | 87 | 57 | 177 | 227 | 45 | 65 | 65 | 66 | 51 | 52 | 4 | B2 |
| CFTR | 14A-3 | 53 | 63 | 53 | 192 | 242 | 45 | 65 | 65 | 66 | 51 | 52 | 4 | B3 |
| CFTR | 6B-1 | — | 88 | 33 | 148 | 198 | 46.5 | 65 | 64 | 66 | 50 | 52 | 4 | C1 |
| CFTR | 5B | — | 92 | 44 | 163 | 213 | 59.6 | 65 | 64 | 66 | 50 | 52 | 4 | C2 |
| CFTR | 23 | 53 | 64 | 55 | 252 | 302 | | | 65 | 67 | 51 | 53 | 5 | A1 |
| CFTR | 14A-1 | 55 | | | 50 | | 45 | 65 | 66 | 68 | 52 | 54 | 5 | A2 |
| CFTR | 9A | — | 60 | 46 | 171 | 221 | 45 | 63.4 | 66 | 67 | 52 | 53 | 5 | |

TABLE E-continued

| Gene | Fragment | PCR Temp | Rating | App Tm | Length | Length_GC | Min PCR | Max PCR | Min Melt | Max Melt | Min Actual | Max Actual | Group | Position |
|---|---|---|---|---|---|---|---|---|---|---|---|---|---|---|
| CFTR | 8B | 53 | 57 | 49 | 227 | 277 | 45 | 65 | 65 | 67 | 51 | 53 | 5 | B1 |
| CFTR | 19A | 50 | 84 | 49 | 166 | 216 | 45 | 65 | 65 | 67 | 51 | 53 | 5 | B2 |
| CFTR | 17A-1 | 55 | 66 | 54 | 181 | 231 | 50.5 | 65 | 66 | 67 | 52 | 53 | 5 | |
| CFTR | 11A | 50 | 67 | 52 | 144 | 194 | 48.2 | 65 | 65 | 67 | 51 | 53 | 5 | F1 |
| CFTR | 18B | 62 | 68 | 52 | 178 | 228 | 45 | 64.6 | 66 | 68 | 52 | 54 | 5 | F2 |
| CFTR | 13F | 50 | 66 | 42 | 312 | 362 | 45 | 65 | 67 | 68 | 53 | 54 | 5 | C1 |
| CFTR | 6A-3 | 50 | 70 | 56 | 153 | 233 | 53.4 | 63 | 66 | 68 | 52 | 54 | 5 | C2 |
| CFTR | 3A | 50 | 72 | 44 | 230 | 280 | 45 | 56.7 | 66 | 68 | 52 | 54 | 5 | D1 |
| CFTR | 14A-2 | 50 | 80 | 55 | 134 | 184 | 53.4 | 65 | 67 | 68 | 53 | 54 | 5 | D2 |
| CFTR | 9B | 60 | 68 | 53 | 167 | 207 | 45 | 65 | 65 | 67 | 51 | 53 | 5 | |
| CFTR | 10 | 60 | 92 | 50 | 356 | 406 | 20.5 | 65 | 65 | 68 | 51 | 54 | 5 | E2 |
| CFTR | 13B | 55 | 64 | 55 | 440 | 490 | 45 | 61.8 | 66.5 | 68.5 | 52.5 | 54.5 | 6 | A1 |
| CFTR | 11B | 45 | 74 | 43 | 180 | 230 | 59.6 | 65 | 67 | 69 | 53 | 55 | 6 | A2 |
| CFTR | 4B | 55 | 92 | 43 | 194 | 244 | 45 | 59 | 67 | 69 | 53 | 55 | 6 | A3 |
| CFTR | 19B | 60 | 48 | 53 | 143 | 193 | 50 | 65 | 67 | 69 | 53 | 55 | 6 | A4 |
| CFTR | 9D | 60 | 53 | 56 | 132 | 182 | 45 | 63.4 | 67 | 69 | 53 | 55 | 6 | |
| CFTR | 13C | 45 | 81 | 55 | 300 | 350 | 45 | 65 | 68 | 70 | 54 | 56 | 7 | A1 |
| CFTR | 18A | 62 | 92 | 49 | 213 | 263 | 50.5 | 63.4 | 68 | 70 | 54 | 56 | 7 | A2 |
| CFTR | 17A-2 | 55 | 59 | 58 | 239 | 289 | 45 | 65 | 68 | 70 | 54 | 56 | 7 | A3 |
| CFTR | 15A | 50 | 82 | 56 | 244 | 294 | 45 | 65 | 69 | 70 | 55 | 56 | 7 | A4 |
| CFTR | 9C | 60 | 65 | 56 | 200 | 250 | 63.4 | 65 | 69 | 70 | 55 | 56 | 7 | B1 |
| CFTR | 22A | 55 | 76 | 53 | 217 | 267 | 45 | 65 | 67.5 | 70 | 53.5 | 56 | 7 | B2 |
| CFTR | 2A | 53 | 80 | 52 | 166 | 216 | 45 | 61.8 | 68 | 70 | 54 | 56 | 7 | B3 |
| CFTR | 21B | | 76 | 38 | 256 | 306 | 45 | 65 | 68 | 70 | 54 | 56 | 7 | B4 |
| CFTR | 7B | 55 | 93 | 61 | 116 | 166 | 45 | 65 | 70 | 71 | 56 | 57 | 8 | A1 |
| CFTR | 14B-2 | 50 | 69 | 56 | 114 | 164 | 45 | 65 | 69 | 71 | 55 | 57 | 8 | A2 |
| CFTR | 22C | 50 | 76 | 47 | 167 | 217 | 45 | 65 | 69 | 71 | 55 | 57 | 8 | A3 |
| CFTR | 19D | 50 | | | | 50 | 45 | 65 | 69.5 | 71.5 | 55.5 | 57.5 | 8 | A4 |
| CFTR | 20 | 50 | 71 | 53 | 228 | 278 | 45 | 65 | 69 | 71 | 55 | 57 | 8 | B1 |
| CFTR | 19C | 53 | 84 | 50 | 226 | 276 | 45 | 65 | 69 | 71 | 55 | 57 | 8 | B2 |
| CFTR | 15B | 45 | 82 | 49 | 205 | 255 | 45 | 53.4 | 69 | 71 | 55 | 57 | 8 | B3 |
| CFTR | 14B-1 | 45 | 75 | 40 | 159 | 209 | 45 | 65 | 70 | 71 | 56 | 57 | 8 | B4 |
| CFTR | 4A | 50 | 79 | 55 | 219 | 269 | 45 | 63.4 | 70 | 72 | 56 | 58 | 9 | A1 |
| CFTR | 13D | 50 | 78 | 55 | 162 | 212 | 48.2 | 56.7 | 70 | 73 | 56 | 59 | 9 | A2 |
| CFTR | 17B-3 | 45 | 89 | 54 | 149 | 199 | 45 | 56.7 | 71 | 72 | 57 | 58 | 9 | B1 |
| CFTR | 22B | 55 | 66 | 58 | 260 | 310 | 45 | 65 | 71 | 73 | 57 | 59 | 10 | A1 |
| CFTR | 17B-2 | 45 | 80 | 56 | 192 | 242 | 45 | 59.6 | 71 | 73 | 57 | 59 | 10 | A2 |
| CFTR | 7C | 55 | 85 | 55 | 253 | 303 | 45 | 65 | 71 | 73 | 57 | 59 | 10 | B1 |
| CFTR | 6A-2 | 50 | 93 | 49 | 127 | 177 | 45 | 65 | 71 | 73 | 57 | 59 | 10 | B2 |
| CFTR | 6A-1 | 50 | 86 | 46 | 292 | 342 | 45 | 65 | 73 | 75 | 59 | 61 | 11 | A1 |
| CFTR | 24B | 50 | 88 | 53 | 183 | 233 | | | 73 | 74 | 59 | 60 | 11 | A2 |
| CFTR | 24A | 50 | 81 | 46 | 215 | 265 | | | 73 | 75 | 59 | 61 | 11 | A3 |
| CFTR | 13E | 50 | | | | 50 | 45 | 65 | 73 | 76.5 | 59 | 62.5 | 12 | A1 |
| CFTR | 1A | 60 | 84 | 62 | 180 | 230 | 56.7 | 65 | 76 | 78 | 62 | 64 | 13 | A1 |
| CFTR | 1B | 60 | 85 | 60 | 165 | 215 | 56.7 | 64.6 | 76 | 77 | 62 | 63 | 13 | A2 |

What is claimed is:

1. A method of identifying the presence or absence of genetic markers in the human cystic fibrosis transmembrane conductance regulator (CFTR) gene of a subject comprising:
providing a DNA sample from said subject;
contacting said DNA sample with at least four primer sets;
generating an extension product from each of said at least four primer sets comprising a region of DNA that includes the location of a genetic marker;
grouping said extension products according to the following grouping assignments, wherein at least one group includes at least four pooled extension products:
Group 1 comprising extension products generated from primer sets SEQ ID NOs 358-359, SEQ ID NOs 364-365, and SEQ ID NOs 186-187;
Group 2 comprising extension products generated from primer sets SEQ ID NOs 235-236, SEQ ID NOs 305-306, SEQ ID NOs 226-227;
Group 3 comprising extension products generated from primer sets SEQ ID NOs 262-263, SEQ ID NOs 330-331, SEQ ID NOs 319-320, SEQ ID NOs 221-222, and SEQ ID NOs 325-326;
Group 4 comprising extension products generated from primer sets SEQ ID NOs 267-268, SEQ ID NOs 203-204, SEQ ID NOs 230-231, SEQ ID NOs 191-192, SEQ ID NOs 284-285, SEQ ID NOs 219-220, and SEQ ID NOs 205-206;
Group 5 comprising extension products generated from primer sets SEQ ID NOs 376-377, SEQ ID NOs 378-379, SEQ ID NOs 280-281, SEQ ID NOs 237-238, SEQ ID NOs 335-336, SEQ ID NOs 312-313, SEQ ID NOs 255-256, SEQ ID NOs 330-331, SEQ ID NOs 277-278, SEQ ID NOs 235-236, SEQ ID NOs 189-190, SEQ ID NOs 282-283, and SEQ ID NOs 248-249;
Group 6 comprising extension products generated from primer sets SEQ ID NOs 269-270 SEQ ID NOs 257-258, SEQ ID NOs 198-199, and SEQ ID NOs 337-338;
Group 7 comprising extension products generated from primer sets SEQ ID NOs 271-272, SEQ ID NOs 328-329, SEQ ID NOs 314-315, SEQ ID NOs 296-297, SEQ ID NOs 242-243, SEQ ID NOs 367-368, SEQ ID NOs 182-183, and SEQ ID NOs 360-361;
Group 8 comprising extension products generated from primer sets SEQ ID NOs 371-372, SEQ ID NOs 341-342, SEQ ID NOs 355-356, SEQ ID NOs 339-340, and SEQ ID NOs 298-299;
Group 9 comprising extension products generated from primer sets SEQ ID NOs 273-274 and SEQ ID NOs 323-324;
Group 10 comprising extension products generated from primer sets SEQ ID NOs 369-370, SEQ ID NOs 321-322, SEQ ID NOs 228-229, and SEQ ID NOs 212-213;
Group 11 comprising extension products generated from primer sets SEQ ID NOs 210-211, SEQ ID NOs 383-384, and SEQ ID NOs 381-382;
Group 12 comprising extension products generated from primer sets SEQ ID NOs 275-276;
Group 13 comprising extension products generated from primer sets SEQ ID NOs 175-176 and SEQ ID NOs 177-178;
separating said extension products on the basis of melting behavior; and
identifying the presence or absence of said genetic markers in said subject by analyzing the melting behavior of said extension products.

2. The method of claim 1, wherein said at least four primer sets comprise at least five primer sets.

3. The method of claim 2, wherein said at least five primer sets comprise at least six primer sets.

4. The method of claim 3, wherein said at least six primer sets comprise at least seven primer sets.

5. The method of claim 4, wherein said at least seven primer sets comprise at least eight primer sets.

6. The method of claim 1, wherein the extension products generated from said primer sets are grouped with those having similar melting behaviors.

7. The method of claim 1, wherein extension products within groups are separated on a same lane of a TTGE gel or in the same run on a DHPLC.

8. The method of claim 2, wherein the extension products generated from said primer sets are grouped with those having similar melting behaviors and separated on the basis of melting behavior on a same lane of a TTGE gel or in the same run on a DHPLC.

9. The method of claim 3, wherein the extension products generated from said primer sets are grouped with those having similar melting behaviors and separated on the basis of melting behavior on a same lane of a TTGE gel or in the same run on a DHPLC.

10. The method of claim 4, wherein the extension products generated from said primer sets are grouped with those having similar melting behaviors and separated on the basis of melting behavior on a same lane of a TTGE gel or in the same run on a DHPLC.

11. The method of claim 5, wherein the extension products generated from said primer sets are grouped with those having similar melting behaviors and separated on the basis of melting behavior on a same lane of a TTGE gel or in the same run on a DHPLC.

* * * * *